(12) United States Patent
Hendrickson et al.

(10) Patent No.: US 6,904,369 B1
(45) Date of Patent: Jun. 7, 2005

(54) CONJUGATED LIGANDS FOR THE STIMULATION OF BLOOD CELL PROLIFERATION BY EFFECTING DIMERIZATION OF THE RECEPTOR FOR STEM CELL FACTOR

(75) Inventors: Wayne A. Hendrickson, New York, NY (US); Xuliang Jiang, Braintree, MA (US); Keith E. Langley, Newbury Park, CA (US); Rashid Syed, Thousand Oaks, CA (US); Yueh-Rong Ann Hsu, Westlake, CA (US)

(73) Assignees: The Trustees of Columbia University in the City of New York, New York, NY (US); Amgen Inc., Thousand Oaks, CA (US)

( * ) Notice: Subject to any disclaimer, the term of this patent is extended or adjusted under 35 U.S.C. 154(b) by 88 days.

(21) Appl. No.: 09/609,027

(22) Filed: Jun. 29, 2000

(51) Int. Cl.[7] .................. G01N 33/48; G01N 33/50; A61K 38/00; C07K 1/00; C07H 21/04
(52) U.S. Cl. ................ 702/19; 702/20; 702/22; 530/300; 530/350; 536/23.1; 536/24.1
(58) Field of Search ................. 530/300, 350; 536/23.1, 24.1; 702/19, 20, 22

(56) References Cited

FOREIGN PATENT DOCUMENTS

WO       WO-9807835 A2  *  2/1998

OTHER PUBLICATIONS

Jan Drenth, "Principles of Protein X–ray Crystallography", pp. 1–19, Springer–Verlag New York, 1994.*
Barleon et al. 1997, *Journal Biological Chemistry*, 272:10382–10388 (Exhibit 1).
Blechman et al. 1993, *Journal Biological Chemistry*, 268:4399–4406 (Exhibit 2).
Lev et al. 1993, *Journal Biological Chemistry*, 267:15970–15977 (Exhibit 3).
Lu et al. 1996, *Journal Biological Chemistry*, 271:11309–11316 (Exhibit 4); and.
Philo et al. (1996), *Journal Biological Chemistry*, 271, 6895–6902 (Exhibit 5).

* cited by examiner

*Primary Examiner*—John Brusca
*Assistant Examiner*—Shubo (Joe) Zhou
(74) *Attorney, Agent, or Firm*—John P. White; Cooper & Dunham LLP

(57) ABSTRACT

This invention provides a computer based method for preparing a stem cell factor (SCF) analog comprising the steps of: (a) providing computer expression of the three dimensional structure of an SCF molecule using its crystal structure; (b) selecting from the computer expression of step (a) at least one site on the SCF molecule for alteration; (c) preparing a SCF molecule having an alteration at said at least one selected site; and (d) optionally, testing the SCF molecule for a desired characteristic. This invention also provides SCF analogs and SCF ligand analogs prepared according to the above-described method. Compositions comprising SCF analogs or SCF ligand analogs prepared according to the above-described method effective to treat a subject and a pharmaceutically acceptable carrier are provided, as are methods of treating a subject comprising administration of pharmaceutical compositions comprising the prepared SCF analogs and SCF ligand analogs prepared by the described methods. This invention also provides methods for designing compounds capable of binding to the SCF receptor site and compounds designed by the above-described methods.

7 Claims, 85 Drawing Sheets

```
             I                                II                           III
     1   EGICRNRVTNNVKDVTKLVANLPKDYMITEKYVPGMDVLPSHCWLSEMVVQLSDSLTDLLDK  62
Human    EGICRNRVTNNVKDVTKLVANLPKDYMITEKYVPGMDVLPSHCWLSEMVVQLSDSLTDLLDK
Mouse    --KE---G-P---I-------N----------------A----LRD--I--L-----R----
Rat      --QE---G-P---I-------N----------------A----LRD--I--L-----R----
Dog      --K----GK-D----------K-A--------------------LV---E--V---------

IV
     63  FSNISEGLSNYYSIIDKLVNIVDDLVECVKENSSKDLKSFKSPEPREFTPEEFFRIFNRSID  124
Human    FSNISEGLSNYYSIIDKLVNIVDDLVECVKENSSKDLKSFKSPEPREFTPEEFFRIFNRSID
Mouse    ------------------GK------L-ME--AP-NI-E-P--R---T--S-----S-----
Rat      ------------------GK------A-ME--AP-NV-E-L--K---T--N-----S-----
Dog      -----------------.K-------TEGY-FENV-AP-----------L------------

V
    125  AFKDF.VVASETSDCVVSSTLSPEKDSRVSVTKPFMLPPVA  164
Human    AFKDF.VVASETSDCVVSSTLSPEKDSRVSVTKPFMLPPVA
Mouse    -----.M---D------------------------------
Rat      -----.M---D------------------------------
Dog      -----.ET--KS-E---------D-----------------
```

Figure 7
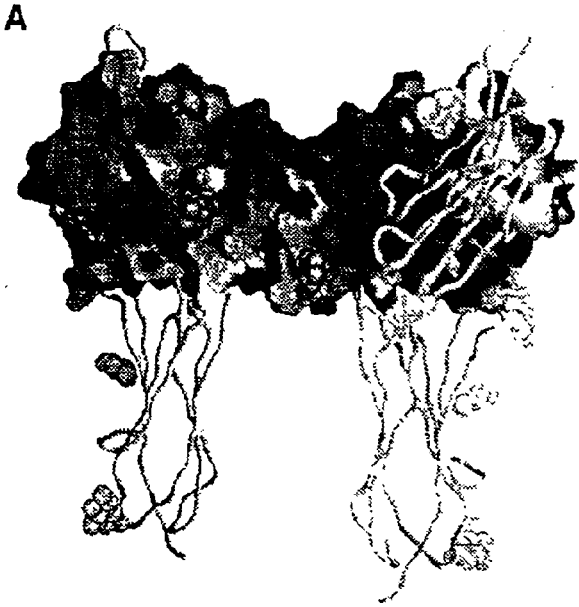
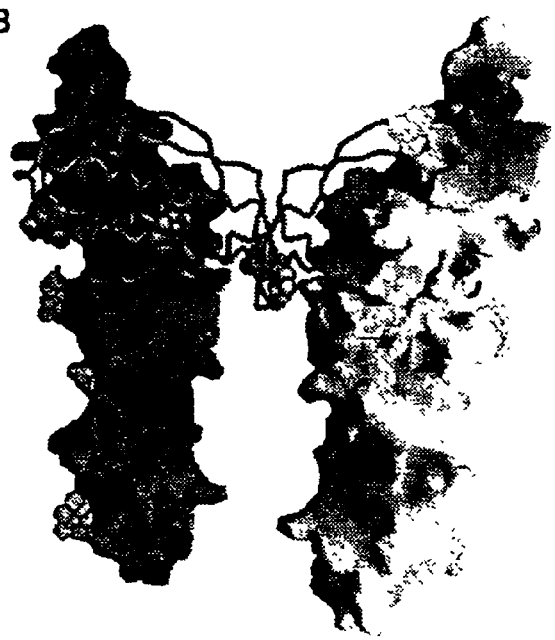

FIGURE 8A-1

```
HEADER      GROWTH FACTOR                                           1SCF
TITLE       HUMAN RECOMBINANT STEM CELL FACTOR
COMPND      MOL_ID: 1;
COMPND     2 MOLECULE: STEM CELL FACTOR;
COMPND     3 CHAIN: A, B, C, D;
COMPND     4 SYNONYM: SCF, SL, MGF, MAST CELL GROWTH FACTOR;
COMPND     5 ENGINEERED: YES;
COMPND     6 BIOLOGICAL_UNIT: DIMER
SOURCE      MOL_ID: 1;
SOURCE     2 ORGANISM_SCIENTIFIC: HOMO SAPIENS;
SOURCE     3 ORGANISM_COMMON: HUMAN;
SOURCE     4 EXPRESSION_SYSTEM: NULL
KEYWDS      HUMAN STEM CELL FACTOR, STEEL FACTOR, KIT LIGAND, MAST CELL
KEYWDS     2 GROWTH FACTOR
EXPDTA      X-RAY DIFFRACTION
AUTHOR      X.JIANG,O.GUREL,K.E.LANGLEY,W.A.HENDRICKSON
JRNL            AUTH   X.JIANG,O.GUREL,K.E.LANGLEY,W.A.HENDRICKSON
JRNL            TITL   CRYSTAL STRUCTURE OF RECOMBINANT HUMAN STEM CELL
JRNL            TITL 2 FACTOR
JRNL            REF    TO BE PUBLISHED
JRNL            REFN                                                0353
REMARK     1
REMARK     2
REMARK     2 RESOLUTION. 2.2 ANGSTROMS.
REMARK     3
REMARK     3 REFINEMENT.
REMARK     3   PROGRAM     : X-PLOR 3.1
REMARK     3   AUTHORS     : BRUNGER
REMARK     3
REMARK     3  DATA USED IN REFINEMENT.
REMARK     3   RESOLUTION RANGE HIGH (ANGSTROMS) : 2.2
REMARK     3   RESOLUTION RANGE LOW  (ANGSTROMS) : 20.0
REMARK     3   DATA CUTOFF            (SIGMA(F)) : 2
REMARK     3   DATA CUTOFF HIGH        (ABS(F))  : 100000
REMARK     3   DATA CUTOFF LOW         (ABS(F))  : 0.1
REMARK     3   COMPLETENESS (WORKING+TEST)   (%) : 96.6
REMARK     3   NUMBER OF REFLECTIONS             : 49851
REMARK     3
REMARK     3  FIT TO DATA USED IN REFINEMENT.
REMARK     3   CROSS-VALIDATION METHOD           : THROUGHOUT
REMARK     3   FREE R VALUE TEST SET SELECTION   : RANDOM
REMARK     3   R VALUE            (WORKING SET)  : 0.199
REMARK     3   FREE R VALUE                      : 0.242
REMARK     3   FREE R VALUE TEST SET SIZE    (%) : 6.0
REMARK     3   FREE R VALUE TEST SET COUNT       : 3016
REMARK     3   ESTIMATED ERROR OF FREE R VALUE   : 0.0044
REMARK     3
REMARK     3  FIT IN THE HIGHEST RESOLUTION BIN.
REMARK     3   TOTAL NUMBER OF BINS USED             : 10
REMARK     3   BIN RESOLUTION RANGE HIGH       (A)   : 2.0
REMARK     3   BIN RESOLUTION RANGE LOW        (A)   : 2.28
REMARK     3   BIN COMPLETENESS (WORKING+TEST) (%)   : 97.0
REMARK     3   REFLECTIONS IN BIN    (WORKING SET)   : 4349
REMARK     3   BIN R VALUE           (WORKING SET)   : 0.3159
REMARK     3   BIN FREE R VALUE                      : 0.3450
REMARK     3   BIN FREE R VALUE TEST SET SIZE  (%)   : 6.4
REMARK     3   BIN FREE R VALUE TEST SET COUNT       : 302
REMARK     3   ESTIMATED ERROR OF BIN FREE R VALUE   : 0.0198
REMARK     3
REMARK     3  NUMBER OF NON-HYDROGEN ATOMS USED IN REFINEMENT.
```

FIGURE 8A-2

```
REMARK   3    PROTEIN ATOMS                      : 3517
REMARK   3    NUCLEIC ACID ATOMS                 : 0
REMARK   3    HETEROGEN ATOMS                    : 19
REMARK   3    SOLVENT ATOMS                      : 264
REMARK   3
REMARK   3   B VALUES.
REMARK   3    FROM WILSON PLOT           (A**2)  : 38.5
REMARK   3    MEAN B VALUE      (OVERALL, A**2)  : 32.1
REMARK   3    OVERALL ANISOTROPIC B VALUE.
REMARK   3     B11 (A**2)  : NULL
REMARK   3     B22 (A**2)  : NULL
REMARK   3     B33 (A**2)  : NULL
REMARK   3     B12 (A**2)  : NULL
REMARK   3     B13 (A**2)  : NULL
REMARK   3     B23 (A**2)  : NULL
REMARK   3
REMARK   3   ESTIMATED COORDINATE ERROR.
REMARK   3    ESD FROM LUZZATI PLOT         (A)  : NULL
REMARK   3    ESD FROM SIGMAA               (A)  : NULL
REMARK   3    LOW RESOLUTION CUTOFF         (A)  : NULL
REMARK   3
REMARK   3   CROSS-VALIDATED ESTIMATED COORDINATE ERROR.
REMARK   3    ESD FROM C-V LUZZATI PLOT     (A)  : NULL
REMARK   3    ESD FROM C-V SIGMAA           (A)  : NULL
REMARK   3
REMARK   3   RMS DEVIATIONS FROM IDEAL VALUES.
REMARK   3    BOND LENGTHS                  (A)  : 0.016
REMARK   3    BOND ANGLES             (DEGREES)  : 2.5
REMARK   3    DIHEDRAL ANGLES         (DEGREES)  : 22.8
REMARK   3    IMPROPER ANGLES         (DEGREES)  : 2.05
REMARK   3
REMARK   3   ISOTROPIC THERMAL MODEL : RESTRAINED
REMARK   3
REMARK   3   ISOTROPIC THERMAL FACTOR RESTRAINTS.    RMS      SIGMA
REMARK   3    MAIN-CHAIN BOND              (A**2) : 1.2    ;  1.5
REMARK   3    MAIN-CHAIN ANGLE             (A**2) : 1.6    ;  2.0
REMARK   3    SIDE-CHAIN BOND              (A**2) : 2.1    ;  2.0
REMARK   3    SIDE-CHAIN ANGLE             (A**2) : 2.4    ;  2.5
REMARK   3
REMARK   3   NCS MODEL : RESTRAINTS
REMARK   3
REMARK   3   NCS RESTRAINTS.                               RMS    SIGMA/WEIGHT
REMARK   3    GROUP  1  POSITIONAL          (A)  : NULL  ; NULL
REMARK   3    GROUP  1  B-FACTOR          (A**2) : NULL  ; NULL
REMARK   3
REMARK   3   PARAMETER FILE   1  : PARAM19_MOD.PRO
REMARK   3   PARAMETER FILE   2  : PARAM19.SOL
REMARK   3   PARAMETER FILE   3  : HETEROPARAM19.PAR
REMARK   3   TOPOLOGY  FILE   1  : TOPH19_MOD.PRO
REMARK   3   TOPOLOGY  FILE   2  : TOPH19.SOL
REMARK   3   TOPOLOGY  FILE   3  : HETERO.TOP
REMARK   3
REMARK   3   OTHER REFINEMENT REMARKS: REFINEMENT WAS PERFORMED WITH
REMARK   3   ANOMALOUS ON; PARAM19_MOD.PRO AND TOPH19_MOD.PRO ARE
REMARK   3   MODIFIED PARAMETER AND TOPOLOGY FILES OF PARAM19.PRO AND
REMARK   3   TOPH19.PRO, RESPECTIVELY, FOR SELENOMETHIONYL PROTEINS.
REMARK   3   NCS RESTRAINTS WERE APPLIED ONLY DURING THE INITIAL
REMARK   3   REFINEMENT.
REMARK   4
REMARK   4  1SCF COMPLIES WITH FORMAT V. 2.3,
```

FIGURE 8A-3

```
REMARK   6
REMARK   6 THE FOLLOWING RESIDUES ARE DISORDERED IN THE STRUCTURE:
REMARK   6 A1-10; A92-103; B1-10; B130-136; B139-141; C1-10; C92-103;
REMARK   6 C127-141; D1-10; D91-103; D128-141
REMARK   7
REMARK   7 THE SIDE CHAINS OF THE FOLLOWING RESIDUES ARE DISORDERED IN
REMARK   7 THE STRUCTURE: A11-13,A91,A127,A133,B11,B13,B93,B96-97,
REMARK   7 B103,B128,B137,C11,C13,C39,D11,D13,D90,D106,D127
REMARK   8
REMARK   8 LYS A 91 IS LAST RESIDUE BEFORE GAP, PHE B 129 IS LAST
REMARK   8 RESIDUE BEFORE GAP, LYS C 91 IS LAST RESIDUE BEFORE GAP,
REMARK   8 PHE C 126 IS LAST RESIDUE BEFORE GAP, VAL D 90 IS LAST
REMARK   8 RESIDUE BEFORE GAP.
REMARK 200
REMARK 200 EXPERIMENTAL DETAILS
REMARK 200  EXPERIMENT TYPE                    : X-RAY DIFFRACTION
REMARK 200  DATE OF DATA COLLECTION            :
REMARK 200  TEMPERATURE           (KELVIN)     : 110
REMARK 200  PH                                 : 7.4
REMARK 200  NUMBER OF CRYSTALS USED            : 1
REMARK 200
REMARK 200  SYNCHROTRON           (Y/N)        : Y
REMARK 200  RADIATION SOURCE                   : NSLS
REMARK 200  BEAMLINE                           : X4A
REMARK 200  X-RAY GENERATOR MODEL              : NULL
REMARK 200  MONOCHROMATIC OR LAUE (M/L)        : M
REMARK 200  WAVELENGTH OR RANGE   (A)          : 0.986
REMARK 200  MONOCHROMATOR                      : SILICON CRYSTAL
REMARK 200  OPTICS                             : MIRRORS
REMARK 200
REMARK 200  DETECTOR TYPE                      : IMAGE PLATE
REMARK 200  DETECTOR MANUFACTURER              : FUJI
REMARK 200  INTENSITY-INTEGRATION SOFTWARE     : DENSO
REMARK 200  DATA SCALING SOFTWARE              : SCALEPACK
REMARK 200
REMARK 200  NUMBER OF UNIQUE REFLECTIONS       : 65689
REMARK 200  RESOLUTION RANGE HIGH    (A)       : 2.0
REMARK 200  RESOLUTION RANGE LOW     (A)       : 25
REMARK 200  REJECTION CRITERIA  (SIGMA(I))     : -3
REMARK 200
REMARK 200 OVERALL.
REMARK 200  COMPLETENESS FOR RANGE   (%)       : 94.9
REMARK 200  DATA REDUNDANCY                    : 2.75
REMARK 200  R MERGE                  (I)       : NULL
REMARK 200  R SYM                    (I)       : 0.056
REMARK 200  <I/SIGMA(I)> FOR THE DATA SET      : 15.3
REMARK 200
REMARK 200 IN THE HIGHEST RESOLUTION SHELL.
REMARK 200  HIGHEST RESOLUTION SHELL, RANGE HIGH (A) : 2.0
REMARK 200  HIGHEST RESOLUTION SHELL, RANGE LOW  (A) : 2.07
REMARK 200  COMPLETENESS FOR SHELL   (%)       : 72
REMARK 200  DATA REDUNDANCY IN SHELL           : 2.23
REMARK 200  R MERGE FOR SHELL        (I)       : NULL
REMARK 200  R SYM FOR SHELL          (I)       : 0.581
REMARK 200  <I/SIGMA(I)> FOR SHELL             : 1.6
REMARK 200
REMARK 200 DIFFRACTION PROTOCOL: NULL
REMARK 200 METHOD USED TO DETERMINE THE STRUCTURE: MAD
REMARK 200 SOFTWARE USED: MADLSQ
REMARK 200 STARTING MODEL: NULL
```

FIGURE 8A-4

```
REMARK 200
REMARK 200 REMARK: NULL
REMARK 280
REMARK 280 CRYSTAL
REMARK 280 SOLVENT CONTENT, VS    (%): NULL
REMARK 280 MATTHEWS COEFFICIENT, VM (ANGSTROMS**3/DA): NULL
REMARK 280
REMARK 280 CRYSTALLIZATION CONDITIONS: PROTEIN WAS CRYSTALLIZED FROM
REMARK 280 22% PEG 400, 220 MM CACL2, 100 MM HEPES, PH 7.4 AND 5MM
REMARK 280 DTT IN 20 DEGREE ROOM
REMARK 290
REMARK 290 CRYSTALLOGRAPHIC SYMMETRY
REMARK 290 SYMMETRY OPERATORS FOR SPACE GROUP: P 21 21 21
REMARK 290
REMARK 290      SYMOP    SYMMETRY
REMARK 290      NNNMMM   OPERATOR
REMARK 290       1555    X,Y,Z
REMARK 290       2555    1/2-X,-Y,1/2+Z
REMARK 290       3555    -X,1/2+Y,1/2-Z
REMARK 290       4555    1/2+X,1/2-Y,-Z
REMARK 290
REMARK 290     WHERE NNN -> OPERATOR NUMBER
REMARK 290           MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
REMARK 290 RELATED MOLECULES.
REMARK 290     SMTRY1   1  1.000000  0.000000  0.000000        0.00000
REMARK 290     SMTRY2   1  0.000000  1.000000  0.000000        0.00000
REMARK 290     SMTRY3   1  0.000000  0.000000  1.000000        0.00000
REMARK 290     SMTRY1   2 -1.000000  0.000000  0.000000       35.90922
REMARK 290     SMTRY2   2  0.000000 -1.000000  0.000000        0.00000
REMARK 290     SMTRY3   2  0.000000  0.000000  1.000000       44.09560
REMARK 290     SMTRY1   3 -1.000000  0.000000  0.000000        0.00000
REMARK 290     SMTRY2   3  0.000000  1.000000  0.000000       41.27456
REMARK 290     SMTRY3   3  0.000000  0.000000 -1.000000       44.09560
REMARK 290     SMTRY1   4  1.000000  0.000000  0.000000       35.90922
REMARK 290     SMTRY2   4  0.000000 -1.000000  0.000000       41.27456
REMARK 290     SMTRY3   4  0.000000  0.000000 -1.000000        0.00000
REMARK 290
REMARK 290 REMARK: NULL
REMARK 295
REMARK 295 NON-CRYSTALLOGRAPHIC SYMMETRY
REMARK 295 THE TRANSFORMATIONS PRESENTED ON THE MTRIX RECORDS BELOW
REMARK 295 DESCRIBE NON-CRYSTALLOGRAPHIC RELATIONSHIPS AMONG ATOMS
REMARK 295 IN THIS ENTRY.  APPLYING THE APPROPRIATE MTRIX
REMARK 295 TRANSFORMATION TO THE RESIDUES LISTED FIRST WILL YIELD
REMARK 295 APPROXIMATE COORDINATES FOR THE RESIDUES LISTED SECOND.
REMARK 295 CHAIN IDENTIFIERS GIVEN AS "?" REFER TO CHAINS FOR WHICH
REMARK 295 ATOMS ARE NOT FOUND IN THIS ENTRY.
REMARK 295
REMARK 295                 APPLIED TO           TRANSFORMED TO
REMARK 295        TRANSFORM CHAIN  RESIDUES     CHAIN  RESIDUES      RMSD
REMARK 295           SSS
REMARK 295          M  1      B    11 .. 91      A    11 .. 91      1.020
REMARK 295          M  2      A    11 .. 91      C    11 .. 91      1.677
REMARK 295          M  3      D    11 .. 91      A    11 .. 91      1.926
REMARK 295          M  4      C    11 .. 91      B    11 .. 91      0.620
REMARK 295          M  5      D    11 .. 91      B    11 .. 91      1.764
```

FIGURE 8A-5

```
REMARK 295      M  6        D  11 .. 91          C  11 .. 91    1.810
REMARK 295      M  7        C  11 .. 91          A  11 .. 91    0.898
REMARK 295
REMARK 295      WHERE SSS -> COLUMNS 8-10 OF MTRIX RECORDS
REMARK 295
REMARK 295 REMARK:
REMARK 295 TRANSFORMATION RELATES CHAIN B TO CHAIN A; INCLUDING
REMARK 295     RESIDUES 11-90 AND 104-126.
REMARK 295 TRANSFORMATION RELATES CHAIN C TO CHAIN A; INCLUDING
REMARK 295     RESIDUES 11-90 AND 104-126.
REMARK 295 TRANSFORMATION RELATES CHAIN D TO CHAIN A; INCLUDING
REMARK 295     RESIDUES 11-90 AND 104-126.
REMARK 295 TRANSFORMATION RELATES CHAIN C TO CHAIN B; INCLUDING
REMARK 295     RESIDUES 11-90 AND 104-126.
REMARK 295 TRANSFORMATION RELATES CHAIN D TO CHAIN B; INCLUDING
REMARK 295     RESIDUES 11-90 AND 104-126.
REMARK 295 TRANSFORMATION RELATES CHAIN D TO CHAIN C; INCLUDING
REMARK 295     RESIDUES 11-90 AND 104-126.
REMARK 295 TRANSFORMATION RELATES CHAIN CD DIMER TO CHAIN AB DIMER;
REMARK 295   INCLUDING RESIDUES A11-91,A104-126,B11-B90,B104-127,
REMARK 295   C11-91,C104-126,D11-90,D104-127
REMARK 470
REMARK 470 MISSING ATOM
REMARK 470 THE FOLLOWING RESIDUES HAVE MISSING ATOMS (M=MODEL NUMBER;
REMARK 470 RES=RESIDUE NAME; C=CHAIN IDENTIFIER; SSEQ=SEQUENCE NUMBER;
REMARK 470 I=INSERTION CODE):
REMARK 470   M RES CSSEQI  ATOMS
REMARK 470     ASN A  11    CG   OD1  ND2
REMARK 470     VAL A  12    CG1  CG2
REMARK 470     LYS A  13    CG   CD   CE   NZ
REMARK 470     LYS A  91    CG   CD   CE   NZ
REMARK 470     LYS A 127    CG   CD   CE   NZ
REMARK 470     SER A 133    OG
REMARK 470     ASN B  11    CG   OD1  ND2
REMARK 470     LYS B  13    CG   CD   CE   NZ
REMARK 470     ASN B  93    CG   OD1  ND2
REMARK 470     LYS B  96    CG   CD   CE   NZ
REMARK 470     ASP B  97    CG   OD1  OD2
REMARK 470     LYS B 103    CG   CD   CE   NZ
REMARK 470     ASP B 128    CG   OD1  OD2
REMARK 470     ASP B 137    CG   OD1  OD2
REMARK 470     ASN C  11    CG   OD1  ND2
REMARK 470     LYS C  13    CG   CD   CE   NZ
REMARK 470     LEU C  39    CG   CD1  CD2
REMARK 470     ASN D  11    CG   OD1  ND2
REMARK 470     LYS D  13    CG   CD   CE   NZ
REMARK 470     VAL D  90    CG1  CG2
REMARK 470     GLU D 106    CG   CD   OE1  OE2
REMARK 470     LYS D 127    CG   CD   CE   NZ
REMARK 500
REMARK 500 GEOMETRY AND STEREOCHEMISTRY
REMARK 500 SUBTOPIC: CLOSE CONTACTS
REMARK 500
REMARK 500 THE FOLLOWING ATOMS THAT ARE RELATED BY CRYSTALLOGRAPHIC
REMARK 500 SYMMETRY ARE IN CLOSE CONTACT.  AN ATOM LOCATED WITHIN 0.15
REMARK 500 ANGSTROMS OF A SYMMETRY RELATED ATOM IS ASSUMED TO BE ON A
REMARK 500 SPECIAL POSITION AND IS, THEREFORE, LISTED IN REMARK 375
REMARK 500 INSTEAD OF REMARK 500.  ATOMS WITH NON-BLANK ALTERNATE
REMARK 500 LOCATION INDICATORS ARE NOT INCLUDED IN THE CALCULATIONS.
REMARK 500
```

FIGURE 8A-6

```
REMARK 500 DISTANCE CUTOFF:
REMARK 500   2.2 ANGSTROMS FOR CONTACTS NOT INVOLVING HYDROGEN ATOMS
REMARK 500   1.6 ANGSTROMS FOR CONTACTS INVOLVING HYDROGEN ATOMS
REMARK 500
REMARK 500   ATM1  RES C  SSEQI     ATM2  RES C  SSEQI   SSYMOP      DISTANCE
REMARK 500   CA    CA     1021      O     VAL A   139.    3655         2.18
REMARK 500
REMARK 500 REMARK: NULL
REMARK 600
REMARK 600 HETEROGEN
REMARK 600   1PE: ONLY PART OF THE PEG400 CHAIN IS ORDERED IN THE
REMARK 600   STRUCTURE.
REMARK 999
REMARK 999 SEQUENCE
REMARK 999 1SCF A      SWS    P21583        1 -   35 NOT IN ATOMS LIST
REMARK 999 1SCF A      SWS    P21583      167 -  273 NOT IN ATOMS LIST
REMARK 999 1SCF B      SWS    P21583        1 -   35 NOT IN ATOMS LIST
REMARK 999 1SCF B      SWS    P21583      164 -  273 NOT IN ATOMS LIST
REMARK 999 1SCF C      SWS    P21583        1 -   35 NOT IN ATOMS LIST
REMARK 999 1SCF C      SWS    P21583      152 -  273 NOT IN ATOMS LIST
REMARK 999 1SCF D      SWS    P21583        1 -   35 NOT IN ATOMS LIST
REMARK 999 1SCF D      SWS    P21583      153 -  273 NOT IN ATOMS LIST
DBREF  1SCF A   11    91  SWS    P21583   SCF_HUMAN       36    116
DBREF  1SCF A  104   141  SWS    P21583   SCF_HUMAN      129    166
DBREF  1SCF B   11   129  SWS    P21583   SCF_HUMAN       36    154
DBREF  1SCF B  137   138  SWS    P21583   SCF_HUMAN      162    163
DBREF  1SCF C   11    91  SWS    P21583   SCF_HUMAN       36    116
DBREF  1SCF C  104   126  SWS    P21583   SCF_HUMAN      129    151
DBREF  1SCF D   11    90  SWS    P21583   SCF_HUMAN       36    115
DBREF  1SCF D  104   127  SWS    P21583   SCF_HUMAN      129    152
SEQADV 1SCF MSE A   27  SWS  P21583    MET    52 MODIFIED
SEQADV 1SCF MSE A   36  SWS  P21583    MET    61 MODIFIED
SEQADV 1SCF MSE A   48  SWS  P21583    MET    73 MODIFIED
SEQADV 1SCF     A       SWS  P21583    GLU   117 GAP IN PDB ENTRY
SEQADV 1SCF     A       SWS  P21583    ASN   118 GAP IN PDB ENTRY
SEQADV 1SCF     A       SWS  P21583    SER   119 GAP IN PDB ENTRY
SEQADV 1SCF     A       SWS  P21583    SER   120 GAP IN PDB ENTRY
SEQADV 1SCF     A       SWS  P21583    LYS   121 GAP IN PDB ENTRY
SEQADV 1SCF     A       SWS  P21583    ASP   122 GAP IN PDB ENTRY
SEQADV 1SCF     A       SWS  P21583    LEU   123 GAP IN PDB ENTRY
SEQADV 1SCF     A       SWS  P21583    LYS   124 GAP IN PDB ENTRY
SEQADV 1SCF     A       SWS  P21583    LYS   125 GAP IN PDB ENTRY
SEQADV 1SCF     A       SWS  P21583    SER   126 GAP IN PDB ENTRY
SEQADV 1SCF     A       SWS  P21583    PHE   127 GAP IN PDB ENTRY
SEQADV 1SCF     A       SWS  P21583    LYS   128 GAP IN PDB ENTRY
SEQADV 1SCF MSE B   27  SWS  P21583    MET    52 MODIFIED
SEQADV 1SCF MSE B   36  SWS  P21583    MET    61 MODIFIED
SEQADV 1SCF MSE B   48  SWS  P21583    MET    73 MODIFIED
SEQADV 1SCF     B       SWS  P21583    VAL   155 GAP IN PDB ENTRY
SEQADV 1SCF     B       SWS  P21583    VAL   156 GAP IN PDB ENTRY
SEQADV 1SCF     B       SWS  P21583    ALA   157 GAP IN PDB ENTRY
SEQADV 1SCF     B       SWS  P21583    SER   158 GAP IN PDB ENTRY
SEQADV 1SCF     B       SWS  P21583    GLU   159 GAP IN PDB ENTRY
SEQADV 1SCF     B       SWS  P21583    THR   160 GAP IN PDB ENTRY
SEQADV 1SCF     B       SWS  P21583    SER   161 GAP IN PDB ENTRY
SEQADV 1SCF MSE C   27  SWS  P21583    MET    52 MODIFIED
SEQADV 1SCF MSE C   36  SWS  P21583    MET    61 MODIFIED
SEQADV 1SCF MSE C   48  SWS  P21583    MET    73 MODIFIED
SEQADV 1SCF     C       SWS  P21583    GLU   117 GAP IN PDB ENTRY
SEQADV 1SCF     C       SWS  P21583    ASN   118 GAP IN PDB ENTRY
```

FIGURE 8A-7

```
SEQADV 1SCF         C       SWS P21583   SER    119 GAP IN PDB ENTRY
SEQADV 1SCF         C       SWS P21583   SER    120 GAP IN PDB ENTRY
SEQADV 1SCF         C       SWS P21583   LYS    121 GAP IN PDB ENTRY
SEQADV 1SCF         C       SWS P21583   ASP    122 GAP IN PDB ENTRY
SEQADV 1SCF         C       SWS P21583   LEU    123 GAP IN PDB ENTRY
SEQADV 1SCF         C       SWS P21583   LYS    124 GAP IN PDB ENTRY
SEQADV 1SCF         C       SWS P21583   LYS    125 GAP IN PDB ENTRY
SEQADV 1SCF         C       SWS P21583   SER    126 GAP IN PDB ENTRY
SEQADV 1SCF         C       SWS P21583   PHE    127 GAP IN PDB ENTRY
SEQADV 1SCF         C       SWS P21583   LYS    128 GAP IN PDB ENTRY
SEQADV 1SCF MSE     D   27  SWS P21583   MET     52 MODIFIED
SEQADV 1SCF MSE     D   36  SWS P21583   MET     61 MODIFIED
SEQADV 1SCF MSE     D   48  SWS P21583   MET     73 MODIFIED
SEQADV 1SCF         D       SWS P21583   LYS    116 GAP IN PDB ENTRY
SEQADV 1SCF         D       SWS P21583   GLU    117 GAP IN PDB ENTRY
SEQADV 1SCF         D       SWS P21583   ASN    118 GAP IN PDB ENTRY
SEQADV 1SCF         D       SWS P21583   SER    119 GAP IN PDB ENTRY
SEQADV 1SCF         D       SWS P21583   SER    120 GAP IN PDB ENTRY
SEQADV 1SCF         D       SWS P21583   LYS    121 GAP IN PDB ENTRY
SEQADV 1SCF         D       SWS P21583   ASP    122 GAP IN PDB ENTRY
SEQADV 1SCF         D       SWS P21583   LEU    123 GAP IN PDB ENTRY
SEQADV 1SCF         D       SWS P21583   LYS    124 GAP IN PDB ENTRY
SEQADV 1SCF         D       SWS P21583   LYS    125 GAP IN PDB ENTRY
SEQADV 1SCF         D       SWS P21583   SER    126 GAP IN PDB ENTRY
SEQADV 1SCF         D       SWS P21583   PHE    127 GAP IN PDB ENTRY
SEQADV 1SCF         D       SWS P21583   LYS    128 GAP IN PDB ENTRY
SEQRES    1 A  273  MET LYS LYS THR GLN THR TRP ILE LEU THR CYS ILE TYR
SEQRES    2 A  273  LEU GLN LEU LEU LEU PHE ASN PRO LEU VAL LYS THR GLU
SEQRES    3 A  273  GLY ILE CYS ARG ASN ARG VAL THR ASN ASN VAL LYS ASP
SEQRES    4 A  273  VAL THR LYS LEU VAL ALA ASN LEU PRO LYS ASP TYR MSE
SEQRES    5 A  273  ILE THR LEU LYS TYR VAL PRO GLY MSE ASP VAL LEU PRO
SEQRES    6 A  273  SER HIS CYS TRP ILE SER GLU MSE VAL VAL GLN LEU SER
SEQRES    7 A  273  ASP SER LEU THR ASP LEU LEU ASP LYS PHE SER ASN ILE
SEQRES    8 A  273  SER GLU GLY LEU SER ASN TYR SER ILE ILE ASP LYS LEU
SEQRES    9 A  273  VAL ASN ILE VAL ASP ASP LEU VAL GLU CYS VAL LYS GLU
SEQRES   10 A  273  ASN SER SER LYS ASP LEU LYS LYS SER PHE LYS SER PRO
SEQRES   11 A  273  GLU PRO ARG LEU PHE THR PRO GLU GLU PHE PHE ARG ILE
SEQRES   12 A  273  PHE ASN ARG SER ILE ASP ALA PHE LYS ASP PHE VAL VAL
SEQRES   13 A  273  ALA SER GLU THR SER ASP CYS VAL VAL SER SER THR LEU
SEQRES   14 A  273  SER PRO GLU LYS ASP SER ARG VAL SER VAL THR LYS PRO
SEQRES   15 A  273  PHE MET LEU PRO PRO VAL ALA ALA SER SER LEU ARG ASN
SEQRES   16 A  273  ASP SER SER SER SER ASN ARG LYS ALA LYS ASN PRO PRO
SEQRES   17 A  273  GLY ASP SER SER LEU HIS TRP ALA ALA MET ALA LEU PRO
SEQRES   18 A  273  ALA LEU PHE SER LEU ILE ILE GLY PHE ALA PHE GLY ALA
SEQRES   19 A  273  LEU TYR TRP LYS LYS ARG GLN PRO SER LEU THR ARG ALA
SEQRES   20 A  273  VAL GLU ASN ILE GLN ILE ASN GLU GLU ASP ASN GLU ILE
SEQRES   21 A  273  SER MET LEU GLN GLU LYS GLU ARG GLU PHE GLN GLU VAL
SEQRES    1 B  273  MET LYS LYS THR GLN THR TRP ILE LEU THR CYS ILE TYR
SEQRES    2 B  273  LEU GLN LEU LEU LEU PHE ASN PRO LEU VAL LYS THR GLU
SEQRES    3 B  273  GLY ILE CYS ARG ASN ARG VAL THR ASN ASN VAL LYS ASP
SEQRES    4 B  273  VAL THR LYS LEU VAL ALA ASN LEU PRO LYS ASP TYR MSE
SEQRES    5 B  273  ILE THR LEU LYS TYR VAL PRO GLY MSE ASP VAL LEU PRO
SEQRES    6 B  273  SER HIS CYS TRP ILE SER GLU MSE VAL VAL GLN LEU SER
SEQRES    7 B  273  ASP SER LEU THR ASP LEU LEU ASP LYS PHE SER ASN ILE
SEQRES    8 B  273  SER GLU GLY LEU SER ASN TYR SER ILE ILE ASP LYS LEU
SEQRES    9 B  273  VAL ASN ILE VAL ASP ASP LEU VAL GLU CYS VAL LYS GLU
SEQRES   10 B  273  ASN SER SER LYS ASP LEU LYS LYS SER PHE LYS SER PRO
SEQRES   11 B  273  GLU PRO ARG LEU PHE THR PRO GLU GLU PHE PHE ARG ILE
SEQRES   12 B  273  PHE ASN ARG SER ILE ASP ALA PHE LYS ASP PHE VAL VAL
SEQRES   13 B  273  ALA SER GLU THR SER ASP CYS VAL VAL SER SER THR LEU
```

FIGURE 8A-8

```
SEQRES   14 B  273  SER PRO GLU LYS ASP SER ARG VAL SER VAL THR LYS PRO
SEQRES   15 B  273  PHE MET LEU PRO PRO VAL ALA ALA SER SER LEU ARG ASN
SEQRES   16 B  273  ASP SER SER SER SER ASN ARG LYS ALA LYS ASN PRO PRO
SEQRES   17 B  273  GLY ASP SER SER LEU HIS TRP ALA ALA MET ALA LEU PRO
SEQRES   18 B  273  ALA LEU PHE SER LEU ILE ILE GLY PHE ALA PHE GLY ALA
SEQRES   19 B  273  LEU TYR TRP LYS LYS ARG GLN PRO SER LEU THR ARG ALA
SEQRES   20 B  273  VAL GLU ASN ILE GLN ILE ASN GLU GLU ASP ASN GLU ILE
SEQRES   21 B  273  SER MET LEU GLN GLU LYS GLU ARG GLU PHE GLN GLU VAL
SEQRES    1 C  273  MET LYS LYS THR GLN THR TRP ILE LEU THR CYS ILE TYR
SEQRES    2 C  273  LEU GLN LEU LEU LEU PHE ASN PRO LEU VAL LYS THR GLU
SEQRES    3 C  273  GLY ILE CYS ARG ASN ARG VAL THR ASN ASN VAL LYS ASP
SEQRES    4 C  273  VAL THR LYS LEU VAL ALA ASN LEU PRO LYS ASP TYR MSE
SEQRES    5 C  273  ILE THR LEU LYS TYR VAL PRO GLY MSE ASP VAL LEU PRO
SEQRES    6 C  273  SER HIS CYS TRP ILE SER GLU MSE VAL VAL GLN LEU SER
SEQRES    7 C  273  ASP SER LEU THR ASP LEU LEU ASP LYS PHE SER ASN ILE
SEQRES    8 C  273  SER GLU GLY LEU SER ASN TYR SER ILE ILE ASP LYS LEU
SEQRES    9 C  273  VAL ASN ILE VAL ASP ASP LEU VAL GLU CYS VAL LYS GLU
SEQRES   10 C  273  ASN SER SER LYS ASP LEU LYS LYS SER PHE LYS SER PRO
SEQRES   11 C  273  GLU PRO ARG LEU PHE THR PRO GLU GLU PHE PHE ARG ILE
SEQRES   12 C  273  PHE ASN ARG SER ILE ASP ALA PHE LYS ASP PHE VAL VAL
SEQRES   13 C  273  ALA SER GLU THR SER ASP CYS VAL VAL SER SER THR LEU
SEQRES   14 C  273  SER PRO GLU LYS ASP SER ARG VAL SER VAL THR LYS PRO
SEQRES   15 C  273  PHE MET LEU PRO PRO VAL ALA ALA SER SER LEU ARG ASN
SEQRES   16 C  273  ASP SER SER SER SER ASN ARG LYS ALA LYS ASN PRO PRO
SEQRES   17 C  273  GLY ASP SER SER LEU HIS TRP ALA ALA MET ALA LEU PRO
SEQRES   18 C  273  ALA LEU PHE SER LEU ILE ILE GLY PHE ALA PHE GLY ALA
SEQRES   19 C  273  LEU TYR TRP LYS LYS ARG GLN PRO SER LEU THR ARG ALA
SEQRES   20 C  273  VAL GLU ASN ILE GLN ILE ASN GLU GLU ASP ASN GLU ILE
SEQRES   21 C  273  SER MET LEU GLN GLU LYS GLU ARG GLU PHE GLN GLU VAL
SEQRES    1 D  273  MET LYS LYS THR GLN THR TRP ILE LEU THR CYS ILE TYR
SEQRES    2 D  273  LEU GLN LEU LEU LEU PHE ASN PRO LEU VAL LYS THR GLU
SEQRES    3 D  273  GLY ILE CYS ARG ASN ARG VAL THR ASN ASN VAL LYS ASP
SEQRES    4 D  273  VAL THR LYS LEU VAL ALA ASN LEU PRO LYS ASP TYR MSE
SEQRES    5 D  273  ILE THR LEU LYS TYR VAL PRO GLY MSE ASP VAL LEU PRO
SEQRES    6 D  273  SER HIS CYS TRP ILE SER GLU MSE VAL VAL GLN LEU SER
SEQRES    7 D  273  ASP SER LEU THR ASP LEU LEU ASP LYS PHE SER ASN ILE
SEQRES    8 D  273  SER GLU GLY LEU SER ASN TYR SER ILE ILE ASP LYS LEU
SEQRES    9 D  273  VAL ASN ILE VAL ASP ASP LEU VAL GLU CYS VAL LYS GLU
SEQRES   10 D  273  ASN SER SER LYS ASP LEU LYS LYS SER PHE LYS SER PRO
SEQRES   11 D  273  GLU PRO ARG LEU PHE THR PRO GLU GLU PHE PHE ARG ILE
SEQRES   12 D  273  PHE ASN ARG SER ILE ASP ALA PHE LYS ASP PHE VAL VAL
SEQRES   13 D  273  ALA SER GLU THR SER ASP CYS VAL VAL SER SER THR LEU
SEQRES   14 D  273  SER PRO GLU LYS ASP SER ARG VAL SER VAL THR LYS PRO
SEQRES   15 D  273  PHE MET LEU PRO PRO VAL ALA ALA SER SER LEU ARG ASN
SEQRES   16 D  273  ASP SER SER SER SER ASN ARG LYS ALA LYS ASN PRO PRO
SEQRES   17 D  273  GLY ASP SER SER LEU HIS TRP ALA ALA MET ALA LEU PRO
SEQRES   18 D  273  ALA LEU PHE SER LEU ILE ILE GLY PHE ALA PHE GLY ALA
SEQRES   19 D  273  LEU TYR TRP LYS LYS ARG GLN PRO SER LEU THR ARG ALA
SEQRES   20 D  273  VAL GLU ASN ILE GLN ILE ASN GLU GLU ASP ASN GLU ILE
SEQRES   21 D  273  SER MET LEU GLN GLU LYS GLU ARG GLU PHE GLN GLU VAL
MODRES 1SCF MSE A   27  MET   SELENOMETHIONINE
MODRES 1SCF MSE A   36  MET   SELENOMETHIONINE
MODRES 1SCF MSE A   48  MET   SELENOMETHIONINE
MODRES 1SCF MSE B   27  MET   SELENOMETHIONINE
MODRES 1SCF MSE B   36  MET   SELENOMETHIONINE
MODRES 1SCF MSE B   48  MET   SELENOMETHIONINE
MODRES 1SCF MSE C   27  MET   SELENOMETHIONINE
MODRES 1SCF MSE C   36  MET   SELENOMETHIONINE
MODRES 1SCF MSE C   48  MET   SELENOMETHIONINE
MODRES 1SCF MSE D   27  MET   SELENOMETHIONINE
```

FIGURE 8A-9

```
MODRES 1SCF MSE D   36    MET    SELENOMETHIONINE
MODRES 1SCF MSE D   48    MET    SELENOMETHIONINE
HET         MSE A   27         8
HET         MSE A   36         8
HET         MSE A   48         8
HET         MSE B   27         8
HET         MSE B   36         8
HET         MSE B   48         8
HET         MSE C   27         8
HET         MSE C   36         8
HET         MSE C   48         8
HET         MSE D   27         8
HET         MSE D   36         8
HET         MSE D   48         8
HET         CA    1021         1
HET         CA    1022         1
HET         CA    1023         1
HET         1PE      1        16
HETNAM      MSE SELENOMETHIONINE
HETNAM      CA CALCIUM ION
HETNAM      1PE POLYETHYLENE GLYCOL
HETSYN      1PE PEG400
FORMUL   1  MSE       3(C5 H11 N1 O2 SE1)
FORMUL   2  MSE       3(C5 H11 N1 O2 SE1)
FORMUL   3  MSE       3(C5 H11 N1 O2 SE1)
FORMUL   4  MSE       3(C5 H11 N1 O2 SE1)
FORMUL   5  CA        3(CA1 2+)
FORMUL   6  1PE       C10 H22 O6
FORMUL   7  HOH     *264(H2 O1)
HELIX    1   1 VAL A    12  ASN A    21  1                                   10
HELIX    2   2 SER A    41  CYS A    43  5                                    3
HELIX    3   3 SER A    46  LYS A    62  5                                   17
HELIX    4   4 ASN A    72  CYS A    89  1                                   18
HELIX    5   5 PRO A   112  LYS A   127  1                                   16
HELIX    6   6 VAL B    12  ASN B    21  1                                   10
HELIX    7   7 SER B    41  CYS B    43  5                                    3
HELIX    8   8 SER B    46  LYS B    62  5                                   17
HELIX    9   9 ASN B    72  GLU B    92  1                                   21
HELIX   10  10 PRO B   112  LYS B   127  1                                   16
HELIX   11  11 VAL C    12  ASN C    21  1                                   10
HELIX   12  12 SER C    41  LYS C    62  1                                   22
HELIX   13  13 ASN C    72  VAL C    90  1                                   19
HELIX   14  14 PRO C   112  ASP C   124  1                                   13
HELIX   15  15 VAL D    12  ASN D    21  1                                   10
HELIX   16  16 SER D    41  CYS D    43  5                                    3
HELIX   17  17 SER D    46  LYS D    62  5                                   17
HELIX   18  18 ASN D    72  CYS D    89  1                                   18
HELIX   19  19 PRO D   112  ALA D   125  1                                   14
SHEET    1   A 2 THR A    29  LYS A    31  0
SHEET    2   A 2 PRO A   107  LEU A   109 -1  N  ARG A 108   O  LEU A  30
SHEET    1   B 2 THR B    29  LYS B    31  0
SHEET    2   B 2 PRO B   107  LEU B   109 -1  N  ARG B 108   O  LEU B  30
SHEET    1   C 2 THR C    29  LYS C    31  0
SHEET    2   C 2 PRO C   107  LEU C   109 -1  N  ARG C 108   O  LEU C  30
SHEET    1   D 2 THR D    29  LYS D    31  0
SHEET    2   D 2 PRO D   107  LEU D   109 -1  N  ARG D 108   O  LEU D  30
SSBOND   1 CYS A    43    CYS A   138
SSBOND   2 CYS B    43    CYS B   138
LINK         N   MSE A  27                 C   TYR A  26
LINK         C   MSE A  27                 N   ILE A  28
```

FIGURE 8A-10

```
LINK         N    MSE A   36              C   GLY A   35
LINK         C    MSE A   35              N   ASP A   37
LINK         N    MSE A   48              C   GLU A   47
LINK         C    MSE A   48              N   VAL A   49
LINK         N    MSE B   27              C   TYR B   26
LINK         C    MSE B   27              N   ILE B   28
LINK         N    MSE B   36              C   GLY B   35
LINK         C    MSE B   36              N   ASP B   37
LINK         N    MSE B   48              C   GLU B   47
LINK         C    MSE B   48              N   VAL B   49
LINK         N    MSE C   27              C   TYR C   26
LINK         C    MSE C   27              N   ILE C   28
LINK         N    MSE C   36              C   GLY C   35
LINK         C    MSE C   36              N   ASP C   37
LINK         N    MSE C   48              C   GLU C   47
LINK         C    MSE C   48              N   VAL C   49
LINK         N    MSE D   27              C   TYR D   26
LINK         C    MSE D   27              N   ILE D   28
LINK         N    MSE D   36              C   GLY D   35
LINK         C    MSE D   36              N   ASP D   37
LINK         N    MSE D   48              C   GLU D   47
LINK         C    MSE D   48              N   VAL D   49
LINK         CA   CA     1021             O   HOH     1024
LINK         CA   CA     1021             O   HOH     1025
LINK         CA   CA     1023             O   HOH     1027
LINK         CA   CA     1023             O   HOH     1028
LINK         CA   CA     1023             O   HOH     1029
CISPEP   1 SER A   104     PRO A   105           0         -0.10
CRYST1   71.820  82.550   88.190  90.00  90.00  90.00 P 21 21 21    4
ORIGX1        1.000000  0.000000  0.000000        0.00000
ORIGX2        0.000000  1.000000  0.000000        0.00000
ORIGX3        0.000000  0.000000  1.000000        0.00000
SCALE1        0.013924  0.000000  0.000000        0.00000
SCALE2        0.000000  0.012114  0.000000        0.00000
SCALE3        0.000000  0.000000  0.011339        0.00000
MTRIX1   1    0.915300  0.368400  0.162800      -10.34380    1
MTRIX2   1    0.357100 -0.929200  0.095000       35.55670    1
MTRIX3   1    0.186300 -0.028800 -0.982100       43.17570    1
MTRIX1   2   -0.935658 -0.315827 -0.157471       63.79985    1
MTRIX2   2   -0.265278  0.923709 -0.276386       17.94411    1
MTRIX3   2    0.232747 -0.216829 -0.948058       63.68074    1
MTRIX1   3   -0.994700  0.088300 -0.051700       54.54720    1
MTRIX2   3   -0.094000 -0.988400  0.119100       48.88150    1
MTRIX3   3   -0.040600  0.123400  0.991500      -20.54390    1
MTRIX1   4   -0.991100  0.100500 -0.087800       55.16840    1
MTRIX2   4   -0.117800 -0.968000  0.221700       45.07210    1
MTRIX3   4   -0.062700  0.230100  0.971100      -21.92400    1
MTRIX1   5   -0.951900 -0.248300  0.179700       52.25270    1
MTRIX2   5   -0.277100  0.947600 -0.158800       13.33780    1
MTRIX3   5   -0.130900 -0.200900 -0.970800       74.41510    1
MTRIX1   6    0.984200  0.147100 -0.098100        0.55340    1
MTRIX2   6    0.142600 -0.988400 -0.052100       52.60730    1
MTRIX3   6   -0.104600  0.037300 -0.993800       86.74100    1
MTRIX1   7   -0.955400 -0.244200  0.166100       52.84290    1
MTRIX2   7   -0.269500  0.950900 -0.152200       12.52990    1
MTRIX3   7   -0.120800 -0.190100 -0.974300       73.76110    1
ATOM     1   N    ASN A   11      10.232   3.110  20.636  1.00 60.07    N
ATOM     2   CA   ASN A   11       9.176   3.892  19.994  1.00 59.79    C
ATOM     3   C    ASN A   11       9.647   5.204  19.309  1.00 59.52    C
ATOM     4   O    ASN A   11       9.661   6.288  19.910  1.00 59.97    O
```

FIGURE 8A-11

| | | | | | | | | | | |
|---|---|---|---|---|---|---|---|---|---|---|
| ATOM | 5 | CB | ASN | A | 11 | 8.113 | 4.228 | 21.038 | 1.00 | 60.46 |
| ATOM | 6 | N | VAL | A | 12 | 10.013 | 5.143 | 18.009 | 1.00 | 57.40 |
| ATOM | 7 | CA | VAL | A | 12 | 10.715 | 6.225 | 17.309 | 1.00 | 53.71 |
| ATOM | 8 | C | VAL | A | 12 | 9.844 | 7.387 | 16.820 | 1.00 | 50.84 |
| ATOM | 9 | O | VAL | A | 12 | 10.343 | 8.268 | 16.130 | 1.00 | 51.46 |
| ATOM | 10 | CB | VAL | A | 12 | 11.541 | 5.657 | 16.126 | 1.00 | 53.25 |
| ATOM | 11 | N | LYS | A | 13 | 8.543 | 7.490 | 17.147 | 1.00 | 49.07 |
| ATOM | 12 | CA | LYS | A | 13 | 7.721 | 8.640 | 16.756 | 1.00 | 44.35 |
| ATOM | 13 | C | LYS | A | 13 | 8.114 | 9.879 | 17.542 | 1.00 | 42.86 |
| ATOM | 14 | O | LYS | A | 13 | 8.271 | 10.995 | 17.007 | 1.00 | 41.79 |
| ATOM | 15 | CB | LYS | A | 13 | 6.258 | 8.378 | 17.093 | 1.00 | 44.76 |
| ATOM | 16 | N | ASP | A | 14 | 8.283 | 9.557 | 18.839 | 1.00 | 38.29 |
| ATOM | 17 | CA | ASP | A | 14 | 8.609 | 10.545 | 19.818 | 1.00 | 35.56 |
| ATOM | 18 | C | ASP | A | 14 | 10.068 | 10.894 | 19.718 | 1.00 | 32.01 |
| ATOM | 19 | O | ASP | A | 14 | 10.389 | 12.060 | 19.896 | 1.00 | 30.80 |
| ATOM | 20 | CB | ASP | A | 14 | 8.151 | 10.072 | 21.200 | 1.00 | 38.77 |
| ATOM | 21 | CG | ASP | A | 14 | 6.725 | 10.518 | 21.630 | 1.00 | 43.77 |
| ATOM | 22 | OD1 | ASP | A | 14 | 6.046 | 11.324 | 20.969 | 1.00 | 45.53 |
| ATOM | 23 | OD2 | ASP | A | 14 | 6.269 | 10.057 | 22.680 | 1.00 | 47.33 |
| ATOM | 24 | N | VAL | A | 15 | 10.939 | 9.938 | 19.360 | 1.00 | 28.31 |
| ATOM | 25 | CA | VAL | A | 15 | 12.335 | 10.224 | 19.089 | 1.00 | 27.35 |
| ATOM | 26 | C | VAL | A | 15 | 12.510 | 11.219 | 17.959 | 1.00 | 29.06 |
| ATOM | 27 | O | VAL | A | 15 | 13.265 | 12.166 | 18.139 | 1.00 | 32.49 |
| ATOM | 28 | CB | VAL | A | 15 | 13.191 | 8.976 | 18.792 | 1.00 | 26.33 |
| ATOM | 29 | CG1 | VAL | A | 15 | 14.623 | 9.347 | 18.405 | 1.00 | 20.32 |
| ATOM | 30 | CG2 | VAL | A | 15 | 13.215 | 8.064 | 20.008 | 1.00 | 24.37 |
| ATOM | 31 | N | THR | A | 16 | 11.858 | 11.085 | 16.807 | 1.00 | 28.42 |
| ATOM | 32 | CA | THR | A | 16 | 11.968 | 12.085 | 15.758 | 1.00 | 27.97 |
| ATOM | 33 | C | THR | A | 16 | 11.386 | 13.413 | 16.208 | 1.00 | 25.43 |
| ATOM | 34 | O | THR | A | 16 | 12.020 | 14.418 | 15.905 | 1.00 | 25.82 |
| ATOM | 35 | CB | THR | A | 16 | 11.357 | 11.646 | 14.385 | 1.00 | 27.70 |
| ATOM | 36 | OG1 | THR | A | 16 | 9.959 | 11.529 | 14.588 | 1.00 | 32.27 |
| ATOM | 37 | CG2 | THR | A | 16 | 11.931 | 10.335 | 13.912 | 1.00 | 25.71 |
| ATOM | 38 | N | LYS | A | 17 | 10.243 | 13.459 | 16.928 | 1.00 | 24.83 |
| ATOM | 39 | CA | LYS | A | 17 | 9.701 | 14.698 | 17.482 | 1.00 | 23.60 |
| ATOM | 40 | C | LYS | A | 17 | 10.659 | 15.401 | 18.410 | 1.00 | 21.54 |
| ATOM | 41 | O | LYS | A | 17 | 10.756 | 16.624 | 18.373 | 1.00 | 23.88 |
| ATOM | 42 | CB | LYS | A | 17 | 8.365 | 14.488 | 18.206 | 1.00 | 27.08 |
| ATOM | 43 | CG | LYS | A | 17 | 7.291 | 14.120 | 17.198 | 1.00 | 34.84 |
| ATOM | 44 | CD | LYS | A | 17 | 5.881 | 14.040 | 17.781 | 1.00 | 40.64 |
| ATOM | 45 | CE | LYS | A | 17 | 4.800 | 13.911 | 16.665 | 1.00 | 45.98 |
| ATOM | 46 | NZ | LYS | A | 17 | 4.607 | 12.559 | 16.140 | 1.00 | 48.58 |
| ATOM | 47 | N | LEU | A | 18 | 11.417 | 14.646 | 19.212 | 1.00 | 19.73 |
| ATOM | 48 | CA | LEU | A | 18 | 12.377 | 15.207 | 20.151 | 1.00 | 17.98 |
| ATOM | 49 | C | LEU | A | 18 | 13.544 | 15.778 | 19.401 | 1.00 | 17.55 |
| ATOM | 50 | O | LEU | A | 18 | 13.813 | 16.959 | 19.523 | 1.00 | 17.68 |
| ATOM | 51 | CB | LEU | A | 18 | 12.875 | 14.144 | 21.121 | 1.00 | 17.63 |
| ATOM | 52 | CG | LEU | A | 18 | 13.850 | 14.582 | 22.216 | 1.00 | 15.34 |
| ATOM | 53 | CD1 | LEU | A | 18 | 13.278 | 15.668 | 23.080 | 1.00 | 15.28 |
| ATOM | 54 | CD2 | LEU | A | 18 | 14.253 | 13.389 | 23.032 | 1.00 | 14.40 |
| ATOM | 55 | N | VAL | A | 19 | 14.189 | 14.952 | 18.577 | 1.00 | 18.35 |
| ATOM | 56 | CA | VAL | A | 19 | 15.187 | 15.421 | 17.628 | 1.00 | 19.40 |
| ATOM | 57 | C | VAL | A | 19 | 14.757 | 16.628 | 16.824 | 1.00 | 18.97 |
| ATOM | 58 | O | VAL | A | 19 | 15.533 | 17.562 | 16.711 | 1.00 | 22.36 |
| ATOM | 59 | CB | VAL | A | 19 | 15.668 | 14.325 | 16.729 | 1.00 | 18.19 |
| ATOM | 60 | CG1 | VAL | A | 19 | 16.675 | 14.817 | 15.708 | 1.00 | 20.68 |
| ATOM | 61 | CG2 | VAL | A | 19 | 16.422 | 13.390 | 17.612 | 1.00 | 19.91 |
| ATOM | 62 | N | ALA | A | 20 | 13.530 | 16.732 | 16.365 | 1.00 | 18.27 |
| ATOM | 63 | CA | ALA | A | 20 | 13.105 | 17.946 | 15.719 | 1.00 | 17.82 |
| ATOM | 64 | C | ALA | A | 20 | 12.923 | 19.074 | 16.711 | 1.00 | 18.90 |

*FIGURE 8A-12*

| | | | | | | | | | | |
|---|---|---|---|---|---|---|---|---|---|---|
| ATOM | 65 | O | ALA | A | 20 | 12.977 | 20.244 | 16.352 | 1.00 20.70 | O |
| ATOM | 66 | CB | ALA | A | 20 | 11.777 | 17.661 | 15.059 | 1.00 17.70 | C |
| ATOM | 67 | N | ASN | A | 21 | 12.677 | 18.787 | 17.979 | 1.00 20.04 | N |
| ATOM | 68 | CA | ASN | A | 21 | 12.450 | 19.852 | 18.933 | 1.00 20.73 | C |
| ATOM | 69 | C | ASN | A | 21 | 13.695 | 20.161 | 19.771 | 1.00 20.34 | C |
| ATOM | 70 | O | ASN | A | 21 | 13.627 | 20.909 | 20.741 | 1.00 21.05 | O |
| ATOM | 71 | CB | ASN | A | 21 | 11.235 | 19.456 | 19.751 | 1.00 20.84 | C |
| ATOM | 72 | CG | ASN | A | 21 | 10.409 | 20.664 | 20.103 | 1.00 21.87 | C |
| ATOM | 73 | OD1 | ASN | A | 21 | 10.157 | 21.501 | 19.250 | 1.00 20.51 | O |
| ATOM | 74 | ND2 | ASN | A | 21 | 9.983 | 20.853 | 21.359 | 1.00 25.03 | N |
| ATOM | 75 | N | LEU | A | 22 | 14.851 | 19.615 | 19.399 | 1.00 18.22 | N |
| ATOM | 76 | CA | LEU | A | 22 | 16.129 | 19.924 | 20.000 | 1.00 17.27 | C |
| ATOM | 77 | C | LEU | A | 22 | 17.023 | 20.733 | 19.051 | 1.00 19.37 | C |
| ATOM | 78 | O | LEU | A | 22 | 17.001 | 20.468 | 17.851 | 1.00 19.69 | O |
| ATOM | 79 | CB | LEU | A | 22 | 16.856 | 18.631 | 20.432 | 1.00 16.17 | C |
| ATOM | 80 | CG | LEU | A | 22 | 16.342 | 17.790 | 21.598 | 1.00 14.77 | C |
| ATOM | 81 | CD1 | LEU | A | 22 | 17.058 | 16.447 | 21.768 | 1.00 14.07 | C |
| ATOM | 82 | CD2 | LEU | A | 22 | 16.463 | 18.606 | 22.862 | 1.00 11.82 | C |
| ATOM | 83 | N | PRO | A | 23 | 17.833 | 21.728 | 19.457 | 1.00 19.42 | N |
| ATOM | 84 | CA | PRO | A | 23 | 18.655 | 22.511 | 18.537 | 1.00 19.17 | C |
| ATOM | 85 | C | PRO | A | 23 | 19.694 | 21.621 | 17.878 | 1.00 20.53 | C |
| ATOM | 86 | O | PRO | A | 23 | 20.318 | 20.832 | 18.575 | 1.00 21.23 | O |
| ATOM | 87 | CB | PRO | A | 23 | 19.341 | 23.468 | 19.459 | 1.00 18.21 | C |
| ATOM | 88 | CG | PRO | A | 23 | 18.549 | 23.480 | 20.755 | 1.00 16.10 | C |
| ATOM | 89 | CD | PRO | A | 23 | 18.206 | 22.015 | 20.846 | 1.00 17.73 | C |
| ATOM | 90 | N | LYS | A | 24 | 19.959 | 21.716 | 16.571 | 1.00 23.65 | N |
| ATOM | 91 | CA | LYS | A | 24 | 20.937 | 20.852 | 15.866 | 1.00 27.23 | C |
| ATOM | 92 | C | LYS | A | 24 | 22.388 | 20.847 | 16.370 | 1.00 25.36 | C |
| ATOM | 93 | O | LYS | A | 24 | 23.179 | 19.918 | 16.149 | 1.00 25.16 | O |
| ATOM | 94 | CB | LYS | A | 24 | 20.931 | 21.150 | 14.332 | 1.00 29.02 | C |
| ATOM | 95 | CG | LYS | A | 24 | 19.550 | 20.939 | 13.680 | 1.00 36.19 | C |
| ATOM | 96 | CD | LYS | A | 24 | 19.557 | 21.512 | 12.245 | 1.00 43.22 | C |
| ATOM | 97 | CE | LYS | A | 24 | 18.207 | 21.800 | 11.585 | 1.00 42.88 | C |
| ATOM | 98 | NZ | LYS | A | 24 | 18.433 | 22.694 | 10.448 | 1.00 48.02 | N |
| ATOM | 99 | N | ASP | A | 25 | 22.712 | 21.900 | 17.110 | 1.00 26.32 | N |
| ATOM | 100 | CA | ASP | A | 25 | 24.060 | 22.087 | 17.653 | 1.00 28.70 | C |
| ATOM | 101 | C | ASP | A | 25 | 24.209 | 22.024 | 19.180 | 1.00 26.91 | C |
| ATOM | 102 | O | ASP | A | 25 | 25.225 | 22.386 | 19.785 | 1.00 27.43 | O |
| ATOM | 103 | CB | ASP | A | 25 | 24.551 | 23.433 | 17.144 | 1.00 30.59 | C |
| ATOM | 104 | CG | ASP | A | 25 | 23.780 | 24.615 | 17.684 | 1.00 33.09 | C |
| ATOM | 105 | OD1 | ASP | A | 25 | 22.556 | 24.529 | 17.847 | 1.00 34.74 | O |
| ATOM | 106 | OD2 | ASP | A | 25 | 24.421 | 25.638 | 17.933 | 1.00 37.53 | O |
| ATOM | 107 | N | TYR | A | 26 | 23.122 | 21.605 | 19.808 | 1.00 24.09 | N |
| ATOM | 108 | CA | TYR | A | 26 | 23.165 | 21.289 | 21.189 | 1.00 20.96 | C |
| ATOM | 109 | C | TYR | A | 26 | 23.821 | 19.937 | 21.246 | 1.00 20.04 | C |
| ATOM | 110 | O | TYR | A | 26 | 23.282 | 18.951 | 20.780 | 1.00 22.61 | O |
| ATOM | 111 | CB | TYR | A | 26 | 21.759 | 21.239 | 21.710 | 1.00 20.00 | C |
| ATOM | 112 | CG | TYR | A | 26 | 21.728 | 20.927 | 23.199 | 1.00 23.05 | C |
| ATOM | 113 | CD1 | TYR | A | 26 | 22.430 | 21.764 | 24.039 | 1.00 20.56 | C |
| ATOM | 114 | CD2 | TYR | A | 26 | 21.015 | 19.843 | 23.683 | 1.00 22.87 | C |
| ATOM | 115 | CE1 | TYR | A | 26 | 22.421 | 21.541 | 25.376 | 1.00 23.76 | C |
| ATOM | 116 | CE2 | TYR | A | 26 | 20.993 | 19.629 | 25.047 | 1.00 22.41 | C |
| ATOM | 117 | CZ | TYR | A | 26 | 21.693 | 20.493 | 25.877 | 1.00 23.68 | C |
| ATOM | 118 | OH | TYR | A | 26 | 21.661 | 20.353 | 27.259 | 1.00 22.67 | O |
| HETATM | 119 | N | MSE | A | 27 | 25.003 | 19.890 | 21.809 | 1.00 21.07 | N |
| HETATM | 120 | CA | MSE | A | 27 | 25.716 | 18.643 | 22.008 | 1.00 21.95 | C |
| HETATM | 121 | C | MSE | A | 27 | 25.325 | 17.906 | 23.296 | 1.00 23.63 | C |
| HETATM | 122 | O | MSE | A | 27 | 25.089 | 18.481 | 24.371 | 1.00 22.77 | O |
| HETATM | 123 | CB | MSE | A | 27 | 27.201 | 18.955 | 22.055 | 1.00 27.32 | C |
| HETATM | 124 | CG | MSE | A | 27 | 27.695 | 19.788 | 20.866 | 1.00 28.96 | C |

FIGURE 8A-13

```
HETATM  125  SE   MSE A  27    27.207  18.877  19.234  1.00  37.24           SE
HETATM  126  CE   MSE A  27    28.489  17.511  19.371  1.00  26.83           C
ATOM    127  N    ILE A  28    25.250  16.576  23.165  1.00  22.91           N
ATOM    128  CA   ILE A  28    24.860  15.666  24.240  1.00  21.29           C
ATOM    129  C    ILE A  28    26.030  14.713  24.494  1.00  21.02           C
ATOM    130  O    ILE A  28    26.530  14.075  23.571  1.00  20.97           O
ATOM    131  CB   ILE A  28    23.550  14.901  23.870  1.00  19.78           C
ATOM    132  CG1  ILE A  28    22.372  15.818  23.534  1.00  17.37           C
ATOM    133  CG2  ILE A  28    23.147  14.006  25.006  1.00  18.93           C
ATOM    134  CD1  ILE A  28    21.207  15.120  22.805  1.00  16.08           C
ATOM    135  N    THR A  29    26.492  14.597  25.744  1.00  20.17           N
ATOM    136  CA   THR A  29    27.592  13.727  26.087  1.00  20.16           C
ATOM    137  C    THR A  29    27.065  12.315  26.319  1.00  20.21           C
ATOM    138  O    THR A  29    26.051  12.081  26.988  1.00  19.29           O
ATOM    139  CB   THR A  29    28.269  14.295  27.333  1.00  21.22           C
ATOM    140  OG1  THR A  29    28.515  15.655  27.048  1.00  24.08           O
ATOM    141  CG2  THR A  29    29.593  13.644  27.634  1.00  23.19           C
ATOM    142  N    LEU A  30    27.767  11.369  25.708  1.00  18.56           N
ATOM    143  CA   LEU A  30    27.462   9.976  25.862  1.00  17.76           C
ATOM    144  C    LEU A  30    28.824   9.351  25.959  1.00  18.41           C
ATOM    145  O    LEU A  30    29.738   9.774  25.283  1.00  20.72           O
ATOM    146  CB   LEU A  30    26.649   9.396  24.642  1.00  19.78           C
ATOM    147  CG   LEU A  30    26.350   7.884  24.473  1.00  14.53           C
ATOM    148  CD1  LEU A  30    25.475   7.478  25.601  1.00  18.04           C
ATOM    149  CD2  LEU A  30    25.629   7.525  23.205  1.00  14.92           C
ATOM    150  N    LYS A  31    28.984   8.378  26.833  1.00  18.64           N
ATOM    151  CA   LYS A  31    30.176   7.575  26.918  1.00  20.71           C
ATOM    152  C    LYS A  31    29.940   6.417  25.999  1.00  21.51           C
ATOM    153  O    LYS A  31    28.966   5.701  26.170  1.00  23.02           O
ATOM    154  CB   LYS A  31    30.411   7.009  28.295  1.00  19.63           C
ATOM    155  CG   LYS A  31    30.788   8.066  29.309  1.00  25.85           C
ATOM    156  CD   LYS A  31    31.154   7.355  30.605  1.00  29.83           C
ATOM    157  CE   LYS A  31    31.652   8.305  31.675  1.00  32.89           C
ATOM    158  NZ   LYS A  31    32.116   7.506  32.799  1.00  39.63           N
ATOM    159  N    TYR A  32    30.845   6.219  25.034  1.00  24.83           N
ATOM    160  CA   TYR A  32    30.565   5.424  23.844  1.00  22.31           C
ATOM    161  C    TYR A  32    31.607   4.359  23.767  1.00  19.55           C
ATOM    162  O    TYR A  32    32.759   4.667  23.946  1.00  22.18           O
ATOM    163  CB   TYR A  32    30.569   6.367  22.640  1.00  25.12           C
ATOM    164  CG   TYR A  32    30.557   5.725  21.262  1.00  27.46           C
ATOM    165  CD1  TYR A  32    31.790   5.449  20.689  1.00  26.41           C
ATOM    166  CD2  TYR A  32    29.369   5.437  20.613  1.00  26.10           C
ATOM    167  CE1  TYR A  32    31.871   4.860  19.452  1.00  27.56           C
ATOM    168  CE2  TYR A  32    29.462   4.854  19.356  1.00  29.60           C
ATOM    169  CZ   TYR A  32    30.710   4.589  18.787  1.00  28.41           C
ATOM    170  OH   TYR A  32    30.844   4.087  17.501  1.00  32.61           O
ATOM    171  N    VAL A  33    31.217   3.108  23.604  1.00  20.21           N
ATOM    172  CA   VAL A  33    32.138   2.022  23.453  1.00  22.23           C
ATOM    173  C    VAL A  33    32.829   2.212  22.110  1.00  24.20           C
ATOM    174  O    VAL A  33    32.156   2.231  21.078  1.00  24.76           O
ATOM    175  CB   VAL A  33    31.400   0.676  23.549  1.00  23.11           C
ATOM    176  CG1  VAL A  33    32.297  -0.537  23.309  1.00  22.36           C
ATOM    177  CG2  VAL A  33    30.857   0.535  24.951  1.00  25.26           C
ATOM    178  N    PRO A  34    34.158   2.380  22.078  1.00  25.19           N
ATOM    179  CA   PRO A  34    34.921   2.477  20.834  1.00  27.43           C
ATOM    180  C    PRO A  34    34.727   1.263  19.907  1.00  27.77           C
ATOM    181  O    PRO A  34    34.907   0.101  20.291  1.00  27.65           O
ATOM    182  CB   PRO A  34    36.381   2.586  21.335  1.00  29.54           C
ATOM    183  CG   PRO A  34    36.224   3.056  22.773  1.00  26.93           C
ATOM    184  CD   PRO A  34    35.043   2.269  23.245  1.00  23.54           C
```

FIGURE 8A-14

| | | | | | | | | | | |
|---|---|---|---|---|---|---|---|---|---|---|
| ATOM | 185 | N | GLY | A | 35 | 34.312 | 1.550 | 18.666 | 1.00 28.92 | N |
| ATOM | 186 | CA | GLY | A | 35 | 34.175 | 0.517 | 17.650 | 1.00 28.59 | C |
| ATOM | 187 | C | GLY | A | 35 | 32.886 | -0.277 | 17.715 | 1.00 28.76 | C |
| ATOM | 188 | O | GLY | A | 35 | 32.743 | -1.224 | 16.957 | 1.00 29.41 | O |
| HETATM | 189 | N | MSE | A | 36 | 31.923 | 0.064 | 18.569 | 1.00 27.95 | N |
| HETATM | 190 | CA | MSE | A | 36 | 30.612 | -0.561 | 18.587 | 1.00 28.65 | C |
| HETATM | 191 | C | MSE | A | 36 | 29.809 | -0.477 | 17.276 | 1.00 28.45 | C |
| HETATM | 192 | O | MSE | A | 36 | 28.824 | -1.189 | 17.098 | 1.00 26.26 | O |
| HETATM | 193 | CB | MSE | A | 36 | 29.774 | 0.036 | 19.739 | 1.00 32.71 | C |
| HETATM | 194 | CG | MSE | A | 36 | 29.232 | 1.427 | 19.485 | 1.00 34.05 | C |
| HETATM | 195 | SE | MSE | A | 36 | 27.946 | 2.252 | 20.676 | 1.00 36.59 | SE |
| HETATM | 196 | CE | MSE | A | 36 | 26.309 | 1.728 | 19.841 | 1.00 26.94 | C |
| ATOM | 197 | N | ASP | A | 37 | 30.212 | 0.393 | 16.338 | 1.00 30.42 | N |
| ATOM | 198 | CA | ASP | A | 37 | 29.736 | 0.418 | 14.935 | 1.00 30.74 | C |
| ATOM | 199 | C | ASP | A | 37 | 30.051 | -0.794 | 14.038 | 1.00 27.32 | C |
| ATOM | 200 | O | ASP | A | 37 | 29.344 | -1.054 | 13.064 | 1.00 28.97 | O |
| ATOM | 201 | CB | ASP | A | 37 | 30.200 | 1.716 | 14.234 | 1.00 33.15 | C |
| ATOM | 202 | CG | ASP | A | 37 | 31.706 | 1.960 | 14.294 | 1.00 35.22 | C |
| ATOM | 203 | OD1 | ASP | A | 37 | 32.230 | 2.247 | 15.374 | 1.00 42.04 | O |
| ATOM | 204 | OD2 | ASP | A | 37 | 32.369 | 1.875 | 13.275 | 1.00 34.84 | O |
| ATOM | 205 | N | VAL | A | 38 | 31.054 | -1.584 | 14.381 | 1.00 23.11 | N |
| ATOM | 206 | CA | VAL | A | 38 | 31.471 | -2.713 | 13.566 | 1.00 23.69 | C |
| ATOM | 207 | C | VAL | A | 38 | 31.568 | -4.045 | 14.389 | 1.00 26.12 | C |
| ATOM | 208 | O | VAL | A | 38 | 31.649 | -5.172 | 13.882 | 1.00 27.25 | O |
| ATOM | 209 | CB | VAL | A | 38 | 32.741 | -2.089 | 12.936 | 1.00 19.85 | C |
| ATOM | 210 | CG1 | VAL | A | 38 | 34.023 | -2.366 | 13.647 | 1.00 16.55 | C |
| ATOM | 211 | CG2 | VAL | A | 38 | 32.825 | -2.379 | 11.512 | 1.00 19.54 | C |
| ATOM | 212 | N | LEU | A | 39 | 31.464 | -3.968 | 15.728 | 1.00 26.26 | N |
| ATOM | 213 | CA | LEU | A | 39 | 31.505 | -5.113 | 16.640 | 1.00 26.07 | C |
| ATOM | 214 | C | LEU | A | 39 | 30.149 | -5.788 | 16.888 | 1.00 25.48 | C |
| ATOM | 215 | O | LEU | A | 39 | 29.130 | -5.109 | 16.842 | 1.00 23.47 | O |
| ATOM | 216 | CB | LEU | A | 39 | 32.061 | -4.671 | 18.014 | 1.00 25.49 | C |
| ATOM | 217 | CG | LEU | A | 39 | 33.515 | -4.307 | 18.156 | 1.00 27.97 | C |
| ATOM | 218 | CD1 | LEU | A | 39 | 33.729 | -3.645 | 19.510 | 1.00 30.79 | C |
| ATOM | 219 | CD2 | LEU | A | 39 | 34.399 | -5.522 | 17.940 | 1.00 23.69 | C |
| ATOM | 220 | N | PRO | A | 40 | 30.017 | -7.086 | 17.192 | 1.00 25.65 | N |
| ATOM | 221 | CA | PRO | A | 40 | 28.734 | -7.665 | 17.563 | 1.00 27.77 | C |
| ATOM | 222 | C | PRO | A | 40 | 28.061 | -7.004 | 18.792 | 1.00 27.59 | C |
| ATOM | 223 | O | PRO | A | 40 | 28.710 | -6.411 | 19.658 | 1.00 26.55 | O |
| ATOM | 224 | CB | PRO | A | 40 | 29.102 | -9.122 | 17.683 | 1.00 27.41 | C |
| ATOM | 225 | CG | PRO | A | 40 | 30.584 | -9.150 | 18.015 | 1.00 26.93 | C |
| ATOM | 226 | CD | PRO | A | 40 | 31.076 | -8.082 | 17.099 | 1.00 26.35 | C |
| ATOM | 227 | N | SER | A | 41 | 26.724 | -7.026 | 18.830 | 1.00 27.40 | N |
| ATOM | 228 | CA | SER | A | 41 | 26.003 | -6.235 | 19.806 | 1.00 26.79 | C |
| ATOM | 229 | C | SER | A | 41 | 26.288 | -6.707 | 21.202 | 1.00 27.70 | C |
| ATOM | 230 | O | SER | A | 41 | 26.451 | -5.903 | 22.097 | 1.00 29.20 | O |
| ATOM | 231 | CB | SER | A | 41 | 24.540 | -6.240 | 19.558 | 1.00 23.46 | C |
| ATOM | 232 | OG | SER | A | 41 | 24.074 | -7.559 | 19.691 | 1.00 25.42 | O |
| ATOM | 233 | N | HIS | A | 42 | 26.526 | -8.007 | 21.355 | 1.00 29.95 | N |
| ATOM | 234 | CA | HIS | A | 42 | 26.853 | -8.594 | 22.636 | 1.00 30.32 | C |
| ATOM | 235 | C | HIS | A | 42 | 28.076 | -7.971 | 23.312 | 1.00 29.42 | C |
| ATOM | 236 | O | HIS | A | 42 | 28.270 | -8.138 | 24.524 | 1.00 28.56 | O |
| ATOM | 237 | CB | HIS | A | 42 | 27.008 | -10.109 | 22.451 | 1.00 35.10 | C |
| ATOM | 238 | CG | HIS | A | 42 | 28.387 | -10.616 | 21.997 | 1.00 39.36 | C |
| ATOM | 239 | ND1 | HIS | A | 42 | 29.424 | -10.993 | 22.752 | 1.00 43.05 | N |
| ATOM | 240 | CD2 | HIS | A | 42 | 28.829 | -10.644 | 20.694 | 1.00 42.30 | C |
| ATOM | 241 | CE1 | HIS | A | 42 | 30.472 | -11.198 | 21.971 | 1.00 42.05 | C |
| ATOM | 242 | NE2 | HIS | A | 42 | 30.103 | -10.969 | 20.735 | 1.00 41.31 | N |
| ATOM | 243 | N | CYS | A | 43 | 28.888 | -7.246 | 22.533 | 1.00 26.69 | N |
| ATOM | 244 | CA | CYS | A | 43 | 30.112 | -6.657 | 23.037 | 1.00 29.55 | C |

FIGURE 8A-15

| | | | | | | | | | | |
|---|---|---|---|---|---|---|---|---|---|---|
| ATOM | 245 | C | CYS | A | 43 | 29.916 | -5.341 | 23.766 | 1.00 29.31 | C |
| ATOM | 246 | O | CYS | A | 43 | 30.779 | -4.912 | 24.512 | 1.00 31.36 | O |
| ATOM | 247 | CB | CYS | A | 43 | 31.140 | -6.395 | 21.915 | 1.00 31.15 | C |
| ATOM | 248 | SG | CYS | A | 43 | 31.674 | -7.929 | 21.120 | 1.00 35.60 | S |
| ATOM | 249 | N | TRP | A | 44 | 28.813 | -4.637 | 23.555 | 1.00 28.24 | N |
| ATOM | 250 | CA | TRP | A | 44 | 28.704 | -3.240 | 23.952 | 1.00 25.54 | C |
| ATOM | 251 | C | TRP | A | 44 | 27.331 | -2.947 | 24.498 | 1.00 25.35 | C |
| ATOM | 252 | O | TRP | A | 44 | 27.173 | -1.924 | 25.113 | 1.00 28.50 | O |
| ATOM | 253 | CB | TRP | A | 44 | 28.965 | -2.299 | 22.746 | 1.00 22.52 | C |
| ATOM | 254 | CG | TRP | A | 44 | 28.207 | -2.626 | 21.450 | 1.00 20.09 | C |
| ATOM | 255 | CD1 | TRP | A | 44 | 28.851 | -3.316 | 20.455 | 1.00 19.03 | C |
| ATOM | 256 | CD2 | TRP | A | 44 | 26.890 | -2.326 | 21.142 | 1.00 20.02 | C |
| ATOM | 257 | NE1 | TRP | A | 44 | 27.948 | -3.464 | 19.527 | 1.00 20.48 | N |
| ATOM | 258 | CE2 | TRP | A | 44 | 26.791 | -2.877 | 19.882 | 1.00 19.41 | C |
| ATOM | 259 | CE3 | TRP | A | 44 | 25.841 | -1.609 | 21.652 | 1.00 18.83 | C |
| ATOM | 260 | CZ2 | TRP | A | 44 | 25.665 | -2.678 | 19.127 | 1.00 16.33 | C |
| ATOM | 261 | CZ3 | TRP | A | 44 | 24.711 | -1.431 | 20.910 | 1.00 16.81 | C |
| ATOM | 262 | CH2 | TRP | A | 44 | 24.617 | -1.962 | 19.653 | 1.00 17.88 | C |
| ATOM | 263 | N | ILE | A | 45 | 26.328 | -3.786 | 24.275 | 1.00 27.39 | N |
| ATOM | 264 | CA | ILE | A | 45 | 24.934 | -3.500 | 24.540 | 1.00 28.48 | C |
| ATOM | 265 | C | ILE | A | 45 | 24.666 | -3.370 | 26.025 | 1.00 29.97 | C |
| ATOM | 266 | O | ILE | A | 45 | 23.770 | -2.622 | 26.389 | 1.00 31.30 | O |
| ATOM | 267 | CB | ILE | A | 45 | 24.055 | -4.601 | 23.904 | 1.00 28.39 | C |
| ATOM | 268 | CG1 | ILE | A | 45 | 22.603 | -4.220 | 23.795 | 1.00 28.24 | C |
| ATOM | 269 | CG2 | ILE | A | 45 | 24.152 | -5.926 | 24.668 | 1.00 28.54 | C |
| ATOM | 270 | CD1 | ILE | A | 45 | 22.371 | -2.868 | 23.098 | 1.00 30.38 | C |
| ATOM | 271 | N | SER | A | 46 | 25.408 | -4.044 | 26.900 | 1.00 30.95 | N |
| ATOM | 272 | CA | SER | A | 46 | 25.200 | -3.897 | 28.337 | 1.00 32.47 | C |
| ATOM | 273 | C | SER | A | 46 | 25.677 | -2.546 | 28.844 | 1.00 30.61 | C |
| ATOM | 274 | O | SER | A | 46 | 24.974 | -1.880 | 29.597 | 1.00 30.88 | O |
| ATOM | 275 | CB | SER | A | 46 | 25.899 | -5.016 | 29.106 | 1.00 35.61 | C |
| ATOM | 276 | OG | SER | A | 46 | 25.387 | -6.311 | 28.746 | 1.00 43.59 | O |
| ATOM | 277 | N | GLU | A | 47 | 26.840 | -2.123 | 28.370 | 1.00 28.57 | N |
| ATOM | 278 | CA | GLU | A | 47 | 27.355 | -0.823 | 28.680 | 1.00 28.90 | C |
| ATOM | 279 | C | GLU | A | 47 | 26.567 | 0.306 | 28.090 | 1.00 27.44 | C |
| ATOM | 280 | O | GLU | A | 47 | 26.383 | 1.323 | 28.735 | 1.00 28.17 | O |
| ATOM | 281 | CB | GLU | A | 47 | 28.791 | -0.702 | 28.244 | 1.00 30.74 | C |
| ATOM | 282 | CG | GLU | A | 47 | 29.439 | 0.554 | 28.818 | 1.00 34.60 | C |
| ATOM | 283 | CD | GLU | A | 47 | 29.550 | 0.665 | 30.351 | 1.00 37.52 | C |
| ATOM | 284 | OE1 | GLU | A | 47 | 28.998 | -0.153 | 31.107 | 1.00 37.54 | O |
| ATOM | 285 | OE2 | GLU | A | 47 | 30.208 | 1.607 | 30.800 | 1.00 38.33 | O |
| HETATM | 286 | N | MSE | A | 48 | 26.073 | 0.098 | 26.879 | 1.00 27.89 | N |
| HETATM | 287 | CA | MSE | A | 48 | 25.327 | 1.113 | 26.154 | 1.00 28.18 | C |
| HETATM | 288 | C | MSE | A | 48 | 23.945 | 1.421 | 26.667 | 1.00 26.21 | C |
| HETATM | 289 | O | MSE | A | 48 | 23.580 | 2.578 | 26.606 | 1.00 27.02 | O |
| HETATM | 290 | CB | MSE | A | 48 | 25.309 | 0.882 | 24.637 | 1.00 29.23 | C |
| HETATM | 291 | CG | MSE | A | 48 | 26.739 | 1.048 | 24.095 | 1.00 28.12 | C |
| HETATM | 292 | SE | MSE | A | 48 | 27.685 | 2.655 | 24.690 | 1.00 35.61 | SE |
| HETATM | 293 | CE | MSE | A | 48 | 26.476 | 3.857 | 23.743 | 1.00 22.58 | C |
| ATOM | 294 | N | VAL | A | 49 | 23.147 | 0.491 | 27.195 | 1.00 27.65 | N |
| ATOM | 295 | CA | VAL | A | 49 | 21.882 | 0.875 | 27.814 | 1.00 27.43 | C |
| ATOM | 296 | C | VAL | A | 49 | 22.017 | 1.680 | 29.115 | 1.00 27.42 | C |
| ATOM | 297 | O | VAL | A | 49 | 21.224 | 2.595 | 29.394 | 1.00 27.48 | O |
| ATOM | 298 | CB | VAL | A | 49 | 20.884 | -0.284 | 27.907 | 1.00 27.18 | C |
| ATOM | 299 | CG1 | VAL | A | 49 | 20.438 | -0.478 | 26.452 | 1.00 27.08 | C |
| ATOM | 300 | CG2 | VAL | A | 49 | 21.421 | -1.534 | 28.610 | 1.00 23.66 | C |
| ATOM | 301 | N | VAL | A | 50 | 23.100 | 1.370 | 29.847 | 1.00 26.26 | N |
| ATOM | 302 | CA | VAL | A | 50 | 23.469 | 2.060 | 31.068 | 1.00 24.75 | C |
| ATOM | 303 | C | VAL | A | 50 | 23.964 | 3.431 | 30.716 | 1.00 25.57 | C |
| ATOM | 304 | O | VAL | A | 50 | 23.485 | 4.384 | 31.320 | 1.00 28.77 | O |

FIGURE 8A-16

| | | | | | | | | | | |
|---|---|---|---|---|---|---|---|---|---|---|
| ATOM | 305 | CB | VAL | A | 50 | 24.545 | 1.307 | 31.812 | 1.00 24.44 | C |
| ATOM | 306 | CG1 | VAL | A | 50 | 25.062 | 2.106 | 32.969 | 1.00 23.79 | C |
| ATOM | 307 | CG2 | VAL | A | 50 | 23.952 | 0.040 | 32.382 | 1.00 24.17 | C |
| ATOM | 308 | N | GLN | A | 51 | 24.888 | 3.551 | 29.758 | 1.00 22.88 | N |
| ATOM | 309 | CA | GLN | A | 51 | 25.315 | 4.841 | 29.294 | 1.00 18.59 | C |
| ATOM | 310 | C | GLN | A | 51 | 24.226 | 5.698 | 28.700 | 1.00 18.17 | C |
| ATOM | 311 | O | GLN | A | 51 | 24.223 | 6.904 | 28.948 | 1.00 20.05 | O |
| ATOM | 312 | CB | GLN | A | 51 | 26.474 | 4.707 | 28.320 | 1.00 21.19 | C |
| ATOM | 313 | CG | GLN | A | 51 | 27.676 | 4.059 | 28.934 | 1.00 17.37 | C |
| ATOM | 314 | CD | GLN | A | 51 | 28.072 | 4.720 | 30.240 | 1.00 21.56 | C |
| ATOM | 315 | OE1 | GLN | A | 51 | 27.879 | 5.913 | 30.476 | 1.00 23.67 | O |
| ATOM | 316 | NE2 | GLN | A | 51 | 28.662 | 3.969 | 31.152 | 1.00 22.77 | N |
| ATOM | 317 | N | LEU | A | 52 | 23.291 | 5.106 | 27.959 | 1.00 15.38 | N |
| ATOM | 318 | CA | LEU | A | 52 | 22.210 | 5.850 | 27.374 | 1.00 16.72 | C |
| ATOM | 319 | C | LEU | A | 52 | 21.199 | 6.284 | 28.411 | 1.00 18.34 | C |
| ATOM | 320 | O | LEU | A | 52 | 20.676 | 7.387 | 28.382 | 1.00 18.73 | O |
| ATOM | 321 | CB | LEU | A | 52 | 21.533 | 5.006 | 26.309 | 1.00 15.91 | C |
| ATOM | 322 | CG | LEU | A | 52 | 22.207 | 5.059 | 24.928 | 1.00 17.11 | C |
| ATOM | 323 | CD1 | LEU | A | 52 | 21.807 | 3.949 | 24.155 | 1.00 14.42 | C |
| ATOM | 324 | CD2 | LEU | A | 52 | 21.886 | 6.330 | 24.184 | 1.00 12.26 | C |
| ATOM | 325 | N | SER | A | 53 | 20.932 | 5.433 | 29.378 | 1.00 20.83 | N |
| ATOM | 326 | CA | SER | A | 53 | 20.098 | 5.806 | 30.505 | 1.00 23.79 | C |
| ATOM | 327 | C | SER | A | 53 | 20.716 | 6.966 | 31.295 | 1.00 24.20 | C |
| ATOM | 328 | O | SER | A | 53 | 19.977 | 7.897 | 31.624 | 1.00 26.42 | O |
| ATOM | 329 | CB | SER | A | 53 | 19.917 | 4.605 | 31.403 | 1.00 23.71 | C |
| ATOM | 330 | OG | SER | A | 53 | 19.285 | 5.024 | 32.601 | 1.00 30.23 | O |
| ATOM | 331 | N | ASP | A | 54 | 22.043 | 6.977 | 31.559 | 1.00 23.25 | N |
| ATOM | 332 | CA | ASP | A | 54 | 22.687 | 8.036 | 32.308 | 1.00 20.61 | C |
| ATOM | 333 | C | ASP | A | 54 | 22.659 | 9.325 | 31.572 | 1.00 19.02 | C |
| ATOM | 334 | O | ASP | A | 54 | 22.303 | 10.358 | 32.142 | 1.00 20.41 | O |
| ATOM | 335 | CB | ASP | A | 54 | 24.114 | 7.682 | 32.740 | 1.00 25.54 | C |
| ATOM | 336 | CG | ASP | A | 54 | 24.207 | 6.579 | 33.815 | 1.00 31.33 | C |
| ATOM | 337 | OD1 | ASP | A | 54 | 23.185 | 5.965 | 34.178 | 1.00 36.02 | O |
| ATOM | 338 | OD2 | ASP | A | 54 | 25.318 | 6.318 | 34.307 | 1.00 32.62 | O |
| ATOM | 339 | N | SER | A | 55 | 22.962 | 9.286 | 30.291 | 1.00 16.79 | N |
| ATOM | 340 | CA | SER | A | 55 | 22.857 | 10.514 | 29.541 | 1.00 17.42 | C |
| ATOM | 341 | C | SER | A | 55 | 21.454 | 11.096 | 29.425 | 1.00 16.81 | C |
| ATOM | 342 | O | SER | A | 55 | 21.293 | 12.318 | 29.474 | 1.00 17.95 | O |
| ATOM | 343 | CB | SER | A | 55 | 23.511 | 10.378 | 28.150 | 1.00 18.91 | C |
| ATOM | 344 | OG | SER | A | 55 | 24.863 | 9.936 | 28.237 | 1.00 22.06 | O |
| ATOM | 345 | N | LEU | A | 56 | 20.439 | 10.249 | 29.243 | 1.00 17.01 | N |
| ATOM | 346 | CA | LEU | A | 56 | 19.073 | 10.726 | 29.162 | 1.00 17.99 | C |
| ATOM | 347 | C | LEU | A | 56 | 18.518 | 11.188 | 30.514 | 1.00 18.27 | C |
| ATOM | 348 | O | LEU | A | 56 | 17.800 | 12.186 | 30.575 | 1.00 18.82 | O |
| ATOM | 349 | CB | LEU | A | 56 | 18.130 | 9.712 | 28.505 | 1.00 17.68 | C |
| ATOM | 350 | CG | LEU | A | 56 | 18.061 | 9.584 | 26.983 | 1.00 18.44 | C |
| ATOM | 351 | CD1 | LEU | A | 56 | 17.381 | 8.280 | 26.613 | 1.00 19.03 | C |
| ATOM | 352 | CD2 | LEU | A | 56 | 17.392 | 10.764 | 26.321 | 1.00 16.39 | C |
| ATOM | 353 | N | THR | A | 57 | 18.835 | 10.532 | 31.616 | 1.00 18.45 | N |
| ATOM | 354 | CA | THR | A | 57 | 18.376 | 11.005 | 32.911 | 1.00 21.42 | C |
| ATOM | 355 | C | THR | A | 57 | 18.975 | 12.383 | 33.205 | 1.00 21.42 | C |
| ATOM | 356 | O | THR | A | 57 | 18.263 | 13.297 | 33.640 | 1.00 21.53 | O |
| ATOM | 357 | CB | THR | A | 57 | 18.680 | 9.942 | 33.948 | 1.00 18.39 | C |
| ATOM | 358 | OG1 | THR | A | 57 | 18.055 | 8.791 | 33.418 | 1.00 20.01 | O |
| ATOM | 359 | CG2 | THR | A | 57 | 17.980 | 10.190 | 35.253 | 1.00 23.58 | C |
| ATOM | 360 | N | ASP | A | 58 | 20.245 | 12.587 | 32.819 | 1.00 23.66 | N |
| ATOM | 361 | CA | ASP | A | 58 | 20.908 | 13.867 | 32.971 | 1.00 24.99 | C |
| ATOM | 362 | C | ASP | A | 58 | 20.269 | 14.969 | 32.162 | 1.00 23.11 | C |
| ATOM | 363 | O | ASP | A | 58 | 20.243 | 16.133 | 32.567 | 1.00 22.89 | O |
| ATOM | 364 | CB | ASP | A | 58 | 22.410 | 13.766 | 32.646 | 1.00 33.60 | C |

FIGURE 8A-17

```
ATOM    365  CG   ASP A   58      23.101  15.151  32.595  1.00 41.66           C
ATOM    366  OD1  ASP A   58      23.500  15.636  33.666  1.00 45.37           O
ATOM    367  OD2  ASP A   58      23.204  15.764  31.502  1.00 43.30           O
ATOM    368  N    LEU A   59      19.762  14.614  30.994  1.00 21.38           N
ATOM    369  CA   LEU A   59      19.106  15.568  30.124  1.00 19.63           C
ATOM    370  C    LEU A   59      17.857  16.179  30.719  1.00 20.35           C
ATOM    371  O    LEU A   59      17.522  17.321  30.413  1.00 19.57           O
ATOM    372  CB   LEU A   59      18.751  14.826  28.859  1.00 19.31           C
ATOM    373  CG   LEU A   59      19.006  15.498  27.551  1.00 18.41           C
ATOM    374  CD1  LEU A   59      20.161  16.496  27.615  1.00 16.32           C
ATOM    375  CD2  LEU A   59      19.225  14.401  26.555  1.00 17.59           C
ATOM    376  N    LEU A   60      17.163  15.410  31.587  1.00 21.63           N
ATOM    377  CA   LEU A   60      15.930  15.857  32.216  1.00 20.55           C
ATOM    378  C    LEU A   60      16.133  17.147  32.974  1.00 22.32           C
ATOM    379  O    LEU A   60      15.264  18.016  32.929  1.00 23.28           O
ATOM    380  CB   LEU A   60      15.389  14.796  33.145  1.00 17.67           C
ATOM    381  CG   LEU A   60      14.680  13.601  32.538  1.00 14.57           C
ATOM    382  CD1  LEU A   60      14.293  12.641  33.643  1.00 12.83           C
ATOM    383  CD2  LEU A   60      13.462  14.048  31.847  1.00  8.22           C
ATOM    384  N    ASP A   61      17.338  17.285  33.558  1.00 22.42           N
ATOM    385  CA   ASP A   61      17.805  18.483  34.247  1.00 22.10           C
ATOM    386  C    ASP A   61      17.810  19.768  33.433  1.00 20.08           C
ATOM    387  O    ASP A   61      17.841  20.870  33.974  1.00 20.02           O
ATOM    388  CB   ASP A   61      19.203  18.169  34.753  1.00 28.60           C
ATOM    389  CG   ASP A   61      19.803  19.159  35.750  1.00 34.29           C
ATOM    390  OD1  ASP A   61      19.459  19.073  36.931  1.00 40.97           O
ATOM    391  OD2  ASP A   61      20.616  20.006  35.356  1.00 37.85           O
ATOM    392  N    LYS A   62      17.721  19.693  32.105  1.00 19.76           N
ATOM    393  CA   LYS A   62      17.839  20.862  31.245  1.00 16.53           C
ATOM    394  C    LYS A   62      16.485  21.335  30.770  1.00 16.75           C
ATOM    395  O    LYS A   62      16.388  22.383  30.130  1.00 17.62           O
ATOM    396  CB   LYS A   62      18.684  20.529  30.020  1.00 18.65           C
ATOM    397  CG   LYS A   62      19.986  19.755  30.233  1.00 16.80           C
ATOM    398  CD   LYS A   62      20.808  20.483  31.276  1.00 18.07           C
ATOM    399  CE   LYS A   62      22.135  19.776  31.535  1.00 23.34           C
ATOM    400  NZ   LYS A   62      22.088  18.331  31.330  1.00 28.06           N
ATOM    401  N    PHE A   63      15.400  20.605  31.068  1.00 16.40           N
ATOM    402  CA   PHE A   63      14.086  20.979  30.586  1.00 16.93           C
ATOM    403  C    PHE A   63      13.110  21.140  31.730  1.00 17.40           C
ATOM    404  O    PHE A   63      13.294  20.626  32.826  1.00 17.50           O
ATOM    405  CB   PHE A   63      13.576  19.942  29.574  1.00 15.08           C
ATOM    406  CG   PHE A   63      14.424  19.850  28.325  1.00 13.39           C
ATOM    407  CD1  PHE A   63      14.261  20.767  27.317  1.00 13.60           C
ATOM    408  CD2  PHE A   63      15.410  18.888  28.252  1.00 14.95           C
ATOM    409  CE1  PHE A   63      15.126  20.740  26.266  1.00 10.99           C
ATOM    410  CE2  PHE A   63      16.305  18.889  27.207  1.00 14.45           C
ATOM    411  CZ   PHE A   63      16.150  19.832  26.229  1.00 10.95           C
ATOM    412  N    SER A   64      12.031  21.843  31.444  1.00 19.14           N
ATOM    413  CA   SER A   64      10.993  22.080  32.407  1.00 21.71           C
ATOM    414  C    SER A   64       9.832  21.125  32.198  1.00 22.87           C
ATOM    415  O    SER A   64       9.431  20.758  31.098  1.00 24.09           O
ATOM    416  CB   SER A   64      10.533  23.508  32.261  1.00 22.47           C
ATOM    417  OG   SER A   64       9.408  23.881  33.049  1.00 29.46           O
ATOM    418  N    ASN A   65       9.298  20.809  33.363  1.00 23.97           N
ATOM    419  CA   ASN A   65       8.233  19.855  33.608  1.00 29.13           C
ATOM    420  C    ASN A   65       6.899  20.530  33.390  1.00 31.34           C
ATOM    421  O    ASN A   65       5.883  19.858  33.203  1.00 35.27           O
ATOM    422  CB   ASN A   65       8.309  19.551  35.119  1.00 30.43           C
ATOM    423  CG   ASN A   65       8.097  18.117  35.514  1.00 33.16           C
ATOM    424  OD1  ASN A   65       7.488  17.258  34.873  1.00 41.60           O
```

FIGURE 8A-18

```
ATOM    425  ND2 ASN A  65       8.641  17.823  36.656  1.00 34.77           N
ATOM    426  N   ILE A  66       6.892  21.862  33.561  1.00 32.62           N
ATOM    427  CA  ILE A  66       5.708  22.691  33.384  1.00 33.83           C
ATOM    428  C   ILE A  66       5.681  23.071  31.918  1.00 35.58           C
ATOM    429  O   ILE A  66       6.450  23.910  31.431  1.00 36.08           O
ATOM    430  CB  ILE A  66       5.752  24.000  34.223  1.00 33.21           C
ATOM    431  CG1 ILE A  66       6.162  23.831  35.672  1.00 33.50           C
ATOM    432  CG2 ILE A  66       4.416  24.708  34.158  1.00 31.21           C
ATOM    433  CD1 ILE A  66       5.330  22.784  36.415  1.00 32.37           C
ATOM    434  N   SER A  67       4.782  22.424  31.201  1.00 37.23           N
ATOM    435  CA  SER A  67       4.669  22.650  29.771  1.00 40.50           C
ATOM    436  C   SER A  67       3.358  22.008  29.327  1.00 42.07           C
ATOM    437  O   SER A  67       3.073  20.841  29.622  1.00 43.86           O
ATOM    438  CB  SER A  67       5.892  21.985  29.075  1.00 40.62           C
ATOM    439  OG  SER A  67       6.244  22.539  27.815  1.00 36.76           O
ATOM    440  N   GLU A  68       2.502  22.765  28.648  1.00 44.40           N
ATOM    441  CA  GLU A  68       1.317  22.183  28.023  1.00 46.43           C
ATOM    442  C   GLU A  68       1.777  21.448  26.758  1.00 46.20           C
ATOM    443  O   GLU A  68       2.874  21.690  26.234  1.00 47.39           O
ATOM    444  CB  GLU A  68       0.364  23.301  27.637  1.00 49.01           C
ATOM    445  CG  GLU A  68      -1.051  22.858  27.256  1.00 53.42           C
ATOM    446  CD  GLU A  68      -2.066  23.229  28.324  1.00 56.12           C
ATOM    447  OE1 GLU A  68      -2.255  22.391  29.223  1.00 58.37           O
ATOM    448  OE2 GLU A  68      -2.634  24.342  28.250  1.00 56.09           O
ATOM    449  N   GLY A  69       0.957  20.523  26.262  1.00 45.44           N
ATOM    450  CA  GLY A  69       1.228  19.834  25.021  1.00 43.62           C
ATOM    451  C   GLY A  69       2.561  19.130  25.029  1.00 42.33           C
ATOM    452  O   GLY A  69       2.944  18.429  25.963  1.00 43.42           O
ATOM    453  N   LEU A  70       3.245  19.412  23.927  1.00 42.01           N
ATOM    454  CA  LEU A  70       4.567  18.856  23.634  1.00 40.66           C
ATOM    455  C   LEU A  70       5.570  19.283  24.688  1.00 37.48           C
ATOM    456  O   LEU A  70       5.769  20.477  24.916  1.00 39.56           O
ATOM    457  CB  LEU A  70       5.069  19.339  22.221  1.00 42.73           C
ATOM    458  CG  LEU A  70       6.365  18.753  21.553  1.00 43.68           C
ATOM    459  CD1 LEU A  70       6.429  17.212  21.539  1.00 40.99           C
ATOM    460  CD2 LEU A  70       6.506  19.318  20.134  1.00 42.81           C
ATOM    461  N   SER A  71       6.203  18.289  25.301  1.00 32.14           N
ATOM    462  CA  SER A  71       7.187  18.514  26.330  1.00 24.30           C
ATOM    463  C   SER A  71       8.394  17.653  26.032  1.00 20.06           C
ATOM    464  O   SER A  71       8.282  16.449  25.900  1.00 21.51           O
ATOM    465  CB  SER A  71       6.519  18.160  27.653  1.00 21.80           C
ATOM    466  OG  SER A  71       7.393  18.171  28.756  1.00 17.14           O
ATOM    467  N   ASN A  72       9.573  18.208  25.883  1.00 18.83           N
ATOM    468  CA  ASN A  72      10.787  17.419  25.827  1.00 16.99           C
ATOM    469  C   ASN A  72      11.079  16.692  27.083  1.00 15.54           C
ATOM    470  O   ASN A  72      11.566  15.578  26.997  1.00 16.64           O
ATOM    471  CB  ASN A  72      11.982  18.277  25.558  1.00 20.15           C
ATOM    472  CG  ASN A  72      11.916  18.839  24.158  1.00 23.44           C
ATOM    473  OD1 ASN A  72      11.109  18.421  23.317  1.00 25.67           O
ATOM    474  ND2 ASN A  72      12.780  19.812  23.894  1.00 24.59           N
ATOM    475  N   TYR A  73      10.823  17.309  28.239  1.00 15.06           N
ATOM    476  CA  TYR A  73      10.835  16.579  29.507  1.00 15.26           C
ATOM    477  C   TYR A  73       9.936  15.319  29.443  1.00 15.85           C
ATOM    478  O   TYR A  73      10.538  14.262  29.740  1.00 18.32           O
ATOM    479  CB  TYR A  73      10.315  17.410  30.733  1.00 12.75           C
ATOM    480  CG  TYR A  73      10.760  16.862  32.082  1.00 10.27           C
ATOM    481  CD1 TYR A  73      11.940  17.306  32.624  1.00 11.84           C
ATOM    482  CD2 TYR A  73       9.993  15.928  32.769  1.00 14.03           C
ATOM    483  CE1 TYR A  73      12.364  16.827  33.839  1.00 12.67           C
ATOM    484  CE2 TYR A  73      10.412  15.419  33.979  1.00 10.24           C
```

FIGURE 8A-19

```
ATOM    485  CZ   TYR A  73      11.592  15.891  34.491  1.00 14.02           C
ATOM    486  OH   TYR A  73      12.042  15.429  35.703  1.00 14.54           O
ATOM    487  N    SER A  74       8.682  15.323  29.087  1.00 18.48           N
ATOM    488  CA   SER A  74       7.947  14.076  29.034  1.00 18.74           C
ATOM    489  C    SER A  74       8.429  13.074  28.017  1.00 18.80           C
ATOM    490  O    SER A  74       8.430  11.882  28.327  1.00 18.69           O
ATOM    491  CB   SER A  74       6.434  14.228  29.002  1.00 21.96           C
ATOM    492  OG   SER A  74       5.847  15.278  28.253  1.00 30.65           O
ATOM    493  N    ILE A  75       8.928  13.522  26.849  1.00 18.95           N
ATOM    494  CA   ILE A  75       9.481  12.602  25.855  1.00 17.82           C
ATOM    495  C    ILE A  75      10.689  11.896  26.422  1.00 17.12           C
ATOM    496  O    ILE A  75      10.679  10.688  26.557  1.00 18.03           O
ATOM    497  CB   ILE A  75       9.750  13.298  24.460  1.00 20.42           C
ATOM    498  CG1  ILE A  75       8.440  13.885  23.860  1.00 19.63           C
ATOM    499  CG2  ILE A  75      10.327  12.283  23.471  1.00 17.30           C
ATOM    500  CD1  ILE A  75       8.582  14.604  22.508  1.00 23.08           C
ATOM    501  N    ILE A  76      11.698  12.625  26.857  1.00 18.46           N
ATOM    502  CA   ILE A  76      12.916  12.070  27.436  1.00 19.33           C
ATOM    503  C    ILE A  76      12.622  11.116  28.592  1.00 19.01           C
ATOM    504  O    ILE A  76      13.199  10.040  28.714  1.00 20.65           O
ATOM    505  CB   ILE A  76      13.816  13.253  27.900  1.00 18.88           C
ATOM    506  CG1  ILE A  76      14.239  14.216  26.789  1.00 17.98           C
ATOM    507  CG2  ILE A  76      15.057  12.732  28.600  1.00 20.53           C
ATOM    508  CD1  ILE A  76      14.950  15.500  27.300  1.00 15.54           C
ATOM    509  N    ASP A  77      11.643  11.474  29.412  1.00 19.90           N
ATOM    510  CA   ASP A  77      11.226  10.682  30.562  1.00 19.93           C
ATOM    511  C    ASP A  77      10.627   9.341  30.177  1.00 21.32           C
ATOM    512  O    ASP A  77      10.832   8.318  30.830  1.00 21.41           O
ATOM    513  CB   ASP A  77      10.189  11.524  31.263  1.00 21.00           C
ATOM    514  CG   ASP A  77       9.506  10.808  32.390  1.00 23.32           C
ATOM    515  OD1  ASP A  77      10.211  10.249  33.204  1.00 26.02           O
ATOM    516  OD2  ASP A  77       8.283  10.750  32.419  1.00 24.74           O
ATOM    517  N    LYS A  78       9.835   9.312  29.101  1.00 23.41           N
ATOM    518  CA   LYS A  78       9.385   8.038  28.606  1.00 23.09           C
ATOM    519  C    LYS A  78      10.529   7.247  27.975  1.00 24.61           C
ATOM    520  O    LYS A  78      10.518   6.000  28.021  1.00 26.85           O
ATOM    521  CB   LYS A  78       8.267   8.237  27.656  1.00 25.84           C
ATOM    522  CG   LYS A  78       7.024   8.643  28.403  1.00 29.26           C
ATOM    523  CD   LYS A  78       5.882   8.766  27.362  1.00 40.97           C
ATOM    524  CE   LYS A  78       6.119   9.815  26.221  1.00 43.91           C
ATOM    525  NZ   LYS A  78       5.056   9.792  25.229  1.00 48.24           N
ATOM    526  N    LEU A  79      11.559   7.936  27.437  1.00 22.19           N
ATOM    527  CA   LEU A  79      12.718   7.253  26.865  1.00 18.09           C
ATOM    528  C    LEU A  79      13.577   6.757  27.968  1.00 16.82           C
ATOM    529  O    LEU A  79      14.146   5.692  27.806  1.00 17.74           O
ATOM    530  CB   LEU A  79      13.580   8.147  25.986  1.00 16.97           C
ATOM    531  CG   LEU A  79      12.928   8.748  24.768  1.00 15.98           C
ATOM    532  CD1  LEU A  79      13.984   9.540  24.058  1.00 16.93           C
ATOM    533  CD2  LEU A  79      12.264   7.721  23.857  1.00 14.76           C
ATOM    534  N    VAL A  80      13.609   7.460  29.101  1.00 16.48           N
ATOM    535  CA   VAL A  80      14.352   6.994  30.249  1.00 13.79           C
ATOM    536  C    VAL A  80      13.697   5.725  30.731  1.00 14.44           C
ATOM    537  O    VAL A  80      14.385   4.763  31.022  1.00 14.81           O
ATOM    538  CB   VAL A  80      14.382   8.054  31.331  1.00 17.12           C
ATOM    539  CG1  VAL A  80      14.937   7.490  32.631  1.00 17.65           C
ATOM    540  CG2  VAL A  80      15.307   9.189  30.910  1.00 13.43           C
ATOM    541  N    ASN A  81      12.383   5.633  30.743  1.00 16.27           N
ATOM    542  CA   ASN A  81      11.696   4.398  31.081  1.00 18.71           C
ATOM    543  C    ASN A  81      11.852   3.174  30.176  1.00 21.49           C
ATOM    544  O    ASN A  81      11.945   2.060  30.691  1.00 22.57           O
```

*FIGURE 8A-20*

```
ATOM    545  CB   ASN A  81      10.244   4.707  31.191  1.00 20.64           C
ATOM    546  CG   ASN A  81       9.968   5.574  32.402  1.00 22.06           C
ATOM    547  OD1  ASN A  81      10.652   5.475  33.422  1.00 22.22           O
ATOM    548  ND2  ASN A  81       8.941   6.409  32.322  1.00 21.76           N
ATOM    549  N    ILE A  82      11.898   3.339  28.846  1.00 21.86           N
ATOM    550  CA   ILE A  82      12.226   2.270  27.917  1.00 23.02           C
ATOM    551  C    ILE A  82      13.602   1.742  28.112  1.00 23.67           C
ATOM    552  O    ILE A  82      13.728   0.536  28.067  1.00 26.85           O
ATOM    553  CB   ILE A  82      12.089   2.768  26.497  1.00 22.79           C
ATOM    554  CG1  ILE A  82      10.613   2.757  26.220  1.00 23.80           C
ATOM    555  CG2  ILE A  82      12.854   1.951  25.474  1.00 21.98           C
ATOM    556  CD1  ILE A  82      10.321   3.659  25.020  1.00 27.18           C
ATOM    557  N    VAL A  83      14.619   2.586  28.254  1.00 25.82           N
ATOM    558  CA   VAL A  83      15.996   2.104  28.338  1.00 27.82           C
ATOM    559  C    VAL A  83      16.212   1.471  29.706  1.00 30.01           C
ATOM    560  O    VAL A  83      16.995   0.522  29.796  1.00 32.08           O
ATOM    561  CB   VAL A  83      17.139   3.137  28.252  1.00 26.25           C
ATOM    562  CG1  VAL A  83      18.343   2.445  27.683  1.00 28.68           C
ATOM    563  CG2  VAL A  83      16.883   4.437  27.569  1.00 28.99           C
ATOM    564  N    ASP A  84      15.602   1.983  30.789  1.00 30.99           N
ATOM    565  CA   ASP A  84      15.711   1.384  32.123  1.00 34.08           C
ATOM    566  C    ASP A  84      15.125  -0.013  32.275  1.00 34.30           C
ATOM    567  O    ASP A  84      15.666  -0.816  33.035  1.00 35.01           O
ATOM    568  CB   ASP A  84      15.148   2.331  33.189  1.00 37.32           C
ATOM    569  CG   ASP A  84      15.909   3.664  33.316  1.00 42.03           C
ATOM    570  OD1  ASP A  84      16.907   3.865  32.621  1.00 43.39           O
ATOM    571  OD2  ASP A  84      15.496   4.523  34.107  1.00 44.86           O
ATOM    572  N    ASP A  85      14.055  -0.335  31.524  1.00 35.79           N
ATOM    573  CA   ASP A  85      13.554  -1.707  31.332  1.00 37.15           C
ATOM    574  C    ASP A  85      14.655  -2.665  30.860  1.00 34.71           C
ATOM    575  O    ASP A  85      14.777  -3.800  31.308  1.00 33.69           O
ATOM    576  CB   ASP A  85      12.434  -1.780  30.233  1.00 42.27           C
ATOM    577  CG   ASP A  85      11.023  -1.216  30.474  1.00 46.16           C
ATOM    578  OD1  ASP A  85      10.747  -0.756  31.587  1.00 46.14           O
ATOM    579  OD2  ASP A  85      10.197  -1.234  29.539  1.00 50.79           O
ATOM    580  N    LEU A  86      15.437  -2.164  29.904  1.00 33.83           N
ATOM    581  CA   LEU A  86      16.527  -2.886  29.288  1.00 33.71           C
ATOM    582  C    LEU A  86      17.747  -2.959  30.177  1.00 34.12           C
ATOM    583  O    LEU A  86      18.440  -3.965  30.083  1.00 34.86           O
ATOM    584  CB   LEU A  86      16.907  -2.260  27.948  1.00 31.87           C
ATOM    585  CG   LEU A  86      15.878  -2.198  26.829  1.00 30.75           C
ATOM    586  CD1  LEU A  86      16.383  -1.351  25.699  1.00 30.54           C
ATOM    587  CD2  LEU A  86      15.521  -3.581  26.349  1.00 29.51           C
ATOM    588  N    VAL A  87      18.033  -1.973  31.039  1.00 33.89           N
ATOM    589  CA   VAL A  87      19.121  -2.074  32.009  1.00 35.56           C
ATOM    590  C    VAL A  87      18.933  -3.223  33.039  1.00 40.73           C
ATOM    591  O    VAL A  87      19.889  -3.890  33.493  1.00 42.23           O
ATOM    592  CB   VAL A  87      19.239  -0.695  32.614  1.00 31.60           C
ATOM    593  CG1  VAL A  87      20.272  -0.634  33.703  1.00 33.57           C
ATOM    594  CG2  VAL A  87      19.680   0.253  31.537  1.00 29.91           C
ATOM    595  N    GLU A  88      17.645  -3.484  33.340  1.00 44.00           N
ATOM    596  CA   GLU A  88      17.191  -4.563  34.217  1.00 47.21           C
ATOM    597  C    GLU A  88      17.016  -5.918  33.542  1.00 48.21           C
ATOM    598  O    GLU A  88      17.359  -6.909  34.169  1.00 47.84           O
ATOM    599  CB   GLU A  88      15.868  -4.200  34.886  1.00 49.05           C
ATOM    600  CG   GLU A  88      15.877  -2.952  35.772  1.00 52.09           C
ATOM    601  CD   GLU A  88      16.809  -3.020  36.976  1.00 53.70           C
ATOM    602  OE1  GLU A  88      16.608  -3.858  37.861  1.00 55.01           O
ATOM    603  OE2  GLU A  88      17.744  -2.221  37.020  1.00 54.23           O
ATOM    604  N    CYS A  89      16.475  -6.018  32.311  1.00 50.79           N
```

*FIGURE 8A-21*

| | | | | | | | | | |
|---|---|---|---|---|---|---|---|---|---|
| ATOM | 605 | CA | CYS | A | 89 | 16.489 | -7.244 | 31.503 | 1.00 54.51 | C |
| ATOM | 606 | C | CYS | A | 89 | 17.952 | -7.703 | 31.459 | 1.00 55.09 | C |
| ATOM | 607 | O | CYS | A | 89 | 18.231 | -8.791 | 31.961 | 1.00 57.42 | O |
| ATOM | 608 | CB | CYS | A | 89 | 15.903 | -6.972 | 30.078 | 1.00 57.17 | C |
| ATOM | 609 | SG | CYS | A | 89 | 15.060 | -8.280 | 29.096 | 1.00 64.80 | S |
| ATOM | 610 | N | VAL | A | 90 | 18.890 | -6.838 | 31.002 | 1.00 55.69 | N |
| ATOM | 611 | CA | VAL | A | 90 | 20.357 | -7.027 | 31.060 | 1.00 55.91 | C |
| ATOM | 612 | C | VAL | A | 90 | 20.906 | -7.397 | 32.450 | 1.00 57.84 | C |
| ATOM | 613 | O | VAL | A | 90 | 22.014 | -7.924 | 32.546 | 1.00 58.27 | O |
| ATOM | 614 | CB | VAL | A | 90 | 21.074 | -5.738 | 30.480 | 1.00 53.45 | C |
| ATOM | 615 | CG1 | VAL | A | 90 | 22.542 | -5.564 | 30.824 | 1.00 52.76 | C |
| ATOM | 616 | CG2 | VAL | A | 90 | 20.965 | -5.689 | 28.978 | 1.00 50.05 | C |
| ATOM | 617 | N | LYS | A | 91 | 20.212 | -7.128 | 33.558 | 1.00 59.29 | N |
| ATOM | 618 | CA | LYS | A | 91 | 20.556 | -7.785 | 34.810 | 1.00 62.11 | C |
| ATOM | 619 | C | LYS | A | 91 | 19.865 | -9.163 | 34.996 | 1.00 63.85 | C |
| ATOM | 620 | O | LYS | A | 91 | 20.517 | -10.061 | 35.533 | 1.00 66.48 | O |
| ATOM | 621 | CB | LYS | A | 91 | 20.305 | -6.837 | 35.993 | 1.00 61.39 | C |
| ATOM | 622 | N | SER | A | 104 | 36.757 | 4.074 | 31.300 | 1.00 64.71 | N |
| ATOM | 623 | CA | SER | A | 104 | 36.147 | 4.043 | 29.974 | 1.00 64.00 | C |
| ATOM | 624 | C | SER | A | 104 | 34.723 | 3.416 | 29.904 | 1.00 61.57 | C |
| ATOM | 625 | O | SER | A | 104 | 34.321 | 2.749 | 30.871 | 1.00 62.78 | O |
| ATOM | 626 | CB | SER | A | 104 | 37.147 | 3.441 | 28.919 | 1.00 65.90 | C |
| ATOM | 627 | OG | SER | A | 104 | 38.150 | 4.399 | 28.533 | 1.00 67.30 | O |
| ATOM | 628 | N | PRO | A | 105 | 33.891 | 3.576 | 28.842 | 1.00 57.26 | N |
| ATOM | 629 | CA | PRO | A | 105 | 34.173 | 4.332 | 27.635 | 1.00 53.19 | C |
| ATOM | 630 | C | PRO | A | 105 | 34.452 | 5.801 | 27.627 | 1.00 51.76 | C |
| ATOM | 631 | O | PRO | A | 105 | 34.107 | 6.397 | 28.843 | 1.00 53.30 | O |
| ATOM | 632 | CB | PRO | A | 105 | 32.968 | 4.091 | 26.813 | 1.00 51.85 | C |
| ATOM | 633 | CG | PRO | A | 105 | 31.869 | 3.765 | 27.755 | 1.00 53.45 | C |
| ATOM | 634 | CD | PRO | A | 105 | 32.618 | 2.880 | 28.698 | 1.00 55.74 | C |
| ATOM | 635 | N | GLU | A | 106 | 35.242 | 6.296 | 26.875 | 1.00 50.80 | N |
| ATOM | 636 | CA | GLU | A | 106 | 35.584 | 7.700 | 26.790 | 1.00 47.97 | C |
| ATOM | 637 | C | GLU | A | 106 | 34.332 | 8.435 | 26.350 | 1.00 44.14 | C |
| ATOM | 638 | O | GLU | A | 106 | 33.684 | 8.006 | 25.400 | 1.00 42.91 | O |
| ATOM | 639 | CB | GLU | A | 106 | 36.796 | 7.970 | 25.858 | 1.00 51.71 | C |
| ATOM | 640 | CG | GLU | A | 106 | 36.873 | 7.196 | 24.509 | 1.00 57.13 | C |
| ATOM | 641 | CD | GLU | A | 106 | 38.045 | 6.192 | 24.389 | 1.00 60.78 | C |
| ATOM | 642 | OE1 | GLU | A | 106 | 38.141 | 5.251 | 25.189 | 1.00 61.59 | O |
| ATOM | 643 | OE2 | GLU | A | 106 | 38.874 | 6.338 | 23.482 | 1.00 63.52 | O |
| ATOM | 644 | N | PRO | A | 107 | 33.936 | 9.481 | 27.092 | 1.00 41.02 | N |
| ATOM | 645 | CA | PRO | A | 107 | 32.846 | 10.386 | 26.770 | 1.00 38.74 | C |
| ATOM | 646 | C | PRO | A | 107 | 33.069 | 11.190 | 25.517 | 1.00 37.93 | C |
| ATOM | 647 | O | PRO | A | 107 | 34.148 | 11.749 | 25.271 | 1.00 40.00 | O |
| ATOM | 648 | CB | PRO | A | 107 | 32.764 | 11.292 | 27.970 | 1.00 39.85 | C |
| ATOM | 649 | CG | PRO | A | 107 | 34.162 | 11.290 | 28.542 | 1.00 40.91 | C |
| ATOM | 650 | CD | PRO | A | 107 | 34.522 | 9.832 | 28.384 | 1.00 41.30 | C |
| ATOM | 651 | N | ARG | A | 108 | 32.000 | 11.208 | 24.724 | 1.00 35.40 | N |
| ATOM | 652 | CA | ARG | A | 108 | 32.006 | 11.864 | 23.436 | 1.00 33.34 | C |
| ATOM | 653 | C | ARG | A | 108 | 30.766 | 12.722 | 23.318 | 1.00 29.75 | C |
| ATOM | 654 | O | ARG | A | 108 | 29.727 | 12.347 | 23.867 | 1.00 29.55 | O |
| ATOM | 655 | CB | ARG | A | 108 | 32.102 | 10.859 | 22.297 | 1.00 35.14 | C |
| ATOM | 656 | CG | ARG | A | 108 | 33.480 | 10.219 | 22.313 | 1.00 39.55 | C |
| ATOM | 657 | CD | ARG | A | 108 | 33.734 | 9.386 | 21.057 | 1.00 44.05 | C |
| ATOM | 658 | NE | ARG | A | 108 | 34.715 | 8.324 | 21.284 | 1.00 45.36 | N |
| ATOM | 659 | CZ | ARG | A | 108 | 34.965 | 7.376 | 20.373 | 1.00 45.18 | C |
| ATOM | 660 | NH1 | ARG | A | 108 | 34.481 | 7.446 | 19.142 | 1.00 46.89 | N |
| ATOM | 661 | NH2 | ARG | A | 108 | 35.679 | 6.306 | 20.712 | 1.00 46.89 | N |
| ATOM | 662 | N | LEU | A | 109 | 30.932 | 13.877 | 22.650 | 1.00 26.42 | N |
| ATOM | 663 | CA | LEU | A | 109 | 29.833 | 14.770 | 22.334 | 1.00 25.17 | C |
| ATOM | 664 | C | LEU | A | 109 | 29.126 | 14.453 | 21.020 | 1.00 25.96 | C |

FIGURE 8A-22

| ATOM | 665 | O   | LEU | A | 109 | 29.774 | 14.229 | 20.002 | 1.00 | 26.43 | O |
|------|-----|-----|-----|---|-----|--------|--------|--------|------|-------|---|
| ATOM | 666 | CB  | LEU | A | 109 | 30.316 | 16.182 | 22.280 | 1.00 | 24.30 | C |
| ATOM | 667 | CG  | LEU | A | 109 | 31.003 | 16.770 | 23.483 | 1.00 | 25.72 | C |
| ATOM | 668 | CD1 | LEU | A | 109 | 31.426 | 18.185 | 23.137 | 1.00 | 26.28 | C |
| ATOM | 669 | CD2 | LEU | A | 109 | 30.097 | 16.820 | 24.677 | 1.00 | 25.67 | C |
| ATOM | 670 | N   | PHE | A | 110 | 27.794 | 14.427 | 20.988 | 1.00 | 24.52 | N |
| ATOM | 671 | CA  | PHE | A | 110 | 27.019 | 14.004 | 19.822 | 1.00 | 22.36 | C |
| ATOM | 672 | C   | PHE | A | 110 | 25.996 | 15.079 | 19.586 | 1.00 | 21.47 | C |
| ATOM | 673 | O   | PHE | A | 110 | 25.618 | 15.777 | 20.525 | 1.00 | 21.05 | O |
| ATOM | 674 | CB  | PHE | A | 110 | 26.227 | 12.725 | 20.075 | 1.00 | 21.69 | C |
| ATOM | 675 | CG  | PHE | A | 110 | 27.133 | 11.561 | 20.318 | 1.00 | 23.01 | C |
| ATOM | 676 | CD1 | PHE | A | 110 | 27.676 | 10.892 | 19.238 | 1.00 | 24.43 | C |
| ATOM | 677 | CD2 | PHE | A | 110 | 27.506 | 11.243 | 21.597 | 1.00 | 21.68 | C |
| ATOM | 678 | CE1 | PHE | A | 110 | 28.614 |  9.897 | 19.463 | 1.00 | 24.92 | C |
| ATOM | 679 | CE2 | PHE | A | 110 | 28.460 | 10.282 | 21.798 | 1.00 | 22.08 | C |
| ATOM | 680 | CZ  | PHE | A | 110 | 29.017 |  9.597 | 20.746 | 1.00 | 23.51 | C |
| ATOM | 681 | N   | THR | A | 111 | 25.557 | 15.239 | 18.339 | 1.00 | 20.40 | N |
| ATOM | 682 | CA  | THR | A | 111 | 24.422 | 16.102 | 18.047 | 1.00 | 19.58 | C |
| ATOM | 683 | C   | THR | A | 111 | 23.175 | 15.367 | 18.473 | 1.00 | 15.81 | C |
| ATOM | 684 | O   | THR | A | 111 | 23.239 | 14.150 | 18.603 | 1.00 | 18.63 | O |
| ATOM | 685 | CB  | THR | A | 111 | 24.305 | 16.421 | 16.578 | 1.00 | 19.96 | C |
| ATOM | 686 | OG1 | THR | A | 111 | 24.145 | 15.178 | 15.907 | 1.00 | 21.91 | O |
| ATOM | 687 | CG2 | THR | A | 111 | 25.487 | 17.252 | 16.118 | 1.00 | 23.08 | C |
| ATOM | 688 | N   | PRO | A | 112 | 22.030 | 15.982 | 18.688 | 1.00 | 15.89 | N |
| ATOM | 689 | CA  | PRO | A | 112 | 20.783 | 15.254 | 18.984 | 1.00 | 16.41 | C |
| ATOM | 690 | C   | PRO | A | 112 | 20.500 | 14.089 | 18.025 | 1.00 | 17.10 | C |
| ATOM | 691 | O   | PRO | A | 112 | 20.329 | 12.954 | 18.431 | 1.00 | 18.32 | O |
| ATOM | 692 | CB  | PRO | A | 112 | 19.794 | 16.375 | 18.870 | 1.00 | 13.89 | C |
| ATOM | 693 | CG  | PRO | A | 112 | 20.581 | 17.559 | 19.386 | 1.00 | 14.36 | C |
| ATOM | 694 | CD  | PRO | A | 112 | 21.876 | 17.424 | 18.685 | 1.00 | 12.46 | C |
| ATOM | 695 | N   | GLU | A | 113 | 20.564 | 14.321 | 16.728 | 1.00 | 20.22 | N |
| ATOM | 696 | CA  | GLU | A | 113 | 20.393 | 13.303 | 15.737 | 1.00 | 24.11 | C |
| ATOM | 697 | C   | GLU | A | 113 | 21.371 | 12.143 | 15.864 | 1.00 | 24.55 | C |
| ATOM | 698 | O   | GLU | A | 113 | 20.963 | 10.982 | 15.866 | 1.00 | 25.38 | O |
| ATOM | 699 | CB  | GLU | A | 113 | 20.539 | 13.991 | 14.420 | 1.00 | 29.66 | C |
| ATOM | 700 | CG  | GLU | A | 113 | 20.432 | 13.029 | 13.250 | 1.00 | 41.26 | C |
| ATOM | 701 | CD  | GLU | A | 113 | 21.253 | 13.476 | 12.042 | 1.00 | 49.84 | C |
| ATOM | 702 | OE1 | GLU | A | 113 | 22.475 | 13.694 | 12.197 | 1.00 | 52.84 | O |
| ATOM | 703 | OE2 | GLU | A | 113 | 20.662 | 13.586 | 10.949 | 1.00 | 55.78 | O |
| ATOM | 704 | N   | GLU | A | 114 | 22.663 | 12.384 | 16.033 | 1.00 | 24.48 | N |
| ATOM | 705 | CA  | GLU | A | 114 | 23.594 | 11.291 | 16.198 | 1.00 | 22.26 | C |
| ATOM | 706 | C   | GLU | A | 114 | 23.398 | 10.486 | 17.471 | 1.00 | 22.80 | C |
| ATOM | 707 | O   | GLU | A | 114 | 23.564 |  9.256 | 17.494 | 1.00 | 23.87 | O |
| ATOM | 708 | CB  | GLU | A | 114 | 24.979 | 11.857 | 16.198 | 1.00 | 26.15 | C |
| ATOM | 709 | CG  | GLU | A | 114 | 25.362 | 12.534 | 14.897 | 1.00 | 32.62 | C |
| ATOM | 710 | CD  | GLU | A | 114 | 26.719 | 13.225 | 15.002 | 1.00 | 38.61 | C |
| ATOM | 711 | OE1 | GLU | A | 114 | 26.860 | 14.093 | 15.867 | 1.00 | 41.67 | O |
| ATOM | 712 | OE2 | GLU | A | 114 | 27.646 | 12.893 | 14.242 | 1.00 | 42.28 | O |
| ATOM | 713 | N   | PHE | A | 115 | 23.035 | 11.181 | 18.558 | 1.00 | 21.59 | N |
| ATOM | 714 | CA  | PHE | A | 115 | 22.812 | 10.544 | 19.850 | 1.00 | 19.30 | C |
| ATOM | 715 | C   | PHE | A | 115 | 21.601 |  9.645 | 19.667 | 1.00 | 17.06 | C |
| ATOM | 716 | O   | PHE | A | 115 | 21.555 |  8.527 | 20.165 | 1.00 | 17.46 | O |
| ATOM | 717 | CB  | PHE | A | 115 | 22.586 | 11.623 | 20.972 | 1.00 | 16.68 | C |
| ATOM | 718 | CG  | PHE | A | 115 | 22.148 | 11.018 | 22.298 | 1.00 | 13.67 | C |
| ATOM | 719 | CD1 | PHE | A | 115 | 20.820 | 10.679 | 22.520 | 1.00 | 15.42 | C |
| ATOM | 720 | CD2 | PHE | A | 115 | 23.081 | 10.752 | 23.261 | 1.00 | 15.56 | C |
| ATOM | 721 | CE1 | PHE | A | 115 | 20.412 | 10.003 | 23.650 | 1.00 | 16.48 | C |
| ATOM | 722 | CE2 | PHE | A | 115 | 22.674 | 10.136 | 24.429 | 1.00 | 17.36 | C |
| ATOM | 723 | CZ  | PHE | A | 115 | 21.351 |  9.750 | 24.617 | 1.00 | 18.29 | C |
| ATOM | 724 | N   | PHE | A | 116 | 20.581 | 10.135 | 18.981 | 1.00 | 18.67 | N |

FIGURE 8A-23

| | | | | | | | | | | | |
|---|---|---|---|---|---|---|---|---|---|---|---|
| ATOM | 725 | CA | PHE | A | 116 | 19.401 | 9.327 | 18.860 | 1.00 | 18.51 | C |
| ATOM | 726 | C | PHE | A | 116 | 19.510 | 8.196 | 17.854 | 1.00 | 22.03 | C |
| ATOM | 727 | O | PHE | A | 116 | 18.768 | 7.213 | 17.892 | 1.00 | 22.83 | O |
| ATOM | 728 | CB | PHE | A | 116 | 18.204 | 10.195 | 18.687 | 1.00 | 19.13 | C |
| ATOM | 729 | CG | PHE | A | 116 | 17.735 | 10.764 | 20.021 | 1.00 | 19.41 | C |
| ATOM | 730 | CD1 | PHE | A | 116 | 17.159 | 9.924 | 20.952 | 1.00 | 19.08 | C |
| ATOM | 731 | CD2 | PHE | A | 116 | 17.991 | 12.079 | 20.343 | 1.00 | 19.60 | C |
| ATOM | 732 | CE1 | PHE | A | 116 | 16.911 | 10.381 | 22.214 | 1.00 | 18.67 | C |
| ATOM | 733 | CE2 | PHE | A | 116 | 17.747 | 12.528 | 21.619 | 1.00 | 21.95 | C |
| ATOM | 734 | CZ | PHE | A | 116 | 17.218 | 11.674 | 22.550 | 1.00 | 19.99 | C |
| ATOM | 735 | N | ARG | A | 117 | 20.510 | 8.249 | 16.986 | 1.00 | 22.43 | N |
| ATOM | 736 | CA | ARG | A | 117 | 20.822 | 7.134 | 16.123 | 1.00 | 21.98 | C |
| ATOM | 737 | C | ARG | A | 117 | 21.453 | 6.076 | 16.971 | 1.00 | 19.70 | C |
| ATOM | 738 | O | ARG | A | 117 | 21.039 | 4.946 | 16.841 | 1.00 | 22.56 | O |
| ATOM | 739 | CB | ARG | A | 117 | 21.769 | 7.623 | 15.052 | 1.00 | 27.63 | C |
| ATOM | 740 | CG | ARG | A | 117 | 22.329 | 6.596 | 14.082 | 1.00 | 36.33 | C |
| ATOM | 741 | CD | ARG | A | 117 | 23.135 | 7.255 | 12.971 | 1.00 | 43.02 | C |
| ATOM | 742 | NE | ARG | A | 117 | 22.296 | 8.207 | 12.239 | 1.00 | 49.61 | N |
| ATOM | 743 | CZ | ARG | A | 117 | 22.704 | 9.468 | 12.008 | 1.00 | 54.02 | C |
| ATOM | 744 | NH1 | ARG | A | 117 | 23.915 | 9.867 | 12.474 | 1.00 | 53.58 | N |
| ATOM | 745 | NH2 | ARG | A | 117 | 21.899 | 10.314 | 11.313 | 1.00 | 53.56 | N |
| ATOM | 746 | N | ILE | A | 118 | 22.394 | 6.348 | 17.874 | 1.00 | 19.56 | N |
| ATOM | 747 | CA | ILE | A | 118 | 22.944 | 5.328 | 18.746 | 1.00 | 18.66 | C |
| ATOM | 748 | C | ILE | A | 118 | 21.888 | 4.776 | 19.673 | 1.00 | 19.62 | C |
| ATOM | 749 | O | ILE | A | 118 | 21.887 | 3.579 | 19.933 | 1.00 | 21.23 | O |
| ATOM | 750 | CB | ILE | A | 118 | 24.054 | 5.970 | 19.533 | 1.00 | 21.60 | C |
| ATOM | 751 | CG1 | ILE | A | 118 | 25.121 | 6.479 | 18.593 | 1.00 | 22.63 | C |
| ATOM | 752 | CG2 | ILE | A | 118 | 24.665 | 5.002 | 20.534 | 1.00 | 22.20 | C |
| ATOM | 753 | CD1 | ILE | A | 118 | 26.178 | 7.330 | 19.285 | 1.00 | 23.90 | C |
| ATOM | 754 | N | PHE | A | 119 | 20.971 | 5.619 | 20.180 | 1.00 | 20.06 | N |
| ATOM | 755 | CA | PHE | A | 119 | 19.827 | 5.124 | 20.943 | 1.00 | 21.07 | C |
| ATOM | 756 | C | PHE | A | 119 | 18.940 | 4.182 | 20.141 | 1.00 | 21.06 | C |
| ATOM | 757 | O | PHE | A | 119 | 18.720 | 3.075 | 20.600 | 1.00 | 22.31 | O |
| ATOM | 758 | CB | PHE | A | 119 | 19.001 | 6.253 | 21.590 | 1.00 | 18.55 | C |
| ATOM | 759 | CG | PHE | A | 119 | 17.726 | 5.856 | 22.342 | 1.00 | 18.55 | C |
| ATOM | 760 | CD1 | PHE | A | 119 | 16.517 | 5.708 | 21.673 | 1.00 | 17.37 | C |
| ATOM | 761 | CD2 | PHE | A | 119 | 17.736 | 5.715 | 23.718 | 1.00 | 21.09 | C |
| ATOM | 762 | CE1 | PHE | A | 119 | 15.348 | 5.439 | 22.351 | 1.00 | 16.37 | C |
| ATOM | 763 | CE2 | PHE | A | 119 | 16.555 | 5.448 | 24.404 | 1.00 | 19.97 | C |
| ATOM | 764 | CZ | PHE | A | 119 | 15.369 | 5.311 | 23.721 | 1.00 | 19.81 | C |
| ATOM | 765 | N | ASN | A | 120 | 18.426 | 4.507 | 18.957 | 1.00 | 22.51 | N |
| ATOM | 766 | CA | ASN | A | 120 | 17.567 | 3.577 | 18.222 | 1.00 | 23.92 | C |
| ATOM | 767 | C | ASN | A | 120 | 18.284 | 2.316 | 17.841 | 1.00 | 25.82 | C |
| ATOM | 768 | O | ASN | A | 120 | 17.653 | 1.274 | 17.841 | 1.00 | 26.73 | O |
| ATOM | 769 | CB | ASN | A | 120 | 16.912 | 4.179 | 16.996 | 1.00 | 20.96 | C |
| ATOM | 770 | CG | ASN | A | 120 | 15.857 | 5.195 | 17.377 | 1.00 | 24.90 | C |
| ATOM | 771 | OD1 | ASN | A | 120 | 14.852 | 4.877 | 18.020 | 1.00 | 30.44 | O |
| ATOM | 772 | ND2 | ASN | A | 120 | 16.044 | 6.458 | 17.023 | 1.00 | 26.09 | N |
| ATOM | 773 | N | ARG | A | 121 | 19.605 | 2.390 | 17.632 | 1.00 | 29.29 | N |
| ATOM | 774 | CA | ARG | A | 121 | 20.447 | 1.234 | 17.314 | 1.00 | 32.15 | C |
| ATOM | 775 | C | ARG | A | 121 | 20.686 | 0.283 | 18.503 | 1.00 | 32.13 | C |
| ATOM | 776 | O | ARG | A | 121 | 20.652 | -0.949 | 18.369 | 1.00 | 32.27 | O |
| ATOM | 777 | CB | ARG | A | 121 | 21.752 | 1.846 | 16.891 | 1.00 | 36.26 | C |
| ATOM | 778 | CG | ARG | A | 121 | 22.606 | 0.988 | 16.001 | 1.00 | 42.80 | C |
| ATOM | 779 | CD | ARG | A | 121 | 24.066 | 1.304 | 16.288 | 1.00 | 45.46 | C |
| ATOM | 780 | NE | ARG | A | 121 | 24.730 | 0.026 | 16.469 | 1.00 | 49.59 | N |
| ATOM | 781 | CZ | ARG | A | 121 | 25.603 | -0.473 | 15.599 | 1.00 | 47.62 | C |
| ATOM | 782 | NH1 | ARG | A | 121 | 26.106 | 0.291 | 14.622 | 1.00 | 50.56 | N |
| ATOM | 783 | NH2 | ARG | A | 121 | 25.907 | -1.764 | 15.692 | 1.00 | 41.39 | N |
| ATOM | 784 | N | SER | A | 122 | 20.925 | 0.856 | 19.695 | 1.00 | 29.65 | N |

FIGURE 8A-24

| | | | | | | | | | | |
|---|---|---|---|---|---|---|---|---|---|---|
| ATOM | 785 | CA | SER | A | 122 | 20.981 | 0.077 | 20.908 | 1.00 27.73 | C |
| ATOM | 786 | C | SER | A | 122 | 19.643 | -0.555 | 21.201 | 1.00 27.23 | C |
| ATOM | 787 | O | SER | A | 122 | 19.603 | -1.652 | 21.716 | 1.00 28.27 | O |
| ATOM | 788 | CB | SER | A | 122 | 21.388 | 0.942 | 22.071 | 1.00 25.31 | C |
| ATOM | 789 | OG | SER | A | 122 | 22.619 | 1.543 | 21.726 | 1.00 25.19 | O |
| ATOM | 790 | N | ILE | A | 123 | 18.530 | 0.087 | 20.884 | 1.00 29.27 | N |
| ATOM | 791 | CA | ILE | A | 123 | 17.210 | -0.453 | 21.140 | 1.00 31.25 | C |
| ATOM | 792 | C | ILE | A | 123 | 16.972 | -1.618 | 20.207 | 1.00 32.43 | C |
| ATOM | 793 | O | ILE | A | 123 | 16.522 | -2.672 | 20.637 | 1.00 32.75 | O |
| ATOM | 794 | CB | ILE | A | 123 | 16.129 | 0.661 | 20.973 | 1.00 33.20 | C |
| ATOM | 795 | CG1 | ILE | A | 123 | 16.103 | 1.685 | 22.130 | 1.00 35.29 | C |
| ATOM | 796 | CG2 | ILE | A | 123 | 14.739 | 0.181 | 20.629 | 1.00 33.87 | C |
| ATOM | 797 | CD1 | ILE | A | 123 | 16.243 | 1.313 | 23.627 | 1.00 32.91 | C |
| ATOM | 798 | N | ASP | A | 124 | 17.325 | -1.466 | 18.937 | 1.00 35.41 | N |
| ATOM | 799 | CA | ASP | A | 124 | 17.064 | -2.502 | 17.973 | 1.00 38.41 | C |
| ATOM | 800 | C | ASP | A | 124 | 17.902 | -3.728 | 18.170 | 1.00 38.55 | C |
| ATOM | 801 | O | ASP | A | 124 | 17.386 | -4.820 | 17.960 | 1.00 39.71 | O |
| ATOM | 802 | CB | ASP | A | 124 | 17.074 | -1.951 | 16.562 | 1.00 43.19 | C |
| ATOM | 803 | CG | ASP | A | 124 | 15.763 | -1.179 | 16.387 | 1.00 51.27 | C |
| ATOM | 804 | OD1 | ASP | A | 124 | 14.700 | -1.790 | 16.620 | 1.00 56.07 | O |
| ATOM | 805 | OD2 | ASP | A | 124 | 15.784 | 0.020 | 16.039 | 1.00 54.65 | O |
| ATOM | 806 | N | ALA | A | 125 | 19.102 | -3.546 | 18.739 | 1.00 37.63 | N |
| ATOM | 807 | CA | ALA | A | 125 | 20.039 | -4.621 | 18.983 | 1.00 37.10 | C |
| ATOM | 808 | C | ALA | A | 125 | 19.555 | -5.682 | 19.944 | 1.00 39.02 | C |
| ATOM | 809 | O | ALA | A | 125 | 20.250 | -6.667 | 20.151 | 1.00 40.94 | O |
| ATOM | 810 | CB | ALA | A | 125 | 21.321 | -4.035 | 19.500 | 1.00 35.16 | C |
| ATOM | 811 | N | PHE | A | 126 | 18.374 | -5.538 | 20.549 | 1.00 41.54 | N |
| ATOM | 812 | CA | PHE | A | 126 | 17.774 | -6.599 | 21.363 | 1.00 45.13 | C |
| ATOM | 813 | C | PHE | A | 126 | 16.837 | -7.482 | 20.578 | 1.00 47.39 | C |
| ATOM | 814 | O | PHE | A | 126 | 16.711 | -8.660 | 20.900 | 1.00 48.19 | O |
| ATOM | 815 | CB | PHE | A | 126 | 16.971 | -6.099 | 22.571 | 1.00 45.19 | C |
| ATOM | 816 | CG | PHE | A | 126 | 17.791 | -5.456 | 23.683 | 1.00 44.53 | C |
| ATOM | 817 | CD1 | PHE | A | 126 | 18.239 | -4.150 | 23.568 | 1.00 43.63 | C |
| ATOM | 818 | CD2 | PHE | A | 126 | 18.073 | -6.184 | 24.815 | 1.00 44.69 | C |
| ATOM | 819 | CE1 | PHE | A | 126 | 19.960 | -3.565 | 24.576 | 1.00 41.80 | C |
| ATOM | 820 | CE2 | PHE | A | 126 | 18.800 | -5.597 | 25.822 | 1.00 43.70 | C |
| ATOM | 821 | CZ | PHE | A | 126 | 19.238 | -4.295 | 25.700 | 1.00 43.96 | C |
| ATOM | 822 | N | LYS | A | 127 | 16.128 | -6.898 | 19.600 | 1.00 50.61 | N |
| ATOM | 823 | CA | LYS | A | 127 | 15.283 | -7.656 | 18.679 | 1.00 53.56 | C |
| ATOM | 824 | C | LYS | A | 127 | 16.149 | -8.640 | 17.856 | 1.00 55.43 | C |
| ATOM | 825 | O | LYS | A | 127 | 16.038 | -9.876 | 17.922 | 1.00 57.14 | O |
| ATOM | 826 | CB | LYS | A | 127 | 14.546 | -6.638 | 17.764 | 1.00 51.56 | C |
| ATOM | 827 | N | ASP | A | 128 | 17.077 | -8.036 | 17.105 | 1.00 57.96 | N |
| ATOM | 828 | CA | ASP | A | 128 | 18.105 | -8.734 | 16.356 | 1.00 59.25 | C |
| ATOM | 829 | C | ASP | A | 128 | 19.292 | -9.249 | 17.190 | 1.00 59.16 | C |
| ATOM | 830 | O | ASP | A | 128 | 20.461 | -8.894 | 17.008 | 1.00 58.89 | O |
| ATOM | 831 | CB | ASP | A | 128 | 18.492 | -7.915 | 15.062 | 1.00 61.00 | C |
| ATOM | 832 | CG | ASP | A | 128 | 18.868 | -6.421 | 15.036 | 1.00 61.70 | C |
| ATOM | 833 | OD1 | ASP | A | 128 | 20.024 | -6.078 | 15.330 | 1.00 63.63 | O |
| ATOM | 834 | OD2 | ASP | A | 128 | 18.015 | -5.603 | 14.667 | 1.00 61.66 | O |
| ATOM | 835 | N | PHE | A | 129 | 18.967 | -10.151 | 18.118 | 1.00 59.49 | N |
| ATOM | 836 | CA | PHE | A | 129 | 19.969 | -10.719 | 19.002 | 1.00 61.20 | C |
| ATOM | 837 | C | PHE | A | 129 | 20.411 | -12.103 | 18.503 | 1.00 61.55 | C |
| ATOM | 838 | O | PHE | A | 129 | 19.596 | -12.979 | 18.179 | 1.00 61.67 | O |
| ATOM | 839 | CB | PHE | A | 129 | 19.410 | -10.801 | 20.440 | 1.00 64.40 | C |
| ATOM | 840 | CG | PHE | A | 129 | 20.326 | -10.282 | 21.561 | 1.00 67.62 | C |
| ATOM | 841 | CD1 | PHE | A | 129 | 21.642 | -10.721 | 21.686 | 1.00 68.55 | C |
| ATOM | 842 | CD2 | PHE | A | 129 | 19.847 | -9.338 | 22.473 | 1.00 69.51 | C |
| ATOM | 843 | CE1 | PHE | A | 129 | 22.464 | -10.192 | 22.672 | 1.00 68.84 | C |
| ATOM | 844 | CE2 | PHE | A | 129 | 20.665 | -8.823 | 23.472 | 1.00 68.79 | C |

FIGURE 8A-25

```
ATOM    845  CZ   PHE A 129      21.976   -9.245  23.561  1.00 69.80           C
ATOM    846  N    VAL A 130      21.737  -12.294  18.417  1.00 60.68           N
ATOM    847  CA   VAL A 130      22.337  -13.577  18.041  1.00 60.72           C
ATOM    848  C    VAL A 130      23.459  -13.949  19.040  1.00 59.57           C
ATOM    849  O    VAL A 130      24.157  -13.076  19.597  1.00 58.08           O
ATOM    850  CB   VAL A 130      22.937  -13.560  16.582  1.00 60.98           C
ATOM    851  CG1  VAL A 130      23.051  -15.001  16.068  1.00 60.93           C
ATOM    852  CG2  VAL A 130      22.229  -12.635  15.579  1.00 58.32           C
ATOM    853  N    VAL A 131      23.635  -15.277  19.213  1.00 57.03           N
ATOM    854  CA   VAL A 131      24.634  -15.872  20.101  1.00 54.98           C
ATOM    855  C    VAL A 131      26.059  -15.336  19.950  1.00 53.17           C
ATOM    856  O    VAL A 131      26.547  -15.173  18.839  1.00 51.72           O
ATOM    857  CB   VAL A 131      24.563  -17.411  19.950  1.00 55.34           C
ATOM    858  CG1  VAL A 131      25.611  -18.162  20.780  1.00 55.30           C
ATOM    859  CG2  VAL A 131      23.145  -17.893  20.297  1.00 54.41           C
ATOM    860  N    ALA A 132      26.660  -15.027  21.117  1.00 52.91           N
ATOM    861  CA   ALA A 132      28.022  -14.512  21.293  1.00 52.69           C
ATOM    862  C    ALA A 132      29.161  -15.433  20.860  1.00 53.47           C
ATOM    863  O    ALA A 132      30.250  -15.019  20.445  1.00 52.96           O
ATOM    864  CB   ALA A 132      28.268  -14.176  22.771  1.00 48.84           C
ATOM    865  N    SER A 133      28.899  -16.725  21.000  1.00 55.81           N
ATOM    866  CA   SER A 133      29.812  -17.748  20.533  1.00 58.09           C
ATOM    867  C    SER A 133      29.744  -17.881  19.005  1.00 59.46           C
ATOM    868  O    SER A 133      30.726  -18.259  18.343  1.00 61.98           O
ATOM    869  CB   SER A 133      29.348  -19.047  21.161  1.00 59.31           C
ATOM    870  N    GLU A 134      28.556  -17.536  18.469  1.00 58.84           N
ATOM    871  CA   GLU A 134      28.251  -17.530  17.031  1.00 57.10           C
ATOM    872  C    GLU A 134      28.550  -16.218  16.298  1.00 54.08           C
ATOM    873  O    GLU A 134      28.319  -16.114  15.094  1.00 50.66           O
ATOM    874  CB   GLU A 134      26.768  -17.808  16.761  1.00 58.33           C
ATOM    875  CG   GLU A 134      26.269  -19.189  17.121  1.00 61.93           C
ATOM    876  CD   GLU A 134      24.955  -19.558  16.436  1.00 65.28           C
ATOM    877  OE1  GLU A 134      24.056  -18.711  16.294  1.00 64.83           O
ATOM    878  OE2  GLU A 134      24.853  -20.726  16.034  1.00 68.18           O
ATOM    879  N    THR A 135      28.999  -15.169  16.988  1.00 52.70           N
ATOM    880  CA   THR A 135      29.366  -13.953  16.291  1.00 51.61           C
ATOM    881  C    THR A 135      30.896  -13.856  16.192  1.00 51.35           C
ATOM    882  O    THR A 135      31.549  -14.721  15.580  1.00 52.93           O
ATOM    883  CB   THR A 135      28.621  -12.683  16.830  1.00 49.31           C
ATOM    884  OG1  THR A 135      29.039  -12.514  18.171  1.00 49.65           O
ATOM    885  CG2  THR A 135      27.108  -12.772  16.767  1.00 48.16           C
ATOM    886  N    SER A 136      31.473  -12.828  16.825  1.00 50.88           N
ATOM    887  CA   SER A 136      32.885  -12.502  16.714  1.00 49.48           C
ATOM    888  C    SER A 136      33.422  -12.163  18.121  1.00 47.44           C
ATOM    889  O    SER A 136      32.624  -12.000  19.056  1.00 46.14           O
ATOM    890  CB   SER A 136      32.966  -11.306  15.767  1.00 50.00           C
ATOM    891  OG   SER A 136      32.146  -11.504  14.615  1.00 52.41           O
ATOM    892  N    ASP A 137      34.760  -12.051  18.314  1.00 44.90           N
ATOM    893  CA   ASP A 137      35.366  -11.578  19.566  1.00 40.01           C
ATOM    894  C    ASP A 137      35.037  -10.093  19.850  1.00 36.45           C
ATOM    895  O    ASP A 137      34.105   -9.570  19.228  1.00 35.34           O
ATOM    896  CB   ASP A 137      36.879  -11.949  19.641  1.00 40.10           C
ATOM    897  CG   ASP A 137      37.915  -11.197  18.783  1.00 44.69           C
ATOM    898  OD1  ASP A 137      37.617  -10.121  18.252  1.00 46.41           O
ATOM    899  OD2  ASP A 137      39.056  -11.661  18.648  1.00 46.87           O
ATOM    900  N    CYS A 138      35.702   -9.337  20.741  1.00 32.95           N
ATOM    901  CA   CYS A 138      35.263   -7.982  21.014  1.00 31.28           C
ATOM    902  C    CYS A 138      36.311   -6.919  20.838  1.00 30.73           C
ATOM    903  O    CYS A 138      36.233   -5.825  21.414  1.00 31.32           O
ATOM    904  CB   CYS A 138      34.557   -7.854  22.361  1.00 32.08           C
```

FIGURE 8A-26

```
ATOM    905  SG   CYS A 138      32.988   -8.777  22.463  1.00 37.40           S
ATOM    906  N    VAL A 139      37.258   -7.242  19.954  1.00 30.63           N
ATOM    907  CA   VAL A 139      38.333   -6.318  19.599  1.00 29.74           C
ATOM    908  C    VAL A 139      38.151   -5.898  18.168  1.00 28.81           C
ATOM    909  O    VAL A 139      37.830   -6.734  17.342  1.00 27.95           O
ATOM    910  CB   VAL A 139      39.769   -6.915  19.600  1.00 28.99           C
ATOM    911  CG1  VAL A 139      40.717   -5.884  20.195  1.00 29.64           C
ATOM    912  CG2  VAL A 139      39.889   -8.307  20.143  1.00 26.32           C
ATOM    913  N    VAL A 140      38.424   -4.646  17.840  1.00 31.00           N
ATOM    914  CA   VAL A 140      38.442   -4.247  16.459  1.00 34.50           C
ATOM    915  C    VAL A 140      39.899   -4.167  16.020  1.00 36.64           C
ATOM    916  O    VAL A 140      40.406   -5.059  15.323  1.00 39.48           O
ATOM    917  CB   VAL A 140      37.758   -2.914  16.217  1.00 36.55           C
ATOM    918  CG1  VAL A 140      37.417   -2.900  14.747  1.00 36.42           C
ATOM    919  CG2  VAL A 140      36.594   -2.569  17.119  1.00 34.81           C
ATOM    920  N    SER A 141      40.566   -3.136  16.529  1.00 37.83           N
ATOM    921  CA   SER A 141      41.905   -2.682  16.123  1.00 41.81           C
ATOM    922  C    SER A 141      41.936   -1.563  15.056  1.00 42.37           C
ATOM    923  O    SER A 141      43.035   -1.174  14.685  1.00 43.60           O
ATOM    924  CB   SER A 141      42.986   -3.811  15.889  1.00 42.08           C
ATOM    925  OG   SER A 141      43.175   -4.693  17.008  1.00 38.01           O
TER     927       SER A 141
ATOM    928  N    ASN B  11       2.666   37.382  21.946  1.00 65.93           N
ATOM    929  CA   ASN B  11       1.945   36.256  22.556  1.00 66.50           C
ATOM    930  C    ASN B  11       2.726   35.510  23.658  1.00 66.17           C
ATOM    931  O    ASN B  11       3.559   34.641  23.372  1.00 66.24           O
ATOM    932  CB   ASN B  11       1.488   35.204  21.515  1.00 66.50           C
ATOM    933  N    VAL B  12       2.404   35.814  24.934  1.00 65.43           N
ATOM    934  CA   VAL B  12       3.197   35.450  26.131  1.00 62.92           C
ATOM    935  C    VAL B  12       3.195   33.985  26.631  1.00 60.27           C
ATOM    936  O    VAL B  12       4.143   33.547  27.294  1.00 59.00           O
ATOM    937  CB   VAL B  12       2.780   36.430  27.299  1.00 64.35           C
ATOM    938  CG1  VAL B  12       1.408   36.086  27.935  1.00 63.94           C
ATOM    939  CG2  VAL B  12       3.908   36.621  28.318  1.00 63.41           C
ATOM    940  N    LYS B  13       2.125   33.208  26.374  1.00 56.82           N
ATOM    941  CA   LYS B  13       2.071   31.821  26.800  1.00 51.85           C
ATOM    942  C    LYS B  13       3.021   31.001  25.927  1.00 48.88           C
ATOM    943  O    LYS B  13       3.595   30.003  26.380  1.00 49.33           O
ATOM    944  CB   LYS B  13       0.640   31.283  26.675  1.00 52.25           C
ATOM    945  N    ASP B  14       3.258   31.456  24.684  1.00 44.12           N
ATOM    946  CA   ASP B  14       4.169   30.783  23.770  1.00 37.71           C
ATOM    947  C    ASP B  14       5.662   30.978  24.040  1.00 31.42           C
ATOM    948  O    ASP B  14       6.413   30.025  23.895  1.00 30.29           O
ATOM    949  CB   ASP B  14       3.763   31.113  22.326  1.00 40.87           C
ATOM    950  CG   ASP B  14       2.497   30.409  21.803  1.00 44.08           C
ATOM    951  OD1  ASP B  14       1.832   29.636  22.531  1.00 44.87           O
ATOM    952  OD2  ASP B  14       2.192   30.662  20.631  1.00 45.27           O
ATOM    953  N    VAL B  15       6.165   32.130  24.468  1.00 25.72           N
ATOM    954  CA   VAL B  15       7.545   32.234  24.906  1.00 24.93           C
ATOM    955  C    VAL B  15       7.872   31.357  26.112  1.00 26.84           C
ATOM    956  O    VAL B  15       8.935   30.739  26.124  1.00 29.81           O
ATOM    957  CB   VAL B  15       7.914   33.670  25.178  1.00 22.45           C
ATOM    958  CG1  VAL B  15       9.335   33.803  25.722  1.00 18.01           C
ATOM    959  CG2  VAL B  15       7.730   34.435  23.895  1.00 21.89           C
ATOM    960  N    THR B  16       6.962   31.275  27.104  1.00 27.60           N
ATOM    961  CA   THR B  16       7.040   30.393  28.276  1.00 28.70           C
ATOM    962  C    THR B  16       7.191   28.905  27.903  1.00 27.24           C
ATOM    963  O    THR B  16       8.063   28.227  28.442  1.00 29.07           O
ATOM    964  CB   THR B  16       5.797   30.649  29.237  1.00 30.92           C
ATOM    965  OG1  THR B  16       5.967   31.920  29.887  1.00 30.85           O
```

FIGURE 8A-27

```
ATOM    966  CG2 THR B  16       5.605  29.577  30.304  1.00 29.47           C
ATOM    967  N   LYS B  17       6.385  28.387  26.979  1.00 24.02           N
ATOM    968  CA  LYS B  17       6.508  27.042  26.455  1.00 25.48           C
ATOM    969  C   LYS B  17       7.776  26.845  25.607  1.00 22.72           C
ATOM    970  O   LYS B  17       8.397  25.806  25.690  1.00 22.89           O
ATOM    971  CB  LYS B  17       5.235  26.851  25.662  1.00 29.47           C
ATOM    972  CG  LYS B  17       5.047  25.479  25.076  1.00 36.80           C
ATOM    973  CD  LYS B  17       3.820  25.460  24.129  1.00 40.47           C
ATOM    974  CE  LYS B  17       3.432  24.008  23.742  1.00 42.23           C
ATOM    975  NZ  LYS B  17       4.518  23.260  23.099  1.00 40.28           N
ATOM    976  N   LEU B  18       8.223  27.840  24.836  1.00 21.80           N
ATOM    977  CA  LEU B  18       9.489  27.797  24.148  1.00 19.84           C
ATOM    978  C   LEU B  18      10.608  27.757  25.151  1.00 19.53           C
ATOM    979  O   LEU B  18      11.425  26.868  24.985  1.00 22.71           O
ATOM    980  CB  LEU B  18       9.660  28.989  23.206  1.00 17.63           C
ATOM    981  CG  LEU B  18      10.954  29.148  22.479  1.00 13.25           C
ATOM    982  CD1 LEU B  18      11.216  27.956  21.627  1.00 16.15           C
ATOM    983  CD2 LEU B  18      10.895  30.338  21.606  1.00 13.19           C
ATOM    984  N   VAL B  19      10.670  28.606  26.187  1.00 17.49           N
ATOM    985  CA  VAL B  19      11.713  28.547  27.193  1.00 15.59           C
ATOM    986  C   VAL B  19      11.708  27.199  27.912  1.00 16.76           C
ATOM    987  O   VAL B  19      12.763  26.598  28.121  1.00 18.54           O
ATOM    988  CB  VAL B  19      11.587  29.741  28.170  1.00 15.79           C
ATOM    989  CG1 VAL B  19      12.566  29.662  29.308  1.00 13.19           C
ATOM    990  CG2 VAL B  19      11.922  31.014  27.489  1.00 12.62           C
ATOM    991  N   ALA B  20      10.533  26.655  28.232  1.00 17.26           N
ATOM    992  CA  ALA B  20      10.415  25.384  28.918  1.00 17.20           C
ATOM    993  C   ALA B  20      10.866  24.235  28.075  1.00 20.20           C
ATOM    994  O   ALA B  20      11.185  23.166  28.578  1.00 22.02           O
ATOM    995  CB  ALA B  20       8.972  25.064  29.185  1.00 18.25           C
ATOM    996  N   ASN B  21      10.854  24.390  26.763  1.00 22.32           N
ATOM    997  CA  ASN B  21      11.373  23.351  25.920  1.00 21.93           C
ATOM    998  C   ASN B  21      12.711  23.661  25.314  1.00 21.34           C
ATOM    999  O   ASN B  21      13.114  22.930  24.441  1.00 23.28           O
ATOM   1000  CB  ASN B  21      10.378  23.022  24.873  1.00 26.17           C
ATOM   1001  CG  ASN B  21       9.256  22.250  25.531  1.00 31.77           C
ATOM   1002  OD1 ASN B  21       9.352  21.054  25.813  1.00 30.41           O
ATOM   1003  ND2 ASN B  21       8.168  22.955  25.820  1.00 34.22           N
ATOM   1004  N   LEU B  22      13.455  24.675  25.727  1.00 20.84           N
ATOM   1005  CA  LEU B  22      14.825  24.880  25.285  1.00 18.95           C
ATOM   1006  C   LEU B  22      15.754  24.358  26.359  1.00 19.14           C
ATOM   1007  O   LEU B  22      15.428  24.560  27.526  1.00 19.71           O
ATOM   1008  CB  LEU B  22      15.097  26.380  25.022  1.00 17.41           C
ATOM   1009  CG  LEU B  22      14.510  27.035  23.750  1.00 15.79           C
ATOM   1010  CD1 LEU B  22      14.718  28.544  23.724  1.00 13.61           C
ATOM   1011  CD2 LEU B  22      15.120  26.381  22.517  1.00 14.80           C
ATOM   1012  N   PRO B  23      16.903  23.701  26.091  1.00 18.35           N
ATOM   1013  CA  PRO B  23      17.831  23.260  27.130  1.00 17.51           C
ATOM   1014  C   PRO B  23      18.329  24.418  28.008  1.00 17.87           C
ATOM   1015  O   PRO B  23      18.703  25.449  27.473  1.00 18.03           O
ATOM   1016  CB  PRO B  23      18.908  22.619  26.307  1.00 13.87           C
ATOM   1017  CG  PRO B  23      18.299  22.223  25.002  1.00 12.84           C
ATOM   1018  CD  PRO B  23      17.457  23.421  24.762  1.00 14.01           C
ATOM   1019  N   LYS B  24      18.327  24.340  29.347  1.00 18.87           N
ATOM   1020  CA  LYS B  24      18.756  25.441  30.226  1.00 21.96           C
ATOM   1021  C   LYS B  24      20.207  25.930  30.039  1.00 21.00           C
ATOM   1022  O   LYS B  24      20.567  27.081  30.304  1.00 21.61           O
ATOM   1023  CB  LYS B  24      18.456  25.044  31.703  1.00 23.68           C
ATOM   1024  CG  LYS B  24      16.956  25.097  32.077  1.00 29.69           C
ATOM   1025  CD  LYS B  24      16.544  24.407  33.429  1.00 34.88           C
```

*FIGURE 8A-28*

| | | | | | | | | | | |
|---|---|---|---|---|---|---|---|---|---|---|
| ATOM | 1026 | CE | LYS | B | 24 | 15.010 | 24.526 | 33.777 | 1.00 39.45 | C |
| ATOM | 1027 | NZ | LYS | B | 24 | 14.493 | 23.773 | 34.927 | 1.00 41.87 | N |
| ATOM | 1028 | N | ASP | B | 25 | 21.040 | 25.044 | 29.503 | 1.00 19.08 | N |
| ATOM | 1029 | CA | ASP | B | 25 | 22.440 | 25.350 | 29.263 | 1.00 20.79 | C |
| ATOM | 1030 | C | ASP | B | 25 | 22.758 | 25.601 | 27.789 | 1.00 19.77 | C |
| ATOM | 1031 | O | ASP | B | 25 | 23.907 | 25.469 | 27.373 | 1.00 20.06 | O |
| ATOM | 1032 | CB | ASP | B | 25 | 23.305 | 24.190 | 29.796 | 1.00 17.87 | C |
| ATOM | 1033 | CG | ASP | B | 25 | 23.063 | 22.836 | 29.175 | 1.00 20.81 | C |
| ATOM | 1034 | OD1 | ASP | B | 25 | 21.975 | 22.598 | 28.651 | 1.00 22.64 | O |
| ATOM | 1035 | OD2 | ASP | B | 25 | 23.964 | 21.991 | 29.214 | 1.00 24.79 | O |
| ATOM | 1036 | N | TYR | B | 26 | 21.753 | 25.866 | 26.950 | 1.00 19.06 | N |
| ATOM | 1037 | CA | TYR | B | 26 | 21.990 | 26.130 | 25.542 | 1.00 18.77 | C |
| ATOM | 1038 | C | TYR | B | 26 | 22.027 | 27.652 | 25.358 | 1.00 18.82 | C |
| ATOM | 1039 | O | TYR | B | 26 | 21.066 | 28.358 | 25.655 | 1.00 19.57 | O |
| ATOM | 1040 | CB | TYR | B | 26 | 20.900 | 25.477 | 24.712 | 1.00 16.23 | C |
| ATOM | 1041 | CG | TYR | B | 26 | 21.007 | 25.766 | 23.228 | 1.00 19.16 | C |
| ATOM | 1042 | CD1 | TYR | B | 26 | 22.034 | 25.216 | 22.492 | 1.00 20.33 | C |
| ATOM | 1043 | CD2 | TYR | B | 26 | 20.097 | 26.629 | 22.632 | 1.00 19.21 | C |
| ATOM | 1044 | CE1 | TYR | B | 26 | 22.125 | 25.531 | 21.150 | 1.00 19.71 | C |
| ATOM | 1045 | CE2 | TYR | B | 26 | 20.180 | 26.936 | 21.294 | 1.00 18.86 | C |
| ATOM | 1046 | CZ | TYR | B | 26 | 21.184 | 26.356 | 20.565 | 1.00 21.21 | C |
| ATOM | 1047 | OH | TYR | B | 26 | 21.209 | 26.560 | 19.204 | 1.00 23.57 | O |
| HETATM | 1048 | N | MSE | B | 27 | 23.136 | 28.207 | 24.891 | 1.00 18.02 | N |
| HETATM | 1049 | CA | MSE | B | 27 | 23.249 | 29.645 | 24.886 | 1.00 20.01 | C |
| HETATM | 1050 | C | MSE | B | 27 | 22.894 | 30.253 | 23.553 | 1.00 20.43 | C |
| HETATM | 1051 | O | MSE | B | 27 | 23.319 | 29.791 | 22.493 | 1.00 22.74 | O |
| HETATM | 1052 | CB | MSE | B | 27 | 24.648 | 30.070 | 25.309 | 1.00 21.80 | C |
| HETATM | 1053 | CG | MSE | B | 27 | 25.179 | 29.494 | 26.646 | 1.00 24.25 | C |
| HETATM | 1054 | SE | MSE | B | 27 | 24.219 | 29.995 | 28.260 | 1.00 30.76 | SE |
| HETATM | 1055 | CE | MSE | B | 27 | 24.936 | 31.691 | 28.317 | 1.00 17.91 | C |
| ATOM | 1056 | N | ILE | B | 28 | 22.071 | 31.294 | 23.642 | 1.00 21.17 | N |
| ATOM | 1057 | CA | ILE | B | 28 | 21.690 | 32.092 | 22.507 | 1.00 20.03 | C |
| ATOM | 1058 | C | ILE | B | 28 | 22.501 | 33.383 | 22.470 | 1.00 20.64 | C |
| ATOM | 1059 | O | ILE | B | 28 | 22.545 | 34.162 | 23.403 | 1.00 19.83 | O |
| ATOM | 1060 | CB | ILE | B | 28 | 20.168 | 32.289 | 22.522 | 1.00 19.56 | C |
| ATOM | 1061 | CG1 | ILE | B | 28 | 19.489 | 30.935 | 22.719 | 1.00 14.81 | C |
| ATOM | 1062 | CG2 | ILE | B | 28 | 19.653 | 32.893 | 21.195 | 1.00 17.30 | C |
| ATOM | 1063 | CD1 | ILE | B | 28 | 17.993 | 31.054 | 22.978 | 1.00 14.38 | C |
| ATOM | 1064 | N | THR | B | 29 | 23.235 | 33.585 | 21.364 | 1.00 22.56 | N |
| ATOM | 1065 | CA | THR | B | 29 | 24.048 | 34.777 | 21.117 | 1.00 21.92 | C |
| ATOM | 1066 | C | THR | B | 29 | 23.167 | 35.926 | 20.723 | 1.00 21.18 | C |
| ATOM | 1067 | O | THR | B | 29 | 22.235 | 35.744 | 19.926 | 1.00 24.05 | O |
| ATOM | 1068 | CB | THR | B | 29 | 25.003 | 34.540 | 19.949 | 1.00 24.32 | C |
| ATOM | 1069 | OG1 | THR | B | 29 | 25.751 | 33.393 | 20.310 | 1.00 26.19 | O |
| ATOM | 1070 | CG2 | THR | B | 29 | 25.901 | 35.743 | 19.657 | 1.00 23.45 | C |
| ATOM | 1071 | N | LEU | B | 30 | 23.485 | 37.110 | 21.229 | 1.00 19.18 | N |
| ATOM | 1072 | CA | LEU | B | 30 | 22.694 | 38.278 | 20.928 | 1.00 19.42 | C |
| ATOM | 1073 | C | LEU | B | 30 | 23.612 | 39.444 | 21.123 | 1.00 20.84 | C |
| ATOM | 1074 | O | LEU | B | 30 | 24.251 | 39.604 | 22.155 | 1.00 22.59 | O |
| ATOM | 1075 | CB | LEU | B | 30 | 21.486 | 38.458 | 21.822 | 1.00 16.57 | C |
| ATOM | 1076 | CG | LEU | B | 30 | 20.712 | 39.739 | 21.692 | 1.00 17.65 | C |
| ATOM | 1077 | CD1 | LEU | B | 30 | 19.907 | 39.690 | 20.405 | 1.00 15.54 | C |
| ATOM | 1078 | CD2 | LEU | B | 30 | 19.875 | 40.004 | 22.946 | 1.00 14.12 | C |
| ATOM | 1079 | N | LYS | B | 31 | 23.641 | 40.271 | 20.085 | 1.00 21.41 | N |
| ATOM | 1080 | CA | LYS | B | 31 | 24.340 | 41.533 | 20.142 | 1.00 22.33 | C |
| ATOM | 1081 | C | LYS | B | 31 | 23.462 | 42.478 | 20.918 | 1.00 21.90 | C |
| ATOM | 1082 | O | LYS | B | 31 | 22.714 | 43.295 | 20.370 | 1.00 24.57 | O |
| ATOM | 1083 | CB | LYS | B | 31 | 24.642 | 42.093 | 18.754 | 1.00 21.18 | C |
| ATOM | 1084 | CG | LYS | B | 31 | 25.844 | 41.479 | 18.111 | 1.00 21.89 | C |
| ATOM | 1085 | CD | LYS | B | 31 | 25.551 | 41.360 | 16.647 | 1.00 29.30 | C |

FIGURE 8A-29

```
ATOM     1086  CE   LYS B  31      26.741  40.957  15.808  1.00 31.29           C
ATOM     1087  NZ   LYS B  31      27.628  42.105  15.688  1.00 39.41           N
ATOM     1088  N    TYR B  32      23.572  42.299  22.227  1.00 21.32           N
ATOM     1089  CA   TYR B  32      22.800  43.101  23.138  1.00 19.60           C
ATOM     1090  C    TYR B  32      23.198  44.586  22.981  1.00 19.96           C
ATOM     1091  O    TYR B  32      24.384  44.940  22.977  1.00 20.37           O
ATOM     1092  CB   TYR B  32      23.094  42.513  24.532  1.00 17.35           C
ATOM     1093  CG   TYR B  32      22.621  43.373  25.710  1.00 17.26           C
ATOM     1094  CD1  TYR B  32      21.298  43.297  26.107  1.00 15.20           C
ATOM     1095  CD2  TYR B  32      23.490  44.280  26.299  1.00 14.00           C
ATOM     1096  CE1  TYR B  32      20.851  44.149  27.086  1.00 13.12           C
ATOM     1097  CE2  TYR B  32      23.013  45.166  27.227  1.00 14.39           C
ATOM     1098  CZ   TYR B  32      21.702  45.070  27.606  1.00 13.82           C
ATOM     1099  OH   TYR B  32      21.213  45.916  28.560  1.00 18.31           O
ATOM     1100  N    VAL B  33      22.179  45.455  22.873  1.00 19.13           N
ATOM     1101  CA   VAL B  33      22.376  46.889  22.818  1.00 19.34           C
ATOM     1102  C    VAL B  33      22.478  47.489  24.223  1.00 22.86           C
ATOM     1103  O    VAL B  33      21.487  47.535  24.979  1.00 23.26           O
ATOM     1104  CB   VAL B  33      21.220  47.609  22.071  1.00 18.33           C
ATOM     1105  CG1  VAL B  33      21.607  49.014  21.732  1.00 17.72           C
ATOM     1106  CG2  VAL B  33      20.868  46.933  20.772  1.00 18.88           C
ATOM     1107  N    PRO B  34      23.669  48.022  24.556  1.00 23.14           N
ATOM     1108  CA   PRO B  34      23.950  48.685  25.814  1.00 25.98           C
ATOM     1109  C    PRO B  34      22.991  49.844  26.052  1.00 27.87           C
ATOM     1110  O    PRO B  34      22.782  50.697  25.173  1.00 28.20           O
ATOM     1111  CB   PRO B  34      25.355  49.247  25.629  1.00 24.52           C
ATOM     1112  CG   PRO B  34      25.947  48.454  24.514  1.00 23.81           C
ATOM     1113  CD   PRO B  34      24.761  48.256  23.617  1.00 23.96           C
ATOM     1114  N    GLY B  35      22.428  49.854  27.265  1.00 27.60           N
ATOM     1115  CA   GLY B  35      21.544  50.919  27.694  1.00 26.85           C
ATOM     1116  C    GLY B  35      20.103  50.509  27.809  1.00 26.95           C
ATOM     1117  O    GLY B  35      19.314  51.234  28.392  1.00 27.06           O
HETATM   1118  N    MSE B  36      19.736  49.361  27.277  1.00 27.66           N
HETATM   1119  CA   MSE B  36      18.444  48.762  27.502  1.00 31.16           C
HETATM   1120  C    MSE B  36      17.873  48.948  28.920  1.00 33.96           C
HETATM   1121  O    MSE B  36      16.708  49.315  29.138  1.00 34.27           O
HETATM   1122  CB   MSE B  36      18.679  47.299  27.225  1.00 34.63           C
HETATM   1123  CG   MSE B  36      17.921  46.622  26.126  1.00 37.69           C
HETATM   1124  SE   MSE B  36      16.954  45.030  26.682  1.00 48.87          SE
HETATM   1125  CE   MSE B  36      16.692  45.161  28.560  1.00 40.22           C
ATOM     1126  N    ASP B  37      18.753  48.712  29.902  1.00 35.95           N
ATOM     1127  CA   ASP B  37      18.421  48.828  31.303  1.00 37.28           C
ATOM     1128  C    ASP B  37      18.228  50.272  31.758  1.00 38.57           C
ATOM     1129  O    ASP B  37      17.189  50.545  32.368  1.00 42.23           O
ATOM     1130  CB   ASP B  37      19.407  48.058  32.203  1.00 38.21           C
ATOM     1131  CG   ASP B  37      20.907  48.280  32.005  1.00 42.18           C
ATOM     1132  OD1  ASP B  37      21.288  49.092  31.150  1.00 44.69           O
ATOM     1133  OD2  ASP B  37      21.709  47.641  32.708  1.00 43.60           O
ATOM     1134  N    VAL B  38      19.111  51.237  31.458  1.00 36.46           N
ATOM     1135  CA   VAL B  38      18.974  52.585  32.008  1.00 34.42           C
ATOM     1136  C    VAL B  38      18.360  53.701  31.150  1.00 35.48           C
ATOM     1137  O    VAL B  38      17.844  54.706  31.662  1.00 35.46           O
ATOM     1138  CB   VAL B  38      20.314  53.047  32.623  1.00 33.96           C
ATOM     1139  CG1  VAL B  38      20.656  52.110  33.757  1.00 33.39           C
ATOM     1140  CG2  VAL B  38      21.452  53.127  31.638  1.00 30.40           C
ATOM     1141  N    LEU B  39      18.466  53.536  29.826  1.00 34.58           N
ATOM     1142  CA   LEU B  39      18.173  54.590  28.859  1.00 33.84           C
ATOM     1143  C    LEU B  39      16.770  54.521  28.304  1.00 34.39           C
ATOM     1144  O    LEU B  39      16.234  53.407  28.274  1.00 37.21           O
ATOM     1145  CB   LEU B  39      19.106  54.513  27.672  1.00 31.59           C
```

*FIGURE 8A-30*

| ATOM | 1146 | CG  | LEU | B | 39  | 20.516 | 54.934 | 27.836 | 1.00 | 30.49 | C |
|------|------|-----|-----|---|-----|--------|--------|--------|------|-------|---|
| ATOM | 1147 | CD1 | LEU | B | 39  | 21.233 | 54.571 | 26.544 | 1.00 | 30.11 | C |
| ATOM | 1148 | CD2 | LEU | B | 39  | 20.556 | 56.416 | 28.187 | 1.00 | 28.81 | C |
| ATOM | 1149 | N   | PRO | B | 40  | 16.124 | 55.613 | 27.821 | 1.00 | 33.22 | N |
| ATOM | 1150 | CA  | PRO | B | 40  | 14.743 | 55.564 | 27.336 | 1.00 | 32.18 | C |
| ATOM | 1151 | C   | PRO | B | 40  | 14.595 | 54.656 | 26.104 | 1.00 | 31.61 | C |
| ATOM | 1152 | O   | PRO | B | 40  | 15.515 | 54.575 | 25.295 | 1.00 | 32.07 | O |
| ATOM | 1153 | CB  | PRO | B | 40  | 14.498 | 57.028 | 27.054 | 1.00 | 31.41 | C |
| ATOM | 1154 | CG  | PRO | B | 40  | 15.395 | 57.749 | 28.027 | 1.00 | 32.72 | C |
| ATOM | 1155 | CD  | PRO | B | 40  | 16.655 | 56.977 | 27.813 | 1.00 | 33.34 | C |
| ATOM | 1156 | N   | SER | B | 41  | 13.487 | 53.949 | 25.885 | 1.00 | 31.04 | N |
| ATOM | 1157 | CA  | SER | B | 41  | 13.422 | 52.973 | 24.819 | 1.00 | 32.48 | C |
| ATOM | 1158 | C   | SER | B | 41  | 13.785 | 53.436 | 23.428 | 1.00 | 32.31 | C |
| ATOM | 1159 | O   | SER | B | 41  | 14.301 | 52.651 | 22.638 | 1.00 | 30.86 | O |
| ATOM | 1160 | CB  | SER | B | 41  | 12.119 | 52.197 | 24.820 | 1.00 | 34.06 | C |
| ATOM | 1161 | OG  | SER | B | 41  | 10.984 | 53.037 | 24.872 | 1.00 | 39.11 | O |
| ATOM | 1162 | N   | HIS | B | 42  | 13.622 | 54.747 | 23.191 | 1.00 | 34.63 | N |
| ATOM | 1163 | CA  | HIS | B | 42  | 13.911 | 55.363 | 21.888 | 1.00 | 36.02 | C |
| ATOM | 1164 | C   | HIS | B | 42  | 15.396 | 55.300 | 21.511 | 1.00 | 36.52 | C |
| ATOM | 1165 | O   | HIS | B | 42  | 15.780 | 55.228 | 20.327 | 1.00 | 34.40 | O |
| ATOM | 1166 | CB  | HIS | B | 42  | 13.316 | 56.805 | 21.755 | 1.00 | 34.27 | C |
| ATOM | 1167 | CG  | HIS | B | 42  | 13.946 | 57.935 | 22.576 | 1.00 | 34.59 | C |
| ATOM | 1168 | ND1 | HIS | B | 42  | 13.588 | 58.408 | 23.772 | 1.00 | 36.14 | N |
| ATOM | 1169 | CD2 | HIS | B | 42  | 15.013 | 58.687 | 22.154 | 1.00 | 32.00 | C |
| ATOM | 1170 | CE1 | HIS | B | 42  | 14.381 | 59.396 | 24.117 | 1.00 | 32.43 | C |
| ATOM | 1171 | NE2 | HIS | B | 42  | 15.227 | 59.539 | 23.124 | 1.00 | 35.02 | N |
| ATOM | 1172 | N   | CYS | B | 43  | 16.177 | 55.249 | 22.615 | 1.00 | 35.96 | N |
| ATOM | 1173 | CA  | CYS | B | 43  | 17.627 | 55.122 | 22.565 | 1.00 | 35.90 | C |
| ATOM | 1174 | C   | CYS | B | 43  | 18.176 | 53.799 | 22.054 | 1.00 | 32.86 | C |
| ATOM | 1175 | O   | CYS | B | 43  | 19.347 | 53.782 | 21.649 | 1.00 | 33.40 | O |
| ATOM | 1176 | CB  | CYS | B | 43  | 18.339 | 55.448 | 23.910 | 1.00 | 40.38 | C |
| ATOM | 1177 | SG  | CYS | B | 43  | 18.099 | 57.127 | 24.542 | 1.00 | 45.68 | S |
| ATOM | 1178 | N   | TRP | B | 44  | 17.380 | 52.707 | 22.075 | 1.00 | 29.25 | N |
| ATOM | 1179 | CA  | TRP | B | 44  | 17.913 | 51.374 | 21.831 | 1.00 | 25.51 | C |
| ATOM | 1180 | C   | TRP | B | 44  | 17.009 | 50.463 | 21.066 | 1.00 | 24.22 | C |
| ATOM | 1181 | O   | TRP | B | 44  | 17.544 | 49.594 | 20.406 | 1.00 | 26.02 | O |
| ATOM | 1182 | CB  | TRP | B | 44  | 18.375 | 50.661 | 23.113 | 1.00 | 21.99 | C |
| ATOM | 1183 | CG  | TRP | B | 44  | 17.351 | 50.644 | 24.234 | 1.00 | 20.34 | C |
| ATOM | 1184 | CD1 | TRP | B | 44  | 17.361 | 51.632 | 25.183 | 1.00 | 18.11 | C |
| ATOM | 1185 | CD2 | TRP | B | 44  | 16.297 | 49.745 | 24.363 | 1.00 | 19.23 | C |
| ATOM | 1186 | NE1 | TRP | B | 44  | 16.293 | 51.390 | 25.908 | 1.00 | 19.12 | N |
| ATOM | 1187 | CE2 | TRP | B | 44  | 15.635 | 50.281 | 25.471 | 1.00 | 18.20 | C |
| ATOM | 1188 | CE3 | TRP | B | 44  | 15.892 | 48.551 | 23.795 | 1.00 | 15.22 | C |
| ATOM | 1189 | CZ2 | TRP | B | 44  | 14.532 | 49.622 | 26.000 | 1.00 | 14.99 | C |
| ATOM | 1190 | CZ3 | TRP | B | 44  | 14.805 | 47.897 | 24.324 | 1.00 | 13.45 | C |
| ATOM | 1191 | CH2 | TRP | B | 44  | 14.130 | 48.434 | 25.405 | 1.00 | 15.50 | C |
| ATOM | 1192 | N   | ILE | B | 45  | 15.680 | 50.626 | 21.096 | 1.00 | 24.85 | N |
| ATOM | 1193 | CA  | ILE | B | 45  | 14.726 | 49.656 | 20.539 | 1.00 | 25.50 | C |
| ATOM | 1194 | C   | ILE | B | 45  | 14.926 | 49.254 | 19.094 | 1.00 | 26.34 | C |
| ATOM | 1195 | O   | ILE | B | 45  | 14.724 | 48.086 | 18.762 | 1.00 | 28.11 | O |
| ATOM | 1196 | CB  | ILE | B | 45  | 13.231 | 50.055 | 20.773 | 1.00 | 26.28 | C |
| ATOM | 1197 | CG1 | ILE | B | 45  | 12.358 | 48.838 | 20.592 | 1.00 | 24.31 | C |
| ATOM | 1198 | CG2 | ILE | B | 45  | 12.716 | 51.206 | 19.885 | 1.00 | 25.51 | C |
| ATOM | 1199 | CD1 | ILE | B | 45  | 12.688 | 47.633 | 21.486 | 1.00 | 19.41 | C |
| ATOM | 1200 | N   | SER | B | 46  | 15.336 | 50.233 | 18.274 | 1.00 | 28.06 | N |
| ATOM | 1201 | CA  | SER | B | 46  | 15.623 | 50.071 | 16.851 | 1.00 | 28.67 | C |
| ATOM | 1202 | C   | SER | B | 46  | 16.739 | 49.059 | 16.553 | 1.00 | 27.51 | C |
| ATOM | 1203 | O   | SER | B | 46  | 16.558 | 48.113 | 15.773 | 1.00 | 26.90 | O |
| ATOM | 1204 | CB  | SER | B | 46  | 15.933 | 51.472 | 16.250 | 1.00 | 28.71 | C |
| ATOM | 1205 | OG  | SER | B | 46  | 16.259 | 51.414 | 14.971 | 1.00 | 31.35 | O |

FIGURE 8A-31

```
ATOM    1206  N   GLU B  47      17.902  49.210  17.203  1.00  26.77           N
ATOM    1207  CA  GLU B  47      18.910  48.173  17.142  1.00  27.22           C
ATOM    1208  C   GLU B  47      18.555  46.912  17.906  1.00  23.80           C
ATOM    1209  O   GLU B  47      19.011  45.850  17.513  1.00  24.85           O
ATOM    1210  CB  GLU B  47      20.209  48.703  17.683  1.00  30.36           C
ATOM    1211  CG  GLU B  47      21.460  47.909  17.269  1.00  31.64           C
ATOM    1212  CD  GLU B  47      21.718  47.840  15.774  1.00  31.93           C
ATOM    1213  OE1 GLU B  47      21.267  48.726  15.034  1.00  32.82           O
ATOM    1214  OE2 GLU B  47      22.391  46.892  15.366  1.00  31.60           O
HETATM  1215  N   MSE B  48      17.739  46.958  18.958  1.00  23.65           N
HETATM  1216  CA  MSE B  48      17.401  45.755  19.709  1.00  21.94           C
HETATM  1217  C   MSE B  48      16.511  44.916  18.837  1.00  22.24           C
HETATM  1218  O   MSE B  48      16.819  43.732  18.731  1.00  24.91           O
HETATM  1219  CB  MSE B  48      16.783  46.061  21.080  1.00  22.86           C
HETATM  1220  CG  MSE B  48      16.875  44.981  22.173  1.00  24.51           C
HETATM  1221  SE  MSE B  48      18.597  44.203  22.615  1.00  30.61          SE
HETATM  1222  CE  MSE B  48      17.982  42.661  21.922  1.00  26.74           C
ATOM    1223  N   VAL B  49      15.506  45.445  18.110  1.00  21.88           N
ATOM    1224  CA  VAL B  49      14.661  44.597  17.276  1.00  20.25           C
ATOM    1225  C   VAL B  49      15.387  43.973  16.098  1.00  20.18           C
ATOM    1226  O   VAL B  49      15.120  42.815  15.790  1.00  22.62           O
ATOM    1227  CB  VAL B  49      13.351  45.252  16.813  1.00  23.22           C
ATOM    1228  CG1 VAL B  49      12.455  45.562  17.992  1.00  24.62           C
ATOM    1229  CG2 VAL B  49      13.551  46.527  16.025  1.00  23.30           C
ATOM    1230  N   VAL B  50      16.363  44.655  15.484  1.00  19.52           N
ATOM    1231  CA  VAL B  50      17.179  44.087  14.408  1.00  19.02           C
ATOM    1232  C   VAL B  50      18.005  42.916  14.897  1.00  19.73           C
ATOM    1233  O   VAL B  50      18.091  41.872  14.232  1.00  19.76           O
ATOM    1234  CB  VAL B  50      18.110  45.171  13.808  1.00  18.29           C
ATOM    1235  CG1 VAL B  50      19.181  44.607  12.925  1.00  16.52           C
ATOM    1236  CG2 VAL B  50      17.290  46.136  13.024  1.00  18.74           C
ATOM    1237  N   GLN B  51      18.617  43.151  16.064  1.00  17.95           N
ATOM    1238  CA  GLN B  51      19.447  42.130  16.677  1.00  18.39           C
ATOM    1239  C   GLN B  51      18.645  40.938  17.084  1.00  16.66           C
ATOM    1240  O   GLN B  51      19.056  39.827  16.830  1.00  18.39           O
ATOM    1241  CB  GLN B  51      20.264  42.655  17.851  1.00  18.87           C
ATOM    1242  CG  GLN B  51      21.265  43.713  17.440  1.00  18.55           C
ATOM    1243  CD  GLN B  51      22.253  43.283  16.370  1.00  23.83           C
ATOM    1244  OE1 GLN B  51      22.400  42.141  15.918  1.00  23.92           O
ATOM    1245  NE2 GLN B  51      23.019  44.265  15.958  1.00  27.04           N
ATOM    1246  N   LEU B  52      17.481  41.149  17.652  1.00  16.16           N
ATOM    1247  CA  LEU B  52      16.615  40.053  18.010  1.00  17.66           C
ATOM    1248  C   LEU B  52      16.106  39.302  16.810  1.00  18.23           C
ATOM    1249  O   LEU B  52      16.012  38.080  16.844  1.00  19.09           O
ATOM    1250  CB  LEU B  52      15.412  40.576  18.771  1.00  19.12           C
ATOM    1251  CG  LEU B  52      15.665  40.840  20.232  1.00  20.87           C
ATOM    1252  CD1 LEU B  52      14.609  41.767  20.734  1.00  20.47           C
ATOM    1253  CD2 LEU B  52      15.692  39.553  21.037  1.00  21.69           C
ATOM    1254  N   SER B  53      15.797  40.014  15.717  1.00  20.42           N
ATOM    1255  CA  SER B  53      15.410  39.376  14.469  1.00  18.47           C
ATOM    1256  C   SER B  53      16.491  38.428  13.973  1.00  18.27           C
ATOM    1257  O   SER B  53      16.259  37.257  13.692  1.00  17.53           O
ATOM    1258  CB  SER B  53      15.188  40.496  13.523  1.00  21.19           C
ATOM    1259  OG  SER B  53      14.858  39.866  12.317  1.00  22.45           O
ATOM    1260  N   ASP B  54      17.729  38.892  13.962  1.00  21.01           N
ATOM    1261  CA  ASP B  54      18.811  38.060  13.483  1.00  25.15           C
ATOM    1262  C   ASP B  54      19.040  36.841  14.339  1.00  24.43           C
ATOM    1263  O   ASP B  54      19.279  35.764  13.782  1.00  24.72           O
ATOM    1264  CB  ASP B  54      20.170  38.731  13.462  1.00  32.20           C
ATOM    1265  CG  ASP B  54      20.366  40.017  12.671  1.00  44.10           C
```

FIGURE 8A-32

| ATOM | 1266 | OD1 | ASP | B | 54 | 19.508 | 40.411 | 11.838 | 1.00 | 48.06 | O |
|---|---|---|---|---|---|---|---|---|---|---|---|
| ATOM | 1267 | OD2 | ASP | B | 54 | 21.429 | 40.630 | 12.924 | 1.00 | 50.40 | O |
| ATOM | 1268 | N | SER | B | 55 | 19.025 | 37.009 | 15.674 | 1.00 | 21.94 | N |
| ATOM | 1269 | CA | SER | B | 55 | 19.197 | 35.872 | 16.589 | 1.00 | 21.29 | C |
| ATOM | 1270 | C | SER | B | 55 | 18.036 | 34.884 | 16.516 | 1.00 | 19.86 | C |
| ATOM | 1271 | O | SER | B | 55 | 18.259 | 33.675 | 16.567 | 1.00 | 20.94 | O |
| ATOM | 1272 | CB | SER | B | 55 | 19.356 | 36.295 | 18.052 | 1.00 | 18.68 | C |
| ATOM | 1273 | OG | SER | B | 55 | 20.384 | 37.208 | 18.406 | 1.00 | 18.26 | O |
| ATOM | 1274 | N | LEU | B | 56 | 16.789 | 35.362 | 16.374 | 1.00 | 20.32 | N |
| ATOM | 1275 | CA | LEU | B | 56 | 15.647 | 34.453 | 16.343 | 1.00 | 20.44 | C |
| ATOM | 1276 | C | LEU | B | 56 | 15.628 | 33.735 | 15.025 | 1.00 | 21.16 | C |
| ATOM | 1277 | O | LEU | B | 56 | 15.299 | 32.552 | 14.968 | 1.00 | 20.64 | O |
| ATOM | 1278 | CB | LEU | B | 56 | 14.335 | 35.169 | 16.568 | 1.00 | 19.08 | C |
| ATOM | 1279 | CG | LEU | B | 56 | 13.967 | 35.545 | 17.993 | 1.00 | 19.76 | C |
| ATOM | 1280 | CD1 | LEU | B | 56 | 12.809 | 36.497 | 18.033 | 1.00 | 18.12 | C |
| ATOM | 1281 | CD2 | LEU | B | 56 | 13.621 | 34.308 | 18.773 | 1.00 | 17.63 | C |
| ATOM | 1282 | N | THR | B | 57 | 16.081 | 34.451 | 13.984 | 1.00 | 22.55 | N |
| ATOM | 1283 | CA | THR | B | 57 | 16.144 | 33.901 | 12.624 | 1.00 | 23.77 | C |
| ATOM | 1284 | C | THR | B | 57 | 17.169 | 32.775 | 12.599 | 1.00 | 25.31 | C |
| ATOM | 1285 | O | THR | B | 57 | 16.904 | 31.674 | 12.109 | 1.00 | 28.36 | O |
| ATOM | 1286 | CB | THR | B | 57 | 16.420 | 35.019 | 11.581 | 1.00 | 22.83 | C |
| ATOM | 1287 | OG1 | THR | B | 57 | 15.245 | 35.800 | 11.520 | 1.00 | 20.28 | O |
| ATOM | 1288 | CG2 | THR | B | 57 | 16.608 | 34.496 | 10.209 | 1.00 | 22.98 | C |
| ATOM | 1289 | N | ASP | B | 58 | 18.331 | 32.975 | 13.229 | 1.00 | 27.29 | N |
| ATOM | 1290 | CA | ASP | B | 58 | 19.328 | 31.934 | 13.394 | 1.00 | 25.16 | C |
| ATOM | 1291 | C | ASP | B | 58 | 18.874 | 30.781 | 14.238 | 1.00 | 22.74 | C |
| ATOM | 1292 | O | ASP | B | 58 | 19.128 | 29.640 | 13.909 | 1.00 | 20.50 | O |
| ATOM | 1293 | CB | ASP | B | 58 | 20.510 | 32.549 | 14.059 | 1.00 | 32.90 | C |
| ATOM | 1294 | CG | ASP | B | 58 | 21.367 | 33.343 | 13.098 | 1.00 | 40.22 | C |
| ATOM | 1295 | OD1 | ASP | B | 58 | 21.635 | 32.807 | 11.999 | 1.00 | 47.28 | O |
| ATOM | 1296 | OD2 | ASP | B | 58 | 21.780 | 34.468 | 13.458 | 1.00 | 42.79 | O |
| ATOM | 1297 | N | LEU | B | 59 | 18.174 | 31.090 | 15.328 | 1.00 | 22.88 | N |
| ATOM | 1298 | CA | LEU | B | 59 | 17.597 | 30.066 | 16.166 | 1.00 | 22.01 | C |
| ATOM | 1299 | C | LEU | B | 59 | 16.596 | 29.206 | 15.391 | 1.00 | 22.75 | C |
| ATOM | 1300 | O | LEU | B | 59 | 16.642 | 27.981 | 15.498 | 1.00 | 24.25 | O |
| ATOM | 1301 | CB | LEU | B | 59 | 16.984 | 30.711 | 17.389 | 1.00 | 21.26 | C |
| ATOM | 1302 | CG | LEU | B | 59 | 16.544 | 29.703 | 18.408 | 1.00 | 21.05 | C |
| ATOM | 1303 | CD1 | LEU | B | 59 | 17.733 | 28.955 | 19.020 | 1.00 | 20.13 | C |
| ATOM | 1304 | CD2 | LEU | B | 59 | 15.718 | 30.419 | 19.413 | 1.00 | 20.68 | C |
| ATOM | 1305 | N | LEU | B | 60 | 15.729 | 29.754 | 14.537 | 1.00 | 22.30 | N |
| ATOM | 1306 | CA | LEU | B | 60 | 14.838 | 28.912 | 13.776 | 1.00 | 21.18 | C |
| ATOM | 1307 | C | LEU | B | 60 | 15.559 | 27.884 | 12.897 | 1.00 | 24.69 | C |
| ATOM | 1308 | O | LEU | B | 60 | 15.084 | 26.761 | 12.702 | 1.00 | 27.59 | O |
| ATOM | 1309 | CB | LEU | B | 60 | 13.949 | 29.829 | 12.982 | 1.00 | 20.34 | C |
| ATOM | 1310 | CG | LEU | B | 60 | 12.805 | 29.256 | 12.208 | 1.00 | 15.11 | C |
| ATOM | 1311 | CD1 | LEU | B | 60 | 11.775 | 28.689 | 13.124 | 1.00 | 14.00 | C |
| ATOM | 1312 | CD2 | LEU | B | 60 | 12.216 | 30.351 | 11.405 | 1.00 | 15.62 | C |
| ATOM | 1313 | N | ASP | B | 61 | 16.768 | 28.142 | 12.405 | 1.00 | 28.19 | N |
| ATOM | 1314 | CA | ASP | B | 61 | 17.425 | 27.134 | 11.587 | 1.00 | 31.01 | C |
| ATOM | 1315 | C | ASP | B | 61 | 17.898 | 25.925 | 12.380 | 1.00 | 30.42 | C |
| ATOM | 1316 | O | ASP | B | 61 | 18.293 | 24.903 | 11.836 | 1.00 | 30.78 | O |
| ATOM | 1317 | CB | ASP | B | 61 | 18.486 | 27.766 | 10.638 | 1.00 | 40.38 | C |
| ATOM | 1318 | CG | ASP | B | 61 | 20.011 | 27.910 | 10.913 | 1.00 | 49.60 | C |
| ATOM | 1319 | OD1 | ASP | B | 61 | 20.632 | 27.086 | 11.630 | 1.00 | 52.10 | O |
| ATOM | 1320 | OD2 | ASP | B | 61 | 20.602 | 28.852 | 10.340 | 1.00 | 54.11 | O |
| ATOM | 1321 | N | LYS | B | 62 | 17.841 | 26.023 | 13.706 | 1.00 | 29.72 | N |
| ATOM | 1322 | CA | LYS | B | 62 | 18.282 | 24.972 | 14.586 | 1.00 | 26.53 | C |
| ATOM | 1323 | C | LYS | B | 62 | 17.227 | 23.920 | 14.754 | 1.00 | 26.40 | C |
| ATOM | 1324 | O | LYS | B | 62 | 17.553 | 22.835 | 15.224 | 1.00 | 28.09 | O |
| ATOM | 1325 | CB | LYS | B | 62 | 18.655 | 25.534 | 15.953 | 1.00 | 25.89 | C |

FIGURE 8A-33

```
ATOM   1326  CG   LYS B  62      19.865  26.451  15.996  1.00 24.99           C
ATOM   1327  CD   LYS B  62      21.053  25.810  15.308  1.00 26.66           C
ATOM   1328  CE   LYS B  62      22.198  26.806  15.251  1.00 28.58           C
ATOM   1329  NZ   LYS B  62      21.868  27.957  14.431  1.00 34.52           N
ATOM   1330  N    PHE B  63      15.986  24.225  14.389  1.00 26.48           N
ATOM   1331  CA   PHE B  63      14.862  23.316  14.568  1.00 29.27           C
ATOM   1332  C    PHE B  63      14.293  22.916  13.220  1.00 31.78           C
ATOM   1333  O    PHE B  63      14.573  23.581  12.227  1.00 34.39           O
ATOM   1334  CB   PHE B  63      13.744  23.920  15.427  1.00 24.13           C
ATOM   1335  CG   PHE B  63      14.261  24.236  16.809  1.00 23.83           C
ATOM   1336  CD1  PHE B  63      14.269  23.261  17.761  1.00 20.94           C
ATOM   1337  CD2  PHE B  63      14.811  25.488  17.066  1.00 25.00           C
ATOM   1338  CE1  PHE B  63      14.872  23.535  18.964  1.00 23.54           C
ATOM   1339  CE2  PHE B  63      15.444  25.741  18.263  1.00 22.33           C
ATOM   1340  CZ   PHE B  63      15.467  24.752  19.211  1.00 21.46           C
ATOM   1341  N    SER B  64      13.565  21.791  13.203  1.00 35.96           N
ATOM   1342  CA   SER B  64      12.847  21.251  12.047  1.00 41.24           C
ATOM   1343  C    SER B  64      11.362  21.237  12.401  1.00 44.87           C
ATOM   1344  O    SER B  64      11.045  21.210  13.593  1.00 45.47           O
ATOM   1345  CB   SER B  64      13.299  19.810  11.723  1.00 39.81           C
ATOM   1346  OG   SER B  64      14.690  19.659  11.441  1.00 41.15           O
ATOM   1347  N    ASN B  65      10.393  21.257  11.464  1.00 50.28           N
ATOM   1348  CA   ASN B  65       8.980  21.293  11.878  1.00 53.31           C
ATOM   1349  C    ASN B  65       8.304  19.970  12.291  1.00 53.88           C
ATOM   1350  O    ASN B  65       8.619  18.877  11.815  1.00 53.27           O
ATOM   1351  CB   ASN B  65       8.137  22.121  10.899  1.00 55.21           C
ATOM   1352  CG   ASN B  65       6.847  22.674  11.525  1.00 58.28           C
ATOM   1353  OD1  ASN B  65       5.829  22.845  10.846  1.00 62.80           O
ATOM   1354  ND2  ASN B  65       6.802  22.997  12.821  1.00 58.83           N
ATOM   1355  N    ILE B  66       7.402  20.111  13.274  1.00 55.78           N
ATOM   1356  CA   ILE B  66       6.604  19.028  13.857  1.00 58.20           C
ATOM   1357  C    ILE B  66       5.128  19.413  13.732  1.00 59.99           C
ATOM   1358  O    ILE B  66       4.679  20.439  14.266  1.00 59.98           O
ATOM   1359  CB   ILE B  66       6.916  18.864  15.373  1.00 58.00           C
ATOM   1360  CG1  ILE B  66       8.393  18.635  15.673  1.00 56.77           C
ATOM   1361  CG2  ILE B  66       6.119  17.713  15.950  1.00 58.43           C
ATOM   1362  CD1  ILE B  66       8.729  18.733  17.169  1.00 53.61           C
ATOM   1363  N    SER B  67       4.387  18.545  13.027  1.00 62.59           N
ATOM   1364  CA   SER B  67       2.945  18.687  12.803  1.00 65.18           C
ATOM   1365  C    SER B  67       2.049  18.114  13.935  1.00 66.39           C
ATOM   1366  O    SER B  67       1.110  17.339  13.725  1.00 68.18           O
ATOM   1367  CB   SER B  67       2.632  18.133  11.385  1.00 65.71           C
ATOM   1368  OG   SER B  67       3.288  16.912  10.995  1.00 67.79           O
ATOM   1369  N    GLU B  68       2.307  18.549  15.184  1.00 66.59           N
ATOM   1370  CA   GLU B  68       1.793  17.929  16.415  1.00 65.52           C
ATOM   1371  C    GLU B  68       0.895  18.865  17.238  1.00 66.78           C
ATOM   1372  O    GLU B  68      -0.333  18.715  17.307  1.00 67.15           O
ATOM   1373  CB   GLU B  68       2.977  17.471  17.301  1.00 66.40           C
ATOM   1374  CG   GLU B  68       2.568  17.163  18.743  1.00 67.84           C
ATOM   1375  CD   GLU B  68       3.745  16.736  19.622  1.00 69.12           C
ATOM   1376  OE1  GLU B  68       4.931  16.661  19.119  1.00 70.46           O
ATOM   1377  OE2  GLU B  68       3.552  16.451  20.865  1.00 71.34           O
ATOM   1378  N    GLY B  69       1.582  19.807  17.897  1.00 65.16           N
ATOM   1379  CA   GLY B  69       1.015  20.935  18.626  1.00 63.26           C
ATOM   1380  C    GLY B  69       2.019  22.049  18.382  1.00 60.63           C
ATOM   1381  O    GLY B  69       2.666  22.081  17.308  1.00 60.82           O
ATOM   1382  N    LEU B  70       2.179  22.963  19.355  1.00 57.50           N
ATOM   1383  CA   LEU B  70       3.254  23.950  19.225  1.00 53.07           C
ATOM   1384  C    LEU B  70       4.610  23.233  19.244  1.00 50.38           C
ATOM   1385  O    LEU B  70       4.879  22.324  20.040  1.00 53.95           O
```

FIGURE 8A-34

| | | | | | | | | | | |
|---|---|---|---|---|---|---|---|---|---|---|
| ATOM | 1386 | CB | LEU | B | 70 | 3.243 | 25.033 | 20.295 | 1.00 52.74 | C |
| ATOM | 1387 | CG | LEU | B | 70 | 2.243 | 26.184 | 20.332 | 1.00 54.01 | C |
| ATOM | 1388 | CD1 | LEU | B | 70 | 2.326 | 26.991 | 19.014 | 1.00 54.05 | C |
| ATOM | 1389 | CD2 | LEU | B | 70 | 0.834 | 25.683 | 20.698 | 1.00 55.75 | C |
| ATOM | 1390 | N | SER | B | 71 | 5.437 | 23.543 | 18.271 | 1.00 43.22 | N |
| ATOM | 1391 | CA | SER | B | 71 | 6.788 | 23.107 | 18.347 | 1.00 37.10 | C |
| ATOM | 1392 | C | SER | B | 71 | 7.676 | 24.348 | 18.452 | 1.00 35.41 | C |
| ATOM | 1393 | O | SER | B | 71 | 7.223 | 25.469 | 18.195 | 1.00 34.32 | O |
| ATOM | 1394 | CB | SER | B | 71 | 7.030 | 22.242 | 17.147 | 1.00 36.36 | C |
| ATOM | 1395 | OG | SER | B | 71 | 6.753 | 22.899 | 15.934 | 1.00 36.82 | O |
| ATOM | 1396 | N | ASN | B | 72 | 8.946 | 24.206 | 18.876 | 1.00 33.26 | N |
| ATOM | 1397 | CA | ASN | B | 72 | 9.888 | 25.327 | 18.974 | 1.00 28.70 | C |
| ATOM | 1398 | C | ASN | B | 72 | 10.013 | 26.017 | 17.631 | 1.00 25.92 | C |
| ATOM | 1399 | O | ASN | B | 72 | 10.086 | 27.234 | 17.591 | 1.00 25.46 | O |
| ATOM | 1400 | CB | ASN | B | 72 | 11.281 | 24.862 | 19.462 | 1.00 28.21 | C |
| ATOM | 1401 | CG | ASN | B | 72 | 11.365 | 24.292 | 20.880 | 1.00 26.47 | C |
| ATOM | 1402 | OD1 | ASN | B | 72 | 10.592 | 24.638 | 21.764 | 1.00 25.38 | O |
| ATOM | 1403 | ND2 | ASN | B | 72 | 12.284 | 23.373 | 21.160 | 1.00 26.66 | N |
| ATOM | 1404 | N | TYR | B | 73 | 9.968 | 25.221 | 16.547 | 1.00 26.29 | N |
| ATOM | 1405 | CA | TYR | B | 73 | 9.940 | 25.723 | 15.179 | 1.00 26.54 | C |
| ATOM | 1406 | C | TYR | B | 73 | 8.760 | 26.639 | 14.993 | 1.00 23.80 | C |
| ATOM | 1407 | O | TYR | B | 73 | 8.967 | 27.809 | 14.726 | 1.00 27.19 | O |
| ATOM | 1408 | CB | TYR | B | 73 | 9.881 | 24.631 | 14.075 | 1.00 28.15 | C |
| ATOM | 1409 | CG | TYR | B | 73 | 10.162 | 25.129 | 12.647 | 1.00 28.60 | C |
| ATOM | 1410 | CD1 | TYR | B | 73 | 9.210 | 25.828 | 11.901 | 1.00 29.58 | C |
| ATOM | 1411 | CD2 | TYR | B | 73 | 11.426 | 24.929 | 12.122 | 1.00 30.26 | C |
| ATOM | 1412 | CE1 | TYR | B | 73 | 9.566 | 26.391 | 10.690 | 1.00 29.50 | C |
| ATOM | 1413 | CE2 | TYR | B | 73 | 11.783 | 25.467 | 10.898 | 1.00 31.02 | C |
| ATOM | 1414 | CZ | TYR | B | 73 | 10.855 | 26.215 | 10.209 | 1.00 32.38 | C |
| ATOM | 1415 | OH | TYR | B | 73 | 11.245 | 26.802 | 9.014 | 1.00 36.91 | O |
| ATOM | 1416 | N | SER | B | 74 | 7.535 | 26.185 | 15.145 | 1.00 23.20 | N |
| ATOM | 1417 | CA | SER | B | 74 | 6.402 | 27.077 | 15.028 | 1.00 24.27 | C |
| ATOM | 1418 | C | SER | B | 74 | 6.449 | 28.270 | 15.935 | 1.00 23.26 | C |
| ATOM | 1419 | O | SER | B | 74 | 6.039 | 29.360 | 15.572 | 1.00 25.85 | O |
| ATOM | 1420 | CB | SER | B | 74 | 5.156 | 26.342 | 15.357 | 1.00 25.27 | C |
| ATOM | 1421 | OG | SER | B | 74 | 5.173 | 25.254 | 14.460 | 1.00 32.42 | O |
| ATOM | 1422 | N | ILE | B | 75 | 6.958 | 28.120 | 17.146 | 1.00 25.08 | N |
| ATOM | 1423 | CA | ILE | B | 75 | 6.913 | 29.248 | 18.057 | 1.00 23.59 | C |
| ATOM | 1424 | C | ILE | B | 75 | 7.908 | 30.294 | 17.620 | 1.00 21.89 | C |
| ATOM | 1425 | O | ILE | B | 75 | 7.509 | 31.437 | 17.519 | 1.00 21.19 | O |
| ATOM | 1426 | CB | ILE | B | 75 | 7.150 | 28.785 | 19.482 | 1.00 23.07 | C |
| ATOM | 1427 | CG1 | ILE | B | 75 | 5.984 | 27.956 | 19.962 | 1.00 23.49 | C |
| ATOM | 1428 | CG2 | ILE | B | 75 | 7.272 | 29.985 | 20.397 | 1.00 22.81 | C |
| ATOM | 1429 | CD1 | ILE | B | 75 | 6.254 | 27.309 | 21.343 | 1.00 21.59 | C |
| ATOM | 1430 | N | ILE | B | 76 | 9.149 | 29.881 | 17.347 | 1.00 21.79 | N |
| ATOM | 1431 | CA | ILE | B | 76 | 10.226 | 30.789 | 16.994 | 1.00 22.16 | C |
| ATOM | 1432 | C | ILE | B | 76 | 9.830 | 31.465 | 15.705 | 1.00 23.36 | C |
| ATOM | 1433 | O | ILE | B | 76 | 9.898 | 32.679 | 15.673 | 1.00 26.09 | O |
| ATOM | 1434 | CB | ILE | B | 76 | 11.611 | 30.123 | 16.831 | 1.00 21.17 | C |
| ATOM | 1435 | CG1 | ILE | B | 76 | 12.075 | 29.444 | 18.092 | 1.00 19.74 | C |
| ATOM | 1436 | CG2 | ILE | B | 76 | 12.661 | 31.169 | 16.489 | 1.00 18.62 | C |
| ATOM | 1437 | CD1 | ILE | B | 76 | 13.143 | 28.388 | 17.846 | 1.00 17.66 | C |
| ATOM | 1438 | N | ASP | B | 77 | 9.353 | 30.734 | 14.702 | 1.00 23.97 | N |
| ATOM | 1439 | CA | ASP | B | 77 | 8.866 | 31.293 | 13.456 | 1.00 25.97 | C |
| ATOM | 1440 | C | ASP | B | 77 | 7.856 | 32.411 | 13.657 | 1.00 26.70 | C |
| ATOM | 1441 | O | ASP | B | 77 | 8.065 | 33.525 | 13.187 | 1.00 28.84 | O |
| ATOM | 1442 | CB | ASP | B | 77 | 8.223 | 30.179 | 12.680 | 1.00 28.57 | C |
| ATOM | 1443 | CG | ASP | B | 77 | 8.018 | 30.507 | 11.212 | 1.00 32.25 | C |
| ATOM | 1444 | OD1 | ASP | B | 77 | 8.957 | 31.036 | 10.598 | 1.00 34.07 | C |
| ATOM | 1445 | OD2 | ASP | B | 77 | 6.927 | 30.224 | 10.704 | 1.00 32.50 | C |

FIGURE 8A-35

| | | | | | | | | | | |
|---|---|---|---|---|---|---|---|---|---|---|
| ATOM | 1446 | N | LYS | B | 78 | 6.797 | 32.211 | 14.443 | 1.00 28.77 | N |
| ATOM | 1447 | CA | LYS | B | 78 | 5.891 | 33.285 | 14.868 | 1.00 28.31 | C |
| ATOM | 1448 | C | LYS | B | 78 | 6.596 | 34.463 | 15.571 | 1.00 26.90 | C |
| ATOM | 1449 | O | LYS | B | 78 | 6.221 | 35.629 | 15.449 | 1.00 26.22 | O |
| ATOM | 1450 | CB | LYS | B | 78 | 4.861 | 32.589 | 15.762 | 1.00 32.30 | C |
| ATOM | 1451 | CG | LYS | B | 78 | 3.767 | 33.491 | 16.290 | 1.00 41.29 | C |
| ATOM | 1452 | CD | LYS | B | 78 | 2.746 | 32.676 | 17.100 | 1.00 49.72 | C |
| ATOM | 1453 | CE | LYS | B | 78 | 1.564 | 33.546 | 17.666 | 1.00 53.37 | C |
| ATOM | 1454 | NZ | LYS | B | 78 | 0.551 | 32.773 | 18.406 | 1.00 54.23 | N |
| ATOM | 1455 | N | LEU | B | 79 | 7.663 | 34.218 | 16.330 | 1.00 25.35 | N |
| ATOM | 1456 | CA | LEU | B | 79 | 8.352 | 35.299 | 17.007 | 1.00 23.52 | C |
| ATOM | 1457 | C | LEU | B | 79 | 9.151 | 36.141 | 16.063 | 1.00 22.42 | C |
| ATOM | 1458 | O | LEU | B | 79 | 9.249 | 37.348 | 16.219 | 1.00 20.72 | O |
| ATOM | 1459 | CB | LEU | B | 79 | 9.292 | 34.752 | 18.074 | 1.00 23.66 | C |
| ATOM | 1460 | CG | LEU | B | 79 | 8.739 | 33.917 | 19.241 | 1.00 21.39 | C |
| ATOM | 1461 | CD1 | LEU | B | 79 | 9.823 | 33.698 | 20.260 | 1.00 17.54 | C |
| ATOM | 1462 | CD2 | LEU | B | 79 | 7.579 | 34.608 | 19.911 | 1.00 21.67 | C |
| ATOM | 1463 | N | VAL | B | 80 | 9.727 | 35.426 | 15.094 | 1.00 25.43 | N |
| ATOM | 1464 | CA | VAL | B | 80 | 10.474 | 35.983 | 13.952 | 1.00 25.77 | C |
| ATOM | 1465 | C | VAL | B | 80 | 9.566 | 36.918 | 13.200 | 1.00 25.42 | C |
| ATOM | 1466 | O | VAL | B | 80 | 9.948 | 38.052 | 12.971 | 1.00 26.43 | O |
| ATOM | 1467 | CB | VAL | B | 80 | 10.989 | 34.920 | 12.949 | 1.00 24.61 | C |
| ATOM | 1468 | CG1 | VAL | B | 80 | 11.693 | 35.588 | 11.801 | 1.00 26.74 | C |
| ATOM | 1469 | CG2 | VAL | B | 80 | 12.018 | 33.999 | 13.521 | 1.00 24.19 | C |
| ATOM | 1470 | N | ASN | B | 81 | 8.352 | 36.466 | 12.893 | 1.00 27.82 | N |
| ATOM | 1471 | CA | ASN | B | 81 | 7.420 | 37.299 | 12.163 | 1.00 29.77 | C |
| ATOM | 1472 | C | ASN | B | 81 | 6.999 | 38.527 | 12.964 | 1.00 29.38 | C |
| ATOM | 1473 | O | ASN | B | 81 | 6.937 | 39.593 | 12.377 | 1.00 32.14 | O |
| ATOM | 1474 | CB | ASN | B | 81 | 6.221 | 36.505 | 11.562 | 1.00 31.24 | C |
| ATOM | 1475 | CG | ASN | B | 81 | 6.543 | 35.379 | 10.564 | 1.00 33.72 | C |
| ATOM | 1476 | OD1 | ASN | B | 81 | 7.608 | 35.271 | 9.962 | 1.00 34.16 | O |
| ATOM | 1477 | ND2 | ASN | B | 81 | 5.614 | 34.454 | 10.332 | 1.00 37.55 | N |
| ATOM | 1478 | N | ILE | B | 82 | 6.761 | 38.515 | 14.283 | 1.00 30.06 | N |
| ATOM | 1479 | CA | ILE | B | 82 | 6.418 | 39.713 | 15.057 | 1.00 27.77 | C |
| ATOM | 1480 | C | ILE | B | 82 | 7.591 | 40.672 | 15.019 | 1.00 28.50 | C |
| ATOM | 1481 | O | ILE | B | 82 | 7.388 | 41.866 | 14.826 | 1.00 30.63 | O |
| ATOM | 1482 | CB | ILE | B | 82 | 6.164 | 39.318 | 16.534 | 1.00 27.91 | C |
| ATOM | 1483 | CG1 | ILE | B | 82 | 4.880 | 38.557 | 16.625 | 1.00 29.24 | C |
| ATOM | 1484 | CG2 | ILE | B | 82 | 6.192 | 40.458 | 17.555 | 1.00 23.22 | C |
| ATOM | 1485 | CD1 | ILE | B | 82 | 4.796 | 37.771 | 17.958 | 1.00 33.77 | C |
| ATOM | 1486 | N | VAL | B | 83 | 8.833 | 40.218 | 15.222 | 1.00 28.54 | N |
| ATOM | 1487 | CA | VAL | B | 83 | 9.884 | 41.192 | 15.413 | 1.00 28.60 | C |
| ATOM | 1488 | C | VAL | B | 83 | 10.348 | 41.752 | 14.061 | 1.00 32.57 | C |
| ATOM | 1489 | O | VAL | B | 83 | 10.849 | 42.878 | 13.989 | 1.00 32.81 | O |
| ATOM | 1490 | CB | VAL | B | 83 | 10.975 | 40.632 | 16.338 | 1.00 26.41 | C |
| ATOM | 1491 | CG1 | VAL | B | 83 | 11.972 | 39.760 | 15.644 | 1.00 26.53 | C |
| ATOM | 1492 | CG2 | VAL | B | 83 | 11.609 | 41.742 | 17.144 | 1.00 25.82 | C |
| ATOM | 1493 | N | ASP | B | 84 | 10.153 | 40.975 | 12.980 | 1.00 33.06 | N |
| ATOM | 1494 | CA | ASP | B | 84 | 10.383 | 41.446 | 11.632 | 1.00 34.79 | C |
| ATOM | 1495 | C | ASP | B | 84 | 9.332 | 42.450 | 11.205 | 1.00 34.82 | C |
| ATOM | 1496 | O | ASP | B | 84 | 9.665 | 43.271 | 10.357 | 1.00 36.49 | O |
| ATOM | 1497 | CB | ASP | B | 84 | 10.391 | 40.329 | 10.601 | 1.00 37.40 | C |
| ATOM | 1498 | CG | ASP | B | 84 | 11.732 | 39.649 | 10.403 | 1.00 41.65 | C |
| ATOM | 1499 | OD1 | ASP | B | 84 | 12.767 | 40.242 | 10.726 | 1.00 45.61 | O |
| ATOM | 1500 | OD2 | ASP | B | 84 | 11.746 | 38.524 | 9.895 | 1.00 45.89 | O |
| ATOM | 1501 | N | ASP | B | 85 | 8.101 | 42.430 | 11.753 | 1.00 33.73 | N |
| ATOM | 1502 | CA | ASP | B | 85 | 7.134 | 43.501 | 11.551 | 1.00 32.67 | C |
| ATOM | 1503 | C | ASP | B | 85 | 7.527 | 44.753 | 12.304 | 1.00 31.61 | C |
| ATOM | 1504 | O | ASP | B | 85 | 7.290 | 45.876 | 11.852 | 1.00 30.78 | O |
| ATOM | 1505 | CB | ASP | B | 85 | 5.689 | 43.092 | 11.967 | 1.00 36.31 | C |

FIGURE 8A-36

```
ATOM   1506  CG   ASP B  85       4.984  42.012  11.146  1.00 36.50      C
ATOM   1507  OD1  ASP B  85       5.491  41.708  10.065  1.00 34.52      O
ATOM   1508  OD2  ASP B  85       3.945  41.485  11.574  1.00 37.36      O
ATOM   1509  N    LEU B  86       8.151  44.567  13.473  1.00 31.94      N
ATOM   1510  CA   LEU B  86       8.695  45.686  14.241  1.00 29.00      C
ATOM   1511  C    LEU B  86       9.945  46.335  13.646  1.00 27.01      C
ATOM   1512  O    LEU B  86      10.158  47.536  13.788  1.00 25.07      O
ATOM   1513  CB   LEU B  86       8.888  45.242  15.703  1.00 29.72      C
ATOM   1514  CG   LEU B  86       7.630  44.973  16.544  1.00 29.69      C
ATOM   1515  CD1  LEU B  86       7.934  44.246  17.825  1.00 29.68      C
ATOM   1516  CD2  LEU B  86       6.938  46.265  16.914  1.00 29.39      C
ATOM   1517  N    VAL B  87      10.774  45.550  12.962  1.00 26.28      N
ATOM   1518  CA   VAL B  87      11.895  46.068  12.214  1.00 29.27      C
ATOM   1519  C    VAL B  87      11.333  47.009  11.163  1.00 32.65      C
ATOM   1520  O    VAL B  87      11.721  48.175  11.164  1.00 35.43      O
ATOM   1521  CB   VAL B  87      12.725  44.966  11.523  1.00 28.93      C
ATOM   1522  CG1  VAL B  87      13.789  45.570  10.630  1.00 25.59      C
ATOM   1523  CG2  VAL B  87      13.417  44.036  12.521  1.00 30.50      C
ATOM   1524  N    GLU B  88      10.392  46.534  10.325  1.00 34.28      N
ATOM   1525  CA   GLU B  88       9.820  47.291   9.217  1.00 34.18      C
ATOM   1526  C    GLU B  88       9.201  48.582   9.702  1.00 34.90      C
ATOM   1527  O    GLU B  88       9.505  49.640   9.178  1.00 35.08      O
ATOM   1528  CB   GLU B  88       8.789  46.446   8.468  1.00 34.62      C
ATOM   1529  CG   GLU B  88       9.361  45.233   7.725  1.00 35.13      C
ATOM   1530  CD   GLU B  88       8.360  44.218   7.145  1.00 37.81      C
ATOM   1531  OE1  GLU B  88       7.241  44.088   7.653  1.00 39.42      O
ATOM   1532  OE2  GLU B  88       8.696  43.539   6.176  1.00 38.59      O
ATOM   1533  N    CYS B  89       8.402  48.520  10.754  1.00 37.74      N
ATOM   1534  CA   CYS B  89       7.803  49.680  11.378  1.00 41.43      C
ATOM   1535  C    CYS B  89       8.798  50.685  11.934  1.00 43.62      C
ATOM   1536  O    CYS B  89       8.578  51.896  11.896  1.00 44.63      O
ATOM   1537  CB   CYS B  89       6.875  49.166  12.472  1.00 43.51      C
ATOM   1538  SG   CYS B  89       6.538  50.326  13.821  1.00 52.54      S
ATOM   1539  N    VAL B  90       9.907  50.205  12.473  1.00 45.45      N
ATOM   1540  CA   VAL B  90      10.919  51.096  13.007  1.00 48.36      C
ATOM   1541  C    VAL B  90      11.787  51.723  11.909  1.00 49.57      C
ATOM   1542  O    VAL B  90      12.399  52.768  12.121  1.00 50.61      O
ATOM   1543  CB   VAL B  90      11.681  50.331  14.107  1.00 48.77      C
ATOM   1544  CG1  VAL B  90      12.903  51.039  14.582  1.00 51.24      C
ATOM   1545  CG2  VAL B  90      10.793  50.256  15.316  1.00 48.76      C
ATOM   1546  N    LYS B  91      11.834  51.181  10.695  1.00 50.84      N
ATOM   1547  CA   LYS B  91      12.492  51.870   9.600  1.00 52.46      C
ATOM   1548  C    LYS B  91      11.615  52.881   8.847  1.00 53.71      C
ATOM   1549  O    LYS B  91      12.139  53.730   8.127  1.00 52.07      O
ATOM   1550  CB   LYS B  91      13.135  50.840   8.721  1.00 54.00      C
ATOM   1551  CG   LYS B  91      14.290  50.209   9.508  1.00 59.12      C
ATOM   1552  CD   LYS B  91      14.955  49.089   8.690  1.00 63.16      C
ATOM   1553  CE   LYS B  91      16.176  48.420   9.367  1.00 66.55      C
ATOM   1554  NZ   LYS B  91      16.631  47.252   8.605  1.00 68.43      N
ATOM   1555  N    GLU B  92      10.283  52.859   9.066  1.00 56.63      N
ATOM   1556  CA   GLU B  92       9.333  53.861   8.565  1.00 59.16      C
ATOM   1557  C    GLU B  92       9.366  55.130   9.381  1.00 60.82      C
ATOM   1558  O    GLU B  92       9.635  56.189   8.802  1.00 61.59      O
ATOM   1559  CB   GLU B  92       7.852  53.434   8.599  1.00 60.60      C
ATOM   1560  CG   GLU B  92       7.388  52.228   7.784  1.00 63.20      C
ATOM   1561  CD   GLU B  92       7.621  52.275   6.273  1.00 66.00      C
ATOM   1562  OE1  GLU B  92       7.843  53.369   5.709  1.00 65.65      O
ATOM   1563  OE2  GLU B  92       7.564  51.187   5.667  1.00 67.41      O
ATOM   1564  N    ASN B  93       9.061  54.977  10.698  1.00 62.57      N
ATOM   1565  CA   ASN B  93       9.063  56.041  11.714  1.00 64.84      C
```

FIGURE 8A-37

```
ATOM   1566  C    ASN B  93      10.247  56.971  11.593  1.00 65.46           C
ATOM   1567  O    ASN B  93      11.368  56.721  12.018  1.00 65.03           O
ATOM   1568  CB   ASN B  93       9.069  55.511  13.153  1.00 63.55           C
ATOM   1569  N    SER B  94       9.868  58.041  10.904  1.00 68.52           N
ATOM   1570  CA   SER B  94      10.773  58.985  10.254  1.00 70.87           C
ATOM   1571  C    SER B  94      11.391  60.076  11.141  1.00 71.17           C
ATOM   1572  O    SER B  94      12.292  60.821  10.689  1.00 72.46           O
ATOM   1573  CB   SER B  94      10.028  59.573   9.039  1.00 71.38           C
ATOM   1574  OG   SER B  94       8.711  60.001   9.407  1.00 73.36           O
ATOM   1575  N    SER B  95      10.923  60.135  12.415  1.00 68.97           N
ATOM   1576  CA   SER B  95      11.564  60.953  13.424  1.00 68.06           C
ATOM   1577  C    SER B  95      13.040  60.572  13.473  1.00 67.28           C
ATOM   1578  O    SER B  95      13.457  59.458  13.839  1.00 64.89           O
ATOM   1579  CB   SER B  95      10.932  60.795  14.794  1.00 68.06           C
ATOM   1580  OG   SER B  95      11.441  61.800  15.670  1.00 59.36           O
ATOM   1581  N    LYS B  96      13.755  61.565  12.916  1.00 66.92           N
ATOM   1582  CA   LYS B  96      15.199  61.518  12.771  1.00 67.27           C
ATOM   1583  C    LYS B  96      15.848  60.974  14.056  1.00 66.10           C
ATOM   1584  O    LYS B  96      16.615  59.996  14.014  1.00 64.46           O
ATOM   1585  CB   LYS B  96      15.699  62.948  12.478  1.00 67.07           C
ATOM   1586  N    ASP B  97      15.289  61.560  15.147  1.00 64.54           N
ATOM   1587  CA   ASP B  97      15.657  61.369  16.562  1.00 62.82           C
ATOM   1588  C    ASP B  97      15.739  59.968  17.239  1.00 60.00           C
ATOM   1589  O    ASP B  97      16.792  59.674  17.852  1.00 59.90           O
ATOM   1590  CB   ASP B  97      14.689  62.230  17.394  1.00 63.85           C
ATOM   1591  N    LEU B  98      14.638  59.137  17.174  1.00 53.67           N
ATOM   1592  CA   LEU B  98      14.641  57.690  17.447  1.00 44.35           C
ATOM   1593  C    LEU B  98      15.837  57.135  16.728  1.00 40.32           C
ATOM   1594  O    LEU B  98      15.868  57.109  15.497  1.00 40.10           O
ATOM   1595  CB   LEU B  98      13.389  56.996  16.916  1.00 41.21           C
ATOM   1596  CG   LEU B  98      13.251  55.479  17.095  1.00 40.48           C
ATOM   1597  CD1  LEU B  98      11.904  55.030  17.695  1.00 39.61           C
ATOM   1598  CD2  LEU B  98      13.519  54.787  15.784  1.00 37.90           C
ATOM   1599  N    LYS B  99      16.815  56.840  17.593  1.00 36.84           N
ATOM   1600  CA   LYS B  99      18.171  56.457  17.229  1.00 35.08           C
ATOM   1601  C    LYS B  99      18.141  55.218  16.365  1.00 34.40           C
ATOM   1602  O    LYS B  99      17.600  54.164  16.712  1.00 34.91           O
ATOM   1603  CB   LYS B  99      19.028  56.193  18.485  1.00 35.16           C
ATOM   1604  CG   LYS B  99      20.550  56.058  18.286  1.00 37.24           C
ATOM   1605  CD   LYS B  99      21.314  55.641  19.556  1.00 36.33           C
ATOM   1606  CE   LYS B  99      22.817  55.994  19.594  1.00 38.98           C
ATOM   1607  NZ   LYS B  99      23.617  55.657  18.428  1.00 38.67           N
ATOM   1608  N    LYS B 100      18.689  55.387  15.174  1.00 34.28           N
ATOM   1609  CA   LYS B 100      18.726  54.285  14.232  1.00 34.35           C
ATOM   1610  C    LYS B 100      20.147  53.964  13.811  1.00 31.26           C
ATOM   1611  O    LYS B 100      20.368  52.917  13.224  1.00 32.09           O
ATOM   1612  CB   LYS B 100      17.832  54.592  13.044  1.00 36.01           C
ATOM   1613  CG   LYS B 100      16.335  54.635  13.349  1.00 38.72           C
ATOM   1614  CD   LYS B 100      15.782  55.851  12.617  1.00 43.22           C
ATOM   1615  CE   LYS B 100      14.290  55.723  12.370  1.00 43.50           C
ATOM   1616  NZ   LYS B 100      13.982  55.990  10.969  1.00 43.57           N
ATOM   1617  N    SER B 101      21.120  54.814  14.159  1.00 29.00           N
ATOM   1618  CA   SER B 101      22.529  54.614  13.871  1.00 28.55           C
ATOM   1619  C    SER B 101      23.351  54.047  15.032  1.00 28.24           C
ATOM   1620  O    SER B 101      23.732  54.783  15.943  1.00 31.98           O
ATOM   1621  CB   SER B 101      23.049  55.977  13.473  1.00 27.88           C
ATOM   1622  OG   SER B 101      24.459  55.979  13.457  1.00 27.09           O
ATOM   1623  N    PHE B 102      23.680  52.766  15.077  1.00 27.56           N
ATOM   1624  CA   PHE B 102      24.364  52.184  16.230  1.00 27.12           C
ATOM   1625  C    PHE B 102      25.620  51.495  15.755  1.00 28.99           C
```

FIGURE 8A-38

| ATOM | 1626 | O   | PHE | B | 102 | 25.613 | 51.001 | 14.627 | 1.00 | 28.31 | O |
|------|------|-----|-----|---|-----|--------|--------|--------|------|-------|---|
| ATOM | 1627 | CB  | PHE | B | 102 | 23.538 | 51.127 | 16.945 | 1.00 | 22.35 | C |
| ATOM | 1628 | CG  | PHE | B | 102 | 22.247 | 51.672 | 17.462 | 1.00 | 20.73 | C |
| ATOM | 1629 | CD1 | PHE | B | 102 | 21.206 | 51.877 | 16.608 | 1.00 | 22.70 | C |
| ATOM | 1630 | CD2 | PHE | B | 102 | 22.105 | 51.932 | 18.801 | 1.00 | 24.01 | C |
| ATOM | 1631 | CE1 | PHE | B | 102 | 20.007 | 52.325 | 17.098 | 1.00 | 23.86 | C |
| ATOM | 1632 | CE2 | PHE | B | 102 | 20.892 | 52.343 | 19.295 | 1.00 | 23.54 | C |
| ATOM | 1633 | CZ  | PHE | B | 102 | 19.837 | 52.536 | 18.435 | 1.00 | 23.17 | C |
| ATOM | 1634 | N   | LYS | B | 103 | 26.691 | 51.459 | 16.575 | 1.00 | 30.21 | N |
| ATOM | 1635 | CA  | LYS | B | 103 | 27.823 | 50.595 | 16.284 | 1.00 | 30.86 | C |
| ATOM | 1636 | C   | LYS | B | 103 | 27.374 | 49.171 | 16.550 | 1.00 | 32.14 | C |
| ATOM | 1637 | O   | LYS | B | 103 | 26.583 | 48.957 | 17.472 | 1.00 | 33.74 | O |
| ATOM | 1638 | CB  | LYS | B | 103 | 28.965 | 50.952 | 17.200 | 1.00 | 32.77 | C |
| ATOM | 1639 | N   | SER | B | 104 | 27.788 | 48.202 | 15.720 | 1.00 | 32.95 | N |
| ATOM | 1640 | CA  | SER | B | 104 | 27.284 | 46.825 | 15.805 | 1.00 | 33.85 | C |
| ATOM | 1641 | C   | SER | B | 104 | 27.695 | 46.249 | 17.145 | 1.00 | 31.14 | C |
| ATOM | 1642 | O   | SER | B | 104 | 28.891 | 46.121 | 17.418 | 1.00 | 32.16 | O |
| ATOM | 1643 | CB  | SER | B | 104 | 27.812 | 45.908 | 14.692 | 1.00 | 36.29 | C |
| ATOM | 1644 | OG  | SER | B | 104 | 28.690 | 46.589 | 13.784 | 1.00 | 44.97 | O |
| ATOM | 1645 | N   | PRO | B | 105 | 26.737 | 45.950 | 18.023 | 1.00 | 28.62 | N |
| ATOM | 1646 | CA  | PRO | B | 105 | 27.026 | 45.601 | 19.393 | 1.00 | 27.39 | C |
| ATOM | 1647 | C   | PRO | B | 105 | 27.816 | 44.315 | 19.472 | 1.00 | 26.85 | C |
| ATOM | 1648 | O   | PRO | B | 105 | 27.947 | 43.532 | 18.527 | 1.00 | 29.04 | O |
| ATOM | 1649 | CB  | PRO | B | 105 | 25.668 | 45.476 | 19.982 | 1.00 | 26.67 | C |
| ATOM | 1650 | CG  | PRO | B | 105 | 24.803 | 46.313 | 19.104 | 1.00 | 26.85 | C |
| ATOM | 1651 | CD  | PRO | B | 105 | 25.308 | 45.910 | 17.747 | 1.00 | 26.48 | C |
| ATOM | 1652 | N   | GLU | B | 106 | 28.426 | 44.160 | 20.628 | 1.00 | 27.12 | N |
| ATOM | 1653 | CA  | GLU | B | 106 | 29.240 | 42.982 | 20.897 | 1.00 | 27.97 | C |
| ATOM | 1654 | C   | GLU | B | 106 | 28.299 | 41.806 | 21.172 | 1.00 | 25.13 | C |
| ATOM | 1655 | O   | GLU | B | 106 | 27.294 | 41.966 | 21.870 | 1.00 | 21.99 | O |
| ATOM | 1656 | CB  | GLU | B | 106 | 30.140 | 43.258 | 22.105 | 1.00 | 30.05 | C |
| ATOM | 1657 | CG  | GLU | B | 106 | 31.418 | 42.451 | 22.220 | 1.00 | 35.47 | C |
| ATOM | 1658 | CD  | GLU | B | 106 | 32.045 | 42.483 | 23.613 | 1.00 | 40.01 | C |
| ATOM | 1659 | OE1 | GLU | B | 106 | 32.162 | 43.570 | 24.198 | 1.00 | 41.10 | O |
| ATOM | 1660 | OE2 | GLU | B | 106 | 32.431 | 41.409 | 24.102 | 1.00 | 42.35 | O |
| ATOM | 1661 | N   | PRO | B | 107 | 28.564 | 40.640 | 20.578 | 1.00 | 23.74 | N |
| ATOM | 1662 | CA  | PRO | B | 107 | 27.806 | 39.423 | 20.817 | 1.00 | 24.07 | C |
| ATOM | 1663 | C   | PRO | B | 107 | 27.906 | 38.967 | 22.264 | 1.00 | 22.95 | C |
| ATOM | 1664 | O   | PRO | B | 107 | 28.989 | 38.920 | 22.832 | 1.00 | 24.47 | O |
| ATOM | 1665 | CB  | PRO | B | 107 | 28.437 | 38.439 | 19.837 | 1.00 | 24.75 | C |
| ATOM | 1666 | CG  | PRO | B | 107 | 28.949 | 39.309 | 18.715 | 1.00 | 25.17 | C |
| ATOM | 1667 | CD  | PRO | B | 107 | 29.556 | 40.448 | 19.512 | 1.00 | 24.46 | C |
| ATOM | 1668 | N   | ARG | B | 108 | 26.765 | 38.677 | 22.884 | 1.00 | 22.39 | N |
| ATOM | 1669 | CA  | ARG | B | 108 | 26.684 | 38.164 | 24.239 | 1.00 | 20.57 | C |
| ATOM | 1670 | C   | ARG | B | 108 | 25.904 | 36.865 | 24.227 | 1.00 | 17.43 | C |
| ATOM | 1671 | O   | ARG | B | 108 | 24.954 | 36.685 | 23.488 | 1.00 | 17.22 | O |
| ATOM | 1672 | CB  | ARG | B | 108 | 26.064 | 39.155 | 25.256 | 1.00 | 20.10 | C |
| ATOM | 1673 | CG  | ARG | B | 108 | 27.007 | 40.157 | 25.848 | 1.00 | 21.68 | C |
| ATOM | 1674 | CD  | ARG | B | 108 | 26.321 | 41.144 | 26.778 | 1.00 | 25.69 | C |
| ATOM | 1675 | NE  | ARG | B | 108 | 25.859 | 40.576 | 28.047 | 1.00 | 27.65 | N |
| ATOM | 1676 | CZ  | ARG | B | 108 | 25.517 | 41.345 | 29.084 | 1.00 | 26.15 | C |
| ATOM | 1677 | NH1 | ARG | B | 108 | 25.637 | 42.653 | 29.004 | 1.00 | 26.98 | N |
| ATOM | 1678 | NH2 | ARG | B | 108 | 25.031 | 40.819 | 30.217 | 1.00 | 27.28 | N |
| ATOM | 1679 | N   | LEU | B | 109 | 26.320 | 35.964 | 25.078 | 1.00 | 16.44 | N |
| ATOM | 1680 | CA  | LEU | B | 109 | 25.649 | 34.700 | 25.242 | 1.00 | 19.58 | C |
| ATOM | 1681 | C   | LEU | B | 109 | 24.667 | 34.827 | 26.384 | 1.00 | 19.57 | C |
| ATOM | 1682 | O   | LEU | B | 109 | 24.963 | 35.423 | 27.418 | 1.00 | 21.90 | O |
| ATOM | 1683 | CB  | LEU | B | 109 | 26.626 | 33.555 | 25.533 | 1.00 | 18.89 | C |
| ATOM | 1684 | CG  | LEU | B | 109 | 27.661 | 33.129 | 24.491 | 1.00 | 20.14 | C |
| ATOM | 1685 | CD1 | LEU | B | 109 | 28.673 | 32.188 | 25.119 | 1.00 | 18.71 | C |

FIGURE 8A-39

| | | | | | | | | | |
|---|---|---|---|---|---|---|---|---|---|
| ATOM | 1686 | CD2 | LEU B | 109 | 26.985 | 32.436 | 23.316 | 1.00 22.74 | C |
| ATOM | 1687 | N | PHE B | 110 | 23.477 | 34.293 | 26.119 | 1.00 19.30 | N |
| ATOM | 1688 | CA | PHE B | 110 | 22.372 | 34.322 | 27.050 | 1.00 18.85 | C |
| ATOM | 1689 | C | PHE B | 110 | 21.748 | 32.939 | 27.188 | 1.00 19.38 | C |
| ATOM | 1690 | O | PHE B | 110 | 21.676 | 32.205 | 26.207 | 1.00 18.43 | O |
| ATOM | 1691 | CB | PHE B | 110 | 21.312 | 35.298 | 26.553 | 1.00 17.38 | C |
| ATOM | 1692 | CG | PHE B | 110 | 21.743 | 36.756 | 26.567 | 1.00 19.20 | C |
| ATOM | 1693 | CD1 | PHE B | 110 | 21.733 | 37.487 | 27.744 | 1.00 20.10 | C |
| ATOM | 1694 | CD2 | PHE B | 110 | 22.198 | 37.350 | 25.408 | 1.00 19.07 | C |
| ATOM | 1695 | CE1 | PHE B | 110 | 22.211 | 38.788 | 27.755 | 1.00 19.86 | C |
| ATOM | 1696 | CE2 | PHE B | 110 | 22.643 | 38.650 | 25.436 | 1.00 15.79 | C |
| ATOM | 1697 | CZ | PHE B | 110 | 22.659 | 39.367 | 26.596 | 1.00 17.86 | C |
| ATOM | 1698 | N | THR B | 111 | 21.246 | 32.547 | 28.376 | 1.00 18.40 | N |
| ATOM | 1699 | CA | THR B | 111 | 20.431 | 31.336 | 28.505 | 1.00 14.95 | C |
| ATOM | 1700 | C | THR B | 111 | 19.077 | 31.537 | 27.823 | 1.00 14.86 | C |
| ATOM | 1701 | O | THR B | 111 | 18.720 | 32.705 | 27.696 | 1.00 18.62 | O |
| ATOM | 1702 | CB | THR B | 111 | 20.254 | 30.986 | 30.016 | 1.00 10.83 | C |
| ATOM | 1703 | OG1 | THR B | 111 | 19.440 | 32.008 | 30.536 | 1.00 14.68 | O |
| ATOM | 1704 | CG2 | THR B | 111 | 21.520 | 31.006 | 30.845 | 1.00 11.33 | C |
| ATOM | 1705 | N | PRO B | 112 | 18.205 | 30.602 | 27.418 | 1.00 14.14 | N |
| ATOM | 1706 | CA | PRO B | 112 | 16.903 | 30.899 | 26.832 | 1.00 12.85 | C |
| ATOM | 1707 | C | PRO B | 112 | 16.055 | 31.789 | 27.714 | 1.00 15.00 | C |
| ATOM | 1708 | O | PRO B | 112 | 15.351 | 32.679 | 27.268 | 1.00 16.67 | O |
| ATOM | 1709 | CB | PRO B | 112 | 16.297 | 29.536 | 26.730 | 1.00 13.18 | C |
| ATOM | 1710 | CG | PRO B | 112 | 17.459 | 28.689 | 26.406 | 1.00 11.71 | C |
| ATOM | 1711 | CD | PRO B | 112 | 18.482 | 29.179 | 27.402 | 1.00 12.63 | C |
| ATOM | 1712 | N | GLU B | 113 | 16.103 | 31.597 | 29.015 | 1.00 17.42 | N |
| ATOM | 1713 | CA | GLU B | 113 | 15.375 | 32.431 | 29.945 | 1.00 19.68 | C |
| ATOM | 1714 | C | GLU B | 113 | 15.802 | 33.888 | 29.901 | 1.00 18.59 | C |
| ATOM | 1715 | O | GLU B | 113 | 14.931 | 34.751 | 29.885 | 1.00 21.48 | O |
| ATOM | 1716 | CB | GLU B | 113 | 15.546 | 31.841 | 31.328 | 1.00 22.92 | C |
| ATOM | 1717 | CG | GLU B | 113 | 14.984 | 32.707 | 32.439 | 1.00 32.95 | C |
| ATOM | 1718 | CD | GLU B | 113 | 15.763 | 32.704 | 33.770 | 1.00 39.93 | C |
| ATOM | 1719 | OE1 | GLU B | 113 | 16.869 | 33.281 | 33.900 | 1.00 41.39 | O |
| ATOM | 1720 | OE2 | GLU B | 113 | 15.193 | 32.144 | 34.712 | 1.00 44.90 | O |
| ATOM | 1721 | N | GLU B | 114 | 17.096 | 34.210 | 29.885 | 1.00 18.49 | N |
| ATOM | 1722 | CA | GLU B | 114 | 17.601 | 35.576 | 29.760 | 1.00 17.43 | C |
| ATOM | 1723 | C | GLU B | 114 | 17.321 | 36.289 | 28.451 | 1.00 16.60 | C |
| ATOM | 1724 | O | GLU B | 114 | 16.910 | 37.449 | 28.404 | 1.00 19.48 | O |
| ATOM | 1725 | CB | GLU B | 114 | 19.090 | 35.543 | 29.980 | 1.00 19.55 | C |
| ATOM | 1726 | CG | GLU B | 114 | 19.486 | 35.319 | 31.442 | 1.00 23.40 | C |
| ATOM | 1727 | CD | GLU B | 114 | 20.962 | 35.034 | 31.718 | 1.00 25.98 | C |
| ATOM | 1728 | OE1 | GLU B | 114 | 21.730 | 34.826 | 30.765 | 1.00 25.41 | O |
| ATOM | 1729 | OE2 | GLU B | 114 | 21.322 | 34.982 | 32.906 | 1.00 28.77 | O |
| ATOM | 1730 | N | PHE B | 115 | 17.507 | 35.551 | 27.379 | 1.00 14.86 | N |
| ATOM | 1731 | CA | PHE B | 115 | 17.212 | 35.998 | 26.023 | 1.00 15.76 | C |
| ATOM | 1732 | C | PHE B | 115 | 15.776 | 36.422 | 25.843 | 1.00 14.74 | C |
| ATOM | 1733 | O | PHE B | 115 | 15.474 | 37.469 | 25.295 | 1.00 16.04 | O |
| ATOM | 1734 | CB | PHE B | 115 | 17.513 | 34.865 | 25.012 | 1.00 14.37 | C |
| ATOM | 1735 | CG | PHE B | 115 | 17.384 | 35.323 | 23.572 | 1.00 16.76 | C |
| ATOM | 1736 | CD1 | PHE B | 115 | 18.400 | 36.062 | 22.990 | 1.00 15.08 | C |
| ATOM | 1737 | CD2 | PHE B | 115 | 16.217 | 35.063 | 22.881 | 1.00 16.51 | C |
| ATOM | 1738 | CE1 | PHE B | 115 | 18.169 | 36.611 | 21.755 | 1.00 15.92 | C |
| ATOM | 1739 | CE2 | PHE B | 115 | 16.024 | 35.579 | 21.619 | 1.00 13.36 | C |
| ATOM | 1740 | CZ | PHE B | 115 | 16.994 | 36.364 | 21.079 | 1.00 14.28 | C |
| ATOM | 1741 | N | PHE B | 116 | 14.897 | 35.549 | 26.284 | 1.00 15.61 | N |
| ATOM | 1742 | CA | PHE B | 116 | 13.497 | 35.810 | 26.150 | 1.00 15.94 | C |
| ATOM | 1743 | C | PHE B | 116 | 12.918 | 36.798 | 27.125 | 1.00 16.92 | C |
| ATOM | 1744 | O | PHE B | 116 | 11.842 | 37.326 | 26.862 | 1.00 18.97 | O |
| ATOM | 1745 | CB | PHE B | 116 | 12.759 | 34.499 | 26.111 | 1.00 16.90 | C |

*FIGURE 8A-40*

```
ATOM   1746  CG   PHE B 116      12.962  33.796  24.776  1.00 16.87           C
ATOM   1747  CD1  PHE B 116      12.315  34.278  23.639  1.00 16.00           C
ATOM   1748  CD2  PHE B 116      13.830  32.714  24.689  1.00 17.13           C
ATOM   1749  CE1  PHE B 116      12.558  33.654  22.429  1.00 17.64           C
ATOM   1750  CE2  PHE B 116      14.079  32.114  23.482  1.00 16.31           C
ATOM   1751  CZ   PHE B 116      13.427  32.582  22.349  1.00 17.77           C
ATOM   1752  N    ARG B 117      13.629  37.094  28.208  1.00 17.01           N
ATOM   1753  CA   ARG B 117      13.292  38.189  29.085  1.00 18.94           C
ATOM   1754  C    ARG B 117      13.636  39.492  28.388  1.00 20.76           C
ATOM   1755  O    ARG B 117      12.988  40.526  28.561  1.00 21.80           O
ATOM   1756  CB   ARG B 117      14.124  38.043  30.361  1.00 22.28           C
ATOM   1757  CG   ARG B 117      13.889  39.003  31.538  1.00 29.21           C
ATOM   1758  CD   ARG B 117      13.292  38.359  32.834  1.00 35.23           C
ATOM   1759  NE   ARG B 117      14.094  37.253  33.357  1.00 37.19           N
ATOM   1760  CZ   ARG B 117      15.408  37.373  33.616  1.00 42.10           C
ATOM   1761  NH1  ARG B 117      16.023  38.568  33.647  1.00 45.58           N
ATOM   1762  NH2  ARG B 117      16.151  36.268  33.794  1.00 43.18           N
ATOM   1763  N    ILE B 118      14.709  39.453  27.596  1.00 20.97           N
ATOM   1764  CA   ILE B 118      15.078  40.588  26.807  1.00 18.77           C
ATOM   1765  C    ILE B 118      14.103  40.799  25.662  1.00 20.54           C
ATOM   1766  O    ILE B 118      13.592  41.896  25.487  1.00 20.49           O
ATOM   1767  CB   ILE B 118      16.498  40.364  26.385  1.00 16.96           C
ATOM   1768  CG1  ILE B 118      17.377  40.504  27.587  1.00 12.82           C
ATOM   1769  CG2  ILE B 118      16.892  41.347  25.310  1.00 15.77           C
ATOM   1770  CD1  ILE B 118      18.851  40.271  27.253  1.00 14.00           C
ATOM   1771  N    PHE B 119      13.817  39.736  24.922  1.00 22.16           N
ATOM   1772  CA   PHE B 119      12.840  39.717  23.864  1.00 23.96           C
ATOM   1773  C    PHE B 119      11.528  40.271  24.356  1.00 26.51           C
ATOM   1774  O    PHE B 119      10.934  41.093  23.674  1.00 29.24           O
ATOM   1775  CB   PHE B 119      12.660  38.299  23.364  1.00 22.84           C
ATOM   1776  CG   PHE B 119      11.555  38.133  22.327  1.00 24.88           C
ATOM   1777  CD1  PHE B 119      11.811  38.512  21.006  1.00 25.69           C
ATOM   1778  CD2  PHE B 119      10.271  37.803  22.727  1.00 24.94           C
ATOM   1779  CE1  PHE B 119      10.748  38.539  20.122  1.00 25.07           C
ATOM   1780  CE2  PHE B 119       9.216  37.831  21.844  1.00 24.69           C
ATOM   1781  CZ   PHE B 119       9.465  38.212  20.539  1.00 25.22           C
ATOM   1782  N    ASN B 120      11.076  39.898  25.540  1.00 29.22           N
ATOM   1783  CA   ASN B 120       9.863  40.470  26.094  1.00 31.04           C
ATOM   1784  C    ASN B 120       9.953  41.939  26.499  1.00 32.79           C
ATOM   1785  O    ASN B 120       9.018  42.684  26.204  1.00 34.41           O
ATOM   1786  CB   ASN B 120       9.343  39.640  27.253  1.00 29.44           C
ATOM   1787  CG   ASN B 120       8.856  38.301  26.738  1.00 33.04           C
ATOM   1788  OD1  ASN B 120       8.264  38.216  25.651  1.00 32.93           O
ATOM   1789  ND2  ASN B 120       9.110  37.237  27.508  1.00 31.91           N
ATOM   1790  N    ARG B 121      11.018  42.436  27.140  1.00 32.47           N
ATOM   1791  CA   ARG B 121      11.117  43.849  27.465  1.00 30.92           C
ATOM   1792  C    ARG B 121      11.067  44.709  26.204  1.00 29.78           C
ATOM   1793  O    ARG B 121      10.444  45.760  26.207  1.00 28.95           O
ATOM   1794  CB   ARG B 121      12.391  44.075  28.271  1.00 33.61           C
ATOM   1795  CG   ARG B 121      12.655  45.523  28.664  1.00 41.90           C
ATOM   1796  CD   ARG B 121      11.463  46.261  29.336  1.00 48.78           C
ATOM   1797  NE   ARG B 121      11.048  47.453  28.567  1.00 55.93           N
ATOM   1798  CZ   ARG B 121      11.568  48.694  28.762  1.00 59.13           C
ATOM   1799  NH1  ARG B 121      12.543  48.894  29.659  1.00 60.86           N
ATOM   1800  NH2  ARG B 121      11.124  49.767  28.074  1.00 60.62           N
ATOM   1801  N    SER B 122      11.680  44.225  25.121  1.00 29.04           N
ATOM   1802  CA   SER B 122      11.818  44.920  23.854  1.00 27.66           C
ATOM   1803  C    SER B 122      10.512  45.006  23.126  1.00 29.01           C
ATOM   1804  O    SER B 122      10.198  46.085  22.634  1.00 30.77           O
ATOM   1805  CB   SER B 122      12.808  44.195  22.954  1.00 24.91           C
```

FIGURE 8A-41

| | | | | | | | | | |
|---|---|---|---|---|---|---|---|---|---|
| ATOM | 1806 | OG | SER B 122 | 14.125 | 44.237 | 23.464 | 1.00 | 21.03 | O |
| ATOM | 1807 | N | ILE B 123 | 9.765 | 43.896 | 23.061 | 1.00 | 30.73 | N |
| ATOM | 1808 | CA | ILE B 123 | 8.427 | 43.886 | 22.488 | 1.00 | 33.96 | C |
| ATOM | 1809 | C | ILE B 123 | 7.513 | 44.857 | 23.232 | 1.00 | 38.09 | C |
| ATOM | 1810 | O | ILE B 123 | 6.743 | 45.579 | 22.610 | 1.00 | 38.61 | O |
| ATOM | 1811 | CB | ILE B 123 | 7.863 | 42.445 | 22.513 | 1.00 | 33.36 | C |
| ATOM | 1812 | CG1 | ILE B 123 | 8.567 | 41.492 | 21.559 | 1.00 | 33.77 | C |
| ATOM | 1813 | CG2 | ILE B 123 | 6.385 | 42.334 | 22.276 | 1.00 | 35.01 | C |
| ATOM | 1814 | CD1 | ILE B 123 | 8.539 | 41.729 | 20.058 | 1.00 | 31.14 | C |
| ATOM | 1815 | N | ASP B 124 | 7.638 | 44.925 | 24.562 | 1.00 | 42.48 | N |
| ATOM | 1816 | CA | ASP B 124 | 6.868 | 45.809 | 25.424 | 1.00 | 45.69 | C |
| ATOM | 1817 | C | ASP B 124 | 7.347 | 47.237 | 25.404 | 1.00 | 45.68 | C |
| ATOM | 1818 | O | ASP B 124 | 6.592 | 48.118 | 25.836 | 1.00 | 46.88 | O |
| ATOM | 1819 | CB | ASP B 124 | 6.915 | 45.381 | 26.912 | 1.00 | 50.45 | C |
| ATOM | 1820 | CG | ASP B 124 | 6.483 | 43.950 | 27.274 | 1.00 | 56.00 | C |
| ATOM | 1821 | OD1 | ASP B 124 | 5.766 | 43.310 | 26.481 | 1.00 | 61.21 | O |
| ATOM | 1822 | OD2 | ASP B 124 | 6.883 | 43.461 | 28.344 | 1.00 | 56.72 | O |
| ATOM | 1823 | N | ALA B 125 | 8.599 | 47.461 | 24.970 | 1.00 | 46.60 | N |
| ATOM | 1824 | CA | ALA B 125 | 9.190 | 48.801 | 24.903 | 1.00 | 47.64 | C |
| ATOM | 1825 | C | ALA B 125 | 8.420 | 49.664 | 23.926 | 1.00 | 48.60 | C |
| ATOM | 1826 | O | ALA B 125 | 8.412 | 50.882 | 24.081 | 1.00 | 48.65 | O |
| ATOM | 1827 | CB | ALA B 125 | 10.643 | 48.781 | 24.422 | 1.00 | 46.01 | C |
| ATOM | 1828 | N | PHE B 126 | 7.752 | 49.014 | 22.960 | 1.00 | 50.56 | N |
| ATOM | 1829 | CA | PHE B 126 | 6.834 | 49.695 | 22.055 | 1.00 | 54.13 | C |
| ATOM | 1830 | C | PHE B 126 | 5.525 | 50.182 | 22.688 | 1.00 | 57.79 | C |
| ATOM | 1831 | O | PHE B 126 | 5.141 | 51.334 | 22.460 | 1.00 | 59.99 | O |
| ATOM | 1832 | CB | PHE B 126 | 6.538 | 48.850 | 20.810 | 1.00 | 51.52 | C |
| ATOM | 1833 | CG | PHE B 126 | 7.721 | 48.691 | 19.873 | 1.00 | 49.43 | C |
| ATOM | 1834 | CD1 | PHE B 126 | 8.650 | 47.685 | 20.086 | 1.00 | 48.93 | C |
| ATOM | 1835 | CD2 | PHE B 126 | 7.872 | 49.550 | 18.804 | 1.00 | 48.24 | C |
| ATOM | 1836 | CE1 | PHE B 126 | 9.721 | 47.531 | 19.226 | 1.00 | 47.28 | C |
| ATOM | 1837 | CE2 | PHE B 126 | 8.960 | 49.402 | 17.969 | 1.00 | 46.11 | C |
| ATOM | 1838 | CZ | PHE B 126 | 9.882 | 48.401 | 18.174 | 1.00 | 45.91 | C |
| ATOM | 1839 | N | LYS B 127 | 4.843 | 49.346 | 23.505 | 1.00 | 61.28 | N |
| ATOM | 1840 | CA | LYS B 127 | 3.558 | 49.636 | 24.178 | 1.00 | 62.20 | C |
| ATOM | 1841 | C | LYS B 127 | 3.454 | 50.906 | 25.026 | 1.00 | 62.03 | C |
| ATOM | 1842 | O | LYS B 127 | 2.394 | 51.539 | 25.092 | 1.00 | 61.71 | O |
| ATOM | 1843 | CB | LYS B 127 | 3.115 | 48.458 | 25.090 | 1.00 | 64.81 | C |
| ATOM | 1844 | CG | LYS B 127 | 2.463 | 47.185 | 24.502 | 1.00 | 65.92 | C |
| ATOM | 1845 | CD | LYS B 127 | 2.082 | 46.311 | 25.702 | 1.00 | 67.81 | C |
| ATOM | 1846 | CE | LYS B 127 | 2.369 | 44.834 | 25.433 | 1.00 | 69.44 | C |
| ATOM | 1847 | NZ | LYS B 127 | 2.594 | 44.129 | 26.691 | 1.00 | 68.14 | N |
| ATOM | 1848 | N | ASP B 128 | 4.561 | 51.200 | 25.719 | 1.00 | 62.76 | N |
| ATOM | 1849 | CA | ASP B 128 | 4.736 | 52.380 | 26.554 | 1.00 | 62.70 | C |
| ATOM | 1850 | C | ASP B 128 | 5.573 | 53.412 | 25.794 | 1.00 | 63.56 | C |
| ATOM | 1851 | O | ASP B 128 | 6.638 | 53.838 | 26.251 | 1.00 | 64.23 | O |
| ATOM | 1852 | CB | ASP B 128 | 5.480 | 51.925 | 27.833 | 1.00 | 62.32 | C |
| ATOM | 1853 | N | PHE B 129 | 5.128 | 53.802 | 24.587 | 1.00 | 64.47 | N |
| ATOM | 1854 | CA | PHE B 129 | 5.813 | 54.828 | 23.801 | 1.00 | 65.58 | C |
| ATOM | 1855 | C | PHE B 129 | 5.172 | 56.224 | 23.900 | 1.00 | 66.25 | C |
| ATOM | 1856 | O | PHE B 129 | 4.145 | 56.473 | 23.258 | 1.00 | 67.17 | O |
| ATOM | 1857 | CB | PHE B 129 | 5.971 | 54.368 | 22.338 | 1.00 | 64.56 | C |
| ATOM | 1858 | CG | PHE B 129 | 7.424 | 54.230 | 21.907 | 1.00 | 63.61 | C |
| ATOM | 1859 | CD1 | PHE B 129 | 8.187 | 55.356 | 21.634 | 1.00 | 64.45 | C |
| ATOM | 1860 | CD2 | PHE B 129 | 7.979 | 52.977 | 21.775 | 1.00 | 62.93 | C |
| ATOM | 1861 | CE1 | PHE B 129 | 9.503 | 55.219 | 21.235 | 1.00 | 64.07 | C |
| ATOM | 1862 | CE2 | PHE B 129 | 9.291 | 52.837 | 21.378 | 1.00 | 63.56 | C |
| ATOM | 1863 | CZ | PHE B 129 | 10.048 | 53.959 | 21.111 | 1.00 | 64.70 | C |
| ATOM | 1864 | N | ASP B 137 | 17.272 | 62.584 | 24.623 | 1.00 | 55.18 | N |
| ATOM | 1865 | CA | ASP B 137 | 18.560 | 63.025 | 24.106 | 1.00 | 54.96 | C |

*FIGURE 8A-42*

```
ATOM   1866  C   ASP B 137      19.597  61.931  23.769  1.00 55.95           C
ATOM   1867  O   ASP B 137      20.291  62.026  22.743  1.00 55.11           O
ATOM   1868  CB  ASP B 137      19.180  63.952  25.136  1.00 53.99           C
ATOM   1869  N   CYS B 138      19.669  60.900  24.656  1.00 55.99           N
ATOM   1870  CA  CYS B 138      20.594  59.741  24.665  1.00 55.50           C
ATOM   1871  C   CYS B 138      22.065  59.964  25.031  1.00 55.10           C
ATOM   1872  O   CYS B 138      22.723  58.973  25.357  1.00 55.77           O
ATOM   1873  CB  CYS B 138      20.486  58.822  23.416  1.00 53.55           C
ATOM   1874  SG  CYS B 138      18.766  58.362  23.058  1.00 53.01           S
TER    1876      CYS B 138
ATOM   1877  N   ASN C  11      51.574  13.978  45.345  1.00 51.40           N
ATOM   1878  CA  ASN C  11      50.150  14.075  45.169  1.00 50.61           C
ATOM   1879  C   ASN C  11      49.636  15.080  46.231  1.00 51.75           C
ATOM   1880  O   ASN C  11      49.446  16.244  45.828  1.00 52.28           O
ATOM   1881  CB  ASN C  11      49.486  12.671  45.271  1.00 48.14           C
ATOM   1882  N   VAL C  12      49.577  14.664  47.548  1.00 49.74           N
ATOM   1883  CA  VAL C  12      48.941  15.269  48.771  1.00 46.17           C
ATOM   1884  C   VAL C  12      49.317  16.681  49.255  1.00 43.47           C
ATOM   1885  O   VAL C  12      48.526  17.397  49.868  1.00 42.02           O
ATOM   1886  CB  VAL C  12      49.032  14.271  50.044  1.00 47.02           C
ATOM   1887  CG1 VAL C  12      50.479  14.042  50.561  1.00 46.01           C
ATOM   1888  CG2 VAL C  12      48.129  14.662  51.233  1.00 44.78           C
ATOM   1889  N   LYS C  13      50.588  17.052  49.054  1.00 43.09           N
ATOM   1890  CA  LYS C  13      51.082  18.424  49.218  1.00 39.49           C
ATOM   1891  C   LYS C  13      50.370  19.321  48.180  1.00 36.49           C
ATOM   1892  O   LYS C  13      49.910  20.435  48.472  1.00 35.14           O
ATOM   1893  CB  LYS C  13      52.643  18.424  48.986  1.00 37.77           C
ATOM   1894  N   ASP C  14      50.231  18.776  46.951  1.00 33.25           N
ATOM   1895  CA  ASP C  14      49.522  19.456  45.898  1.00 27.29           C
ATOM   1896  C   ASP C  14      48.042  19.262  45.991  1.00 21.51           C
ATOM   1897  O   ASP C  14      47.408  20.205  45.602  1.00 20.53           O
ATOM   1898  CB  ASP C  14      50.101  19.142  44.565  1.00 31.10           C
ATOM   1899  CG  ASP C  14      51.439  19.856  44.288  1.00 35.88           C
ATOM   1900  OD1 ASP C  14      52.043  20.514  45.155  1.00 37.80           O
ATOM   1901  OD2 ASP C  14      51.890  19.755  43.143  1.00 37.19           O
ATOM   1902  N   VAL C  15      47.447  18.202  46.526  1.00 15.89           N
ATOM   1903  CA  VAL C  15      46.073  18.270  46.962  1.00 16.75           C
ATOM   1904  C   VAL C  15      45.796  19.433  47.938  1.00 17.73           C
ATOM   1905  O   VAL C  15      44.821  20.167  47.775  1.00 18.15           O
ATOM   1906  CB  VAL C  15      45.653  16.905  47.548  1.00 17.03           C
ATOM   1907  CG1 VAL C  15      44.266  16.920  48.161  1.00 15.16           C
ATOM   1908  CG2 VAL C  15      45.656  15.889  46.430  1.00 17.49           C
ATOM   1909  N   THR C  16      46.659  19.692  48.910  1.00 17.16           N
ATOM   1910  CA  THR C  16      46.513  20.824  49.806  1.00 16.51           C
ATOM   1911  C   THR C  16      46.660  22.151  49.096  1.00 15.07           C
ATOM   1912  O   THR C  16      45.901  23.049  49.418  1.00 16.99           O
ATOM   1913  CB  THR C  16      47.533  20.674  51.000  1.00 17.35           C
ATOM   1914  OG1 THR C  16      47.059  19.546  51.734  1.00 19.10           O
ATOM   1915  CG2 THR C  16      47.615  21.868  51.934  1.00 11.74           C
ATOM   1916  N   LYS C  17      47.562  22.381  48.160  1.00 13.81           N
ATOM   1917  CA  LYS C  17      47.496  23.602  47.390  1.00 15.88           C
ATOM   1918  C   LYS C  17      46.197  23.789  46.541  1.00 16.97           C
ATOM   1919  O   LYS C  17      45.608  24.877  46.465  1.00 17.88           O
ATOM   1920  CB  LYS C  17      48.702  23.598  46.505  1.00 18.13           C
ATOM   1921  CG  LYS C  17      50.006  23.615  47.257  1.00 21.24           C
ATOM   1922  CD  LYS C  17      51.103  23.441  46.198  1.00 24.88           C
ATOM   1923  CE  LYS C  17      52.486  23.537  46.798  1.00 28.59           C
ATOM   1924  NZ  LYS C  17      52.730  24.883  47.284  1.00 31.31           N
ATOM   1925  N   LEU C  18      45.682  22.736  45.880  1.00 14.39           N
ATOM   1926  CA  LEU C  18      44.454  22.764  45.149  1.00 11.22           C
```

FIGURE 8A-43

| | | | | | | | | | | |
|---|---|---|---|---|---|---|---|---|---|---|
| ATOM | 1927 | C | LEU | C | 18 | 43.333 | 23.111 | 46.047 | 1.00 | 10.78 | C |
| ATOM | 1928 | O | LEU | C | 18 | 42.612 | 24.032 | 45.691 | 1.00 | 16.08 | O |
| ATOM | 1929 | CB | LEU | C | 18 | 44.129 | 21.412 | 44.609 | 1.00 | 12.69 | C |
| ATOM | 1930 | CG | LEU | C | 18 | 42.973 | 21.312 | 43.632 | 1.00 | 15.70 | C |
| ATOM | 1931 | CD1 | LEU | C | 18 | 43.151 | 22.220 | 42.429 | 1.00 | 9.04 | C |
| ATOM | 1932 | CD2 | LEU | C | 18 | 42.864 | 19.875 | 43.248 | 1.00 | 15.11 | C |
| ATOM | 1933 | N | VAL | C | 19 | 43.155 | 22.484 | 47.210 | 1.00 | 11.81 | N |
| ATOM | 1934 | CA | VAL | C | 19 | 42.092 | 22.868 | 48.138 | 1.00 | 12.12 | C |
| ATOM | 1935 | C | VAL | C | 19 | 42.159 | 24.359 | 48.569 | 1.00 | 13.12 | C |
| ATOM | 1936 | O | VAL | C | 19 | 41.144 | 25.056 | 48.607 | 1.00 | 14.59 | O |
| ATOM | 1937 | CB | VAL | C | 19 | 42.041 | 21.868 | 49.328 | 1.00 | 12.63 | C |
| ATOM | 1938 | CG1 | VAL | C | 19 | 40.984 | 22.267 | 50.328 | 1.00 | 11.49 | C |
| ATOM | 1939 | CG2 | VAL | C | 19 | 41.661 | 20.496 | 48.835 | 1.00 | 12.48 | C |
| ATOM | 1940 | N | ALA | C | 20 | 43.362 | 24.909 | 48.321 | 1.00 | 13.02 | N |
| ATOM | 1941 | CA | ALA | C | 20 | 43.532 | 26.278 | 49.252 | 1.00 | 11.77 | C |
| ATOM | 1942 | C | ALA | C | 20 | 43.254 | 27.224 | 48.126 | 1.00 | 11.25 | C |
| ATOM | 1943 | O | ALA | C | 20 | 42.888 | 28.357 | 48.344 | 1.00 | 14.74 | O |
| ATOM | 1944 | CB | ALA | C | 20 | 44.975 | 26.452 | 49.635 | 1.00 | 10.68 | C |
| ATOM | 1945 | N | ASN | C | 21 | 43.461 | 26.757 | 46.895 | 1.00 | 15.11 | N |
| ATOM | 1946 | CA | ASN | C | 21 | 43.197 | 27.471 | 45.648 | 1.00 | 13.34 | C |
| ATOM | 1947 | C | ASN | C | 21 | 41.898 | 27.107 | 44.949 | 1.00 | 13.09 | C |
| ATOM | 1948 | O | ASN | C | 21 | 41.663 | 27.533 | 43.815 | 1.00 | 18.62 | O |
| ATOM | 1949 | CB | ASN | C | 21 | 44.318 | 27.149 | 44.717 | 1.00 | 12.84 | C |
| ATOM | 1950 | CG | ASN | C | 21 | 45.401 | 28.151 | 44.755 | 1.00 | 12.42 | C |
| ATOM | 1951 | OD1 | ASN | C | 21 | 45.277 | 29.229 | 45.315 | 1.00 | 14.66 | O |
| ATOM | 1952 | ND2 | ASN | C | 21 | 46.503 | 27.827 | 44.131 | 1.00 | 12.99 | N |
| ATOM | 1953 | N | LEU | C | 22 | 41.041 | 26.311 | 45.536 | 1.00 | 12.25 | N |
| ATOM | 1954 | CA | LEU | C | 22 | 39.691 | 26.194 | 45.063 | 1.00 | 12.28 | C |
| ATOM | 1955 | C | LEU | C | 22 | 38.831 | 27.012 | 45.972 | 1.00 | 12.85 | C |
| ATOM | 1956 | O | LEU | C | 22 | 39.216 | 27.109 | 47.126 | 1.00 | 17.11 | O |
| ATOM | 1957 | CB | LEU | C | 22 | 39.202 | 24.755 | 45.039 | 1.00 | 10.06 | C |
| ATOM | 1958 | CG | LEU | C | 22 | 39.745 | 23.906 | 43.936 | 1.00 | 9.08 | C |
| ATOM | 1959 | CD1 | LEU | C | 22 | 39.380 | 22.464 | 44.120 | 1.00 | 8.06 | C |
| ATOM | 1960 | CD2 | LEU | C | 22 | 39.124 | 24.394 | 42.666 | 1.00 | 11.26 | C |
| ATOM | 1961 | N | PRO | C | 23 | 37.706 | 27.649 | 45.629 | 1.00 | 12.49 | N |
| ATOM | 1962 | CA | PRO | C | 23 | 36.902 | 28.384 | 46.592 | 1.00 | 12.26 | C |
| ATOM | 1963 | C | PRO | C | 23 | 36.214 | 27.457 | 47.604 | 1.00 | 13.42 | C |
| ATOM | 1964 | O | PRO | C | 23 | 35.695 | 26.416 | 47.320 | 1.00 | 13.22 | O |
| ATOM | 1965 | CB | PRO | C | 23 | 35.923 | 29.108 | 45.681 | 1.00 | 13.14 | C |
| ATOM | 1966 | CG | PRO | C | 23 | 36.407 | 29.009 | 44.237 | 1.00 | 9.94 | C |
| ATOM | 1967 | CD | PRO | C | 23 | 37.094 | 27.667 | 44.292 | 1.00 | 12.73 | C |
| ATOM | 1968 | N | LYS | C | 24 | 36.216 | 27.796 | 48.898 | 1.00 | 13.54 | N |
| ATOM | 1969 | CA | LYS | C | 24 | 35.515 | 27.039 | 49.919 | 1.00 | 17.03 | C |
| ATOM | 1970 | C | LYS | C | 24 | 34.053 | 26.703 | 49.596 | 1.00 | 17.41 | C |
| ATOM | 1971 | O | LYS | C | 24 | 33.500 | 25.693 | 50.011 | 1.00 | 15.96 | O |
| ATOM | 1972 | CB | LYS | C | 24 | 35.591 | 27.845 | 51.228 | 1.00 | 17.76 | C |
| ATOM | 1973 | CG | LYS | C | 24 | 36.918 | 27.585 | 51.896 | 1.00 | 22.90 | C |
| ATOM | 1974 | CD | LYS | C | 24 | 37.423 | 28.782 | 52.700 | 1.00 | 24.73 | C |
| ATOM | 1975 | CE | LYS | C | 24 | 38.893 | 28.608 | 53.191 | 1.00 | 25.32 | C |
| ATOM | 1976 | NZ | LYS | C | 24 | 39.427 | 29.914 | 53.578 | 1.00 | 27.67 | N |
| ATOM | 1977 | N | ASP | C | 25 | 33.380 | 27.526 | 48.807 | 1.00 | 20.45 | N |
| ATOM | 1978 | CA | ASP | C | 25 | 31.969 | 27.349 | 48.579 | 1.00 | 20.93 | C |
| ATOM | 1979 | C | ASP | C | 25 | 31.690 | 26.924 | 47.164 | 1.00 | 19.35 | C |
| ATOM | 1980 | O | ASP | C | 25 | 30.617 | 27.146 | 46.603 | 1.00 | 21.38 | O |
| ATOM | 1981 | CB | ASP | C | 25 | 31.316 | 28.665 | 48.909 | 1.00 | 23.07 | C |
| ATOM | 1982 | CG | ASP | C | 25 | 31.726 | 29.820 | 48.014 | 1.00 | 28.48 | C |
| ATOM | 1983 | OD1 | ASP | C | 25 | 32.736 | 29.755 | 47.329 | 1.00 | 29.48 | O |
| ATOM | 1984 | OD2 | ASP | C | 25 | 31.018 | 30.829 | 48.006 | 1.00 | 35.37 | O |
| ATOM | 1985 | N | TYR | C | 26 | 32.684 | 26.330 | 46.570 | 1.00 | 17.08 | N |
| ATOM | 1986 | CA | TYR | C | 26 | 32.486 | 25.784 | 45.270 | 1.00 | 18.09 | C |

FIGURE 8A-44

```
ATOM    1987  C    TYR C  26      32.066  24.352  45.473  1.00 20.16           C
ATOM    1988  O    TYR C  26      32.672  23.586  45.210  1.00 20.74           O
ATOM    1989  CB   TYR C  26      33.787  25.925  44.505  1.00 18.65           C
ATOM    1990  CG   TYR C  26      33.779  25.389  43.087  1.00 15.43           C
ATOM    1991  CD1  TYR C  26      32.863  25.870  42.180  1.00 14.28           C
ATOM    1992  CD2  TYR C  26      34.687  24.394  42.740  1.00 18.66           C
ATOM    1993  CE1  TYR C  26      32.828  25.305  40.916  1.00 18.89           C
ATOM    1994  CE2  TYR C  26      34.630  23.853  41.457  1.00 18.57           C
ATOM    1995  CZ   TYR C  26      33.736  24.325  40.567  1.00 17.94           C
ATOM    1996  OH   TYR C  26      33.702  23.844  39.293  1.00 20.05           O
HETATM  1997  N    MSE C  27      30.992  23.977  44.306  1.00 22.38           N
HETATM  1998  CA   MSE C  27      30.472  22.643  44.960  1.00 23.82           C
HETATM  1999  C    MSE C  27      30.902  21.790  43.796  1.00 23.07           C
HETATM  2000  O    MSE C  27      30.675  22.180  42.659  1.00 22.78           O
HETATM  2001  CB   MSE C  27      28.966  22.685  45.023  1.00 27.76           C
HETATM  2002  CG   MSE C  27      28.476  23.440  46.222  1.00 33.28           C
HETATM  2003  SE   MSE C  27      29.250  22.864  47.919  1.00 47.63          SE
HETATM  2004  CE   MSE C  27      28.807  24.413  48.975  1.00 42.81           C
ATOM    2005  N    ILE C  28      31.514  20.637  44.127  1.00 23.36           N
ATOM    2006  CA   ILE C  28      31.890  19.552  43.196  1.00 24.49           C
ATOM    2007  C    ILE C  28      30.924  18.334  43.195  1.00 25.21           C
ATOM    2008  O    ILE C  28      30.568  17.795  44.237  1.00 24.49           O
ATOM    2009  CB   ILE C  28      33.364  19.075  43.497  1.00 21.68           C
ATOM    2010  CG1  ILE C  28      34.379  20.215  43.453  1.00 19.99           C
ATOM    2011  CG2  ILE C  28      33.796  18.049  42.485  1.00 19.57           C
ATOM    2012  CD1  ILE C  28      35.761  19.859  43.991  1.00 18.85           C
ATOM    2013  N    THR C  29      30.508  17.846  42.017  1.00 26.46           N
ATOM    2014  CA   THR C  29      29.637  16.688  41.888  1.00 26.80           C
ATOM    2015  C    THR C  29      30.388  15.361  41.957  1.00 27.21           C
ATOM    2016  O    THR C  29      31.299  15.084  41.182  1.00 26.27           O
ATOM    2017  CB   THR C  29      28.824  16.736  40.580  1.00 25.22           C
ATOM    2018  OG1  THR C  29      28.137  17.962  40.566  1.00 28.05           O
ATOM    2019  CG2  THR C  29      27.773  15.659  40.545  1.00 26.26           C
ATOM    2020  N    LEU C  30      29.980  14.498  42.878  1.00 27.91           N
ATOM    2021  CA   LEU C  30      30.519  13.157  42.943  1.00 29.69           C
ATOM    2022  C    LEU C  30      29.354  12.189  43.168  1.00 31.34           C
ATOM    2023  O    LEU C  30      28.542  12.362  44.080  1.00 30.99           O
ATOM    2024  CB   LEU C  30      31.578  13.070  44.051  1.00 25.27           C
ATOM    2025  CG   LEU C  30      32.157  11.727  44.434  1.00 23.15           C
ATOM    2026  CD1  LEU C  30      32.879  11.106  43.274  1.00 22.85           C
ATOM    2027  CD2  LEU C  30      33.110  11.943  45.570  1.00 25.04           C
ATOM    2028  N    LYS C  31      29.246  11.172  42.300  1.00 34.65           N
ATOM    2029  CA   LYS C  31      28.335  10.045  42.513  1.00 36.49           C
ATOM    2030  C    LYS C  31      28.910   9.150  43.620  1.00 36.03           C
ATOM    2031  O    LYS C  31      29.741   8.287  43.370  1.00 36.42           O
ATOM    2032  CB   LYS C  31      28.121   9.241  41.218  1.00 36.56           C
ATOM    2033  CG   LYS C  31      27.475   9.966  40.056  1.00 39.42           C
ATOM    2034  CD   LYS C  31      26.867   8.902  39.121  1.00 47.68           C
ATOM    2035  CE   LYS C  31      25.930   9.427  37.990  1.00 51.31           C
ATOM    2036  NZ   LYS C  31      24.859   8.496  37.602  1.00 51.86           N
ATOM    2037  N    TYR C  32      28.514   9.411  44.868  1.00 38.89           N
ATOM    2038  CA   TYR C  32      29.122   8.846  46.061  1.00 40.86           C
ATOM    2039  C    TYR C  32      28.594   7.437  46.265  1.00 43.51           C
ATOM    2040  O    TYR C  32      27.425   7.204  45.953  1.00 45.02           O
ATOM    2041  CB   TYR C  32      28.707   9.747  47.229  1.00 37.67           C
ATOM    2042  CG   TYR C  32      29.138   9.317  48.610  1.00 41.48           C
ATOM    2043  CD1  TYR C  32      30.459   9.438  48.984  1.00 43.11           C
ATOM    2044  CD2  TYR C  32      28.190   8.877  49.536  1.00 43.18           C
ATOM    2045  CE1  TYR C  32      30.812   9.172  50.302  1.00 44.55           C
ATOM    2046  CE2  TYR C  32      28.542   8.584  50.847  1.00 44.09           C
```

FIGURE 8A-45

| | | | | | | | | | | |
|---|---|---|---|---|---|---|---|---|---|---|
| ATOM | 2047 | CZ | TYR | C | 32 | 29.862 | 8.758 | 51.230 | 1.00 45.88 | C |
| ATOM | 2048 | OH | TYR | C | 32 | 30.238 | 8.549 | 52.557 | 1.00 49.38 | O |
| ATOM | 2049 | N | VAL | C | 33 | 29.391 | 6.459 | 46.718 | 1.00 46.10 | N |
| ATOM | 2050 | CA | VAL | C | 33 | 28.866 | 5.097 | 46.885 | 1.00 48.63 | C |
| ATOM | 2051 | C | VAL | C | 33 | 28.323 | 4.935 | 48.307 | 1.00 50.48 | C |
| ATOM | 2052 | O | VAL | C | 33 | 29.088 | 5.086 | 49.265 | 1.00 49.75 | O |
| ATOM | 2053 | CB | VAL | C | 33 | 29.900 | 4.000 | 46.501 | 1.00 49.02 | C |
| ATOM | 2054 | CG1 | VAL | C | 33 | 29.390 | 2.594 | 46.823 | 1.00 50.53 | C |
| ATOM | 2055 | CG2 | VAL | C | 33 | 30.216 | 4.072 | 45.014 | 1.00 47.63 | C |
| ATOM | 2056 | N | PRO | C | 34 | 27.006 | 4.682 | 48.505 | 1.00 53.29 | N |
| ATOM | 2057 | CA | PRO | C | 34 | 26.385 | 4.695 | 49.834 | 1.00 55.66 | C |
| ATOM | 2058 | C | PRO | C | 34 | 27.121 | 3.734 | 50.767 | 1.00 58.89 | C |
| ATOM | 2059 | O | PRO | C | 34 | 27.426 | 2.568 | 50.448 | 1.00 59.22 | O |
| ATOM | 2060 | CB | PRO | C | 34 | 24.936 | 4.297 | 49.549 | 1.00 54.96 | C |
| ATOM | 2061 | CG | PRO | C | 34 | 24.701 | 4.825 | 48.139 | 1.00 51.80 | C |
| ATOM | 2062 | CD | PRO | C | 34 | 26.002 | 4.428 | 47.456 | 1.00 51.86 | C |
| ATOM | 2063 | N | GLY | C | 35 | 27.545 | 4.399 | 51.850 | 1.00 60.51 | N |
| ATOM | 2064 | CA | GLY | C | 35 | 28.272 | 3.744 | 52.925 | 1.00 62.88 | C |
| ATOM | 2065 | C | GLY | C | 35 | 29.632 | 3.266 | 52.457 | 1.00 63.14 | C |
| ATOM | 2066 | O | GLY | C | 35 | 29.852 | 2.077 | 52.214 | 1.00 64.01 | O |
| HETATM | 2067 | N | MSE | C | 36 | 30.521 | 4.240 | 52.301 | 1.00 62.92 | N |
| HETATM | 2068 | CA | MSE | C | 36 | 31.881 | 3.970 | 51.881 | 1.00 63.09 | C |
| HETATM | 2069 | C | MSE | C | 36 | 32.945 | 4.485 | 52.836 | 1.00 64.77 | C |
| HETATM | 2070 | O | MSE | C | 36 | 34.148 | 4.357 | 52.599 | 1.00 65.03 | O |
| HETATM | 2071 | CB | MSE | C | 36 | 32.115 | 4.582 | 50.531 | 1.00 62.61 | C |
| HETATM | 2072 | CG | MSE | C | 36 | 31.973 | 6.068 | 50.551 | 1.00 60.55 | C |
| HETATM | 2073 | SE | MSE | C | 36 | 33.277 | 6.879 | 49.401 | 1.00 61.18 | SE |
| HETATM | 2074 | CE | MSE | C | 36 | 34.541 | 7.346 | 50.777 | 1.00 55.15 | C |
| ATOM | 2075 | N | ASP | C | 37 | 32.430 | 5.163 | 53.363 | 1.00 66.73 | N |
| ATOM | 2076 | CA | ASP | C | 37 | 33.149 | 5.583 | 55.061 | 1.00 67.41 | C |
| ATOM | 2077 | C | ASP | C | 37 | 33.215 | 4.481 | 56.132 | 1.00 66.85 | C |
| ATOM | 2078 | O | ASP | C | 37 | 34.130 | 4.393 | 56.957 | 1.00 67.21 | O |
| ATOM | 2079 | CB | ASP | C | 37 | 32.478 | 6.867 | 55.589 | 1.00 69.00 | C |
| ATOM | 2080 | CG | ASP | C | 37 | 30.982 | 6.808 | 55.935 | 1.00 70.25 | C |
| ATOM | 2081 | OD1 | ASP | C | 37 | 30.143 | 6.538 | 55.061 | 1.00 69.81 | O |
| ATOM | 2082 | OD2 | ASP | C | 37 | 30.657 | 7.058 | 57.097 | 1.00 71.69 | O |
| ATOM | 2083 | N | VAL | C | 38 | 32.224 | 3.593 | 56.068 | 1.00 65.94 | N |
| ATOM | 2084 | CA | VAL | C | 38 | 32.091 | 2.461 | 56.960 | 1.00 64.55 | C |
| ATOM | 2085 | C | VAL | C | 38 | 32.395 | 1.200 | 56.170 | 1.00 65.94 | C |
| ATOM | 2086 | O | VAL | C | 38 | 33.340 | 0.521 | 56.584 | 1.00 68.33 | O |
| ATOM | 2087 | CB | VAL | C | 38 | 30.694 | 2.475 | 57.631 | 1.00 63.05 | C |
| ATOM | 2088 | CG1 | VAL | C | 38 | 29.960 | 1.135 | 57.787 | 1.00 62.73 | C |
| ATOM | 2089 | CG2 | VAL | C | 38 | 30.915 | 3.097 | 58.990 | 1.00 61.39 | C |
| ATOM | 2090 | N | LEU | C | 39 | 31.700 | 0.861 | 55.059 | 1.00 64.32 | N |
| ATOM | 2091 | CA | LEU | C | 39 | 31.997 | -0.365 | 54.328 | 1.00 63.23 | C |
| ATOM | 2092 | C | LEU | C | 39 | 33.487 | -0.412 | 53.952 | 1.00 62.57 | C |
| ATOM | 2093 | O | LEU | C | 39 | 34.084 | 0.647 | 53.713 | 1.00 63.24 | O |
| ATOM | 2094 | CB | LEU | C | 39 | 31.130 | -0.449 | 53.078 | 1.00 62.74 | C |
| ATOM | 2095 | N | PRO | C | 40 | 34.161 | -1.578 | 54.006 | 1.00 61.57 | N |
| ATOM | 2096 | CA | PRO | C | 40 | 35.608 | -1.719 | 53.761 | 1.00 59.74 | C |
| ATOM | 2097 | C | PRO | C | 40 | 36.009 | -1.462 | 52.318 | 1.00 57.52 | C |
| ATOM | 2098 | O | PRO | C | 40 | 35.183 | -1.629 | 51.418 | 1.00 54.10 | O |
| ATOM | 2099 | CB | PRO | C | 40 | 35.861 | -3.170 | 54.123 | 1.00 60.55 | C |
| ATOM | 2100 | CG | PRO | C | 40 | 34.550 | -3.363 | 53.762 | 1.00 60.74 | C |
| ATOM | 2101 | CD | PRO | C | 40 | 33.546 | -2.868 | 54.329 | 1.00 61.16 | C |
| ATOM | 2102 | N | SER | C | 41 | 37.282 | -1.110 | 52.111 | 1.00 56.39 | N |
| ATOM | 2103 | CA | SER | C | 41 | 37.779 | -0.735 | 50.798 | 1.00 56.77 | C |
| ATOM | 2104 | C | SER | C | 41 | 37.271 | -1.553 | 49.602 | 1.00 56.41 | C |
| ATOM | 2105 | O | SER | C | 41 | 36.627 | -0.992 | 48.727 | 1.00 56.58 | O |
| ATOM | 2106 | CB | SER | C | 41 | 39.292 | -0.643 | 50.831 | 1.00 57.36 | C |

FIGURE 8A-46

```
ATOM   2107  OG   SER C  41      39.964  -1.877  50.695  1.00 60.69           O
ATOM   2108  N    HIS C  42      37.404  -2.882  49.580  1.00 56.11           N
ATOM   2109  CA   HIS C  42      36.947  -3.739  48.482  1.00 56.80           C
ATOM   2110  C    HIS C  42      35.473  -3.664  48.079  1.00 56.34           C
ATOM   2111  O    HIS C  42      35.062  -4.139  47.007  1.00 55.64           O
ATOM   2112  CB   HIS C  42      37.301  -5.217  48.795  1.00 60.78           C
ATOM   2113  CG   HIS C  42      36.205  -6.095  49.445  1.00 63.24           C
ATOM   2114  ND1  HIS C  42      35.894  -6.211  50.736  1.00 63.50           N
ATOM   2115  CD2  HIS C  42      35.244  -6.788  48.711  1.00 63.78           C
ATOM   2116  CE1  HIS C  42      34.762  -6.882  50.802  1.00 64.65           C
ATOM   2117  NE2  HIS C  42      34.371  -7.201  49.584  1.00 64.49           N
ATOM   2118  N    CYS C  43      34.669  -3.175  49.027  1.00 56.27           N
ATOM   2119  CA   CYS C  43      33.239  -3.012  48.806  1.00 56.25           C
ATOM   2120  C    CYS C  43      32.953  -1.871  47.844  1.00 54.69           C
ATOM   2121  O    CYS C  43      32.104  -2.006  46.959  1.00 56.17           O
ATOM   2122  CB   CYS C  43      32.488  -2.787  50.120  1.00 57.47           C
ATOM   2123  SG   CYS C  43      31.647  -4.253  50.786  1.00 60.51           S
ATOM   2124  N    TRP C  44      33.695  -0.766  47.973  1.00 51.41           N
ATOM   2125  CA   TRP C  44      33.338   0.464  47.287  1.00 47.58           C
ATOM   2126  C    TRP C  44      34.349   0.946  46.300  1.00 46.08           C
ATOM   2127  O    TRP C  44      33.969   1.593  45.341  1.00 46.29           O
ATOM   2128  CB   TRP C  44      33.089   1.587  48.271  1.00 47.09           C
ATOM   2129  CG   TRP C  44      34.199   1.801  49.301  1.00 46.63           C
ATOM   2130  CD1  TRP C  44      34.221   1.046  50.444  1.00 47.77           C
ATOM   2131  CD2  TRP C  44      35.261   2.660  49.225  1.00 45.55           C
ATOM   2132  NE1  TRP C  44      35.307   1.419  51.078  1.00 47.46           N
ATOM   2133  CE2  TRP C  44      35.948   2.361  50.389  1.00 44.86           C
ATOM   2134  CE3  TRP C  44      35.723   3.640  48.403  1.00 42.70           C
ATOM   2135  CZ2  TRP C  44      37.122   2.956  50.754  1.00 43.79           C
ATOM   2136  CZ3  TRP C  44      36.886   4.263  48.782  1.00 43.82           C
ATOM   2137  CH2  TRP C  44      37.597   3.925  49.920  1.00 42.91           C
ATOM   2138  N    ILE C  45      35.615   0.635  46.539  1.00 45.14           N
ATOM   2139  CA   ILE C  45      36.735   1.252  45.851  1.00 47.08           C
ATOM   2140  C    ILE C  45      36.657   1.198  44.329  1.00 47.61           C
ATOM   2141  O    ILE C  45      36.955   2.157  43.619  1.00 48.87           O
ATOM   2142  CB   ILE C  45      38.085   0.681  46.427  1.00 47.91           C
ATOM   2143  CG1  ILE C  45      39.316   1.515  46.123  1.00 46.35           C
ATOM   2144  CG2  ILE C  45      38.420  -0.723  45.905  1.00 50.05           C
ATOM   2145  CD1  ILE C  45      39.180   2.995  46.462  1.00 43.72           C
ATOM   2146  N    SER C  46      36.158   0.077  43.850  1.00 47.61           N
ATOM   2147  CA   SER C  46      36.069  -0.245  42.437  1.00 48.09           C
ATOM   2148  C    SER C  46      35.166   0.685  41.595  1.00 47.26           C
ATOM   2149  O    SER C  46      35.598   1.186  40.555  1.00 46.49           O
ATOM   2150  CB   SER C  46      35.688  -1.728  42.427  1.00 50.90           C
ATOM   2151  OG   SER C  46      35.093  -2.219  43.664  1.00 54.24           O
ATOM   2152  N    GLU C  47      33.932   0.997  42.039  1.00 46.80           N
ATOM   2153  CA   GLU C  47      33.095   2.037  41.430  1.00 45.94           C
ATOM   2154  C    GLU C  47      33.599   3.449  41.776  1.00 43.82           C
ATOM   2155  O    GLU C  47      33.532   4.348  40.947  1.00 43.16           O
ATOM   2156  CB   GLU C  47      31.602   1.843  41.831  1.00 47.29           C
ATOM   2157  CG   GLU C  47      30.478   2.752  41.246  1.00 52.00           C
ATOM   2158  CD   GLU C  47      29.748   2.394  39.936  1.00 54.16           C
ATOM   2159  OE1  GLU C  47      28.894   1.494  39.926  1.00 57.21           O
ATOM   2160  OE2  GLU C  47      29.989   3.052  38.922  1.00 54.36           O
HETATM 2161  N    MSE C  48      34.170   3.670  42.967  1.00 43.01           N
HETATM 2162  CA   MSE C  48      34.601   4.979  43.448  1.00 40.77           C
HETATM 2163  C    MSE C  48      35.795   5.538  42.724  1.00 37.10           C
HETATM 2164  O    MSE C  48      35.799   6.739  42.563  1.00 39.16           O
HETATM 2165  CB   MSE C  48      34.926   4.968  44.927  1.00 43.83           C
HETATM 2166  CG   MSE C  48      34.667   6.334  45.551  1.00 49.60           C
```

FIGURE 8A-47

| | | | | | | | | | | |
|---|---|---|---|---|---|---|---|---|---|---|
| HETATM | 2167 | SE | MSE | C | 48 | 32.809 | 6.850 | 45.340 | 1.00 57.46 | SE |
| HETATM | 2168 | CE | MSE | C | 48 | 32.917 | 8.464 | 46.266 | 1.00 52.90 | C |
| ATOM | 2169 | N | VAL | C | 49 | 36.793 | 4.773 | 42.266 | 1.00 34.29 | N |
| ATOM | 2170 | CA | VAL | C | 49 | 37.855 | 5.271 | 41.388 | 1.00 30.22 | C |
| ATOM | 2171 | C | VAL | C | 49 | 37.372 | 5.680 | 39.997 | 1.00 31.03 | C |
| ATOM | 2172 | O | VAL | C | 49 | 37.936 | 6.572 | 39.365 | 1.00 30.17 | O |
| ATOM | 2173 | CB | VAL | C | 49 | 39.021 | 4.288 | 41.268 | 1.00 27.65 | C |
| ATOM | 2174 | CG1 | VAL | C | 49 | 39.719 | 4.131 | 42.581 | 1.00 27.80 | C |
| ATOM | 2175 | CG2 | VAL | C | 49 | 38.591 | 2.924 | 40.828 | 1.00 27.38 | C |
| ATOM | 2176 | N | VAL | C | 50 | 36.319 | 5.056 | 39.478 | 1.00 29.68 | N |
| ATOM | 2177 | CA | VAL | C | 50 | 35.727 | 5.548 | 38.255 | 1.00 29.53 | C |
| ATOM | 2178 | C | VAL | C | 50 | 34.932 | 6.806 | 38.559 | 1.00 28.57 | C |
| ATOM | 2179 | O | VAL | C | 50 | 35.069 | 7.755 | 37.800 | 1.00 30.41 | O |
| ATOM | 2180 | CB | VAL | C | 50 | 34.904 | 4.446 | 37.554 | 1.00 30.06 | C |
| ATOM | 2181 | CG1 | VAL | C | 50 | 34.026 | 4.900 | 36.371 | 1.00 28.50 | C |
| ATOM | 2182 | CG2 | VAL | C | 50 | 35.916 | 3.457 | 37.070 | 1.00 29.52 | C |
| ATOM | 2183 | N | GLN | C | 51 | 34.147 | 6.917 | 39.639 | 1.00 28.05 | N |
| ATOM | 2184 | CA | GLN | C | 51 | 33.421 | 8.148 | 39.945 | 1.00 27.55 | C |
| ATOM | 2185 | C | GLN | C | 51 | 34.267 | 9.336 | 40.379 | 1.00 26.77 | C |
| ATOM | 2186 | O | GLN | C | 51 | 33.957 | 10.480 | 40.061 | 1.00 27.78 | O |
| ATOM | 2187 | CB | GLN | C | 51 | 32.276 | 7.962 | 40.944 | 1.00 27.95 | C |
| ATOM | 2188 | CG | GLN | C | 51 | 31.142 | 7.029 | 40.503 | 1.00 31.66 | C |
| ATOM | 2189 | CD | GLN | C | 51 | 30.518 | 7.274 | 39.121 | 1.00 35.14 | C |
| ATOM | 2190 | OE1 | GLN | C | 51 | 30.531 | 8.353 | 38.510 | 1.00 34.94 | O |
| ATOM | 2191 | NE2 | GLN | C | 51 | 29.945 | 6.214 | 38.566 | 1.00 36.11 | N |
| ATOM | 2192 | N | LEU | C | 52 | 35.349 | 9.130 | 41.113 | 1.00 24.84 | N |
| ATOM | 2193 | CA | LEU | C | 52 | 36.290 | 10.188 | 41.316 | 1.00 24.73 | C |
| ATOM | 2194 | C | LEU | C | 52 | 36.914 | 10.560 | 40.004 | 1.00 25.82 | C |
| ATOM | 2195 | O | LEU | C | 52 | 37.061 | 11.752 | 39.750 | 1.00 26.91 | O |
| ATOM | 2196 | CB | LEU | C | 52 | 37.349 | 9.754 | 42.251 | 1.00 25.92 | C |
| ATOM | 2197 | CG | LEU | C | 52 | 36.831 | 9.701 | 43.653 | 1.00 27.26 | C |
| ATOM | 2198 | CD1 | LEU | C | 52 | 37.880 | 9.090 | 44.510 | 1.00 27.86 | C |
| ATOM | 2199 | CD2 | LEU | C | 52 | 36.473 | 11.078 | 44.141 | 1.00 27.93 | C |
| ATOM | 2200 | N | SER | C | 53 | 37.211 | 9.566 | 39.148 | 1.00 27.18 | N |
| ATOM | 2201 | CA | SER | C | 53 | 37.788 | 9.790 | 37.838 | 1.00 24.69 | C |
| ATOM | 2202 | C | SER | C | 53 | 36.859 | 10.558 | 36.918 | 1.00 26.00 | C |
| ATOM | 2203 | O | SER | C | 53 | 37.336 | 11.388 | 36.166 | 1.00 26.97 | O |
| ATOM | 2204 | CB | SER | C | 53 | 38.172 | 8.499 | 37.198 | 1.00 25.64 | C |
| ATOM | 2205 | OG | SER | C | 53 | 38.902 | 8.772 | 36.019 | 1.00 24.45 | O |
| ATOM | 2206 | N | ASP | C | 54 | 35.544 | 10.421 | 36.932 | 1.00 27.50 | N |
| ATOM | 2207 | CA | ASP | C | 54 | 34.743 | 11.292 | 36.113 | 1.00 29.13 | C |
| ATOM | 2208 | C | ASP | C | 54 | 34.719 | 12.679 | 36.663 | 1.00 27.20 | C |
| ATOM | 2209 | O | ASP | C | 54 | 34.826 | 13.616 | 35.906 | 1.00 30.75 | O |
| ATOM | 2210 | CB | ASP | C | 54 | 33.314 | 10.874 | 36.099 | 1.00 35.74 | C |
| ATOM | 2211 | CG | ASP | C | 54 | 33.056 | 9.521 | 35.502 | 1.00 43.27 | C |
| ATOM | 2212 | OD1 | ASP | C | 54 | 33.871 | 9.016 | 34.694 | 1.00 44.80 | O |
| ATOM | 2213 | OD2 | ASP | C | 54 | 31.996 | 8.988 | 35.876 | 1.00 47.24 | O |
| ATOM | 2214 | N | SER | C | 55 | 34.554 | 12.829 | 37.966 | 1.00 26.41 | N |
| ATOM | 2215 | CA | SER | C | 55 | 34.470 | 14.119 | 38.610 | 1.00 23.34 | C |
| ATOM | 2216 | C | SER | C | 55 | 35.676 | 14.964 | 38.382 | 1.00 19.99 | C |
| ATOM | 2217 | O | SER | C | 55 | 35.544 | 16.157 | 38.175 | 1.00 20.42 | O |
| ATOM | 2218 | CB | SER | C | 55 | 34.306 | 13.948 | 40.105 | 1.00 24.40 | C |
| ATOM | 2219 | OG | SER | C | 55 | 33.079 | 13.321 | 40.431 | 1.00 24.29 | O |
| ATOM | 2220 | N | LEU | C | 56 | 36.837 | 14.338 | 38.432 | 1.00 19.40 | N |
| ATOM | 2221 | CA | LEU | C | 56 | 38.082 | 15.062 | 38.245 | 1.00 21.98 | C |
| ATOM | 2222 | C | LEU | C | 56 | 38.333 | 15.488 | 36.797 | 1.00 23.22 | C |
| ATOM | 2223 | O | LEU | C | 56 | 38.922 | 16.543 | 36.512 | 1.00 21.76 | O |
| ATOM | 2224 | CB | LEU | C | 56 | 39.301 | 14.271 | 38.793 | 1.00 21.06 | C |
| ATOM | 2225 | CG | LEU | C | 56 | 39.614 | 14.342 | 40.291 | 1.00 19.56 | C |
| ATOM | 2226 | CD1 | LEU | C | 56 | 40.647 | 13.313 | 40.678 | 1.00 18.16 | C |

FIGURE 8A-48

| | | | | | | | | | | |
|---|---|---|---|---|---|---|---|---|---|---|
| ATOM | 2227 | CD2 | LEU | C | 56 | 40.132 | 15.717 | 40.651 | 1.00 16.61 | C |
| ATOM | 2228 | N | THR | C | 57 | 37.873 | 14.624 | 35.881 | 1.00 25.77 | N |
| ATOM | 2229 | CA | THR | C | 57 | 37.991 | 14.906 | 34.462 | 1.00 28.23 | C |
| ATOM | 2230 | C | THR | C | 57 | 37.020 | 16.004 | 34.104 | 1.00 28.03 | C |
| ATOM | 2231 | O | THR | C | 57 | 37.390 | 16.908 | 33.364 | 1.00 31.55 | O |
| ATOM | 2232 | CB | THR | C | 57 | 37.813 | 13.669 | 33.596 | 1.00 30.08 | C |
| ATOM | 2233 | OG1 | THR | C | 57 | 38.904 | 12.849 | 33.972 | 1.00 32.28 | O |
| ATOM | 2234 | CG2 | THR | C | 57 | 38.044 | 13.945 | 32.109 | 1.00 33.98 | C |
| ATOM | 2235 | N | ASP | C | 58 | 35.831 | 16.009 | 34.675 | 1.00 26.77 | N |
| ATOM | 2236 | CA | ASP | C | 58 | 34.940 | 17.120 | 34.486 | 1.00 29.31 | C |
| ATOM | 2237 | C | ASP | C | 58 | 35.387 | 18.422 | 35.173 | 1.00 28.49 | C |
| ATOM | 2238 | O | ASP | C | 58 | 35.241 | 19.515 | 34.614 | 1.00 29.44 | O |
| ATOM | 2239 | CB | ASP | C | 58 | 33.489 | 16.679 | 34.870 | 1.00 36.00 | C |
| ATOM | 2240 | CG | ASP | C | 58 | 32.849 | 15.532 | 34.032 | 1.00 40.53 | C |
| ATOM | 2241 | OD1 | ASP | C | 58 | 33.503 | 14.924 | 33.151 | 1.00 41.90 | O |
| ATOM | 2242 | OD2 | ASP | C | 58 | 31.673 | 15.229 | 34.294 | 1.00 42.29 | O |
| ATOM | 2243 | N | LEU | C | 59 | 35.964 | 18.350 | 36.383 | 1.00 26.07 | N |
| ATOM | 2244 | CA | LEU | C | 59 | 36.486 | 19.508 | 37.074 | 1.00 21.52 | C |
| ATOM | 2245 | C | LEU | C | 59 | 37.611 | 20.115 | 36.285 | 1.00 19.04 | C |
| ATOM | 2246 | O | LEU | C | 59 | 37.748 | 21.317 | 36.312 | 1.00 20.31 | O |
| ATOM | 2247 | CB | LEU | C | 59 | 37.028 | 19.118 | 38.444 | 1.00 19.27 | C |
| ATOM | 2248 | CG | LEU | C | 59 | 37.519 | 20.223 | 39.377 | 1.00 18.52 | C |
| ATOM | 2249 | CD1 | LEU | C | 59 | 36.411 | 21.181 | 39.805 | 1.00 14.85 | C |
| ATOM | 2250 | CD2 | LEU | C | 59 | 38.147 | 19.538 | 40.574 | 1.00 18.90 | C |
| ATOM | 2251 | N | LEU | C | 60 | 38.399 | 19.348 | 35.353 | 1.00 19.17 | N |
| ATOM | 2252 | CA | LEU | C | 60 | 39.549 | 19.854 | 34.840 | 1.00 20.10 | C |
| ATOM | 2253 | C | LEU | C | 60 | 39.173 | 20.833 | 33.766 | 1.00 22.23 | C |
| ATOM | 2254 | O | LEU | C | 60 | 39.912 | 21.768 | 33.474 | 1.00 24.00 | O |
| ATOM | 2255 | CB | LEU | C | 60 | 40.290 | 18.718 | 34.206 | 1.00 18.56 | C |
| ATOM | 2256 | CG | LEU | C | 60 | 41.582 | 19.115 | 33.520 | 1.00 19.76 | C |
| ATOM | 2257 | CD1 | LEU | C | 60 | 42.638 | 19.404 | 34.561 | 1.00 17.43 | C |
| ATOM | 2258 | CD2 | LEU | C | 60 | 42.018 | 18.002 | 32.555 | 1.00 20.53 | C |
| ATOM | 2259 | N | ASP | C | 61 | 37.984 | 20.629 | 33.214 | 1.00 25.53 | N |
| ATOM | 2260 | CA | ASP | C | 61 | 37.471 | 21.478 | 32.157 | 1.00 27.32 | C |
| ATOM | 2261 | C | ASP | C | 61 | 36.950 | 22.809 | 32.666 | 1.00 24.92 | C |
| ATOM | 2262 | O | ASP | C | 61 | 36.768 | 23.738 | 31.883 | 1.00 26.04 | O |
| ATOM | 2263 | CB | ASP | C | 61 | 36.365 | 20.729 | 31.389 | 1.00 35.92 | C |
| ATOM | 2264 | CG | ASP | C | 61 | 36.753 | 19.367 | 30.759 | 1.00 45.09 | C |
| ATOM | 2265 | OD1 | ASP | C | 61 | 37.808 | 19.241 | 30.086 | 1.00 48.21 | O |
| ATOM | 2266 | OD2 | ASP | C | 61 | 35.970 | 18.414 | 30.956 | 1.00 49.47 | O |
| ATOM | 2267 | N | LYS | C | 62 | 36.733 | 22.956 | 33.979 | 1.00 22.12 | N |
| ATOM | 2268 | CA | LYS | C | 62 | 36.379 | 24.234 | 34.559 | 1.00 18.62 | C |
| ATOM | 2269 | C | LYS | C | 62 | 37.603 | 25.082 | 34.727 | 1.00 17.52 | C |
| ATOM | 2270 | O | LYS | C | 62 | 37.491 | 26.205 | 35.176 | 1.00 19.68 | O |
| ATOM | 2271 | CB | LYS | C | 62 | 35.718 | 24.064 | 35.888 | 1.00 17.21 | C |
| ATOM | 2272 | CG | LYS | C | 62 | 34.590 | 23.048 | 35.893 | 1.00 20.59 | C |
| ATOM | 2273 | CD | LYS | C | 62 | 33.552 | 23.302 | 34.802 | 1.00 23.94 | C |
| ATOM | 2274 | CE | LYS | C | 62 | 32.302 | 22.398 | 34.907 | 1.00 27.69 | C |
| ATOM | 2275 | NZ | LYS | C | 62 | 32.621 | 20.990 | 35.112 | 1.00 33.53 | N |
| ATOM | 2276 | N | PHE | C | 63 | 38.792 | 24.629 | 34.385 | 1.00 16.95 | N |
| ATOM | 2277 | CA | PHE | C | 63 | 39.980 | 25.398 | 34.650 | 1.00 18.75 | C |
| ATOM | 2278 | C | PHE | C | 63 | 40.714 | 25.584 | 33.363 | 1.00 20.52 | C |
| ATOM | 2279 | O | PHE | C | 63 | 40.491 | 24.894 | 32.375 | 1.00 22.83 | O |
| ATOM | 2280 | CB | PHE | C | 63 | 40.890 | 24.728 | 35.712 | 1.00 16.49 | C |
| ATOM | 2281 | CG | PHE | C | 63 | 40.280 | 24.790 | 37.109 | 1.00 15.86 | C |
| ATOM | 2282 | CD1 | PHE | C | 63 | 40.413 | 25.931 | 37.893 | 1.00 15.21 | C |
| ATOM | 2283 | CD2 | PHE | C | 63 | 39.475 | 23.764 | 37.555 | 1.00 16.14 | C |
| ATOM | 2284 | CE1 | PHE | C | 63 | 39.717 | 26.070 | 39.078 | 1.00 11.64 | C |
| ATOM | 2285 | CE2 | PHE | C | 63 | 38.742 | 23.932 | 38.732 | 1.00 17.01 | C |
| ATOM | 2286 | CZ | PHE | C | 63 | 38.864 | 25.086 | 39.487 | 1.00 11.68 | C |

FIGURE 8A-49

| ATOM | 2287 | N   | SER | C | 64 | 41.606 | 26.540 | 33.393 | 1.00 | 22.26 | N |
|------|------|-----|-----|---|----|--------|--------|--------|------|-------|---|
| ATOM | 2288 | CA  | SER | C | 64 | 42.458 | 26.748 | 32.268 | 1.00 | 25.03 | C |
| ATOM | 2289 | C   | SER | C | 64 | 43.928 | 26.724 | 32.651 | 1.00 | 27.32 | C |
| ATOM | 2290 | O   | SER | C | 64 | 44.339 | 27.274 | 33.668 | 1.00 | 29.54 | O |
| ATOM | 2291 | CB  | SER | C | 64 | 41.951 | 28.036 | 31.682 | 1.00 | 27.42 | C |
| ATOM | 2292 | OG  | SER | C | 64 | 42.936 | 28.782 | 30.987 | 1.00 | 33.90 | O |
| ATOM | 2293 | N   | ASN | C | 65 | 44.750 | 26.056 | 31.838 | 1.00 | 29.09 | N |
| ATOM | 2294 | CA  | ASN | C | 65 | 46.183 | 25.967 | 32.048 | 1.00 | 29.94 | C |
| ATOM | 2295 | C   | ASN | C | 65 | 46.912 | 27.280 | 31.894 | 1.00 | 31.16 | C |
| ATOM | 2296 | O   | ASN | C | 65 | 46.482 | 28.228 | 31.252 | 1.00 | 32.15 | O |
| ATOM | 2297 | CB  | ASN | C | 65 | 46.770 | 24.950 | 31.088 | 1.00 | 31.52 | C |
| ATOM | 2298 | CG  | ASN | C | 65 | 48.076 | 24.325 | 31.558 | 1.00 | 31.71 | C |
| ATOM | 2299 | OD1 | ASN | C | 65 | 48.626 | 24.591 | 32.636 | 1.00 | 30.12 | O |
| ATOM | 2300 | ND2 | ASN | C | 65 | 48.554 | 23.457 | 30.676 | 1.00 | 32.43 | N |
| ATOM | 2301 | N   | ILE | C | 66 | 48.053 | 27.328 | 32.558 | 1.00 | 34.70 | N |
| ATOM | 2302 | CA  | ILE | C | 66 | 48.822 | 28.549 | 32.743 | 1.00 | 38.02 | C |
| ATOM | 2303 | C   | ILE | C | 66 | 50.279 | 28.139 | 32.567 | 1.00 | 39.89 | C |
| ATOM | 2304 | O   | ILE | C | 66 | 50.733 | 27.095 | 33.077 | 1.00 | 40.56 | O |
| ATOM | 2305 | CB  | ILE | C | 66 | 48.560 | 29.130 | 34.181 | 1.00 | 37.96 | C |
| ATOM | 2306 | CG1 | ILE | C | 66 | 47.097 | 29.513 | 34.381 | 1.00 | 37.79 | C |
| ATOM | 2307 | CG2 | ILE | C | 66 | 49.443 | 30.334 | 34.443 | 1.00 | 37.53 | C |
| ATOM | 2308 | CD1 | ILE | C | 66 | 46.677 | 29.759 | 35.833 | 1.00 | 39.98 | C |
| ATOM | 2309 | N   | SER | C | 67 | 50.960 | 29.038 | 31.828 | 1.00 | 41.75 | N |
| ATOM | 2310 | CA  | SER | C | 67 | 52.349 | 28.856 | 31.397 | 1.00 | 44.33 | C |
| ATOM | 2311 | C   | SER | C | 67 | 53.320 | 28.647 | 32.536 | 1.00 | 44.00 | C |
| ATOM | 2312 | O   | SER | C | 67 | 54.160 | 27.762 | 32.527 | 1.00 | 44.13 | O |
| ATOM | 2313 | CB  | SER | C | 67 | 52.833 | 30.063 | 30.588 | 1.00 | 45.04 | C |
| ATOM | 2314 | OG  | SER | C | 67 | 52.984 | 31.250 | 31.372 | 1.00 | 50.12 | O |
| ATOM | 2315 | N   | GLU | C | 68 | 53.150 | 29.510 | 33.517 | 1.00 | 46.29 | N |
| ATOM | 2316 | CA  | GLU | C | 68 | 53.969 | 29.520 | 34.702 | 1.00 | 49.75 | C |
| ATOM | 2317 | C   | GLU | C | 68 | 53.215 | 29.731 | 36.043 | 1.00 | 48.90 | C |
| ATOM | 2318 | O   | GLU | C | 68 | 52.374 | 30.624 | 36.267 | 1.00 | 49.09 | O |
| ATOM | 2319 | CB  | GLU | C | 68 | 55.066 | 30.581 | 34.479 | 1.00 | 53.81 | C |
| ATOM | 2320 | CG  | GLU | C | 68 | 56.220 | 30.174 | 33.547 | 1.00 | 59.46 | C |
| ATOM | 2321 | CD  | GLU | C | 68 | 57.364 | 29.378 | 34.192 | 1.00 | 63.46 | C |
| ATOM | 2322 | OE1 | GLU | C | 68 | 57.165 | 28.736 | 35.239 | 1.00 | 65.40 | O |
| ATOM | 2323 | OE2 | GLU | C | 68 | 58.477 | 29.413 | 33.642 | 1.00 | 65.78 | O |
| ATOM | 2324 | N   | GLY | C | 69 | 53.643 | 28.896 | 36.995 | 1.00 | 46.18 | N |
| ATOM | 2325 | CA  | GLY | C | 69 | 52.938 | 28.734 | 38.244 | 1.00 | 41.09 | C |
| ATOM | 2326 | C   | GLY | C | 69 | 52.252 | 27.398 | 38.142 | 1.00 | 37.69 | C |
| ATOM | 2327 | O   | GLY | C | 69 | 51.845 | 26.975 | 37.057 | 1.00 | 38.22 | O |
| ATOM | 2328 | N   | LEU | C | 70 | 52.181 | 26.712 | 39.279 | 1.00 | 34.58 | N |
| ATOM | 2329 | CA  | LEU | C | 70 | 51.394 | 25.484 | 39.339 | 1.00 | 30.54 | C |
| ATOM | 2330 | C   | LEU | C | 70 | 49.895 | 25.821 | 39.513 | 1.00 | 28.30 | C |
| ATOM | 2331 | O   | LEU | C | 70 | 49.411 | 26.367 | 40.513 | 1.00 | 29.19 | O |
| ATOM | 2332 | CB  | LEU | C | 70 | 51.895 | 24.714 | 40.615 | 1.00 | 28.69 | C |
| ATOM | 2333 | CG  | LEU | C | 70 | 51.380 | 23.328 | 40.950 | 1.00 | 27.08 | C |
| ATOM | 2334 | CD1 | LEU | C | 70 | 51.749 | 22.340 | 39.816 | 1.00 | 26.63 | C |
| ATOM | 2335 | CD2 | LEU | C | 70 | 51.914 | 22.939 | 42.329 | 1.00 | 22.67 | C |
| ATOM | 2336 | N   | SER | C | 71 | 49.173 | 25.536 | 38.430 | 1.00 | 23.37 | N |
| ATOM | 2337 | CA  | SER | C | 71 | 47.795 | 25.909 | 38.342 | 1.00 | 18.79 | C |
| ATOM | 2338 | C   | SER | C | 71 | 46.961 | 24.732 | 38.737 | 1.00 | 14.59 | C |
| ATOM | 2339 | O   | SER | C | 71 | 47.420 | 23.616 | 38.830 | 1.00 | 13.92 | O |
| ATOM | 2340 | CB  | SER | C | 71 | 47.499 | 26.362 | 36.929 | 1.00 | 19.04 | C |
| ATOM | 2341 | OG  | SER | C | 71 | 47.794 | 25.282 | 36.073 | 1.00 | 21.34 | O |
| ATOM | 2342 | N   | ASN | C | 72 | 45.691 | 25.004 | 38.938 | 1.00 | 15.21 | N |
| ATOM | 2343 | CA  | ASN | C | 72 | 44.712 | 24.002 | 39.262 | 1.00 | 16.38 | C |
| ATOM | 2344 | C   | ASN | C | 72 | 44.530 | 23.023 | 38.120 | 1.00 | 17.89 | C |
| ATOM | 2345 | O   | ASN | C | 72 | 44.330 | 21.836 | 38.358 | 1.00 | 19.68 | O |
| ATOM | 2346 | CB  | ASN | C | 72 | 43.395 | 24.668 | 39.627 | 1.00 | 14.20 | C |

FIGURE 8A-50

| | | | | | | | | | |
|---|---|---|---|---|---|---|---|---|---|
| ATOM | 2347 | CG | ASN | C | 72 | 43.443 | 25.398 | 40.958 | 1.00 16.98 |
| ATOM | 2348 | OD1 | ASN | C | 72 | 44.439 | 25.399 | 41.698 | 1.00 15.50 |
| ATOM | 2349 | ND2 | ASN | C | 72 | 42.348 | 26.051 | 41.315 | 1.00 16.58 |
| ATOM | 2350 | N | TYR | C | 73 | 44.626 | 23.493 | 36.878 | 1.00 17.45 |
| ATOM | 2351 | CA | TYR | C | 73 | 44.546 | 22.649 | 35.715 | 1.00 16.35 |
| ATOM | 2352 | C | TYR | C | 73 | 45.628 | 21.603 | 35.846 | 1.00 16.88 |
| ATOM | 2353 | O | TYR | C | 73 | 45.388 | 20.407 | 35.803 | 1.00 18.90 |
| ATOM | 2354 | CB | TYR | C | 73 | 44.797 | 23.540 | 34.503 | 1.00 14.79 |
| ATOM | 2355 | CG | TYR | C | 73 | 44.618 | 22.779 | 33.215 | 1.00 18.01 |
| ATOM | 2356 | CD1 | TYR | C | 73 | 45.649 | 22.000 | 32.745 | 1.00 18.75 |
| ATOM | 2357 | CD2 | TYR | C | 73 | 43.428 | 22.809 | 32.544 | 1.00 17.80 |
| ATOM | 2358 | CE1 | TYR | C | 73 | 45.507 | 21.189 | 31.632 | 1.00 23.12 |
| ATOM | 2359 | CE2 | TYR | C | 73 | 43.282 | 22.000 | 31.424 | 1.00 23.77 |
| ATOM | 2360 | CZ | TYR | C | 73 | 44.300 | 21.160 | 30.987 | 1.00 22.85 |
| ATOM | 2361 | OH | TYR | C | 73 | 44.105 | 20.242 | 29.959 | 1.00 27.47 |
| ATOM | 2362 | N | SER | C | 74 | 46.846 | 22.071 | 36.054 | 1.00 19.27 |
| ATOM | 2363 | CA | SER | C | 74 | 48.037 | 21.234 | 36.196 | 1.00 18.80 |
| ATOM | 2364 | C | SER | C | 74 | 47.939 | 20.205 | 37.316 | 1.00 18.49 |
| ATOM | 2365 | O | SER | C | 74 | 48.192 | 19.026 | 37.062 | 1.00 18.14 |
| ATOM | 2366 | CB | SER | C | 74 | 49.160 | 22.197 | 36.410 | 1.00 19.97 |
| ATOM | 2367 | OG | SER | C | 74 | 50.345 | 21.552 | 36.749 | 1.00 27.05 |
| ATOM | 2368 | N | ILE | C | 75 | 47.536 | 20.603 | 38.532 | 1.00 17.15 |
| ATOM | 2369 | CA | ILE | C | 75 | 47.360 | 19.670 | 39.640 | 1.00 15.78 |
| ATOM | 2370 | C | ILE | C | 75 | 46.266 | 18.688 | 39.303 | 1.00 15.56 |
| ATOM | 2371 | O | ILE | C | 75 | 46.392 | 17.487 | 39.540 | 1.00 15.90 |
| ATOM | 2372 | CB | ILE | C | 75 | 47.004 | 20.373 | 40.994 | 1.00 14.47 |
| ATOM | 2373 | CG1 | ILE | C | 75 | 48.069 | 21.396 | 41.311 | 1.00 15.08 |
| ATOM | 2374 | CG2 | ILE | C | 75 | 46.847 | 19.406 | 42.151 | 1.00 9.44 |
| ATOM | 2375 | CD1 | ILE | C | 75 | 47.662 | 22.494 | 42.334 | 1.00 16.06 |
| ATOM | 2376 | N | ILE | C | 76 | 45.174 | 19.165 | 38.739 | 1.00 15.87 |
| ATOM | 2377 | CA | ILE | C | 76 | 44.072 | 18.254 | 38.540 | 1.00 16.45 |
| ATOM | 2378 | C | ILE | C | 76 | 44.423 | 17.278 | 37.416 | 1.00 18.42 |
| ATOM | 2379 | O | ILE | C | 76 | 44.047 | 16.107 | 37.479 | 1.00 21.96 |
| ATOM | 2380 | CB | ILE | C | 76 | 42.777 | 19.029 | 38.276 | 1.00 16.99 |
| ATOM | 2381 | CG1 | ILE | C | 76 | 42.407 | 20.014 | 39.366 | 1.00 18.36 |
| ATOM | 2382 | CG2 | ILE | C | 76 | 41.661 | 18.026 | 38.294 | 1.00 18.72 |
| ATOM | 2383 | CD1 | ILE | C | 76 | 41.376 | 21.090 | 38.981 | 1.00 13.71 |
| ATOM | 2384 | N | ASP | C | 77 | 45.169 | 17.686 | 36.395 | 1.00 19.28 |
| ATOM | 2385 | CA | ASP | C | 77 | 45.673 | 16.806 | 35.340 | 1.00 20.35 |
| ATOM | 2386 | C | ASP | C | 77 | 46.477 | 15.616 | 35.867 | 1.00 18.75 |
| ATOM | 2387 | O | ASP | C | 77 | 46.259 | 14.474 | 35.483 | 1.00 20.55 |
| ATOM | 2388 | CB | ASP | C | 77 | 46.528 | 17.679 | 34.388 | 1.00 23.72 |
| ATOM | 2389 | CG | ASP | C | 77 | 46.796 | 17.143 | 32.984 | 1.00 27.17 |
| ATOM | 2390 | OD1 | ASP | C | 77 | 46.195 | 16.148 | 32.611 | 1.00 29.11 |
| ATOM | 2391 | OD2 | ASP | C | 77 | 47.586 | 17.723 | 32.239 | 1.00 31.91 |
| ATOM | 2392 | N | LYS | C | 78 | 47.401 | 15.826 | 36.791 | 1.00 18.00 |
| ATOM | 2393 | CA | LYS | C | 78 | 48.064 | 14.729 | 37.494 | 1.00 19.18 |
| ATOM | 2394 | C | LYS | C | 78 | 47.114 | 13.802 | 38.229 | 1.00 16.84 |
| ATOM | 2395 | O | LYS | C | 78 | 47.200 | 12.586 | 38.170 | 1.00 18.34 |
| ATOM | 2396 | CB | LYS | C | 78 | 49.017 | 15.288 | 38.533 | 1.00 21.80 |
| ATOM | 2397 | CG | LYS | C | 78 | 50.492 | 15.453 | 38.249 | 1.00 26.26 |
| ATOM | 2398 | CD | LYS | C | 78 | 50.799 | 16.212 | 36.977 | 1.00 33.33 |
| ATOM | 2399 | CE | LYS | C | 78 | 51.977 | 17.190 | 37.154 | 1.00 36.36 |
| ATOM | 2400 | NZ | LYS | C | 78 | 51.538 | 18.516 | 37.592 | 1.00 40.57 |
| ATOM | 2401 | N | LEU | C | 79 | 46.160 | 14.358 | 38.937 | 1.00 17.71 |
| ATOM | 2402 | CA | LEU | C | 79 | 45.282 | 13.528 | 39.739 | 1.00 19.39 |
| ATOM | 2403 | C | LEU | C | 79 | 44.465 | 12.641 | 38.836 | 1.00 19.34 |
| ATOM | 2404 | O | LEU | C | 79 | 44.358 | 11.479 | 39.161 | 1.00 22.92 |
| ATOM | 2405 | CB | LEU | C | 79 | 44.412 | 14.342 | 40.708 | 1.00 15.20 |
| ATOM | 2406 | CG | LEU | C | 79 | 45.179 | 15.238 | 41.695 | 1.00 14.54 |

FIGURE 8A-51

| | | | | | | | | | | | |
|---|---|---|---|---|---|---|---|---|---|---|---|
| ATOM | 2407 | CD1 | LEU | C | 79 | 44.276 | 15.934 | 42.683 | 1.00 | 15.95 | C |
| ATOM | 2408 | CD2 | LEU | C | 79 | 46.119 | 14.401 | 42.497 | 1.00 | 14.50 | C |
| ATOM | 2409 | N | VAL | C | 80 | 43.974 | 13.115 | 37.694 | 1.00 | 20.79 | N |
| ATOM | 2410 | CA | VAL | C | 80 | 43.210 | 12.349 | 36.719 | 1.00 | 19.75 | C |
| ATOM | 2411 | C | VAL | C | 80 | 44.068 | 11.231 | 36.229 | 1.00 | 20.92 | C |
| ATOM | 2412 | O | VAL | C | 80 | 43.583 | 10.133 | 36.160 | 1.00 | 19.45 | O |
| ATOM | 2413 | CB | VAL | C | 80 | 42.850 | 13.201 | 35.502 | 1.00 | 20.41 | C |
| ATOM | 2414 | CG1 | VAL | C | 80 | 42.103 | 12.364 | 34.477 | 1.00 | 22.80 | C |
| ATOM | 2415 | CG2 | VAL | C | 80 | 41.915 | 14.311 | 35.902 | 1.00 | 19.35 | C |
| ATOM | 2416 | N | ASN | C | 81 | 45.344 | 11.472 | 35.936 | 1.00 | 24.00 | N |
| ATOM | 2417 | CA | ASN | C | 81 | 46.215 | 10.435 | 35.447 | 1.00 | 24.32 | C |
| ATOM | 2418 | C | ASN | C | 81 | 46.460 | 9.366 | 36.474 | 1.00 | 25.83 | C |
| ATOM | 2419 | O | ASN | C | 81 | 46.405 | 8.188 | 36.168 | 1.00 | 27.41 | O |
| ATOM | 2420 | CB | ASN | C | 81 | 47.505 | 11.049 | 35.027 | 1.00 | 25.29 | C |
| ATOM | 2421 | CG | ASN | C | 81 | 47.389 | 11.689 | 33.658 | 1.00 | 27.98 | C |
| ATOM | 2422 | OD1 | ASN | C | 81 | 47.347 | 10.977 | 32.667 | 1.00 | 30.37 | O |
| ATOM | 2423 | ND2 | ASN | C | 81 | 47.387 | 13.000 | 33.477 | 1.00 | 27.47 | N |
| ATOM | 2424 | N | ILE | C | 82 | 46.690 | 9.750 | 37.714 | 1.00 | 27.31 | N |
| ATOM | 2425 | CA | ILE | C | 82 | 46.839 | 8.819 | 38.814 | 1.00 | 27.48 | C |
| ATOM | 2426 | C | ILE | C | 82 | 45.586 | 7.971 | 39.042 | 1.00 | 29.22 | C |
| ATOM | 2427 | O | ILE | C | 82 | 45.705 | 6.766 | 39.266 | 1.00 | 32.26 | O |
| ATOM | 2428 | CB | ILE | C | 82 | 47.228 | 9.685 | 40.022 | 1.00 | 26.77 | C |
| ATOM | 2429 | CG1 | ILE | C | 82 | 48.662 | 10.131 | 39.852 | 1.00 | 24.85 | C |
| ATOM | 2430 | CG2 | ILE | C | 82 | 47.046 | 8.977 | 41.344 | 1.00 | 26.49 | C |
| ATOM | 2431 | CD1 | ILE | C | 82 | 49.159 | 11.193 | 40.833 | 1.00 | 24.34 | C |
| ATOM | 2432 | N | VAL | C | 83 | 44.371 | 8.547 | 38.968 | 1.00 | 30.80 | N |
| ATOM | 2433 | CA | VAL | C | 83 | 43.099 | 7.834 | 39.209 | 1.00 | 29.90 | C |
| ATOM | 2434 | C | VAL | C | 83 | 42.793 | 6.906 | 38.019 | 1.00 | 30.67 | C |
| ATOM | 2435 | O | VAL | C | 83 | 42.229 | 5.824 | 38.195 | 1.00 | 29.90 | O |
| ATOM | 2436 | CB | VAL | C | 83 | 41.888 | 8.816 | 39.455 | 1.00 | 27.23 | C |
| ATOM | 2437 | CG1 | VAL | C | 83 | 40.651 | 8.141 | 39.973 | 1.00 | 28.89 | C |
| ATOM | 2438 | CG2 | VAL | C | 83 | 42.154 | 9.759 | 40.558 | 1.00 | 28.33 | C |
| ATOM | 2439 | N | ASP | C | 84 | 43.174 | 7.298 | 36.797 | 1.00 | 31.05 | N |
| ATOM | 2440 | CA | ASP | C | 84 | 42.971 | 6.473 | 35.629 | 1.00 | 31.24 | C |
| ATOM | 2441 | C | ASP | C | 84 | 43.761 | 5.196 | 35.686 | 1.00 | 32.41 | C |
| ATOM | 2442 | O | ASP | C | 84 | 43.233 | 4.156 | 35.291 | 1.00 | 32.47 | O |
| ATOM | 2443 | CB | ASP | C | 84 | 43.296 | 7.192 | 34.350 | 1.00 | 31.90 | C |
| ATOM | 2444 | CG | ASP | C | 84 | 42.233 | 8.181 | 33.899 | 1.00 | 36.65 | C |
| ATOM | 2445 | OD1 | ASP | C | 84 | 41.105 | 8.177 | 34.417 | 1.00 | 37.73 | O |
| ATOM | 2446 | OD2 | ASP | C | 84 | 42.537 | 8.969 | 33.000 | 1.00 | 40.83 | O |
| ATOM | 2447 | N | ASP | C | 85 | 44.988 | 5.287 | 36.202 | 1.00 | 31.95 | N |
| ATOM | 2448 | CA | ASP | C | 85 | 45.770 | 4.128 | 36.589 | 1.00 | 34.69 | C |
| ATOM | 2449 | C | ASP | C | 85 | 45.189 | 3.114 | 37.564 | 1.00 | 34.70 | C |
| ATOM | 2450 | O | ASP | C | 85 | 45.464 | 1.921 | 37.471 | 1.00 | 34.86 | O |
| ATOM | 2451 | CB | ASP | C | 85 | 47.030 | 4.593 | 37.248 | 1.00 | 37.43 | C |
| ATOM | 2452 | CG | ASP | C | 85 | 48.101 | 5.028 | 36.290 | 1.00 | 41.26 | C |
| ATOM | 2453 | OD1 | ASP | C | 85 | 47.860 | 4.978 | 35.077 | 1.00 | 45.93 | O |
| ATOM | 2454 | OD2 | ASP | C | 85 | 49.169 | 5.423 | 36.776 | 1.00 | 43.39 | O |
| ATOM | 2455 | N | LEU | C | 86 | 44.445 | 3.587 | 38.552 | 1.00 | 34.35 | N |
| ATOM | 2456 | CA | LEU | C | 86 | 43.783 | 2.717 | 39.498 | 1.00 | 34.80 | C |
| ATOM | 2457 | C | LEU | C | 86 | 42.525 | 2.164 | 38.889 | 1.00 | 34.98 | C |
| ATOM | 2458 | O | LEU | C | 86 | 42.117 | 1.094 | 39.288 | 1.00 | 36.02 | O |
| ATOM | 2459 | CB | LEU | C | 86 | 43.443 | 3.508 | 40.735 | 1.00 | 35.24 | C |
| ATOM | 2460 | CG | LEU | C | 86 | 44.591 | 4.321 | 41.331 | 1.00 | 37.43 | C |
| ATOM | 2461 | CD1 | LEU | C | 86 | 44.052 | 5.240 | 42.407 | 1.00 | 38.91 | C |
| ATOM | 2462 | CD2 | LEU | C | 86 | 45.728 | 3.422 | 41.825 | 1.00 | 37.75 | C |
| ATOM | 2463 | N | VAL | C | 87 | 41.886 | 2.866 | 37.939 | 1.00 | 37.37 | N |
| ATOM | 2464 | CA | VAL | C | 87 | 40.748 | 2.365 | 37.175 | 1.00 | 38.56 | C |
| ATOM | 2465 | C | VAL | C | 87 | 41.236 | 1.205 | 36.320 | 1.00 | 41.43 | C |
| ATOM | 2466 | O | VAL | C | 87 | 40.621 | 0.154 | 36.337 | 1.00 | 43.44 | O |

FIGURE 8A-52

| | | | | | | | | | | |
|---|---|---|---|---|---|---|---|---|---|---|
| ATOM | 2467 | CB | VAL | C | 87 | 40.167 | 3.478 | 36.302 | 1.00 36.61 | C |
| ATOM | 2468 | CG1 | VAL | C | 87 | 39.054 | 2.945 | 35.450 | 1.00 37.46 | C |
| ATOM | 2469 | CG2 | VAL | C | 87 | 39.592 | 4.584 | 37.139 | 1.00 35.39 | C |
| ATOM | 2470 | N | GLU | C | 88 | 42.356 | 1.329 | 35.613 | 1.00 45.33 | N |
| ATOM | 2471 | CA | GLU | C | 88 | 42.933 | 0.237 | 34.842 | 1.00 50.04 | C |
| ATOM | 2472 | C | GLU | C | 88 | 43.480 | -0.856 | 35.761 | 1.00 52.28 | C |
| ATOM | 2473 | O | GLU | C | 88 | 43.503 | -2.015 | 35.374 | 1.00 53.46 | O |
| ATOM | 2474 | CB | GLU | C | 88 | 44.048 | 0.728 | 33.869 | 1.00 52.22 | C |
| ATOM | 2475 | CG | GLU | C | 88 | 43.776 | 1.785 | 32.749 | 1.00 56.99 | C |
| ATOM | 2476 | CD | GLU | C | 88 | 42.784 | 1.451 | 31.610 | 1.00 62.14 | C |
| ATOM | 2477 | OE1 | GLU | C | 88 | 42.853 | 0.348 | 31.046 | 1.00 66.19 | O |
| ATOM | 2478 | OE2 | GLU | C | 88 | 41.926 | 2.286 | 31.266 | 1.00 62.89 | O |
| ATOM | 2479 | N | CYS | C | 89 | 43.930 | -0.535 | 36.982 | 1.00 55.77 | N |
| ATOM | 2480 | CA | CYS | C | 89 | 44.471 | -1.508 | 37.936 | 1.00 58.72 | C |
| ATOM | 2481 | C | CYS | C | 89 | 43.372 | -2.333 | 38.578 | 1.00 60.22 | C |
| ATOM | 2482 | O | CYS | C | 89 | 43.624 | -3.464 | 39.000 | 1.00 61.13 | O |
| ATOM | 2483 | CB | CYS | C | 89 | 45.285 | -0.819 | 39.048 | 1.00 59.69 | C |
| ATOM | 2484 | SG | CYS | C | 89 | 46.103 | -1.924 | 40.239 | 1.00 65.48 | S |
| ATOM | 2485 | N | VAL | C | 90 | 42.159 | -1.749 | 38.657 | 1.00 61.71 | N |
| ATOM | 2486 | CA | VAL | C | 90 | 40.963 | -2.396 | 39.210 | 1.00 62.70 | C |
| ATOM | 2487 | C | VAL | C | 90 | 40.453 | -3.516 | 38.278 | 1.00 64.64 | C |
| ATOM | 2488 | O | VAL | C | 90 | 40.010 | -4.562 | 38.779 | 1.00 65.07 | O |
| ATOM | 2489 | CB | VAL | C | 90 | 39.934 | -1.260 | 39.622 | 1.00 60.49 | C |
| ATOM | 2490 | CG1 | VAL | C | 90 | 38.477 | -1.428 | 39.231 | 1.00 58.30 | C |
| ATOM | 2491 | CG2 | VAL | C | 90 | 40.023 | -1.060 | 41.125 | 1.00 58.40 | C |
| ATOM | 2492 | N | LYS | C | 91 | 40.591 | -3.348 | 36.938 | 1.00 66.41 | N |
| ATOM | 2493 | CA | LYS | C | 91 | 40.281 | -4.402 | 35.971 | 1.00 68.79 | C |
| ATOM | 2494 | C | LYS | C | 91 | 41.219 | -5.638 | 36.092 | 1.00 70.22 | C |
| ATOM | 2495 | O | LYS | C | 91 | 40.715 | -6.728 | 36.404 | 1.00 72.46 | O |
| ATOM | 2496 | CB | LYS | C | 91 | 40.233 | -3.836 | 34.530 | 1.00 68.55 | C |
| ATOM | 2497 | CG | LYS | C | 91 | 39.560 | -4.821 | 33.535 | 1.00 71.09 | C |
| ATOM | 2498 | CD | LYS | C | 91 | 39.779 | -4.534 | 32.028 | 1.00 71.78 | C |
| ATOM | 2499 | CE | LYS | C | 91 | 39.128 | -3.245 | 31.514 | 1.00 70.74 | C |
| ATOM | 2500 | NZ | LYS | C | 91 | 39.730 | -2.834 | 30.259 | 1.00 70.64 | N |
| ATOM | 2501 | N | SER | C | 104 | 25.399 | 2.470 | 38.962 | 1.00 56.13 | N |
| ATOM | 2502 | CA | SER | C | 104 | 25.444 | 3.921 | 38.739 | 1.00 55.65 | C |
| ATOM | 2503 | C | SER | C | 104 | 24.850 | 4.688 | 39.939 | 1.00 52.95 | C |
| ATOM | 2504 | O | SER | C | 104 | 23.647 | 4.968 | 39.947 | 1.00 53.89 | O |
| ATOM | 2505 | CB | SER | C | 104 | 24.797 | 4.326 | 37.337 | 1.00 57.16 | C |
| ATOM | 2506 | OG | SER | C | 104 | 23.517 | 3.792 | 36.940 | 1.00 56.67 | O |
| ATOM | 2507 | N | PRO | C | 105 | 25.618 | 5.024 | 41.000 | 1.00 49.29 | N |
| ATOM | 2508 | CA | PRO | C | 105 | 25.119 | 5.676 | 42.224 | 1.00 46.42 | C |
| ATOM | 2509 | C | PRO | C | 105 | 24.631 | 7.146 | 42.171 | 1.00 44.43 | C |
| ATOM | 2510 | O | PRO | C | 105 | 24.768 | 7.791 | 41.134 | 1.00 42.75 | O |
| ATOM | 2511 | CB | PRO | C | 105 | 26.265 | 5.445 | 43.181 | 1.00 45.66 | C |
| ATOM | 2512 | CG | PRO | C | 105 | 27.467 | 5.523 | 42.277 | 1.00 46.43 | C |
| ATOM | 2513 | CD | PRO | C | 105 | 27.036 | 4.706 | 41.089 | 1.00 47.56 | C |
| ATOM | 2514 | N | GLU | C | 106 | 24.023 | 7.707 | 43.240 | 1.00 44.38 | N |
| ATOM | 2515 | CA | GLU | C | 106 | 23.436 | 9.055 | 43.238 | 1.00 43.85 | C |
| ATOM | 2516 | C | GLU | C | 106 | 24.414 | 10.202 | 43.420 | 1.00 42.61 | C |
| ATOM | 2517 | O | GLU | C | 106 | 25.293 | 10.113 | 44.289 | 1.00 42.69 | O |
| ATOM | 2518 | CB | GLU | C | 106 | 22.321 | 9.281 | 44.289 | 1.00 45.50 | C |
| ATOM | 2519 | CG | GLU | C | 106 | 20.936 | 8.664 | 44.035 | 1.00 46.22 | C |
| ATOM | 2520 | CD | GLU | C | 106 | 20.404 | 8.761 | 42.607 | 1.00 45.82 | C |
| ATOM | 2521 | OE1 | GLU | C | 106 | 20.257 | 9.861 | 42.067 | 1.00 41.34 | O |
| ATOM | 2522 | OE2 | GLU | C | 106 | 20.152 | 7.699 | 42.032 | 1.00 48.83 | O |
| ATOM | 2523 | N | PRO | C | 107 | 24.254 | 11.291 | 42.632 | 1.00 41.36 | N |
| ATOM | 2524 | CA | PRO | C | 107 | 25.096 | 12.486 | 42.637 | 1.00 39.50 | C |
| ATOM | 2525 | C | PRO | C | 107 | 24.873 | 13.318 | 43.850 | 1.00 38.28 | C |
| ATOM | 2526 | O | PRO | C | 107 | 23.767 | 13.685 | 44.226 | 1.00 39.34 | O |

*FIGURE 8A-53*

| | | | | | | | | | |
|---|---|---|---|---|---|---|---|---|---|
| ATOM | 2527 | CB | PRO | C 107 | 24.680 | 13.288 | 41.434 | 1.00 40.28 | C |
| ATOM | 2528 | CG | PRO | C 107 | 24.151 | 12.214 | 40.519 | 1.00 42.95 | C |
| ATOM | 2529 | CD | PRO | C 107 | 23.353 | 11.358 | 41.490 | 1.00 41.93 | C |
| ATOM | 2530 | N | ARG | C 108 | 26.012 | 13.570 | 44.436 | 1.00 35.97 | N |
| ATOM | 2531 | CA | ARG | C 108 | 26.055 | 14.439 | 45.561 | 1.00 35.65 | C |
| ATOM | 2532 | C | ARG | C 108 | 26.953 | 15.609 | 45.219 | 1.00 34.88 | C |
| ATOM | 2533 | O | ARG | C 108 | 27.707 | 15.585 | 44.244 | 1.00 35.60 | O |
| ATOM | 2534 | CB | ARG | C 108 | 26.617 | 13.701 | 46.756 | 1.00 39.40 | C |
| ATOM | 2535 | CG | ARG | C 108 | 25.710 | 12.742 | 47.530 | 1.00 44.75 | C |
| ATOM | 2536 | CD | ARG | C 108 | 25.959 | 12.906 | 49.053 | 1.00 48.86 | C |
| ATOM | 2537 | NE | ARG | C 108 | 25.401 | 11.801 | 49.824 | 1.00 52.47 | N |
| ATOM | 2538 | CZ | ARG | C 108 | 25.920 | 11.400 | 50.988 | 1.00 54.55 | C |
| ATOM | 2539 | NH1 | ARG | C 108 | 26.919 | 12.095 | 51.582 | 1.00 55.13 | N |
| ATOM | 2540 | NH2 | ARG | C 108 | 25.427 | 10.267 | 51.532 | 1.00 54.84 | N |
| ATOM | 2541 | N | LEU | C 109 | 26.850 | 16.651 | 46.046 | 1.00 32.80 | N |
| ATOM | 2542 | CA | LEU | C 109 | 27.686 | 17.851 | 45.949 | 1.00 31.31 | C |
| ATOM | 2543 | C | LEU | C 109 | 28.544 | 17.984 | 47.198 | 1.00 27.53 | C |
| ATOM | 2544 | O | LEU | C 109 | 28.058 | 17.849 | 48.335 | 1.00 29.29 | O |
| ATOM | 2545 | CB | LEU | C 109 | 26.876 | 19.173 | 45.813 | 1.00 30.72 | C |
| ATOM | 2546 | CG | LEU | C 109 | 25.837 | 19.411 | 44.752 | 1.00 29.60 | C |
| ATOM | 2547 | CD1 | LEU | C 109 | 25.143 | 20.697 | 45.150 | 1.00 31.86 | C |
| ATOM | 2548 | CD2 | LEU | C 109 | 26.433 | 19.432 | 43.347 | 1.00 30.24 | C |
| ATOM | 2549 | N | PHE | C 110 | 29.841 | 18.247 | 46.995 | 1.00 24.61 | N |
| ATOM | 2550 | CA | PHE | C 110 | 30.784 | 18.289 | 48.116 | 1.00 20.67 | C |
| ATOM | 2551 | C | PHE | C 110 | 31.579 | 19.548 | 48.013 | 1.00 17.66 | C |
| ATOM | 2552 | O | PHE | C 110 | 31.746 | 20.049 | 46.924 | 1.00 19.14 | O |
| ATOM | 2553 | CB | PHE | C 110 | 31.721 | 17.098 | 48.021 | 1.00 23.08 | C |
| ATOM | 2554 | CG | PHE | C 110 | 31.049 | 15.733 | 48.163 | 1.00 22.91 | C |
| ATOM | 2555 | CD1 | PHE | C 110 | 30.793 | 15.226 | 49.426 | 1.00 20.89 | C |
| ATOM | 2556 | CD2 | PHE | C 110 | 30.737 | 15.008 | 47.024 | 1.00 23.49 | C |
| ATOM | 2557 | CE1 | PHE | C 110 | 30.269 | 13.969 | 49.565 | 1.00 21.28 | C |
| ATOM | 2558 | CE2 | PHE | C 110 | 30.186 | 13.751 | 47.178 | 1.00 24.67 | C |
| ATOM | 2559 | CZ | PHE | C 110 | 29.974 | 13.233 | 48.444 | 1.00 24.36 | C |
| ATOM | 2560 | N | THR | C 111 | 32.071 | 20.116 | 49.084 | 1.00 17.78 | N |
| ATOM | 2561 | CA | THR | C 111 | 32.961 | 21.249 | 48.978 | 1.00 18.25 | C |
| ATOM | 2562 | C | THR | C 111 | 34.337 | 20.763 | 48.509 | 1.00 21.30 | C |
| ATOM | 2563 | O | THR | C 111 | 34.518 | 19.547 | 48.617 | 1.00 26.22 | O |
| ATOM | 2564 | CB | THR | C 111 | 33.057 | 21.895 | 50.359 | 1.00 19.78 | C |
| ATOM | 2565 | OG1 | THR | C 111 | 33.780 | 20.989 | 51.199 | 1.00 19.58 | O |
| ATOM | 2566 | CG2 | THR | C 111 | 31.663 | 22.215 | 50.913 | 1.00 18.93 | C |
| ATOM | 2567 | N | PRO | C 112 | 35.360 | 21.512 | 48.024 | 1.00 19.29 | N |
| ATOM | 2568 | CA | PRO | C 112 | 36.675 | 20.962 | 47.729 | 1.00 18.39 | C |
| ATOM | 2569 | C | PRO | C 112 | 37.225 | 20.086 | 48.855 | 1.00 21.30 | C |
| ATOM | 2570 | O | PRO | C 112 | 37.605 | 18.953 | 48.611 | 1.00 22.05 | O |
| ATOM | 2571 | CB | PRO | C 112 | 37.455 | 22.226 | 47.520 | 1.00 18.00 | C |
| ATOM | 2572 | CG | PRO | C 112 | 36.455 | 23.100 | 46.801 | 1.00 16.59 | C |
| ATOM | 2573 | CD | PRO | C 112 | 35.265 | 22.919 | 47.660 | 1.00 14.34 | C |
| ATOM | 2574 | N | GLU | C 113 | 37.221 | 20.521 | 50.119 | 1.00 22.83 | N |
| ATOM | 2575 | CA | GLU | C 113 | 37.717 | 19.735 | 51.235 | 1.00 24.32 | C |
| ATOM | 2576 | C | GLU | C 113 | 37.046 | 18.394 | 51.408 | 1.00 23.52 | C |
| ATOM | 2577 | O | GLU | C 113 | 37.729 | 17.385 | 51.549 | 1.00 23.92 | O |
| ATOM | 2578 | CB | GLU | C 113 | 37.496 | 20.463 | 52.524 | 1.00 27.24 | C |
| ATOM | 2579 | CG | GLU | C 113 | 38.700 | 20.955 | 53.281 | 1.00 35.37 | C |
| ATOM | 2580 | CD | GLU | C 113 | 38.282 | 21.200 | 54.724 | 1.00 39.80 | C |
| ATOM | 2581 | OE1 | GLU | C 113 | 37.915 | 20.230 | 55.387 | 1.00 41.11 | O |
| ATOM | 2582 | OE2 | GLU | C 113 | 38.296 | 22.339 | 55.182 | 1.00 41.53 | O |
| ATOM | 2583 | N | GLU | C 114 | 35.712 | 18.350 | 51.386 | 1.00 23.35 | N |
| ATOM | 2584 | CA | GLU | C 114 | 34.968 | 17.107 | 51.535 | 1.00 23.29 | C |
| ATOM | 2585 | C | GLU | C 114 | 35.168 | 16.200 | 50.344 | 1.00 22.72 | C |
| ATOM | 2586 | O | GLU | C 114 | 35.160 | 14.981 | 50.518 | 1.00 23.79 | O |

FIGURE 8A-54

```
ATOM   2587  CB   GLU C 114     33.470  17.344  51.622  1.00 26.84           C
ATOM   2588  CG   GLU C 114     32.974  18.114  52.849  1.00 31.67           C
ATOM   2589  CD   GLU C 114     31.578  18.736  52.701  1.00 37.47           C
ATOM   2590  OE1  GLU C 114     30.884  18.533  51.681  1.00 35.31           O
ATOM   2591  OE2  GLU C 114     31.202  19.468  53.633  1.00 40.13           O
ATOM   2592  N    PHE C 115     35.320  16.775  49.143  1.00 20.03           N
ATOM   2593  CA   PHE C 115     35.606  15.979  47.971  1.00 18.15           C
ATOM   2594  C    PHE C 115     36.997  15.397  48.157  1.00 17.33           C
ATOM   2595  O    PHE C 115     37.214  14.205  48.013  1.00 18.05           O
ATOM   2596  CB   PHE C 115     35.524  16.833  46.705  1.00 15.90           C
ATOM   2597  CG   PHE C 115     35.825  16.063  45.429  1.00 17.09           C
ATOM   2598  CD1  PHE C 115     34.861  15.299  44.845  1.00 16.21           C
ATOM   2599  CD2  PHE C 115     37.094  16.093  44.890  1.00 18.64           C
ATOM   2600  CE1  PHE C 115     35.193  14.558  43.744  1.00 19.14           C
ATOM   2601  CE2  PHE C 115     37.425  15.336  43.795  1.00 18.76           C
ATOM   2602  CZ   PHE C 115     36.463  14.570  43.217  1.00 19.41           C
ATOM   2603  N    PHE C 116     38.010  16.167  48.509  1.00 19.36           N
ATOM   2604  CA   PHE C 116     39.361  15.618  48.454  1.00 17.90           C
ATOM   2605  C    PHE C 116     39.621  14.678  49.623  1.00 18.24           C
ATOM   2606  O    PHE C 116     40.505  13.855  49.549  1.00 19.98           O
ATOM   2607  CB   PHE C 116     40.376  16.744  48.162  1.00 16.33           C
ATOM   2608  CG   PHE C 116     40.442  17.170  46.679  1.00 15.27           C
ATOM   2609  CD1  PHE C 116     41.052  16.328  45.753  1.00 14.80           C
ATOM   2610  CD2  PHE C 116     39.806  18.324  46.240  1.00 12.85           C
ATOM   2611  CE1  PHE C 116     40.967  16.602  44.409  1.00 12.34           C
ATOM   2612  CE2  PHE C 116     39.715  18.569  44.885  1.00 14.12           C
ATOM   2613  CZ   PHE C 116     40.289  17.711  43.980  1.00 10.60           C
ATOM   2614  N    ARG C 117     38.755  14.664  50.641  1.00 20.78           N
ATOM   2615  CA   ARG C 117     38.796  13.751  51.770  1.00 21.33           C
ATOM   2616  C    ARG C 117     38.412  12.368  51.308  1.00 20.46           C
ATOM   2617  O    ARG C 117     39.076  11.405  51.639  1.00 21.70           O
ATOM   2618  CB   ARG C 117     37.823  14.244  52.840  1.00 21.70           C
ATOM   2619  CG   ARG C 117     37.838  13.513  54.177  1.00 27.63           C
ATOM   2620  CD   ARG C 117     36.826  14.115  55.165  1.00 29.36           C
ATOM   2621  NE   ARG C 117     37.230  15.464  55.616  1.00 32.11           N
ATOM   2622  CZ   ARG C 117     36.411  16.535  55.565  1.00 32.37           C
ATOM   2623  NH1  ARG C 117     35.179  16.464  55.047  1.00 32.61           N
ATOM   2624  NH2  ARG C 117     36.836  17.701  56.025  1.00 30.98           N
ATOM   2625  N    ILE C 118     37.342  12.263  50.540  1.00 21.91           N
ATOM   2626  CA   ILE C 118     36.897  11.031  49.882  1.00 22.55           C
ATOM   2627  C    ILE C 118     37.944  10.504  48.890  1.00 23.60           C
ATOM   2628  O    ILE C 118     38.254   9.316  48.853  1.00 24.72           O
ATOM   2629  CB   ILE C 118     35.527  11.358  49.213  1.00 22.47           C
ATOM   2630  CG1  ILE C 118     34.467  11.506  50.293  1.00 21.67           C
ATOM   2631  CG2  ILE C 118     35.117  10.338  48.161  1.00 21.48           C
ATOM   2632  CD1  ILE C 118     33.164  12.169  49.825  1.00 21.12           C
ATOM   2633  N    PHE C 119     38.544  11.402  48.103  1.00 23.86           N
ATOM   2634  CA   PHE C 119     39.633  11.098  47.186  1.00 22.73           C
ATOM   2635  C    PHE C 119     40.816  10.488  47.916  1.00 24.24           C
ATOM   2636  O    PHE C 119     41.233   9.416  47.511  1.00 24.28           O
ATOM   2637  CB   PHE C 119     40.038  12.357  46.426  1.00 15.88           C
ATOM   2638  CG   PHE C 119     41.297  12.224  45.624  1.00 15.30           C
ATOM   2639  CD1  PHE C 119     41.231  11.724  44.354  1.00 15.03           C
ATOM   2640  CD2  PHE C 119     42.495  12.639  46.172  1.00 12.85           C
ATOM   2641  CE1  PHE C 119     42.412  11.623  43.653  1.00 15.97           C
ATOM   2642  CE2  PHE C 119     43.675  12.526  45.473  1.00 15.16           C
ATOM   2643  CZ   PHE C 119     43.630  12.003  44.206  1.00 16.33           C
ATOM   2644  N    ASN C 120     41.396  11.145  48.936  1.00 26.61           N
ATOM   2645  CA   ASN C 120     42.511  10.621  49.728  1.00 27.10           C
ATOM   2646  C    ASN C 120     42.225   9.301  50.400  1.00 28.31           C
```

FIGURE 8A-55

| | | | | | | | | | | |
|---|---|---|---|---|---|---|---|---|---|---|
| ATOM | 2647 | O | ASN | C | 120 | 43.081 | 8.433 | 50.376 | 1.00 28.63 | O |
| ATOM | 2648 | CB | ASN | C | 120 | 42.959 | 11.590 | 50.783 | 1.00 24.50 | C |
| ATOM | 2649 | CG | ASN | C | 120 | 43.837 | 12.659 | 50.215 | 1.00 27.34 | C |
| ATOM | 2650 | OD1 | ASN | C | 120 | 43.864 | 13.757 | 50.761 | 1.00 32.26 | O |
| ATOM | 2651 | ND2 | ASN | C | 120 | 44.628 | 12.420 | 49.169 | 1.00 29.64 | N |
| ATOM | 2652 | N | ARG | C | 121 | 41.017 | 9.136 | 50.947 | 1.00 30.80 | N |
| ATOM | 2653 | CA | ARG | C | 121 | 40.549 | 7.862 | 51.441 | 1.00 35.49 | C |
| ATOM | 2654 | C | ARG | C | 121 | 40.514 | 6.767 | 50.357 | 1.00 36.43 | C |
| ATOM | 2655 | O | ARG | C | 121 | 40.859 | 5.615 | 50.628 | 1.00 38.58 | O |
| ATOM | 2656 | CB | ARG | C | 121 | 39.202 | 8.103 | 52.138 | 1.00 37.63 | C |
| ATOM | 2657 | CG | ARG | C | 121 | 38.534 | 6.865 | 52.651 | 1.00 42.24 | C |
| ATOM | 2658 | CD | ARG | C | 121 | 37.240 | 7.194 | 53.373 | 1.00 47.82 | C |
| ATOM | 2659 | NE | ARG | C | 121 | 36.399 | 6.001 | 53.529 | 1.00 51.79 | N |
| ATOM | 2660 | CZ | ARG | C | 121 | 36.788 | 4.912 | 54.233 | 1.00 55.38 | C |
| ATOM | 2661 | NH1 | ARG | C | 121 | 38.016 | 4.799 | 54.783 | 1.00 57.12 | N |
| ATOM | 2662 | NH2 | ARG | C | 121 | 35.928 | 3.904 | 54.446 | 1.00 55.34 | N |
| ATOM | 2663 | N | SER | C | 122 | 40.171 | 7.089 | 49.106 | 1.00 36.49 | N |
| ATOM | 2664 | CA | SER | C | 122 | 40.274 | 6.177 | 47.974 | 1.00 36.44 | C |
| ATOM | 2665 | C | SER | C | 122 | 41.660 | 5.723 | 47.529 | 1.00 37.85 | C |
| ATOM | 2666 | O | SER | C | 122 | 41.874 | 4.556 | 47.235 | 1.00 39.23 | O |
| ATOM | 2667 | CB | SER | C | 122 | 39.613 | 6.814 | 46.788 | 1.00 34.58 | C |
| ATOM | 2668 | OG | SER | C | 122 | 38.296 | 7.132 | 47.155 | 1.00 34.47 | O |
| ATOM | 2669 | N | ILE | C | 123 | 42.638 | 6.599 | 47.409 | 1.00 38.85 | N |
| ATOM | 2670 | CA | ILE | C | 123 | 43.949 | 6.180 | 46.985 | 1.00 43.11 | C |
| ATOM | 2671 | C | ILE | C | 123 | 44.589 | 5.456 | 48.157 | 1.00 46.18 | C |
| ATOM | 2672 | O | ILE | C | 123 | 45.449 | 4.614 | 47.937 | 1.00 47.69 | O |
| ATOM | 2673 | CB | ILE | C | 123 | 44.843 | 7.378 | 46.505 | 1.00 42.65 | C |
| ATOM | 2674 | CG1 | ILE | C | 123 | 44.147 | 8.410 | 45.599 | 1.00 38.38 | C |
| ATOM | 2675 | CG2 | ILE | C | 123 | 46.146 | 6.866 | 45.872 | 1.00 43.09 | C |
| ATOM | 2676 | CD1 | ILE | C | 123 | 43.242 | 7.872 | 44.489 | 1.00 35.80 | C |
| ATOM | 2677 | N | ASP | C | 124 | 44.206 | 5.755 | 49.402 | 1.00 50.61 | N |
| ATOM | 2678 | CA | ASP | C | 124 | 44.805 | 5.095 | 50.564 | 1.00 54.85 | C |
| ATOM | 2679 | C | ASP | C | 124 | 44.197 | 3.730 | 50.882 | 1.00 54.20 | C |
| ATOM | 2680 | O | ASP | C | 124 | 44.774 | 2.898 | 51.586 | 1.00 54.57 | O |
| ATOM | 2681 | CB | ASP | C | 124 | 44.788 | 5.989 | 51.823 | 1.00 59.47 | C |
| ATOM | 2682 | CG | ASP | C | 124 | 45.794 | 7.151 | 51.915 | 1.00 63.36 | C |
| ATOM | 2683 | OD1 | ASP | C | 124 | 45.935 | 7.919 | 50.949 | 1.00 63.45 | O |
| ATOM | 2684 | OD2 | ASP | C | 124 | 46.414 | 7.295 | 52.988 | 1.00 66.94 | O |
| ATOM | 2685 | N | ALA | C | 125 | 43.039 | 3.460 | 50.281 | 1.00 54.57 | N |
| ATOM | 2686 | CA | ALA | C | 125 | 42.427 | 2.137 | 50.314 | 1.00 56.99 | C |
| ATOM | 2687 | C | ALA | C | 125 | 43.150 | 1.108 | 49.440 | 1.00 58.85 | C |
| ATOM | 2688 | O | ALA | C | 125 | 42.617 | 0.022 | 49.161 | 1.00 59.46 | O |
| ATOM | 2689 | CB | ALA | C | 125 | 40.982 | 2.263 | 49.824 | 1.00 56.08 | C |
| ATOM | 2690 | N | PHE | C | 126 | 44.343 | 1.552 | 48.975 | 1.00 60.81 | N |
| ATOM | 2691 | CA | PHE | C | 126 | 45.408 | 0.793 | 48.316 | 1.00 62.82 | C |
| ATOM | 2692 | C | PHE | C | 126 | 46.675 | 0.603 | 49.241 | 1.00 64.91 | C |
| ATOM | 2693 | O | PHE | C | 126 | 47.801 | 0.492 | 48.731 | 1.00 65.88 | O |
| ATOM | 2694 | CB | PHE | C | 126 | 45.715 | 1.476 | 46.898 | 1.00 60.15 | C |
| ATOM | 2695 | CG | PHE | C | 126 | 44.638 | 1.419 | 45.778 | 1.00 57.55 | C |
| ATOM | 2696 | CD1 | PHE | C | 126 | 43.594 | 2.334 | 45.731 | 1.00 56.09 | C |
| ATOM | 2697 | CD2 | PHE | C | 126 | 44.655 | 0.421 | 44.813 | 1.00 56.90 | C |
| ATOM | 2698 | CE1 | PHE | C | 126 | 42.568 | 2.227 | 44.807 | 1.00 52.24 | C |
| ATOM | 2699 | CE2 | PHE | C | 126 | 43.627 | 0.319 | 43.884 | 1.00 54.42 | C |
| ATOM | 2700 | CZ | PHE | C | 126 | 42.573 | 1.208 | 43.889 | 1.00 52.99 | C |
| TER | 2702 | | PHE | C | 126 | | | | | |
| ATOM | 2703 | N | ASN | D | 11 | 47.774 | 44.287 | 38.626 | 1.00 52.77 | N |
| ATOM | 2704 | CA | ASN | D | 11 | 46.416 | 43.904 | 38.273 | 1.00 53.01 | C |
| ATOM | 2705 | C | ASN | D | 11 | 46.383 | 43.039 | 36.995 | 1.00 52.04 | C |
| ATOM | 2706 | O | ASN | D | 11 | 46.673 | 41.852 | 37.139 | 1.00 53.30 | O |
| ATOM | 2707 | CB | ASN | D | 11 | 45.488 | 45.136 | 38.154 | 1.00 52.37 | C |

FIGURE 8A-56

```
ATOM   2708  N    VAL D  12      46.135  43.551  35.763  1.00 49.81           N
ATOM   2709  CA   VAL D  12      45.936  42.823  34.490  1.00 45.10           C
ATOM   2710  C    VAL D  12      46.697  41.529  34.194  1.00 40.73           C
ATOM   2711  O    VAL D  12      46.109  40.477  33.958  1.00 39.20           O
ATOM   2712  CB   VAL D  12      46.118  43.863  33.336  1.00 46.99           C
ATOM   2713  CG1  VAL D  12      46.377  43.229  31.966  1.00 47.11           C
ATOM   2714  CG2  VAL D  12      44.888  44.784  33.225  1.00 46.26           C
ATOM   2715  N    LYS D  13      48.014  41.610  34.165  1.00 37.97           N
ATOM   2716  CA   LYS D  13      48.844  40.432  34.132  1.00 36.45           C
ATOM   2717  C    LYS D  13      48.402  39.322  35.117  1.00 36.18           C
ATOM   2718  O    LYS D  13      48.194  38.166  34.709  1.00 37.38           O
ATOM   2719  CB   LYS D  13      50.258  40.905  34.451  1.00 35.89           C
ATOM   2720  N    ASP D  14      48.190  39.643  36.410  1.00 33.96           N
ATOM   2721  CA   ASP D  14      47.703  38.684  37.372  1.00 29.22           C
ATOM   2722  C    ASP D  14      46.220  38.409  37.305  1.00 25.55           C
ATOM   2723  O    ASP D  14      45.799  37.316  37.647  1.00 25.36           O
ATOM   2724  CB   ASP D  14      48.158  39.126  38.726  1.00 33.71           C
ATOM   2725  CG   ASP D  14      49.573  38.623  39.084  1.00 41.45           C
ATOM   2726  OD1  ASP D  14      50.178  37.858  38.316  1.00 45.64           O
ATOM   2727  OD2  ASP D  14      50.083  38.981  40.161  1.00 44.73           O
ATOM   2728  N    VAL D  15      45.421  39.347  36.809  1.00 22.15           N
ATOM   2729  CA   VAL D  15      44.000  39.173  36.672  1.00 19.73           C
ATOM   2730  C    VAL D  15      43.683  38.044  35.731  1.00 21.56           C
ATOM   2731  O    VAL D  15      42.825  37.217  36.016  1.00 23.37           O
ATOM   2732  CB   VAL D  15      43.294  40.462  36.234  1.00 18.49           C
ATOM   2733  CG1  VAL D  15      41.883  40.238  35.684  1.00 17.31           C
ATOM   2734  CG2  VAL D  15      43.093  41.327  37.450  1.00 17.77           C
ATOM   2735  N    THR D  16      44.387  37.974  34.623  1.00 22.81           N
ATOM   2736  CA   THR D  16      44.166  36.943  33.605  1.00 24.47           C
ATOM   2737  C    THR D  16      44.517  35.513  34.082  1.00 21.91           C
ATOM   2738  O    THR D  16      43.904  34.526  33.676  1.00 20.78           O
ATOM   2739  CB   THR D  16      44.991  37.520  32.381  1.00 26.36           C
ATOM   2740  OG1  THR D  16      44.076  38.310  31.630  1.00 28.31           O
ATOM   2741  CG2  THR D  16      45.721  36.529  31.530  1.00 28.93           C
ATOM   2742  N    LYS D  17      45.470  35.415  35.016  1.00 20.72           N
ATOM   2743  CA   LYS D  17      45.958  34.179  35.596  1.00 20.21           C
ATOM   2744  C    LYS D  17      45.019  33.719  36.683  1.00 18.63           C
ATOM   2745  O    LYS D  17      44.754  32.526  36.783  1.00 21.04           O
ATOM   2746  CB   LYS D  17      47.277  34.522  36.207  1.00 24.75           C
ATOM   2747  CG   LYS D  17      48.163  33.373  36.590  1.00 29.44           C
ATOM   2748  CD   LYS D  17      49.365  33.928  37.347  1.00 32.96           C
ATOM   2749  CE   LYS D  17      50.423  34.474  36.422  1.00 36.20           C
ATOM   2750  NZ   LYS D  17      51.313  35.272  37.230  1.00 39.87           N
ATOM   2751  N    LEU D  18      44.483  34.656  37.468  1.00 16.11           N
ATOM   2752  CA   LEU D  18      43.391  34.389  38.362  1.00 13.77           C
ATOM   2753  C    LEU D  18      42.158  33.926  37.636  1.00 14.10           C
ATOM   2754  O    LEU D  18      41.662  32.898  38.072  1.00 17.61           O
ATOM   2755  CB   LEU D  18      43.070  35.599  39.180  1.00 14.87           C
ATOM   2756  CG   LEU D  18      42.103  35.485  40.362  1.00 15.58           C
ATOM   2757  CD1  LEU D  18      42.567  34.568  41.470  1.00 11.31           C
ATOM   2758  CD2  LEU D  18      41.872  36.849  40.952  1.00 15.28           C
ATOM   2759  N    VAL D  19      41.617  34.544  36.551  1.00 15.42           N
ATOM   2760  CA   VAL D  19      40.479  34.034  35.786  1.00 13.39           C
ATOM   2761  C    VAL D  19      40.704  32.587  35.335  1.00 14.30           C
ATOM   2762  O    VAL D  19      39.824  31.744  35.542  1.00 13.93           O
ATOM   2763  CB   VAL D  19      40.251  34.838  34.439  1.00 14.39           C
ATOM   2764  CG1  VAL D  19      39.059  34.330  33.694  1.00 11.41           C
ATOM   2765  CG2  VAL D  19      39.913  36.255  34.797  1.00 12.80           C
ATOM   2766  N    ALA D  20      41.911  32.288  34.876  1.00 14.50           N
ATOM   2767  CA   ALA D  20      42.319  30.924  34.543  1.00 15.90           C
```

*FIGURE 8A-57*

```
ATOM    2768  C   ALA D  20      42.340  29.894  35.680  1.00 16.27           C
ATOM    2769  O   ALA D  20      42.153  28.697  35.464  1.00 14.91           O
ATOM    2770  CB  ALA D  20      43.719  30.983  33.946  1.00 16.48           C
ATOM    2771  N   ASN D  21      42.543  30.396  36.914  1.00 16.20           N
ATOM    2772  CA  ASN D  21      42.665  29.549  38.081  1.00 14.59           C
ATOM    2773  C   ASN D  21      41.408  29.513  38.923  1.00 15.22           C
ATOM    2774  O   ASN D  21      41.343  28.894  39.982  1.00 14.76           O
ATOM    2775  CB  ASN D  21      43.863  30.085  38.853  1.00 15.31           C
ATOM    2776  CG  ASN D  21      44.760  29.000  39.360  1.00 12.22           C
ATOM    2777  OD1 ASN D  21      45.002  28.023  38.669  1.00 15.31           O
ATOM    2778  ND2 ASN D  21      45.313  29.122  40.545  1.00 14.81           N
ATOM    2779  N   LEU D  22      40.364  30.201  38.493  1.00 15.62           N
ATOM    2780  CA  LEU D  22      39.069  30.126  39.157  1.00 15.32           C
ATOM    2781  C   LEU D  22      38.172  29.241  38.319  1.00 15.81           C
ATOM    2782  O   LEU D  22      38.337  29.289  37.109  1.00 18.22           O
ATOM    2783  CB  LEU D  22      38.470  31.498  39.326  1.00 11.04           C
ATOM    2784  CG  LEU D  22      39.203  32.454  40.210  1.00 10.12           C
ATOM    2785  CD1 LEU D  22      38.580  33.801  40.004  1.00 11.85           C
ATOM    2786  CD2 LEU D  22      39.108  32.071  41.671  1.00 10.74           C
ATOM    2787  N   PRO D  23      37.246  28.422  38.825  1.00 16.11           N
ATOM    2788  CA  PRO D  23      36.365  27.588  38.004  1.00 15.30           C
ATOM    2789  C   PRO D  23      35.533  28.456  37.064  1.00 16.55           C
ATOM    2790  O   PRO D  23      35.044  29.485  37.502  1.00 18.78           O
ATOM    2791  CB  PRO D  23      35.474  26.944  39.027  1.00 14.03           C
ATOM    2792  CG  PRO D  23      36.252  27.043  40.317  1.00 16.22           C
ATOM    2793  CD  PRO D  23      36.854  28.409  40.228  1.00 15.04           C
ATOM    2794  N   LYS D  24      35.319  28.105  35.785  1.00 19.22           N
ATOM    2795  CA  LYS D  24      34.492  28.864  34.822  1.00 19.57           C
ATOM    2796  C   LYS D  24      33.027  28.975  35.241  1.00 18.94           C
ATOM    2797  O   LYS D  24      32.381  29.956  34.910  1.00 22.65           O
ATOM    2798  CB  LYS D  24      34.575  28.214  33.425  1.00 20.25           C
ATOM    2799  CG  LYS D  24      35.853  28.425  32.655  1.00 19.83           C
ATOM    2800  CD  LYS D  24      36.049  27.261  31.683  1.00 20.33           C
ATOM    2801  CE  LYS D  24      37.542  27.297  31.291  1.00 25.04           C
ATOM    2802  NZ  LYS D  24      38.019  26.084  30.523  1.00 27.36           N
ATOM    2803  N   ASP D  25      32.490  28.011  36.007  1.00 20.97           N
ATOM    2804  CA  ASP D  25      31.146  27.984  36.585  1.00 20.24           C
ATOM    2805  C   ASP D  25      31.084  28.420  38.037  1.00 20.26           C
ATOM    2806  O   ASP D  25      30.092  28.177  38.714  1.00 24.64           O
ATOM    2807  CB  ASP D  25      30.557  26.555  36.502  1.00 21.95           C
ATOM    2808  CG  ASP D  25      31.274  25.501  37.333  1.00 26.54           C
ATOM    2809  OD1 ASP D  25      32.429  25.721  37.693  1.00 28.24           O
ATOM    2810  OD2 ASP D  25      30.697  24.445  37.616  1.00 29.75           O
ATOM    2811  N   TYR D  26      32.109  29.038  38.591  1.00 19.65           N
ATOM    2812  CA  TYR D  26      31.978  29.716  39.865  1.00 19.99           C
ATOM    2813  C   TYR D  26      31.327  31.078  39.666  1.00 20.55           C
ATOM    2814  O   TYR D  26      31.837  31.882  38.892  1.00 23.24           O
ATOM    2815  CB  TYR D  26      33.388  29.886  40.446  1.00 18.93           C
ATOM    2816  CG  TYR D  26      33.487  30.459  41.844  1.00 18.30           C
ATOM    2817  CD1 TYR D  26      32.718  29.938  42.855  1.00 17.48           C
ATOM    2818  CD2 TYR D  26      34.309  31.538  42.057  1.00 19.75           C
ATOM    2819  CE1 TYR D  26      32.689  30.542  44.078  1.00 17.10           C
ATOM    2820  CE2 TYR D  26      34.304  32.124  43.291  1.00 21.03           C
ATOM    2821  CZ  TYR D  26      33.494  31.613  44.276  1.00 19.84           C
ATOM    2822  OH  TYR D  26      33.553  32.163  45.538  1.00 26.79           O
HETATM  2823  N   MSE D  27      30.240  31.351  40.390  1.00 20.11           N
HETATM  2824  CA  MSE D  27      29.563  32.640  40.409  1.00 19.68           C
HETATM  2825  C   MSE D  27      29.972  33.547  41.554  1.00 19.24           C
HETATM  2826  O   MSE D  27      29.844  33.217  42.722  1.00 18.84           O
HETATM  2827  CB  MSE D  27      28.030  32.478  40.470  1.00 25.00           C
```

FIGURE 8A-58

| | | | | | | | | | | |
|---|---|---|---|---|---|---|---|---|---|---|
| HETATM | 2828 | CG | MSE | D | 27 | 27.356 | 31.633 | 39.361 | 1.00 27.34 | C |
| HETATM | 2829 | SE | MSE | D | 27 | 28.005 | 31.953 | 37.549 | 1.00 33.76 | SE |
| HETATM | 2830 | CE | MSE | D | 27 | 27.146 | 33.538 | 37.334 | 1.00 29.16 | C |
| ATOM | 2831 | N | ILE | D | 28 | 30.503 | 34.700 | 41.191 | 1.00 18.26 | N |
| ATOM | 2832 | CA | ILE | D | 28 | 30.838 | 35.733 | 42.127 | 1.00 18.98 | C |
| ATOM | 2833 | C | ILE | D | 28 | 29.668 | 36.703 | 42.239 | 1.00 19.61 | C |
| ATOM | 2834 | O | ILE | D | 28 | 29.151 | 37.088 | 41.196 | 1.00 22.18 | O |
| ATOM | 2835 | CB | ILE | D | 28 | 32.136 | 36.421 | 41.662 | 1.00 15.61 | C |
| ATOM | 2836 | CG1 | ILE | D | 28 | 33.234 | 35.398 | 41.469 | 1.00 12.73 | C |
| ATOM | 2837 | CG2 | ILE | D | 28 | 32.593 | 37.471 | 42.693 | 1.00 15.00 | C |
| ATOM | 2838 | CD1 | ILE | D | 28 | 34.487 | 35.969 | 40.818 | 1.00 10.07 | C |
| ATOM | 2839 | N | THR | D | 29 | 29.199 | 37.105 | 43.433 | 1.00 20.30 | N |
| ATOM | 2840 | CA | THR | D | 29 | 28.142 | 38.118 | 43.587 | 1.00 18.55 | C |
| ATOM | 2841 | C | THR | D | 29 | 28.720 | 39.514 | 43.593 | 1.00 18.51 | C |
| ATOM | 2842 | O | THR | D | 29 | 29.681 | 39.757 | 44.305 | 1.00 20.24 | O |
| ATOM | 2843 | CB | THR | D | 29 | 27.248 | 37.915 | 44.853 | 1.00 18.42 | C |
| ATOM | 2844 | OG1 | THR | D | 29 | 26.791 | 36.570 | 44.817 | 1.00 20.41 | O |
| ATOM | 2845 | CG2 | THR | D | 29 | 25.982 | 38.747 | 44.836 | 1.00 16.39 | C |
| ATOM | 2846 | N | LEU | D | 30 | 28.205 | 40.455 | 42.785 | 1.00 18.52 | N |
| ATOM | 2847 | CA | LEU | D | 30 | 28.610 | 41.845 | 42.783 | 1.00 17.78 | C |
| ATOM | 2848 | C | LEU | D | 30 | 27.305 | 42.598 | 42.724 | 1.00 19.35 | C |
| ATOM | 2849 | O | LEU | D | 30 | 26.420 | 42.245 | 41.946 | 1.00 19.98 | O |
| ATOM | 2850 | CB | LEU | D | 30 | 29.390 | 42.149 | 41.505 | 1.00 18.28 | C |
| ATOM | 2851 | CG | LEU | D | 30 | 29.905 | 43.557 | 41.154 | 1.00 15.52 | C |
| ATOM | 2852 | CD1 | LEU | D | 30 | 30.720 | 44.170 | 42.241 | 1.00 15.62 | C |
| ATOM | 2853 | CD2 | LEU | D | 30 | 30.732 | 43.522 | 39.879 | 1.00 17.11 | C |
| ATOM | 2854 | N | LYS | D | 31 | 27.150 | 43.613 | 43.560 | 1.00 20.05 | N |
| ATOM | 2855 | CA | LYS | D | 31 | 26.046 | 44.522 | 43.409 | 1.00 21.35 | C |
| ATOM | 2856 | C | LYS | D | 31 | 26.413 | 45.564 | 42.354 | 1.00 23.46 | C |
| ATOM | 2857 | O | LYS | D | 31 | 27.223 | 46.470 | 42.561 | 1.00 23.96 | O |
| ATOM | 2858 | CB | LYS | D | 31 | 25.702 | 45.148 | 44.722 | 1.00 21.22 | C |
| ATOM | 2859 | CG | LYS | D | 31 | 25.353 | 44.109 | 45.756 | 1.00 23.53 | C |
| ATOM | 2860 | CD | LYS | D | 31 | 24.738 | 44.814 | 46.976 | 1.00 28.13 | C |
| ATOM | 2861 | CE | LYS | D | 31 | 24.583 | 43.890 | 48.132 | 1.00 29.07 | C |
| ATOM | 2862 | NZ | LYS | D | 31 | 23.982 | 44.617 | 49.293 | 1.00 34.24 | N |
| ATOM | 2863 | N | TYR | D | 32 | 25.818 | 45.356 | 41.172 | 1.00 25.01 | N |
| ATOM | 2864 | CA | TYR | D | 32 | 26.219 | 46.004 | 39.925 | 1.00 25.06 | C |
| ATOM | 2865 | C | TYR | D | 32 | 25.377 | 47.248 | 39.752 | 1.00 26.53 | C |
| ATOM | 2866 | O | TYR | D | 32 | 24.167 | 47.293 | 40.046 | 1.00 27.71 | O |
| ATOM | 2867 | CB | TYR | D | 32 | 26.050 | 44.978 | 38.778 | 1.00 25.42 | C |
| ATOM | 2868 | CG | TYR | D | 32 | 26.196 | 45.465 | 37.336 | 1.00 24.15 | C |
| ATOM | 2869 | CD1 | TYR | D | 32 | 27.433 | 45.460 | 36.728 | 1.00 22.29 | C |
| ATOM | 2870 | CD2 | TYR | D | 32 | 25.071 | 45.915 | 36.672 | 1.00 23.90 | C |
| ATOM | 2871 | CE1 | TYR | D | 32 | 27.558 | 45.961 | 35.459 | 1.00 24.06 | C |
| ATOM | 2872 | CE2 | TYR | D | 32 | 25.183 | 46.427 | 35.409 | 1.00 25.00 | C |
| ATOM | 2873 | CZ | TYR | D | 32 | 26.427 | 46.458 | 34.822 | 1.00 26.48 | C |
| ATOM | 2874 | OH | TYR | D | 32 | 26.533 | 47.012 | 33.598 | 1.00 26.81 | O |
| ATOM | 2875 | N | VAL | D | 33 | 26.099 | 48.297 | 39.333 | 1.00 28.52 | N |
| ATOM | 2876 | CA | VAL | D | 33 | 25.505 | 49.613 | 39.093 | 1.00 27.57 | C |
| ATOM | 2877 | C | VAL | D | 33 | 24.973 | 49.634 | 37.670 | 1.00 27.14 | C |
| ATOM | 2878 | O | VAL | D | 33 | 25.769 | 49.693 | 36.750 | 1.00 28.15 | O |
| ATOM | 2879 | CB | VAL | D | 33 | 26.529 | 50.724 | 39.288 | 1.00 26.82 | C |
| ATOM | 2880 | CG1 | VAL | D | 33 | 25.931 | 52.066 | 38.921 | 1.00 25.83 | C |
| ATOM | 2881 | CG2 | VAL | D | 33 | 26.880 | 50.758 | 40.795 | 1.00 25.22 | C |
| ATOM | 2882 | N | PRO | D | 34 | 23.674 | 49.548 | 37.434 | 1.00 27.51 | N |
| ATOM | 2883 | CA | PRO | D | 34 | 23.085 | 49.608 | 36.105 | 1.00 28.26 | C |
| ATOM | 2884 | C | PRO | D | 34 | 23.491 | 50.909 | 35.413 | 1.00 31.20 | C |
| ATOM | 2885 | O | PRO | D | 34 | 23.649 | 51.980 | 36.012 | 1.00 32.62 | O |
| ATOM | 2886 | CB | PRO | D | 34 | 21.617 | 49.574 | 36.407 | 1.00 27.82 | C |
| ATOM | 2887 | CG | PRO | D | 34 | 21.523 | 48.866 | 37.750 | 1.00 29.77 | C |

FIGURE 8A-59

```
ATOM    2888  CD   PRO D  34      22.668  49.494  38.488  1.00  27.97           C
ATOM    2889  N    GLY D  35      23.756  50.780  34.117  1.00  32.89           N
ATOM    2890  CA   GLY D  35      24.265  51.891  33.338  1.00  34.68           C
ATOM    2891  C    GLY D  35      25.749  52.065  33.438  1.00  34.91           C
ATOM    2892  O    GLY D  35      26.271  53.066  32.991  1.00  38.32           O
HETATM  2893  N    MSE D  36      26.456  51.105  33.995  1.00  36.03           N
HETATM  2894  CA   MSE D  36      27.910  51.084  34.060  1.00  38.11           C
HETATM  2895  C    MSE D  36      28.634  51.193  32.726  1.00  38.57           C
HETATM  2896  O    MSE D  36      29.741  51.717  32.594  1.00  39.99           O
HETATM  2897  CB   MSE D  36      28.255  49.744  34.622  1.00  41.60           C
HETATM  2898  CG   MSE D  36      28.972  49.795  35.911  1.00  45.00           C
HETATM  2899  SE   MSE D  36      30.412  48.532  35.745  1.00  54.90           SE
HETATM  2900  CE   MSE D  36      30.966  48.492  33.897  1.00  45.21           C
ATOM    2901  N    ASP D  37      27.956  50.571  31.760  1.00  39.01           N
ATOM    2902  CA   ASP D  37      28.357  50.446  30.370  1.00  37.84           C
ATOM    2903  C    ASP D  37      28.125  51.687  29.525  1.00  37.29           C
ATOM    2904  O    ASP D  37      29.067  52.169  28.896  1.00  40.17           O
ATOM    2905  CB   ASP D  37      27.725  49.194  29.760  1.00  37.35           C
ATOM    2906  CG   ASP D  37      26.258  48.854  30.083  1.00  40.62           C
ATOM    2907  OD1  ASP D  37      25.560  49.672  30.709  1.00  39.43           O
ATOM    2908  OD2  ASP D  37      25.813  47.752  29.705  1.00  41.13           O
ATOM    2909  N    VAL D  38      26.930  52.266  29.525  1.00  36.85           N
ATOM    2910  CA   VAL D  38      26.665  53.462  28.719  1.00  38.43           C
ATOM    2911  C    VAL D  38      27.021  54.828  29.311  1.00  39.02           C
ATOM    2912  O    VAL D  38      27.395  55.748  28.581  1.00  39.83           O
ATOM    2913  CB   VAL D  38      25.212  53.466  28.171  1.00  36.76           C
ATOM    2914  CG1  VAL D  38      25.086  52.227  27.356  1.00  36.24           C
ATOM    2915  CG2  VAL D  38      24.081  53.482  29.175  1.00  36.31           C
ATOM    2916  N    LEU D  39      26.886  54.965  30.641  1.00  39.92           N
ATOM    2917  CA   LEU D  39      27.031  56.231  31.341  1.00  38.96           C
ATOM    2918  C    LEU D  39      28.495  56.624  31.625  1.00  41.40           C
ATOM    2919  O    LEU D  39      29.397  55.777  31.589  1.00  40.82           O
ATOM    2920  CB   LEU D  39      26.208  56.247  32.637  1.00  35.81           C
ATOM    2921  CG   LEU D  39      24.706  56.030  32.689  1.00  34.18           C
ATOM    2922  CD1  LEU D  39      24.285  56.206  34.141  1.00  33.76           C
ATOM    2923  CD2  LEU D  39      23.900  56.980  31.827  1.00  31.66           C
ATOM    2924  N    PRO D  40      28.807  57.926  31.852  1.00  44.17           N
ATOM    2925  CA   PRO D  40      30.141  58.383  32.244  1.00  44.44           C
ATOM    2926  C    PRO D  40      30.420  58.032  33.699  1.00  42.47           C
ATOM    2927  O    PRO D  40      29.550  58.003  34.562  1.00  42.05           O
ATOM    2928  CB   PRO D  40      30.115  59.908  32.011  1.00  45.14           C
ATOM    2929  CG   PRO D  40      28.674  60.256  32.263  1.00  45.10           C
ATOM    2930  CD   PRO D  40      27.934  59.092  31.603  1.00  46.22           C
ATOM    2931  N    SER D  41      31.694  57.749  33.906  1.00  42.00           N
ATOM    2932  CA   SER D  41      32.266  57.360  35.166  1.00  39.50           C
ATOM    2933  C    SER D  41      31.724  58.115  36.365  1.00  38.61           C
ATOM    2934  O    SER D  41      31.345  57.439  37.303  1.00  38.99           O
ATOM    2935  CB   SER D  41      33.760  57.491  35.009  1.00  40.43           C
ATOM    2936  OG   SER D  41      34.204  56.814  33.824  1.00  45.16           O
ATOM    2937  N    HIS D  42      31.550  59.442  36.396  1.00  38.17           N
ATOM    2938  CA   HIS D  42      31.018  60.127  37.567  1.00  36.99           C
ATOM    2939  C    HIS D  42      29.633  59.685  38.068  1.00  38.51           C
ATOM    2940  O    HIS D  42      29.219  59.978  39.190  1.00  39.73           O
ATOM    2941  CB   HIS D  42      31.062  61.646  37.328  1.00  36.53           C
ATOM    2942  CG   HIS D  42      29.988  62.146  36.370  1.00  34.40           C
ATOM    2943  ND1  HIS D  42      30.070  62.275  35.063  1.00  35.82           N
ATOM    2944  CD2  HIS D  42      28.694  62.443  36.749  1.00  36.22           C
ATOM    2945  CE1  HIS D  42      28.872  62.607  34.629  1.00  35.92           C
ATOM    2946  NE2  HIS D  42      28.050  62.680  35.644  1.00  37.56           N
ATOM    2947  N    CYS D  43      28.848  58.974  37.261  1.00  40.38           N
```

FIGURE 8A-60

| | | | | | | | | | | |
|---|---|---|---|---|---|---|---|---|---|---|
| ATOM | 2948 | CA | CYS D | 43 | 27.521 | 58.516 | 37.662 | 1.00 | 40.95 | C |
| ATOM | 2949 | C | CYS D | 43 | 27.545 | 57.165 | 38.394 | 1.00 | 38.66 | C |
| ATOM | 2950 | O | CYS D | 43 | 26.556 | 56.769 | 39.027 | 1.00 | 38.58 | O |
| ATOM | 2951 | CB | CYS D | 43 | 26.561 | 58.489 | 36.426 | 1.00 | 43.16 | C |
| ATOM | 2952 | SG | CYS D | 43 | 25.889 | 60.126 | 35.971 | 1.00 | 50.07 | S |
| ATOM | 2953 | N | TRP D | 44 | 28.677 | 56.450 | 38.300 | 1.00 | 34.96 | N |
| ATOM | 2954 | CA | TRP D | 44 | 28.763 | 55.094 | 38.789 | 1.00 | 32.27 | C |
| ATOM | 2955 | C | TRP D | 44 | 30.055 | 54.754 | 39.486 | 1.00 | 32.35 | C |
| ATOM | 2956 | O | TRP D | 44 | 30.010 | 53.891 | 40.349 | 1.00 | 34.30 | O |
| ATOM | 2957 | CB | TRP D | 44 | 28.502 | 54.045 | 37.688 | 1.00 | 29.74 | C |
| ATOM | 2958 | CG | TRP D | 44 | 29.428 | 54.039 | 36.479 | 1.00 | 25.62 | C |
| ATOM | 2959 | CD1 | TRP D | 44 | 29.034 | 54.689 | 35.340 | 1.00 | 24.56 | C |
| ATOM | 2960 | CD2 | TRP D | 44 | 30.636 | 53.392 | 36.360 | 1.00 | 24.29 | C |
| ATOM | 2961 | NE1 | TRP D | 44 | 30.006 | 54.462 | 34.497 | 1.00 | 26.57 | N |
| ATOM | 2962 | CE2 | TRP D | 44 | 30.972 | 53.705 | 35.046 | 1.00 | 25.16 | C |
| ATOM | 2963 | CE3 | TRP D | 44 | 31.442 | 52.536 | 37.072 | 1.00 | 21.05 | C |
| ATOM | 2964 | CZ2 | TRP D | 44 | 32.119 | 53.210 | 34.446 | 1.00 | 23.57 | C |
| ATOM | 2965 | CZ3 | TRP D | 44 | 32.600 | 52.058 | 36.490 | 1.00 | 21.72 | C |
| ATOM | 2966 | CH2 | TRP D | 44 | 32.956 | 52.395 | 35.194 | 1.00 | 23.72 | C |
| ATOM | 2967 | N | ILE D | 45 | 31.191 | 55.378 | 39.216 | 1.00 | 31.34 | N |
| ATOM | 2968 | CA | ILE D | 45 | 32.444 | 54.851 | 39.687 | 1.00 | 34.23 | C |
| ATOM | 2969 | C | ILE D | 45 | 32.627 | 54.719 | 41.206 | 1.00 | 35.04 | C |
| ATOM | 2970 | O | ILE D | 45 | 33.222 | 53.726 | 41.618 | 1.00 | 36.05 | O |
| ATOM | 2971 | CB | ILE D | 45 | 33.586 | 55.584 | 38.980 | 1.00 | 35.62 | C |
| ATOM | 2972 | CG1 | ILE D | 45 | 34.959 | 54.917 | 39.068 | 1.00 | 36.05 | C |
| ATOM | 2973 | CG2 | ILE D | 45 | 33.716 | 56.959 | 39.592 | 1.00 | 37.86 | C |
| ATOM | 2974 | CD1 | ILE D | 45 | 35.020 | 53.482 | 38.545 | 1.00 | 36.81 | C |
| ATOM | 2975 | N | SER D | 46 | 32.100 | 55.591 | 42.080 | 1.00 | 35.07 | N |
| ATOM | 2976 | CA | SER D | 46 | 32.421 | 55.538 | 43.500 | 1.00 | 35.85 | C |
| ATOM | 2977 | C | SER D | 46 | 31.651 | 54.443 | 44.213 | 1.00 | 35.51 | C |
| ATOM | 2978 | O | SER D | 46 | 32.169 | 53.858 | 45.165 | 1.00 | 38.41 | O |
| ATOM | 2979 | CB | SER D | 46 | 32.165 | 56.852 | 44.223 | 1.00 | 36.96 | C |
| ATOM | 2980 | OG | SER D | 46 | 30.786 | 57.005 | 44.534 | 1.00 | 40.12 | O |
| ATOM | 2981 | N | GLU D | 47 | 30.419 | 54.185 | 43.770 | 1.00 | 33.93 | N |
| ATOM | 2982 | CA | GLU D | 47 | 29.656 | 53.051 | 44.230 | 1.00 | 32.65 | C |
| ATOM | 2983 | C | GLU D | 47 | 30.197 | 51.773 | 43.648 | 1.00 | 31.56 | C |
| ATOM | 2984 | O | GLU D | 47 | 30.216 | 50.761 | 44.339 | 1.00 | 31.25 | O |
| ATOM | 2985 | CB | GLU D | 47 | 28.206 | 53.193 | 43.842 | 1.00 | 36.42 | C |
| ATOM | 2986 | CG | GLU D | 47 | 27.306 | 51.989 | 44.164 | 1.00 | 45.32 | C |
| ATOM | 2987 | CD | GLU D | 47 | 26.964 | 51.716 | 45.628 | 1.00 | 48.90 | C |
| ATOM | 2988 | OE1 | GLU D | 47 | 27.839 | 51.323 | 46.399 | 1.00 | 52.24 | O |
| ATOM | 2989 | OE2 | GLU D | 47 | 25.797 | 51.872 | 45.995 | 1.00 | 52.95 | O |
| HETATM | 2990 | N | MSE D | 48 | 30.646 | 51.788 | 42.398 | 1.00 | 30.45 | N |
| HETATM | 2991 | CA | MSE D | 48 | 31.189 | 50.592 | 41.798 | 1.00 | 31.67 | C |
| HETATM | 2992 | C | MSE D | 48 | 32.499 | 50.155 | 42.444 | 1.00 | 30.88 | C |
| HETATM | 2993 | O | MSE D | 48 | 32.694 | 48.961 | 42.577 | 1.00 | 33.46 | O |
| HETATM | 2994 | CB | MSE D | 48 | 31.394 | 50.777 | 40.342 | 1.00 | 32.74 | C |
| HETATM | 2995 | CG | MSE D | 48 | 31.510 | 49.459 | 39.632 | 1.00 | 36.29 | C |
| HETATM | 2996 | SE | MSE D | 48 | 29.910 | 48.366 | 39.787 | 1.00 | 47.34 | SE |
| HETATM | 2997 | CE | MSE D | 48 | 30.895 | 46.927 | 39.264 | 1.00 | 38.75 | C |
| ATOM | 2998 | N | VAL D | 49 | 33.433 | 50.984 | 42.904 | 1.00 | 30.60 | N |
| ATOM | 2999 | CA | VAL D | 49 | 34.605 | 50.504 | 43.671 | 1.00 | 29.47 | C |
| ATOM | 3000 | C | VAL D | 49 | 34.285 | 50.012 | 45.074 | 1.00 | 27.89 | C |
| ATOM | 3001 | O | VAL D | 49 | 34.967 | 49.128 | 45.596 | 1.00 | 27.63 | O |
| ATOM | 3002 | CB | VAL D | 49 | 35.828 | 51.488 | 43.781 | 1.00 | 30.38 | C |
| ATOM | 3003 | CG1 | VAL D | 49 | 36.552 | 51.617 | 42.439 | 1.00 | 30.57 | C |
| ATOM | 3004 | CG2 | VAL D | 49 | 35.440 | 52.863 | 44.340 | 1.00 | 30.43 | C |
| ATOM | 3005 | N | VAL D | 50 | 33.263 | 50.622 | 45.679 | 1.00 | 25.21 | N |
| ATOM | 3006 | CA | VAL D | 50 | 32.754 | 50.149 | 46.945 | 1.00 | 24.70 | C |
| ATOM | 3007 | C | VAL D | 50 | 32.153 | 48.745 | 46.832 | 1.00 | 24.08 | C |

FIGURE 8A-61

| ATOM | 3008 | O   | VAL | D | 50  | 32.438 | 47.921 | 47.699 | 1.00 | 25.08 | O |
|------|------|-----|-----|---|-----|--------|--------|--------|------|-------|---|
| ATOM | 3009 | CB  | VAL | D | 50  | 31.757 | 51.172 | 47.504 | 1.00 | 24.15 | C |
| ATOM | 3010 | CG1 | VAL | D | 50  | 30.945 | 50.583 | 48.650 | 1.00 | 24.85 | C |
| ATOM | 3011 | CG2 | VAL | D | 50  | 32.484 | 52.411 | 47.974 | 1.00 | 21.01 | C |
| ATOM | 3012 | N   | GLN | D | 51  | 31.343 | 48.470 | 45.796 | 1.00 | 22.06 | N |
| ATOM | 3013 | CA  | GLN | D | 51  | 30.807 | 47.154 | 45.522 | 1.00 | 22.13 | C |
| ATOM | 3014 | C   | GLN | D | 51  | 31.810 | 46.099 | 45.123 | 1.00 | 20.89 | C |
| ATOM | 3015 | O   | GLN | D | 51  | 31.663 | 44.940 | 45.479 | 1.00 | 21.33 | O |
| ATOM | 3016 | CB  | GLN | D | 51  | 29.719 | 47.249 | 44.434 | 1.00 | 24.57 | C |
| ATOM | 3017 | CG  | GLN | D | 51  | 28.496 | 47.999 | 45.018 | 1.00 | 26.12 | C |
| ATOM | 3018 | CD  | GLN | D | 51  | 27.936 | 47.379 | 46.304 | 1.00 | 26.75 | C |
| ATOM | 3019 | OE1 | GLN | D | 51  | 28.128 | 46.194 | 46.616 | 1.00 | 25.54 | O |
| ATOM | 3020 | NE2 | GLN | D | 51  | 27.234 | 48.198 | 47.088 | 1.00 | 26.23 | N |
| ATOM | 3021 | N   | LEU | D | 52  | 32.839 | 46.544 | 44.123 | 1.00 | 19.69 | N |
| ATOM | 3022 | CA  | LEU | D | 52  | 33.966 | 45.728 | 44.057 | 1.00 | 20.34 | C |
| ATOM | 3023 | C   | LEU | D | 52  | 34.831 | 45.383 | 45.250 | 1.00 | 20.47 | C |
| ATOM | 3024 | O   | LEU | D | 52  | 35.199 | 44.215 | 45.356 | 1.00 | 23.75 | O |
| ATOM | 3025 | CB  | LEU | D | 52  | 34.866 | 46.398 | 42.976 | 1.00 | 19.72 | C |
| ATOM | 3026 | CG  | LEU | D | 52  | 34.402 | 46.541 | 41.509 | 1.00 | 18.02 | C |
| ATOM | 3027 | CD1 | LEU | D | 52  | 35.404 | 47.412 | 40.807 | 1.00 | 14.47 | C |
| ATOM | 3028 | CD2 | LEU | D | 52  | 34.217 | 45.177 | 40.844 | 1.00 | 14.93 | C |
| ATOM | 3029 | N   | SER | D | 53  | 35.178 | 46.294 | 46.165 | 1.00 | 21.36 | N |
| ATOM | 3030 | CA  | SER | D | 53  | 35.913 | 45.942 | 47.377 | 1.00 | 22.45 | C |
| ATOM | 3031 | C   | SER | D | 53  | 35.173 | 44.873 | 48.166 | 1.00 | 22.70 | C |
| ATOM | 3032 | O   | SER | D | 53  | 35.770 | 43.895 | 48.565 | 1.00 | 24.55 | O |
| ATOM | 3033 | CB  | SER | D | 53  | 36.117 | 47.178 | 48.233 | 1.00 | 25.43 | C |
| ATOM | 3034 | OG  | SER | D | 53  | 36.882 | 46.917 | 49.410 | 1.00 | 32.17 | O |
| ATOM | 3035 | N   | ASP | D | 54  | 33.852 | 44.962 | 48.286 | 1.00 | 23.74 | N |
| ATOM | 3036 | CA  | ASP | D | 54  | 33.021 | 44.038 | 49.030 | 1.00 | 25.51 | C |
| ATOM | 3037 | C   | ASP | D | 54  | 33.119 | 42.633 | 48.500 | 1.00 | 22.56 | C |
| ATOM | 3038 | O   | ASP | D | 54  | 33.390 | 41.711 | 49.250 | 1.00 | 22.33 | O |
| ATOM | 3039 | CB  | ASP | D | 54  | 31.565 | 44.500 | 48.963 | 1.00 | 32.00 | C |
| ATOM | 3040 | CG  | ASP | D | 54  | 30.624 | 43.913 | 50.019 | 1.00 | 42.23 | C |
| ATOM | 3041 | OD1 | ASP | D | 54  | 30.117 | 42.792 | 49.841 | 1.00 | 45.21 | O |
| ATOM | 3042 | OD2 | ASP | D | 54  | 30.364 | 44.607 | 51.018 | 1.00 | 49.94 | O |
| ATOM | 3043 | N   | SER | D | 55  | 32.943 | 42.520 | 47.192 | 1.00 | 19.99 | N |
| ATOM | 3044 | CA  | SER | D | 55  | 32.933 | 41.258 | 46.504 | 1.00 | 16.42 | C |
| ATOM | 3045 | C   | SER | D | 55  | 34.279 | 40.596 | 46.521 | 1.00 | 14.71 | C |
| ATOM | 3046 | O   | SER | D | 55  | 34.395 | 39.393 | 46.693 | 1.00 | 15.83 | O |
| ATOM | 3047 | CB  | SER | D | 55  | 32.503 | 41.468 | 45.066 | 1.00 | 16.29 | C |
| ATOM | 3048 | OG  | SER | D | 55  | 31.170 | 41.909 | 44.886 | 1.00 | 19.97 | O |
| ATOM | 3049 | N   | LEU | D | 56  | 35.296 | 41.406 | 46.315 | 1.00 | 15.85 | N |
| ATOM | 3050 | CA  | LEU | D | 56  | 36.638 | 40.884 | 46.345 | 1.00 | 17.57 | C |
| ATOM | 3051 | C   | LEU | D | 56  | 37.034 | 40.485 | 47.744 | 1.00 | 17.75 | C |
| ATOM | 3052 | O   | LEU | D | 56  | 37.782 | 39.527 | 47.863 | 1.00 | 19.01 | O |
| ATOM | 3053 | CB  | LEU | D | 56  | 37.619 | 41.904 | 45.848 | 1.00 | 17.61 | C |
| ATOM | 3054 | CG  | LEU | D | 56  | 37.813 | 42.091 | 44.344 | 1.00 | 21.27 | C |
| ATOM | 3055 | CD1 | LEU | D | 56  | 38.577 | 43.396 | 44.141 | 1.00 | 19.96 | C |
| ATOM | 3056 | CD2 | LEU | D | 56  | 38.540 | 40.936 | 43.687 | 1.00 | 16.32 | C |
| ATOM | 3057 | N   | THR | D | 57  | 36.560 | 41.169 | 48.803 | 1.00 | 19.07 | N |
| ATOM | 3058 | CA  | THR | D | 57  | 36.864 | 40.818 | 50.189 | 1.00 | 17.97 | C |
| ATOM | 3059 | C   | THR | D | 57  | 36.126 | 39.571 | 50.556 | 1.00 | 18.20 | C |
| ATOM | 3060 | O   | THR | D | 57  | 36.674 | 38.746 | 51.266 | 1.00 | 20.89 | O |
| ATOM | 3061 | CB  | THR | D | 57  | 36.521 | 41.984 | 51.099 | 1.00 | 19.37 | C |
| ATOM | 3062 | OG1 | THR | D | 57  | 37.503 | 42.932 | 50.741 | 1.00 | 20.91 | O |
| ATOM | 3063 | CG2 | THR | D | 57  | 36.778 | 41.786 | 52.575 | 1.00 | 26.13 | C |
| ATOM | 3064 | N   | ASP | D | 58  | 34.924 | 39.346 | 50.085 | 1.00 | 18.03 | N |
| ATOM | 3065 | CA  | ASP | D | 58  | 34.293 | 38.066 | 50.220 | 1.00 | 18.76 | C |
| ATOM | 3066 | C   | ASP | D | 58  | 34.958 | 37.009 | 49.397 | 1.00 | 20.46 | C |
| ATOM | 3067 | O   | ASP | D | 58  | 35.041 | 35.878 | 49.865 | 1.00 | 20.47 | O |

*FIGURE 8A-62*

| ATOM | 3068 | CB | ASP | D | 58 | 32.859 | 38.102 | 49.791 | 1.00 | 21.24 | C |
| ATOM | 3069 | CG | ASP | D | 58 | 32.043 | 39.157 | 50.517 | 1.00 | 26.19 | C |
| ATOM | 3070 | OD1 | ASP | D | 58 | 32.458 | 39.665 | 51.572 | 1.00 | 26.83 | O |
| ATOM | 3071 | OD2 | ASP | D | 58 | 30.970 | 39.481 | 49.993 | 1.00 | 30.50 | O |
| ATOM | 3072 | N | LEU | D | 59 | 35.449 | 37.324 | 48.197 | 1.00 | 19.65 | N |
| ATOM | 3073 | CA | LEU | D | 59 | 36.099 | 36.331 | 47.383 | 1.00 | 18.09 | C |
| ATOM | 3074 | C | LEU | D | 59 | 37.345 | 35.878 | 48.090 | 1.00 | 19.12 | C |
| ATOM | 3075 | O | LEU | D | 59 | 37.553 | 34.694 | 48.251 | 1.00 | 23.04 | O |
| ATOM | 3076 | CB | LEU | D | 59 | 36.392 | 36.893 | 46.028 | 1.00 | 16.75 | C |
| ATOM | 3077 | CG | LEU | D | 59 | 36.808 | 35.864 | 45.048 | 1.00 | 17.14 | C |
| ATOM | 3078 | CD1 | LEU | D | 59 | 35.714 | 34.823 | 44.909 | 1.00 | 16.41 | C |
| ATOM | 3079 | CD2 | LEU | D | 59 | 37.209 | 36.546 | 43.769 | 1.00 | 16.93 | C |
| ATOM | 3080 | N | LEU | D | 60 | 38.132 | 36.764 | 48.667 | 1.00 | 21.47 | N |
| ATOM | 3081 | CA | LEU | D | 60 | 39.332 | 36.428 | 49.431 | 1.00 | 22.73 | C |
| ATOM | 3082 | C | LEU | D | 60 | 39.173 | 35.401 | 50.564 | 1.00 | 24.38 | C |
| ATOM | 3083 | O | LEU | D | 60 | 40.084 | 34.626 | 50.853 | 1.00 | 25.12 | O |
| ATOM | 3084 | CB | LEU | D | 60 | 39.852 | 37.726 | 50.017 | 1.00 | 21.70 | C |
| ATOM | 3085 | CG | LEU | D | 60 | 41.196 | 37.710 | 50.670 | 1.00 | 23.77 | C |
| ATOM | 3086 | CD1 | LEU | D | 60 | 42.256 | 37.514 | 49.598 | 1.00 | 22.63 | C |
| ATOM | 3087 | CD2 | LEU | D | 60 | 41.446 | 38.985 | 51.425 | 1.00 | 24.99 | C |
| ATOM | 3088 | N | ASP | D | 61 | 38.005 | 35.386 | 51.224 | 1.00 | 26.63 | N |
| ATOM | 3089 | CA | ASP | D | 61 | 37.705 | 34.524 | 52.363 | 1.00 | 25.59 | C |
| ATOM | 3090 | C | ASP | D | 61 | 37.428 | 33.112 | 51.872 | 1.00 | 22.43 | C |
| ATOM | 3091 | O | ASP | D | 61 | 37.373 | 32.161 | 52.646 | 1.00 | 23.39 | O |
| ATOM | 3092 | CB | ASP | D | 61 | 36.497 | 35.146 | 53.120 | 1.00 | 33.33 | C |
| ATOM | 3093 | CG | ASP | D | 61 | 35.889 | 34.390 | 54.325 | 1.00 | 40.36 | C |
| ATOM | 3094 | OD1 | ASP | D | 61 | 36.478 | 34.403 | 55.424 | 1.00 | 44.78 | O |
| ATOM | 3095 | OD2 | ASP | D | 61 | 34.807 | 33.794 | 54.169 | 1.00 | 43.10 | O |
| ATOM | 3096 | N | LYS | D | 62 | 37.289 | 32.899 | 50.575 | 1.00 | 17.94 | N |
| ATOM | 3097 | CA | LYS | D | 62 | 37.048 | 31.574 | 50.058 | 1.00 | 13.29 | C |
| ATOM | 3098 | C | LYS | D | 62 | 38.344 | 30.855 | 49.757 | 1.00 | 12.68 | C |
| ATOM | 3099 | O | LYS | D | 62 | 38.308 | 29.692 | 49.387 | 1.00 | 15.69 | O |
| ATOM | 3100 | CB | LYS | D | 62 | 36.292 | 31.712 | 48.771 | 1.00 | 13.99 | C |
| ATOM | 3101 | CG | LYS | D | 62 | 35.036 | 32.517 | 48.890 | 1.00 | 16.25 | C |
| ATOM | 3102 | CD | LYS | D | 62 | 34.086 | 31.871 | 49.870 | 1.00 | 21.21 | C |
| ATOM | 3103 | CE | LYS | D | 62 | 32.997 | 32.898 | 50.166 | 1.00 | 23.50 | C |
| ATOM | 3104 | NZ | LYS | D | 62 | 32.319 | 33.267 | 48.937 | 1.00 | 30.45 | N |
| ATOM | 3105 | N | PHE | D | 63 | 39.504 | 31.504 | 49.885 | 1.00 | 12.18 | N |
| ATOM | 3106 | CA | PHE | D | 63 | 40.797 | 30.938 | 49.594 | 1.00 | 13.29 | C |
| ATOM | 3107 | C | PHE | D | 63 | 41.659 | 30.965 | 50.837 | 1.00 | 16.38 | C |
| ATOM | 3108 | O | PHE | D | 63 | 41.401 | 31.701 | 51.798 | 1.00 | 16.40 | O |
| ATOM | 3109 | CB | PHE | D | 63 | 41.495 | 31.773 | 48.552 | 1.00 | 11.01 | C |
| ATOM | 3110 | CG | PHE | D | 63 | 40.776 | 31.641 | 47.229 | 1.00 | 13.33 | C |
| ATOM | 3111 | CD1 | PHE | D | 63 | 40.917 | 30.478 | 46.491 | 1.00 | 11.26 | C |
| ATOM | 3112 | CD2 | PHE | D | 63 | 39.904 | 32.635 | 46.823 | 1.00 | 13.18 | C |
| ATOM | 3113 | CE1 | PHE | D | 63 | 40.140 | 30.299 | 45.367 | 1.00 | 9.84 | C |
| ATOM | 3114 | CE2 | PHE | D | 63 | 39.126 | 32.436 | 45.690 | 1.00 | 13.90 | C |
| ATOM | 3115 | CZ | PHE | D | 63 | 39.251 | 31.264 | 44.964 | 1.00 | 10.53 | C |
| ATOM | 3116 | N | SER | D | 64 | 42.725 | 30.164 | 50.773 | 1.00 | 16.82 | N |
| ATOM | 3117 | CA | SER | D | 64 | 43.703 | 30.208 | 51.822 | 1.00 | 16.74 | C |
| ATOM | 3118 | C | SER | D | 64 | 45.123 | 30.230 | 51.275 | 1.00 | 16.89 | C |
| ATOM | 3119 | O | SER | D | 64 | 45.377 | 29.918 | 50.120 | 1.00 | 16.97 | O |
| ATOM | 3120 | CB | SER | D | 64 | 43.430 | 29.068 | 52.849 | 1.00 | 18.93 | C |
| ATOM | 3121 | OG | SER | D | 64 | 44.080 | 27.847 | 52.508 | 1.00 | 28.24 | O |
| ATOM | 3122 | N | ASN | D | 65 | 46.080 | 30.661 | 52.095 | 1.00 | 16.96 | N |
| ATOM | 3123 | CA | ASN | D | 65 | 47.479 | 30.684 | 51.746 | 1.00 | 15.98 | C |
| ATOM | 3124 | C | ASN | D | 65 | 48.027 | 29.319 | 51.496 | 1.00 | 15.15 | C |
| ATOM | 3125 | O | ASN | D | 65 | 47.472 | 28.362 | 52.000 | 1.00 | 17.07 | O |
| ATOM | 3126 | CB | ASN | D | 65 | 48.341 | 31.398 | 52.774 | 1.00 | 17.48 | C |
| ATOM | 3127 | CG | ASN | D | 65 | 48.232 | 32.904 | 52.634 | 1.00 | 19.71 | C |

FIGURE 8A-63

```
ATOM   3128  OD1  ASN D  65      48.695  33.551  51.752  1.00  25.73        O
ATOM   3129  ND2  ASN D  65      47.621  33.560  53.640  1.00  22.21        N
ATOM   3130  N    ILE D  66      49.077  29.253  50.672  1.00  15.61        N
ATOM   3131  CA   ILE D  66      49.778  28.029  50.363  1.00  16.53        C
ATOM   3132  C    ILE D  66      51.232  28.235  50.711  1.00  16.49        C
ATOM   3133  O    ILE D  66      51.633  29.383  50.813  1.00  17.79        O
ATOM   3134  CB   ILE D  66      49.594  27.623  48.869  1.00  16.19        C
ATOM   3135  CG1  ILE D  66      50.149  28.660  47.906  1.00  16.66        C
ATOM   3136  CG2  ILE D  66      48.115  27.329  48.611  1.00  12.63        C
ATOM   3137  CD1  ILE D  66      50.081  28.036  46.478  1.00  18.10        C
ATOM   3138  N    SER D  67      52.041  27.187  50.853  1.00  18.84        N
ATOM   3139  CA   SER D  67      53.442  27.347  51.233  1.00  23.17        C
ATOM   3140  C    SER D  67      54.305  28.078  50.214  1.00  23.34        C
ATOM   3141  O    SER D  67      55.250  28.779  50.552  1.00  25.92        O
ATOM   3142  CB   SER D  67      54.084  26.006  51.543  1.00  23.00        C
ATOM   3143  OG   SER D  67      53.971  25.139  50.419  1.00  30.06        O
ATOM   3144  N    GLU D  68      53.981  27.968  48.942  1.00  25.32        N
ATOM   3145  CA   GLU D  68      54.755  28.626  47.914  1.00  27.08        C
ATOM   3146  C    GLU D  68      54.045  28.401  46.597  1.00  25.08        C
ATOM   3147  O    GLU D  68      53.391  27.373  46.403  1.00  24.26        O
ATOM   3148  CB   GLU D  68      56.190  28.061  47.921  1.00  30.32        C
ATOM   3149  CG   GLU D  68      56.711  27.081  46.883  1.00  40.98        C
ATOM   3150  CD   GLU D  68      56.009  25.744  46.778  1.00  46.80        C
ATOM   3151  OE1  GLU D  68      55.947  24.998  47.773  1.00  50.12        O
ATOM   3152  OE2  GLU D  68      55.508  25.470  45.676  1.00  52.68        O
ATOM   3153  N    GLY D  69      54.121  29.389  45.723  1.00  23.65        N
ATOM   3154  CA   GLY D  69      53.784  29.192  44.320  1.00  24.95        C
ATOM   3155  C    GLY D  69      52.580  30.012  43.952  1.00  23.05        C
ATOM   3156  O    GLY D  69      52.270  30.941  44.691  1.00  24.04        O
ATOM   3157  N    LEU D  70      51.883  29.667  42.870  1.00  22.75        N
ATOM   3158  CA   LEU D  70      50.768  30.474  42.415  1.00  23.31        C
ATOM   3159  C    LEU D  70      49.618  30.380  43.412  1.00  21.85        C
ATOM   3160  O    LEU D  70      49.170  29.262  43.689  1.00  23.27        O
ATOM   3161  CB   LEU D  70      50.307  29.902  41.114  1.00  22.88        C
ATOM   3162  CG   LEU D  70      49.652  30.850  40.145  1.00  22.31        C
ATOM   3163  CD1  LEU D  70      49.073  29.925  39.038  1.00  24.98        C
ATOM   3164  CD2  LEU D  70      48.576  31.722  40.710  1.00  21.90        C
ATOM   3165  N    SER D  71      49.143  31.526  43.918  1.00  19.05        N
ATOM   3166  CA   SER D  71      48.132  31.561  44.977  1.00  16.36        C
ATOM   3167  C    SER D  71      47.008  32.518  44.667  1.00  15.90        C
ATOM   3168  O    SER D  71      47.262  33.701  44.521  1.00  18.19        O
ATOM   3169  CB   SER D  71      48.747  32.015  46.298  1.00  15.26        C
ATOM   3170  OG   SER D  71      47.822  32.217  47.360  1.00  16.34        O
ATOM   3171  N    ASN D  72      45.757  32.053  44.598  1.00  17.24        N
ATOM   3172  CA   ASN D  72      44.604  32.871  44.335  1.00  14.30        C
ATOM   3173  C    ASN D  72      44.451  33.836  45.493  1.00  16.33        C
ATOM   3174  O    ASN D  72      44.170  35.023  45.236  1.00  16.94        O
ATOM   3175  CB   ASN D  72      43.399  31.967  44.208  1.00  14.51        C
ATOM   3176  CG   ASN D  72      43.311  31.102  42.953  1.00  14.36        C
ATOM   3177  OD1  ASN D  72      44.170  31.156  42.089  1.00  15.41        O
ATOM   3178  ND2  ASN D  72      42.291  30.261  42.779  1.00  14.10        N
ATOM   3179  N    TYR D  73      44.711  33.348  46.720  1.00  16.70        N
ATOM   3180  CA   TYR D  73      44.709  34.222  47.893  1.00  17.86        C
ATOM   3181  C    TYR D  73      45.580  35.466  47.698  1.00  17.22        C
ATOM   3182  O    TYR D  73      45.047  36.559  47.813  1.00  19.51        O
ATOM   3183  CB   TYR D  73      45.171  33.479  49.182  1.00  15.83        C
ATOM   3184  CG   TYR D  73      44.962  34.331  50.421  1.00  11.11        C
ATOM   3185  CD1  TYR D  73      43.755  34.297  51.064  1.00  13.95        C
ATOM   3186  CD2  TYR D  73      45.932  35.212  50.823  1.00  14.63        C
ATOM   3187  CE1  TYR D  73      43.474  35.194  52.080  1.00  15.34        C
```

FIGURE 8A-64

```
ATOM   3188  CE2  TYR D  73      45.663  36.140  51.814  1.00  15.34           C
ATOM   3189  CZ   TYR D  73      44.430  36.108  52.407  1.00  16.30           C
ATOM   3190  OH   TYR D  73      44.123  37.051  53.334  1.00  22.01           O
ATOM   3191  N    SER D  74      46.888  35.357  47.402  1.00  18.57           N
ATOM   3192  CA   SER D  74      47.786  36.498  47.221  1.00  17.90           C
ATOM   3193  C    SER D  74      47.420  37.417  46.121  1.00  16.44           C
ATOM   3194  O    SER D  74      47.636  38.600  46.291  1.00  18.01           O
ATOM   3195  CB   SER D  74      49.180  36.125  46.829  1.00  18.93           C
ATOM   3196  OG   SER D  74      49.623  35.176  47.760  1.00  25.77           O
ATOM   3197  N    ILE D  75      46.890  36.866  45.027  1.00  16.68           N
ATOM   3198  CA   ILE D  75      46.470  37.645  43.893  1.00  16.88           C
ATOM   3199  C    ILE D  75      45.256  38.493  44.244  1.00  16.78           C
ATOM   3200  O    ILE D  75      45.237  39.693  43.968  1.00  20.42           O
ATOM   3201  CB   ILE D  75      46.184  36.709  42.711  1.00  16.41           C
ATOM   3202  CG1  ILE D  75      47.380  35.898  42.295  1.00  16.78           C
ATOM   3203  CG2  ILE D  75      45.861  37.615  41.567  1.00  16.46           C
ATOM   3204  CD1  ILE D  75      47.146  34.967  41.097  1.00  19.66           C
ATOM   3205  N    ILE D  76      44.230  37.936  44.901  1.00  18.21           N
ATOM   3206  CA   ILE D  76      43.023  38.678  45.220  1.00  15.41           C
ATOM   3207  C    ILE D  76      43.340  39.669  46.286  1.00  17.60           C
ATOM   3208  O    ILE D  76      42.870  40.796  46.215  1.00  20.17           O
ATOM   3209  CB   ILE D  76      41.941  37.743  45.711  1.00  16.42           C
ATOM   3210  CG1  ILE D  76      41.615  36.789  44.588  1.00  14.92           C
ATOM   3211  CG2  ILE D  76      40.695  38.481  46.200  1.00  11.21           C
ATOM   3212  CD1  ILE D  76      40.745  35.613  45.055  1.00  13.69           C
ATOM   3213  N    ASP D  77      44.162  39.271  47.248  1.00  19.35           N
ATOM   3214  CA   ASP D  77      44.561  40.150  48.321  1.00  21.77           C
ATOM   3215  C    ASP D  77      45.248  41.436  47.858  1.00  22.56           C
ATOM   3216  O    ASP D  77      44.924  42.515  48.376  1.00  22.07           O
ATOM   3217  CB   ASP D  77      45.433  39.385  49.282  1.00  24.17           C
ATOM   3218  CG   ASP D  77      45.713  40.148  50.571  1.00  28.55           C
ATOM   3219  OD1  ASP D  77      44.842  40.889  51.067  1.00  33.63           O
ATOM   3220  OD2  ASP D  77      46.822  39.988  51.073  1.00  28.53           O
ATOM   3221  N    LYS D  78      46.139  41.344  46.851  1.00  22.27           N
ATOM   3222  CA   LYS D  78      46.692  42.534  46.222  1.00  21.32           C
ATOM   3223  C    LYS D  78      45.654  43.318  45.471  1.00  19.56           C
ATOM   3224  O    LYS D  78      45.786  44.524  45.417  1.00  22.75           O
ATOM   3225  CB   LYS D  78      47.807  42.270  45.230  1.00  23.87           C
ATOM   3226  CG   LYS D  78      49.036  41.600  45.795  1.00  30.71           C
ATOM   3227  CD   LYS D  78      50.269  41.917  44.947  1.00  37.30           C
ATOM   3228  CE   LYS D  78      51.317  40.799  45.004  1.00  40.34           C
ATOM   3229  NZ   LYS D  78      50.843  39.671  44.214  1.00  44.85           N
ATOM   3230  N    LEU D  79      44.634  42.714  44.882  1.00  18.00           N
ATOM   3231  CA   LEU D  79      43.570  43.462  44.247  1.00  16.42           C
ATOM   3232  C    LEU D  79      42.696  44.124  45.273  1.00  18.98           C
ATOM   3233  O    LEU D  79      42.215  45.218  45.035  1.00  21.86           O
ATOM   3234  CB   LEU D  79      42.687  42.543  43.451  1.00  13.71           C
ATOM   3235  CG   LEU D  79      43.383  41.746  42.358  1.00  13.81           C
ATOM   3236  CD1  LEU D  79      42.294  41.091  41.522  1.00  14.16           C
ATOM   3237  CD2  LEU D  79      44.240  42.627  41.462  1.00  11.49           C
ATOM   3238  N    VAL D  80      42.438  43.524  46.430  1.00  19.01           N
ATOM   3239  CA   VAL D  80      41.624  44.124  47.462  1.00  20.11           C
ATOM   3240  C    VAL D  80      42.369  45.343  47.920  1.00  21.57           C
ATOM   3241  O    VAL D  80      41.759  46.389  47.987  1.00  25.14           O
ATOM   3242  CB   VAL D  80      41.480  43.093  48.603  1.00  22.94           C
ATOM   3243  CG1  VAL D  80      40.920  43.647  49.896  1.00  25.85           C
ATOM   3244  CG2  VAL D  80      40.511  42.003  48.246  1.00  20.39           C
ATOM   3245  N    ASN D  81      43.678  45.313  48.167  1.00  24.08           N
ATOM   3246  CA   ASN D  81      44.375  46.498  48.626  1.00  23.59           C
ATOM   3247  C    ASN D  81      44.363  47.632  47.620  1.00  26.17           C
```

*FIGURE 8A-65*

```
ATOM  3248  O    ASN D 81    44.334  48.756  48.114  1.00  28.26    O
ATOM  3249  CB   ASN D 81    45.761  46.180  49.097  1.00  21.14    C
ATOM  3250  CG   ASN D 81    45.684  45.257  50.278  1.00  23.73    C
ATOM  3251  OD1  ASN D 81    44.871  45.422  51.175  1.00  31.16    O
ATOM  3252  ND2  ASN D 81    46.490  44.231  50.357  1.00  25.26    N
ATOM  3253  N    ILE D 82    44.340  47.414  46.280  1.00  25.02    N
ATOM  3254  CA   ILE D 82    44.088  48.469  45.268  1.00  25.82    C
ATOM  3255  C    ILE D 82    42.671  49.103  45.287  1.00  25.89    C
ATOM  3256  O    ILE D 82    42.512  50.323  45.196  1.00  25.87    O
ATOM  3257  CB   ILE D 82    44.444  48.002  43.347  1.00  23.39    C
ATOM  3258  CG1  ILE D 82    45.885  47.557  43.751  1.00  25.26    C
ATOM  3259  CG2  ILE D 82    44.317  49.150  42.894  1.00  23.94    C
ATOM  3260  CD1  ILE D 82    46.185  46.717  42.500  1.00  24.24    C
ATOM  3261  N    VAL D 83    41.595  48.324  45.443  1.00  27.50    N
ATOM  3262  CA   VAL D 83    40.240  48.859  45.486  1.00  27.69    C
ATOM  3263  C    VAL D 83    40.017  49.556  46.841  1.00  30.42    C
ATOM  3264  O    VAL D 83    39.190  50.454  46.938  1.00  29.44    O
ATOM  3265  CB   VAL D 83    39.230  47.758  45.201  1.00  23.07    C
ATOM  3266  CG1  VAL D 83    37.910  48.384  44.868  1.00  24.95    C
ATOM  3267  CG2  VAL D 83    39.634  47.000  43.979  1.00  23.59    C
ATOM  3268  N    ASP D 84    40.772  49.192  47.892  1.00  32.89    N
ATOM  3269  CA   ASP D 84    40.753  49.840  49.206  1.00  35.85    C
ATOM  3270  C    ASP D 84    41.361  51.238  49.084  1.00  35.75    C
ATOM  3271  O    ASP D 84    40.779  52.212  49.557  1.00  35.62    O
ATOM  3272  CB   ASP D 84    41.531  49.029  50.294  1.00  39.03    C
ATOM  3273  CG   ASP D 84    40.827  48.006  51.221  1.00  41.67    C
ATOM  3274  OD1  ASP D 84    39.593  47.858  51.172  1.00  43.23    O
ATOM  3275  OD2  ASP D 84    41.536  47.352  52.008  1.00  43.54    O
ATOM  3276  N    ASP D 85    42.500  51.382  48.417  1.00  35.24    N
ATOM  3277  CA   ASP D 85    43.039  52.689  48.095  1.00  39.54    C
ATOM  3278  C    ASP D 85    42.055  53.620  47.372  1.00  40.48    C
ATOM  3279  O    ASP D 85    41.712  54.706  47.853  1.00  42.05    O
ATOM  3280  CB   ASP D 85    44.343  52.540  47.287  1.00  41.18    C
ATOM  3281  CG   ASP D 85    45.534  51.871  48.001  1.00  43.42    C
ATOM  3282  OD1  ASP D 85    45.537  51.723  49.243  1.00  41.35    O
ATOM  3283  OD2  ASP D 85    46.465  51.488  47.276  1.00  42.78    O
ATOM  3284  N    LEU D 86    41.518  53.157  46.238  1.00  41.90    N
ATOM  3285  CA   LEU D 86    40.526  53.903  45.456  1.00  39.57    C
ATOM  3286  C    LEU D 86    39.249  54.172  46.203  1.00  38.81    C
ATOM  3287  O    LEU D 86    38.614  55.176  45.924  1.00  40.16    O
ATOM  3288  CB   LEU D 86    40.142  53.164  44.191  1.00  36.00    C
ATOM  3289  CG   LEU D 86    41.234  52.732  43.251  1.00  34.91    C
ATOM  3290  CD1  LEU D 86    40.618  52.075  42.047  1.00  33.95    C
ATOM  3291  CD2  LEU D 86    42.096  53.907  42.858  1.00  32.40    C
ATOM  3292  N    VAL D 87    38.840  53.303  47.125  1.00  40.82    N
ATOM  3293  CA   VAL D 87    37.680  53.589  47.958  1.00  44.87    C
ATOM  3294  C    VAL D 87    37.965  54.754  48.933  1.00  47.95    C
ATOM  3295  O    VAL D 87    37.085  55.580  49.176  1.00  49.04    O
ATOM  3296  CB   VAL D 87    37.191  52.311  48.682  1.00  42.48    C
ATOM  3297  CG1  VAL D 87    36.094  52.685  49.647  1.00  43.30    C
ATOM  3298  CG2  VAL D 87    36.572  51.285  47.749  1.00  39.59    C
ATOM  3299  N    GLU D 88    39.185  54.862  49.472  1.00  51.32    N
ATOM  3300  CA   GLU D 88    39.548  55.935  50.387  1.00  55.88    C
ATOM  3301  C    GLU D 88    39.807  57.235  49.672  1.00  57.32    C
ATOM  3302  O    GLU D 88    39.717  58.303  50.291  1.00  59.78    O
ATOM  3303  CB   GLU D 88    40.786  55.627  51.225  1.00  57.84    C
ATOM  3304  CG   GLU D 88    40.534  54.935  52.572  1.00  61.46    C
ATOM  3305  CD   GLU D 88    41.737  54.106  53.056  1.00  65.66    C
ATOM  3306  OE1  GLU D 88    42.872  54.610  53.000  1.00  65.91    O
ATOM  3307  OE2  GLU D 88    41.543  52.947  53.479  1.00  68.20    O
```

FIGURE 8A-66

| ATOM | 3308 | N   | CYS | D | 89  | 40.147 | 57.130 | 48.382 | 1.00 | 57.61 | N |
|------|------|-----|-----|---|-----|--------|--------|--------|------|-------|---|
| ATOM | 3309 | CA  | CYS | D | 89  | 40.273 | 58.307 | 47.528 | 1.00 | 58.46 | C |
| ATOM | 3310 | C   | CYS | D | 89  | 38.895 | 58.970 | 47.344 | 1.00 | 58.39 | C |
| ATOM | 3311 | O   | CYS | D | 89  | 38.791 | 60.197 | 47.378 | 1.00 | 58.21 | O |
| ATOM | 3312 | CB  | CYS | D | 89  | 40.931 | 57.880 | 46.221 | 1.00 | 57.54 | C |
| ATOM | 3313 | SG  | CYS | D | 89  | 41.341 | 59.181 | 45.038 | 1.00 | 58.90 | S |
| ATOM | 3314 | N   | VAL | D | 90  | 37.809 | 58.179 | 47.271 | 1.00 | 58.70 | N |
| ATOM | 3315 | CA  | VAL | D | 90  | 36.453 | 58.684 | 47.150 | 1.00 | 59.63 | C |
| ATOM | 3316 | C   | VAL | D | 90  | 35.871 | 59.210 | 48.484 | 1.00 | 61.73 | C |
| ATOM | 3317 | O   | VAL | D | 90  | 34.680 | 59.004 | 48.763 | 1.00 | 62.80 | O |
| ATOM | 3318 | CB  | VAL | D | 90  | 35.602 | 57.544 | 46.539 | 1.00 | 58.55 | C |
| ATOM | 3319 | N   | SER | D | 104 | 20.665 | 52.244 | 45.909 | 1.00 | 56.19 | N |
| ATOM | 3320 | CA  | SER | D | 104 | 21.629 | 51.156 | 45.958 | 1.00 | 53.75 | C |
| ATOM | 3321 | C   | SER | D | 104 | 21.476 | 50.204 | 44.750 | 1.00 | 51.69 | C |
| ATOM | 3322 | O   | SER | D | 104 | 20.519 | 50.365 | 43.954 | 1.00 | 53.93 | O |
| ATOM | 3323 | CB  | SER | D | 104 | 21.454 | 50.421 | 47.297 | 1.00 | 55.38 | C |
| ATOM | 3324 | OG  | SER | D | 104 | 22.506 | 49.503 | 47.610 | 1.00 | 56.37 | O |
| ATOM | 3325 | N   | PRO | D | 105 | 22.446 | 49.277 | 44.526 | 1.00 | 45.68 | N |
| ATOM | 3326 | CA  | PRO | D | 105 | 22.366 | 48.292 | 43.470 | 1.00 | 41.30 | C |
| ATOM | 3327 | C   | PRO | D | 105 | 22.138 | 46.887 | 43.955 | 1.00 | 37.99 | C |
| ATOM | 3328 | O   | PRO | D | 105 | 22.529 | 46.478 | 45.049 | 1.00 | 38.93 | O |
| ATOM | 3329 | CB  | PRO | D | 105 | 23.661 | 48.481 | 42.741 | 1.00 | 40.55 | C |
| ATOM | 3330 | CG  | PRO | D | 105 | 24.631 | 48.664 | 43.862 | 1.00 | 42.00 | C |
| ATOM | 3331 | CD  | PRO | D | 105 | 23.856 | 49.476 | 44.863 | 1.00 | 42.72 | C |
| ATOM | 3332 | N   | GLU | D | 106 | 21.459 | 46.177 | 43.075 | 1.00 | 33.70 | N |
| ATOM | 3333 | CA  | GLU | D | 106 | 20.971 | 44.880 | 43.417 | 1.00 | 32.02 | C |
| ATOM | 3334 | C   | GLU | D | 106 | 21.976 | 43.812 | 43.085 | 1.00 | 32.36 | C |
| ATOM | 3335 | O   | GLU | D | 106 | 22.715 | 43.942 | 42.111 | 1.00 | 32.37 | O |
| ATOM | 3336 | CB  | GLU | D | 106 | 19.734 | 44.553 | 42.624 | 1.00 | 32.57 | C |
| ATOM | 3337 | N   | PRO | D | 107 | 22.006 | 42.732 | 43.886 | 1.00 | 32.45 | N |
| ATOM | 3338 | CA  | PRO | D | 107 | 22.855 | 41.549 | 43.686 | 1.00 | 31.86 | C |
| ATOM | 3339 | C   | PRO | D | 107 | 22.724 | 40.845 | 42.340 | 1.00 | 29.45 | C |
| ATOM | 3340 | O   | PRO | D | 107 | 21.623 | 40.491 | 41.911 | 1.00 | 29.62 | O |
| ATOM | 3341 | CB  | PRO | D | 107 | 22.403 | 40.614 | 44.801 | 1.00 | 32.83 | C |
| ATOM | 3342 | CG  | PRO | D | 107 | 22.040 | 41.574 | 45.904 | 1.00 | 34.59 | C |
| ATOM | 3343 | CD  | PRO | D | 107 | 21.299 | 42.658 | 45.165 | 1.00 | 31.98 | C |
| ATOM | 3344 | N   | ARG | D | 108 | 23.893 | 40.580 | 41.745 | 1.00 | 27.04 | N |
| ATOM | 3345 | CA  | ARG | D | 108 | 23.966 | 39.882 | 40.479 | 1.00 | 24.37 | C |
| ATOM | 3346 | C   | ARG | D | 108 | 25.090 | 38.834 | 40.442 | 1.00 | 22.83 | C |
| ATOM | 3347 | O   | ARG | D | 108 | 26.084 | 39.002 | 41.124 | 1.00 | 21.26 | O |
| ATOM | 3348 | CB  | ARG | D | 108 | 24.090 | 40.981 | 39.431 | 1.00 | 27.20 | C |
| ATOM | 3349 | CG  | ARG | D | 108 | 23.924 | 40.490 | 38.015 | 1.00 | 32.52 | C |
| ATOM | 3350 | CD  | ARG | D | 108 | 23.488 | 41.587 | 37.051 | 1.00 | 35.27 | C |
| ATOM | 3351 | NE  | ARG | D | 108 | 23.846 | 41.160 | 35.712 | 1.00 | 38.19 | N |
| ATOM | 3352 | CZ  | ARG | D | 108 | 23.536 | 41.872 | 34.627 | 1.00 | 38.97 | C |
| ATOM | 3353 | NH1 | ARG | D | 108 | 22.798 | 43.008 | 34.720 | 1.00 | 34.64 | N |
| ATOM | 3354 | NH2 | ARG | D | 108 | 23.995 | 41.398 | 33.454 | 1.00 | 39.61 | N |
| ATOM | 3355 | N   | LEU | D | 109 | 24.984 | 37.734 | 39.681 | 1.00 | 21.95 | N |
| ATOM | 3356 | CA  | LEU | D | 109 | 25.996 | 36.697 | 39.565 | 1.00 | 20.44 | C |
| ATOM | 3357 | C   | LEU | D | 109 | 26.760 | 36.756 | 38.265 | 1.00 | 18.72 | C |
| ATOM | 3358 | O   | LEU | D | 109 | 26.191 | 36.725 | 37.175 | 1.00 | 19.50 | O |
| ATOM | 3359 | CB  | LEU | D | 109 | 25.392 | 35.304 | 39.657 | 1.00 | 21.02 | C |
| ATOM | 3360 | CG  | LEU | D | 109 | 24.434 | 34.895 | 40.779 | 1.00 | 23.43 | C |
| ATOM | 3361 | CD1 | LEU | D | 109 | 24.170 | 33.404 | 40.648 | 1.00 | 24.08 | C |
| ATOM | 3362 | CD2 | LEU | D | 109 | 24.939 | 35.187 | 42.193 | 1.00 | 25.25 | C |
| ATOM | 3363 | N   | PHE | D | 110 | 28.080 | 36.753 | 38.437 | 1.00 | 17.94 | N |
| ATOM | 3364 | CA  | PHE | D | 110 | 29.031 | 36.804 | 37.333 | 1.00 | 17.25 | C |
| ATOM | 3365 | C   | PHE | D | 110 | 30.013 | 35.649 | 37.345 | 1.00 | 16.87 | C |
| ATOM | 3366 | O   | PHE | D | 110 | 30.417 | 35.198 | 38.404 | 1.00 | 19.49 | O |
| ATOM | 3367 | CB  | PHE | D | 110 | 29.848 | 38.070 | 37.366 | 1.00 | 16.08 | C |

FIGURE 8A-67

| | | | | | | | | | |
|---|---|---|---|---|---|---|---|---|---|
| ATOM | 3368 | CG | PHE | D | 110 | 28.993 | 39.305 | 37.265 | 1.00 18.38 | C |
| ATOM | 3369 | CD1 | PHE | D | 110 | 28.573 | 39.743 | 36.029 | 1.00 19.11 | C |
| ATOM | 3370 | CD2 | PHE | D | 110 | 28.633 | 39.977 | 38.408 | 1.00 16.78 | C |
| ATOM | 3371 | CE1 | PHE | D | 110 | 27.802 | 40.874 | 35.946 | 1.00 16.73 | C |
| ATOM | 3372 | CE2 | PHE | D | 110 | 27.850 | 41.103 | 38.321 | 1.00 18.17 | C |
| ATOM | 3373 | CZ | PHE | D | 110 | 27.445 | 41.553 | 37.081 | 1.00 21.53 | C |
| ATOM | 3374 | N | THR | D | 111 | 30.425 | 35.107 | 36.216 | 1.00 15.24 | N |
| ATOM | 3375 | CA | THR | D | 111 | 31.539 | 34.192 | 36.176 | 1.00 14.72 | C |
| ATOM | 3376 | C | THR | D | 111 | 32.811 | 34.994 | 36.443 | 1.00 12.40 | C |
| ATOM | 3377 | O | THR | D | 111 | 32.752 | 36.218 | 36.400 | 1.00 13.27 | O |
| ATOM | 3378 | CB | THR | D | 111 | 31.579 | 33.435 | 34.828 | 1.00 17.12 | C |
| ATOM | 3379 | OG1 | THR | D | 111 | 31.630 | 34.415 | 33.809 | 1.00 17.68 | O |
| ATOM | 3380 | CG2 | THR | D | 111 | 30.451 | 32.446 | 34.621 | 1.00 14.81 | C |
| ATOM | 3381 | N | PRO | D | 112 | 33.974 | 34.412 | 36.757 | 1.00 12.31 | N |
| ATOM | 3382 | CA | PRO | D | 112 | 35.219 | 35.126 | 36.935 | 1.00 11.10 | C |
| ATOM | 3383 | C | PRO | D | 112 | 35.594 | 36.046 | 35.783 | 1.00 14.02 | C |
| ATOM | 3384 | O | PRO | D | 112 | 35.884 | 37.215 | 36.011 | 1.00 13.17 | O |
| ATOM | 3385 | CB | PRO | D | 112 | 36.189 | 33.965 | 37.074 | 1.00 9.39 | C |
| ATOM | 3386 | CG | PRO | D | 112 | 35.413 | 32.952 | 37.854 | 1.00 7.72 | C |
| ATOM | 3387 | CD | PRO | D | 112 | 34.151 | 32.972 | 37.061 | 1.00 11.01 | C |
| ATOM | 3388 | N | GLU | D | 113 | 35.611 | 35.572 | 34.517 | 1.00 16.22 | N |
| ATOM | 3389 | CA | GLU | D | 113 | 35.905 | 36.456 | 33.395 | 1.00 16.17 | C |
| ATOM | 3390 | C | GLU | D | 113 | 35.026 | 37.679 | 33.272 | 1.00 13.99 | C |
| ATOM | 3391 | O | GLU | D | 113 | 35.508 | 38.761 | 32.985 | 1.00 15.09 | O |
| ATOM | 3392 | CB | GLU | D | 113 | 35.913 | 35.703 | 32.092 | 1.00 17.91 | C |
| ATOM | 3393 | CG | GLU | D | 113 | 34.636 | 34.985 | 31.713 | 1.00 19.43 | C |
| ATOM | 3394 | CD | GLU | D | 113 | 34.621 | 34.539 | 30.277 | 1.00 22.34 | C |
| ATOM | 3395 | OE1 | GLU | D | 113 | 35.652 | 34.599 | 29.608 | 1.00 23.91 | O |
| ATOM | 3396 | OE2 | GLU | D | 113 | 33.558 | 34.139 | 29.810 | 1.00 24.64 | O |
| ATOM | 3397 | N | GLU | D | 114 | 33.747 | 37.539 | 33.559 | 1.00 14.85 | N |
| ATOM | 3398 | CA | GLU | D | 114 | 32.837 | 38.649 | 33.596 | 1.00 15.81 | C |
| ATOM | 3399 | C | GLU | D | 114 | 33.063 | 39.567 | 34.769 | 1.00 15.50 | C |
| ATOM | 3400 | O | GLU | D | 114 | 33.085 | 40.783 | 34.557 | 1.00 15.87 | O |
| ATOM | 3401 | CB | GLU | D | 114 | 31.402 | 38.208 | 33.707 | 1.00 19.13 | C |
| ATOM | 3402 | CG | GLU | D | 114 | 30.883 | 37.422 | 32.539 | 1.00 21.49 | C |
| ATOM | 3403 | CD | GLU | D | 114 | 29.605 | 36.642 | 32.816 | 1.00 24.09 | C |
| ATOM | 3404 | OE1 | GLU | D | 114 | 29.017 | 36.697 | 33.897 | 1.00 26.51 | O |
| ATOM | 3405 | OE2 | GLU | D | 114 | 29.185 | 35.937 | 31.907 | 1.00 29.29 | O |
| ATOM | 3406 | N | PHE | D | 115 | 33.204 | 39.041 | 35.990 | 1.00 13.99 | N |
| ATOM | 3407 | CA | PHE | D | 115 | 33.464 | 39.892 | 37.125 | 1.00 12.83 | C |
| ATOM | 3408 | C | PHE | D | 115 | 34.753 | 40.667 | 36.905 | 1.00 13.21 | C |
| ATOM | 3409 | O | PHE | D | 115 | 34.827 | 41.855 | 37.193 | 1.00 14.99 | O |
| ATOM | 3410 | CB | PHE | D | 115 | 33.650 | 39.018 | 38.359 | 1.00 10.89 | C |
| ATOM | 3411 | CG | PHE | D | 115 | 33.982 | 39.867 | 39.569 | 1.00 11.83 | C |
| ATOM | 3412 | CD1 | PHE | D | 115 | 32.951 | 40.361 | 40.344 | 1.00 12.60 | C |
| ATOM | 3413 | CD2 | PHE | D | 115 | 35.296 | 40.133 | 39.917 | 1.00 14.96 | C |
| ATOM | 3414 | CE1 | PHE | D | 115 | 33.251 | 41.093 | 41.480 | 1.00 12.59 | C |
| ATOM | 3415 | CE2 | PHE | D | 115 | 35.605 | 40.892 | 41.033 | 1.00 13.04 | C |
| ATOM | 3416 | CZ | PHE | D | 115 | 34.560 | 41.373 | 41.810 | 1.00 14.57 | C |
| ATOM | 3417 | N | PHE | D | 116 | 35.833 | 40.025 | 36.477 | 1.00 15.07 | N |
| ATOM | 3418 | CA | PHE | D | 116 | 37.102 | 40.718 | 36.297 | 1.00 13.94 | C |
| ATOM | 3419 | C | PHE | D | 116 | 37.181 | 41.563 | 35.036 | 1.00 15.79 | C |
| ATOM | 3420 | O | PHE | D | 116 | 38.014 | 42.455 | 34.965 | 1.00 16.79 | O |
| ATOM | 3421 | CB | PHE | D | 116 | 38.273 | 39.775 | 36.373 | 1.00 13.55 | C |
| ATOM | 3422 | CG | PHE | D | 116 | 38.548 | 39.261 | 37.759 | 1.00 10.27 | C |
| ATOM | 3423 | CD1 | PHE | D | 116 | 39.105 | 40.100 | 38.692 | 1.00 12.82 | C |
| ATOM | 3424 | CD2 | PHE | D | 116 | 38.143 | 37.990 | 38.132 | 1.00 11.47 | C |
| ATOM | 3425 | CE1 | PHE | D | 116 | 39.169 | 39.689 | 40.025 | 1.00 14.46 | C |
| ATOM | 3426 | CE2 | PHE | D | 116 | 38.216 | 37.584 | 39.457 | 1.00 10.67 | C |
| ATOM | 3427 | CZ | PHE | D | 116 | 38.709 | 38.439 | 40.407 | 1.00 11.80 | C |

FIGURE 8A-68

```
ATOM   3428  N    ARG D 117      36.361  41.405  34.011  1.00  16.57          N
ATOM   3429  CA   ARG D 117      36.293  42.421  32.990  1.00  20.64          C
ATOM   3430  C    ARG D 117      35.668  43.700  33.548  1.00  22.51          C
ATOM   3431  O    ARG D 117      36.089  44.803  33.174  1.00  23.89          O
ATOM   3432  CB   ARG D 117      35.446  41.879  31.860  1.00  26.52          C
ATOM   3433  CG   ARG D 117      35.518  42.709  30.598  1.00  31.58          C
ATOM   3434  CD   ARG D 117      34.496  42.146  29.640  1.00  35.05          C
ATOM   3435  NE   ARG D 117      34.394  43.021  28.483  1.00  38.58          N
ATOM   3436  CZ   ARG D 117      33.828  42.656  27.326  1.00  37.56          C
ATOM   3437  NH1  ARG D 117      33.169  41.506  27.170  1.00  33.95          N
ATOM   3438  NH2  ARG D 117      34.002  43.473  26.286  1.00  37.95          N
ATOM   3439  N    ILE D 118      34.656  43.594  34.445  1.00  22.03          N
ATOM   3440  CA   ILE D 118      34.052  44.753  35.121  1.00  19.63          C
ATOM   3441  C    ILE D 118      35.047  45.368  36.086  1.00  19.88          C
ATOM   3442  O    ILE D 118      35.183  46.586  36.085  1.00  23.21          O
ATOM   3443  CB   ILE D 118      32.781  44.357  35.874  1.00  20.68          C
ATOM   3444  CG1  ILE D 118      31.691  43.843  34.951  1.00  19.48          C
ATOM   3445  CG2  ILE D 118      32.255  45.562  36.619  1.00  20.52          C
ATOM   3446  CD1  ILE D 118      30.567  43.143  35.727  1.00  18.63          C
ATOM   3447  N    PHE D 119      35.741  44.577  36.908  1.00  16.07          N
ATOM   3448  CA   PHE D 119      36.853  45.059  37.683  1.00  15.72          C
ATOM   3449  C    PHE D 119      37.853  45.894  36.880  1.00  17.75          C
ATOM   3450  O    PHE D 119      38.208  47.006  37.267  1.00  20.22          O
ATOM   3451  CB   PHE D 119      37.545  43.866  38.359  1.00  12.02          C
ATOM   3452  CG   PHE D 119      38.822  44.222  39.100  1.00  13.89          C
ATOM   3453  CD1  PHE D 119      38.760  44.766  40.389  1.00  14.47          C
ATOM   3454  CD2  PHE D 119      40.057  44.030  38.492  1.00  10.48          C
ATOM   3455  CE1  PHE D 119      39.944  45.148  41.032  1.00  13.14          C
ATOM   3456  CE2  PHE D 119      41.219  44.387  39.149  1.00  10.95          C
ATOM   3457  CZ   PHE D 119      41.163  44.965  40.405  1.00  10.47          C
ATOM   3458  N    ASN D 120      38.349  45.343  35.779  1.00  18.18          N
ATOM   3459  CA   ASN D 120      39.325  45.994  34.955  1.00  18.15          C
ATOM   3460  C    ASN D 120      38.709  47.263  34.387  1.00  20.79          C
ATOM   3461  O    ASN D 120      39.348  48.303  34.408  1.00  22.36          O
ATOM   3462  CB   ASN D 120      39.805  45.078  33.812  1.00  18.05          C
ATOM   3463  CG   ASN D 120      40.849  44.026  34.137  1.00  17.71          C
ATOM   3464  OD1  ASN D 120      41.770  44.210  34.918  1.00  21.36          O
ATOM   3465  ND2  ASN D 120      40.765  42.860  33.538  1.00  17.03          N
ATOM   3466  N    ARG D 121      37.463  47.256  33.941  1.00  22.71          N
ATOM   3467  CA   ARG D 121      36.824  48.438  33.431  1.00  24.59          C
ATOM   3468  C    ARG D 121      36.703  49.523  34.494  1.00  27.41          C
ATOM   3469  O    ARG D 121      36.971  50.683  34.192  1.00  30.49          O
ATOM   3470  CB   ARG D 121      35.468  47.993  32.953  1.00  26.42          C
ATOM   3471  CG   ARG D 121      34.608  49.156  32.549  1.00  33.46          C
ATOM   3472  CD   ARG D 121      34.760  49.641  31.105  1.00  37.32          C
ATOM   3473  NE   ARG D 121      34.149  50.962  30.882  1.00  39.99          N
ATOM   3474  CZ   ARG D 121      32.836  51.217  31.020  1.00  39.01          C
ATOM   3475  NH1  ARG D 121      31.955  50.306  31.426  1.00  37.27          N
ATOM   3476  NH2  ARG D 121      32.392  52.439  30.747  1.00  40.47          N
ATOM   3477  N    SER D 122      36.364  49.186  35.754  1.00  28.07          N
ATOM   3478  CA   SER D 122      36.147  50.153  36.820  1.00  24.66          C
ATOM   3479  C    SER D 122      37.455  50.758  37.250  1.00  25.38          C
ATOM   3480  O    SER D 122      37.536  51.971  37.401  1.00  24.85          O
ATOM   3481  CB   SER D 122      35.452  49.505  37.983  1.00  20.76          C
ATOM   3482  OG   SER D 122      34.236  48.886  37.591  1.00  19.10          O
ATOM   3483  N    ILE D 123      38.513  49.954  37.389  1.00  28.58          N
ATOM   3484  CA   ILE D 123      39.853  50.468  37.718  1.00  31.03          C
ATOM   3485  C    ILE D 123      40.396  51.464  36.684  1.00  33.54          C
ATOM   3486  O    ILE D 123      40.998  52.471  37.040  1.00  33.54          O
ATOM   3487  CB   ILE D 123      40.821  49.267  38.041  1.00  31.69          C
```

FIGURE 8A-69

| | | | | | | | | | | |
|---|---|---|---|---|---|---|---|---|---|---|
| ATOM | 3488 | CG1 | ILE | D | 123 | 40.899 | 48.877 | 39.544 | 1.00 30.91 | C |
| ATOM | 3489 | CG2 | ILE | D | 123 | 42.262 | 49.504 | 37.583 | 1.00 31.27 | C |
| ATOM | 3490 | CD1 | ILE | D | 123 | 39.609 | 48.826 | 40.377 | 1.00 31.19 | C |
| ATOM | 3491 | N | ASP | D | 124 | 40.123 | 51.244 | 35.395 | 1.00 36.80 | N |
| ATOM | 3492 | CA | ASP | D | 124 | 40.562 | 52.125 | 34.333 | 1.00 38.72 | C |
| ATOM | 3493 | C | ASP | D | 124 | 39.846 | 53.455 | 34.353 | 1.00 39.18 | C |
| ATOM | 3494 | O | ASP | D | 124 | 40.487 | 54.491 | 34.186 | 1.00 39.94 | O |
| ATOM | 3495 | CB | ASP | D | 124 | 40.383 | 51.461 | 32.981 | 1.00 42.50 | C |
| ATOM | 3496 | CG | ASP | D | 124 | 40.847 | 52.342 | 31.828 | 1.00 47.69 | C |
| ATOM | 3497 | OD1 | ASP | D | 124 | 42.058 | 52.554 | 31.645 | 1.00 50.62 | O |
| ATOM | 3498 | OD2 | ASP | D | 124 | 39.972 | 52.837 | 31.116 | 1.00 51.18 | O |
| ATOM | 3499 | N | ALA | D | 125 | 38.538 | 53.440 | 34.590 | 1.00 39.43 | N |
| ATOM | 3500 | CA | ALA | D | 125 | 37.731 | 54.649 | 34.586 | 1.00 41.04 | C |
| ATOM | 3501 | C | ALA | D | 125 | 38.028 | 55.640 | 35.712 | 1.00 44.24 | C |
| ATOM | 3502 | O | ALA | D | 125 | 37.580 | 56.792 | 35.729 | 1.00 46.63 | O |
| ATOM | 3503 | CB | ALA | D | 125 | 36.289 | 54.232 | 34.688 | 1.00 37.89 | C |
| ATOM | 3504 | N | PHE | D | 126 | 38.795 | 55.189 | 36.693 | 1.00 47.55 | N |
| ATOM | 3505 | CA | PHE | D | 126 | 39.342 | 56.063 | 37.709 | 1.00 52.08 | C |
| ATOM | 3506 | C | PHE | D | 126 | 40.409 | 57.058 | 37.208 | 1.00 55.06 | C |
| ATOM | 3507 | O | PHE | D | 126 | 40.531 | 58.167 | 37.751 | 1.00 57.33 | O |
| ATOM | 3508 | CB | PHE | D | 126 | 39.877 | 55.182 | 38.838 | 1.00 51.90 | C |
| ATOM | 3509 | CG | PHE | D | 126 | 39.154 | 55.489 | 40.124 | 1.00 50.92 | C |
| ATOM | 3510 | CD1 | PHE | D | 126 | 39.155 | 56.780 | 40.620 | 1.00 52.88 | C |
| ATOM | 3511 | CD2 | PHE | D | 126 | 38.437 | 54.505 | 40.745 | 1.00 50.11 | C |
| ATOM | 3512 | CE1 | PHE | D | 126 | 38.390 | 57.105 | 41.721 | 1.00 54.34 | C |
| ATOM | 3513 | CE2 | PHE | D | 126 | 37.688 | 54.827 | 41.851 | 1.00 52.08 | C |
| ATOM | 3514 | CZ | PHE | D | 126 | 37.653 | 56.117 | 42.336 | 1.00 53.64 | C |
| ATOM | 3515 | N | LYS | D | 127 | 41.187 | 56.667 | 36.177 | 1.00 56.75 | N |
| ATOM | 3516 | CA | LYS | D | 127 | 42.055 | 57.566 | 35.420 | 1.00 57.29 | C |
| ATOM | 3517 | C | LYS | D | 127 | 41.257 | 58.229 | 34.273 | 1.00 58.91 | C |
| ATOM | 3518 | O | LYS | D | 127 | 41.376 | 57.826 | 33.098 | 1.00 60.03 | O |
| ATOM | 3519 | CB | LYS | D | 127 | 43.225 | 56.735 | 34.882 | 1.00 56.61 | C |
| TER | 3521 | | LYS | D | 127 | | | | | |
| HETATM | 3522 | CA | CA | | 1021 | 34.563 | 32.796 | 27.927 | 1.00 28.47 | CA |
| HETATM | 3523 | CA | CA | | 1022 | 29.874 | 41.216 | 51.866 | 1.00 42.93 | CA |
| HETATM | 3524 | CA | CA | | 1023 | 46.453 | 8.630 | 31.415 | 1.00 34.99 | CA |
| HETATM | 3525 | OH2 | 1PE | | 1 | 18.016 | 39.096 | 31.870 | 1.00 54.04 | O |
| HETATM | 3526 | C12 | 1PE | | 1 | 19.233 | 39.467 | 31.241 | 1.00 52.50 | C |
| HETATM | 3527 | C22 | 1PE | | 1 | 20.344 | 39.764 | 32.285 | 1.00 52.87 | C |
| HETATM | 3528 | OH3 | 1PE | | 1 | 21.455 | 40.455 | 31.657 | 1.00 50.81 | O |
| HETATM | 3529 | C13 | 1PE | | 1 | 21.887 | 42.392 | 30.182 | 1.00 41.29 | C |
| HETATM | 3530 | C23 | 1PE | | 1 | 20.971 | 41.737 | 31.213 | 1.00 45.45 | C |
| HETATM | 3531 | OH4 | 1PE | | 1 | 23.085 | 42.870 | 30.757 | 1.00 37.80 | O |
| HETATM | 3532 | C14 | 1PE | | 1 | 24.265 | 44.731 | 31.534 | 1.00 39.00 | C |
| HETATM | 3533 | C24 | 1PE | | 1 | 22.866 | 44.120 | 31.391 | 1.00 35.49 | C |
| HETATM | 3534 | OH5 | 1PE | | 1 | 25.158 | 43.676 | 31.917 | 1.00 39.07 | O |
| HETATM | 3535 | C15 | 1PE | | 1 | 27.396 | 42.942 | 31.976 | 1.00 36.51 | C |
| HETATM | 3536 | C25 | 1PE | | 1 | 26.476 | 44.138 | 32.222 | 1.00 37.63 | C |
| HETATM | 3537 | OH6 | 1PE | | 1 | 26.797 | 41.817 | 32.602 | 1.00 37.94 | O |
| HETATM | 3538 | C16 | 1PE | | 1 | 28.795 | 40.537 | 32.878 | 1.00 44.86 | C |
| HETATM | 3539 | C26 | 1PE | | 1 | 27.405 | 40.589 | 32.251 | 1.00 38.90 | C |
| HETATM | 3540 | OH7 | 1PE | | 1 | 29.817 | 40.999 | 31.987 | 1.00 53.59 | O |
| HETATM | 3541 | O | HOH | | 1024 | 36.890 | 32.430 | 27.721 | 1.00 24.58 | O |
| HETATM | 3542 | O | HOH | | 1025 | 35.049 | 30.934 | 29.322 | 1.00 27.97 | O |
| HETATM | 3543 | O | HOH | | 1026 | 31.347 | 42.865 | 52.839 | 1.00 31.45 | O |
| HETATM | 3544 | O | HOH | | 1027 | 44.819 | 10.251 | 32.056 | 1.00 31.08 | O |
| HETATM | 3545 | O | HOH | | 1028 | 47.508 | 7.695 | 33.365 | 1.00 35.15 | O |
| HETATM | 3546 | O | HOH | | 1029 | 46.695 | 9.256 | 30.957 | 1.00 29.22 | O |
| HETATM | 3547 | O | HOH | | 1105 | 33.704 | 13.935 | 20.986 | 1.00 32.21 | O |
| HETATM | 3548 | O | HOH | | 1106 | 22.707 | 17.800 | 13.006 | 1.00 51.74 | O |

*FIGURE 8A-70*

| | | | | | | | | | |
|---|---|---|---|---|---|---|---|---|---|
| HETATM | 3549 | O | HOH | 1107 | 25.589 | 22.952 | 23.068 | 1.00 | 38.86 |
| HETATM | 3550 | O | HOH | 1108 | 20.410 | 17.104 | 15.299 | 1.00 | 29.07 |
| HETATM | 3551 | O | HOH | 1109 | 26.763 | 8.355 | 29.315 | 1.00 | 19.21 |
| HETATM | 3552 | O | HOH | 1110 | 25.744 | 13.365 | 30.461 | 1.00 | 32.06 |
| HETATM | 3553 | O | HOH | 1111 | 27.532 | 6.721 | 32.848 | 1.00 | 38.65 |
| HETATM | 3554 | O | HOH | 1112 | 18.245 | 13.266 | 16.629 | 1.00 | 28.39 |
| HETATM | 3555 | O | HOH | 1113 | 23.260 | 14.366 | 29.164 | 1.00 | 21.00 |
| HETATM | 3556 | O | HOH | 1114 | 15.116 | 22.225 | 22.815 | 1.00 | 19.32 |
| HETATM | 3557 | O | HOH | 1115 | 15.033 | 21.355 | 35.696 | 1.00 | 38.95 |
| HETATM | 3558 | O | HOH | 1116 | 20.651 | 6.306 | 35.427 | 1.00 | 25.08 |
| HETATM | 3559 | O | HOH | 1117 | 15.267 | 18.912 | 37.475 | 1.00 | 41.62 |
| HETATM | 3560 | O | HOH | 1118 | 13.693 | 14.872 | 13.312 | 1.00 | 29.91 |
| HETATM | 3561 | O | HOH | 1119 | 10.257 | 20.310 | 28.411 | 1.00 | 19.75 |
| HETATM | 3562 | O | HOH | 1120 | 17.034 | 0.246 | 35.599 | 1.00 | 32.81 |
| HETATM | 3563 | O | HOH | 1121 | 6.051 | 17.933 | 31.202 | 1.00 | 21.61 |
| HETATM | 3564 | O | HOH | 1122 | 4.997 | 14.576 | 24.993 | 1.00 | 33.94 |
| HETATM | 3565 | O | HOH | 1123 | 0.916 | 19.643 | 30.618 | 1.00 | 37.91 |
| HETATM | 3566 | O | HOH | 1124 | 5.906 | 11.136 | 30.408 | 1.00 | 46.39 |
| HETATM | 3567 | O | HOH | 1125 | 6.559 | 5.604 | 30.508 | 1.00 | 37.39 |
| HETATM | 3568 | O | HOH | 1126 | 8.033 | 4.439 | 28.006 | 1.00 | 43.67 |
| HETATM | 3569 | O | HOH | 1127 | 5.753 | 3.756 | 33.445 | 1.00 | 43.48 |
| HETATM | 3570 | O | HOH | 1128 | 44.059 | 26.360 | 36.277 | 1.00 | 22.42 |
| HETATM | 3571 | O | HOH | 1129 | 34.421 | 31.639 | 20.635 | 1.00 | 57.58 |
| HETATM | 3572 | O | HOH | 1130 | 50.215 | 13.426 | 34.211 | 1.00 | 31.74 |
| HETATM | 3573 | O | HOH | 1132 | 22.455 | 45.496 | 39.519 | 1.00 | 46.16 |
| HETATM | 3574 | O | HOH | 1133 | 13.246 | 35.686 | 8.764 | 1.00 | 63.66 |
| HETATM | 3575 | O | HOH | 1134 | 34.029 | 21.538 | 54.154 | 1.00 | 48.71 |
| HETATM | 3576 | O | HOH | 1135 | 46.505 | 41.139 | 53.506 | 1.00 | 25.80 |
| HETATM | 3577 | O | HOH | 1136 | 14.868 | 40.514 | 7.810 | 1.00 | 46.95 |
| HETATM | 3578 | O | HOH | 1138 | 37.977 | 45.274 | 53.726 | 1.00 | 41.75 |
| HETATM | 3579 | O | HOH | 1139 | 10.511 | 41.610 | 30.508 | 1.00 | 54.06 |
| HETATM | 3580 | O | HOH | 1140 | 21.928 | 44.651 | 36.769 | 1.00 | 27.65 |
| HETATM | 3581 | O | HOH | 1141 | 9.657 | 38.390 | 31.085 | 1.00 | 36.52 |
| HETATM | 3582 | O | HOH | 1142 | 35.556 | 55.905 | 31.455 | 1.00 | 33.05 |
| HETATM | 3583 | O | HOH | 1143 | 52.337 | 31.433 | 47.975 | 1.00 | 42.15 |
| HETATM | 3584 | O | HOH | 1144 | 32.915 | 38.699 | 23.494 | 1.00 | 40.84 |
| HETATM | 3585 | O | HOH | 1145 | 29.548 | 21.469 | 24.434 | 1.00 | 44.50 |
| HETATM | 3586 | O | HOH | 1146 | 26.181 | 34.331 | 29.323 | 1.00 | 34.71 |
| HETATM | 3587 | O | HOH | 1147 | 39.069 | 5.943 | 33.085 | 1.00 | 53.70 |
| HETATM | 3588 | O | HOH | 1148 | 34.970 | 24.222 | 52.427 | 1.00 | 40.12 |
| HETATM | 3589 | O | HOH | 1149 | 59.825 | 24.478 | 48.580 | 1.00 | 40.98 |
| HETATM | 3590 | O | HOH | 1150 | 28.412 | 33.531 | 47.673 | 1.00 | 44.44 |
| HETATM | 3591 | O | HOH | 1151 | 25.454 | 33.933 | 32.960 | 1.00 | 35.88 |
| HETATM | 3592 | O | HOH | 1152 | 41.875 | 59.115 | 53.350 | 1.00 | 51.54 |
| HETATM | 3593 | O | HOH | 1153 | 45.977 | 17.661 | 29.654 | 1.00 | 48.44 |
| HETATM | 3594 | O | HOH | 1154 | 16.374 | 19.854 | 15.198 | 1.00 | 26.92 |
| HETATM | 3595 | O | HOH | 1156 | 2.909 | 45.550 | 9.710 | 1.00 | 33.50 |
| HETATM | 3596 | O | HOH | 1157 | 27.955 | 42.970 | 52.054 | 1.00 | 42.09 |
| HETATM | 3597 | O | HOH | 1158 | 18.671 | 28.692 | 31.947 | 1.00 | 31.92 |
| HETATM | 3598 | O | HOH | 1160 | 31.097 | 11.069 | 39.837 | 1.00 | 22.54 |
| HETATM | 3599 | O | HOH | 1161 | 24.551 | 47.693 | 13.911 | 1.00 | 39.92 |
| HETATM | 3600 | O | HOH | 1162 | 19.328 | 46.523 | 39.555 | 1.00 | 49.64 |
| HETATM | 3601 | O | HOH | 1163 | 14.463 | 28.577 | 32.747 | 1.00 | 33.62 |
| HETATM | 3602 | O | HOH | 1164 | 42.334 | 34.141 | 31.684 | 1.00 | 25.02 |
| HETATM | 3603 | O | HOH | 1165 | 26.640 | 35.518 | 34.853 | 1.00 | 25.40 |
| HETATM | 3604 | O | HOH | 1166 | 41.719 | 26.191 | 52.537 | 1.00 | 54.23 |
| HETATM | 3605 | O | HOH | 1167 | 11.799 | 43.370 | 8.564 | 1.00 | 42.64 |
| HETATM | 3606 | O | HOH | 1169 | 39.695 | 23.691 | 29.775 | 1.00 | 46.55 |
| HETATM | 3607 | O | HOH | 1170 | 25.519 | -10.203 | 13.390 | 1.00 | 29.39 |
| HETATM | 3608 | O | HOH | 1172 | 15.639 | 30.378 | 9.410 | 1.00 | 35.98 |

FIGURE 8A-71

```
HETATM 3609  O  HOH 1173  26.042  53.508  19.228  1.00 35.35           O
HETATM 3610  O  HOH 1174  16.723  43.317   9.437  1.00 70.54           O
HETATM 3611  O  HOH 1175  11.039  27.202  31.989  1.00 35.23           O
HETATM 3612  O  HOH 1176  26.492  54.880  14.660  1.00 45.35           O
HETATM 3613  O  HOH 1177  48.739   5.603  40.080  1.00 46.72           O
HETATM 3614  O  HOH 1179  38.452  10.611  56.410  1.00 33.18           O
HETATM 3615  O  HOH 1180  25.173  41.020  50.981  1.00 37.80           O
HETATM 3616  O  HOH 1181  26.009  21.500  26.306  1.00 37.33           O
HETATM 3617  O  HOH 1185  32.901  61.354  32.974  1.00 47.36           O
HETATM 3618  O  HOH 1186  49.199  44.404  48.616  1.00 55.72           O
HETATM 3619  O  HOH 1187  28.401  31.064  46.621  1.00 25.46           O
HETATM 3620  O  HOH 1189  50.488  34.252  43.662  1.00 27.11           O
HETATM 3621  O  HOH 1190  25.015  38.231  32.413  1.00 46.20           O
HETATM 3622  O  HOH 1191  13.328  45.647   6.880  1.00 50.19           O
HETATM 3623  O  HOH 1192   9.102  28.582  30.815  1.00 28.84           O
HETATM 3624  O  HOH 1194  16.216  53.125  18.778  1.00 20.19           O
HETATM 3625  O  HOH 1195  48.924  37.778  50.511  1.00 41.81           O
HETATM 3626  O  HOH 1196  29.151  29.120  42.414  1.00 25.51           O
HETATM 3627  O  HOH 1197  10.760  56.327  24.871  1.00 25.61           O
HETATM 3628  O  HOH 1198  19.161  31.540  33.429  1.00 41.50           O
HETATM 3629  O  HOH 1201  31.584  19.545  39.778  1.00 41.14           O
HETATM 3630  O  HOH 1202  31.499  33.130  31.243  1.00 30.94           O
HETATM 3631  O  HOH 1203  33.475  31.251  32.729  1.00 30.16           O
HETATM 3632  O  HOH 1204  25.323  26.251  24.066  1.00 29.38           O
HETATM 3633  O  HOH 1205  18.912  50.780  14.345  1.00 28.88           O
HETATM 3634  O  HOH 1206  28.562  46.055  22.818  1.00 37.71           O
HETATM 3635  O  HOH 1207  31.212  15.396  37.505  1.00 38.29           O
HETATM 3636  O  HOH 1208  21.188  13.368  44.376  1.00 22.37           O
HETATM 3637  O  HOH 1209  17.682  38.715  10.160  1.00 31.02           O
HETATM 3638  O  HOH 1210  50.214  11.867  37.111  1.00 50.09           O
HETATM 3639  O  HOH 1212  28.768  41.646  47.276  1.00 22.35           O
HETATM 3640  O  HOH 1214  49.993  18.233  34.806  1.00 44.55           O
HETATM 3641  O  HOH 1215  32.815  34.522  46.504  1.00 35.13           O
HETATM 3642  O  HOH 1216  39.893  28.328  41.896  1.00 12.01           O
HETATM 3643  O  HOH 1217  15.338  26.949  28.916  1.00 11.70           O
HETATM 3644  O  HOH 1218  35.548  32.617  33.681  1.00 18.33           O
HETATM 3645  O  HOH 1219  39.368  28.656  34.414  1.00 16.49           O
HETATM 3646  O  HOH 1220  10.631  22.205  16.485  1.00 23.48           O
HETATM 3647  O  HOH 1221  38.404  33.931  29.548  1.00 20.31           O
HETATM 3648  O  HOH 1222  29.170  43.940  45.652  1.00 17.85           O
HETATM 3649  O  HOH 1223  16.493  28.977  30.383  1.00 19.55           O
HETATM 3650  O  HOH 1224  50.201  26.750  43.278  1.00 23.76           O
HETATM 3651  O  HOH 1225  38.642  25.017  49.298  1.00 24.48           O
HETATM 3652  O  HOH 1226  22.132  37.260  38.648  1.00 21.90           O
HETATM 3653  O  HOH 1227  39.985  27.256  49.971  1.00 19.31           O
HETATM 3654  O  HOH 1228  46.680  26.589  41.727  1.00 24.34           O
HETATM 3655  O  HOH 1229  45.783  30.693  47.582  1.00 25.33           O
HETATM 3656  O  HOH 1230  37.132  23.521  50.764  1.00 25.39           O
HETATM 3657  O  HOH 1231  37.666  45.416  31.269  1.00 22.37           O
HETATM 3658  O  HOH 1232  12.017  34.217  29.751  1.00 24.35           O
HETATM 3659  O  HOH 1233  26.995  45.967  27.617  1.00 23.52           O
HETATM 3660  O  HOH 1234  26.536  25.536  28.250  1.00 29.21           O
HETATM 3661  O  HOH 1235  25.412  37.399  29.161  1.00 27.51           O
HETATM 3662  O  HOH 1236  37.339  31.390  35.413  1.00 25.38           O
HETATM 3663  O  HOH 1237  49.870  32.179  49.678  1.00 25.92           O
HETATM 3664  O  HOH 1238  22.061  39.616  17.387  1.00 15.04           O
HETATM 3665  O  HOH 1239  14.228  24.366  29.787  1.00 22.47           O
HETATM 3666  O  HOH 1240  23.022  47.566  29.327  1.00 39.50           O
HETATM 3667  O  HOH 1241  21.098  32.679  17.559  1.00 35.09           O
HETATM 3668  O  HOH 1242  23.864  37.449  16.707  1.00 37.28           O
```

FIGURE 8A-72

| | | | | | | | | | |
|---|---|---|---|---|---|---|---|---|---|
| HETATM | 3669 | O | HOH | 1243 | 32.934 | 17.639 | 38.491 | 1.00 30.00 | O |
| HETATM | 3670 | O | HOH | 1244 | 30.081 | 39.275 | 47.475 | 1.00 27.25 | O |
| HETATM | 3671 | O | HOH | 1245 | 40.219 | 10.507 | 54.210 | 1.00 42.36 | O |
| HETATM | 3672 | O | HOH | 1246 | 20.198 | 57.839 | 14.584 | 1.00 26.12 | O |
| HETATM | 3673 | O | HOH | 1247 | 22.701 | 31.034 | 19.118 | 1.00 26.32 | O |
| HETATM | 3674 | O | HOH | 1248 | 50.529 | 25.000 | 51.117 | 1.00 16.36 | O |
| HETATM | 3675 | O | HOH | 1249 | 27.308 | 27.122 | 38.575 | 1.00 29.98 | O |
| HETATM | 3676 | O | HOH | 1250 | 41.664 | 46.630 | 31.018 | 1.00 29.42 | O |
| HETATM | 3677 | O | HOH | 1251 | 27.841 | 34.202 | 44.699 | 1.00 37.98 | O |
| HETATM | 3678 | O | HOH | 1252 | 28.946 | 26.204 | 44.341 | 1.00 51.94 | O |
| HETATM | 3679 | O | HOH | 1253 | 26.643 | 43.795 | 23.560 | 1.00 23.03 | O |
| HETATM | 3680 | O | HOH | 1254 | 52.894 | 25.886 | 44.095 | 1.00 33.52 | O |
| HETATM | 3681 | O | HOH | 1255 | 42.339 | 26.613 | 55.952 | 1.00 36.97 | O |
| HETATM | 3682 | O | HOH | 1256 | 48.804 | 2.432 | 50.876 | 1.00 36.59 | O |
| HETATM | 3683 | O | HOH | 1257 | 51.244 | 18.531 | 40.805 | 1.00 33.51 | O |
| HETATM | 3684 | O | HOH | 1260 | 49.903 | 39.828 | 48.137 | 1.00 44.77 | O |
| HETATM | 3685 | O | HOH | 1261 | 45.720 | 4.638 | 32.384 | 1.00 54.41 | O |
| HETATM | 3686 | O | HOH | 1262 | 32.871 | 29.567 | 30.088 | 1.00 39.72 | O |
| HETATM | 3687 | O | HOH | 1263 | 23.890 | 51.918 | 23.175 | 1.00 37.61 | O |
| HETATM | 3688 | O | HOH | 1264 | 13.550 | 26.049 | 31.905 | 1.00 33.45 | O |
| HETATM | 3689 | O | HOH | 1266 | 10.689 | 31.547 | 31.432 | 1.00 47.94 | O |
| HETATM | 3690 | O | HOH | 1269 | 26.086 | -7.425 | 31.507 | 1.00 39.58 | O |
| HETATM | 3691 | O | HOH | 1271 | 22.022 | 54.673 | 22.853 | 1.00 37.03 | O |
| HETATM | 3692 | O | HOH | 1274 | 28.901 | 24.308 | 41.027 | 1.00 41.39 | O |
| HETATM | 3693 | O | HOH | 1276 | 45.609 | -2.697 | 31.603 | 1.00 49.62 | O |
| HETATM | 3694 | O | HOH | 1277 | 9.649 | 26.708 | 34.475 | 1.00 36.02 | O |
| HETATM | 3695 | O | HOH | 1279 | 21.970 | 8.818 | 36.303 | 1.00 45.69 | O |
| HETATM | 3696 | O | HOH | 1280 | 7.956 | 56.039 | 27.031 | 1.00 55.41 | O |
| HETATM | 3697 | O | HOH | 1281 | 15.342 | 17.025 | 12.461 | 1.00 55.13 | O |
| HETATM | 3698 | O | HOH | 1284 | 12.862 | 44.437 | 3.810 | 1.00 49.95 | O |
| HETATM | 3699 | O | HOH | 1286 | 34.675 | 64.010 | 47.159 | 1.00 47.97 | O |
| HETATM | 3700 | O | HOH | 1287 | 41.049 | 11.857 | 30.681 | 1.00 29.94 | O |
| HETATM | 3701 | O | HOH | 1288 | 34.457 | 19.302 | 55.855 | 1.00 47.88 | O |
| HETATM | 3702 | O | HOH | 1289 | 28.546 | 31.433 | 28.564 | 1.00 47.71 | O |
| HETATM | 3703 | O | HOH | 1291 | 33.220 | 60.645 | 39.548 | 1.00 52.03 | O |
| HETATM | 3704 | O | HOH | 1292 | 30.910 | 54.312 | 27.471 | 1.00 48.06 | O |
| HETATM | 3705 | O | HOH | 1293 | 23.058 | 27.656 | 32.358 | 1.00 45.02 | O |
| HETATM | 3706 | O | HOH | 1294 | 28.377 | 27.865 | 25.772 | 1.00 37.73 | O |
| HETATM | 3707 | O | HOH | 1295 | 17.851 | 13.033 | 47.051 | 1.00 31.43 | O |
| HETATM | 3708 | O | HOH | 1297 | 22.435 | 24.151 | 33.420 | 1.00 39.38 | O |
| HETATM | 3709 | O | HOH | 1298 | 29.292 | 20.833 | 37.423 | 1.00 52.78 | O |
| HETATM | 3710 | O | HOH | 1299 | 26.196 | 40.554 | 47.655 | 1.00 52.83 | O |
| HETATM | 3711 | O | HOH | 1300 | 6.687 | 28.384 | 34.247 | 1.00 45.71 | O |
| HETATM | 3712 | O | HOH | 1303 | 41.624 | 1.272 | 27.661 | 1.00 61.55 | O |
| HETATM | 3713 | O | HOH | 1306 | 24.865 | 48.368 | 49.108 | 1.00 53.05 | O |
| HETATM | 3714 | O | HOH | 1308 | 43.375 | 33.196 | 54.115 | 1.00 34.68 | O |
| HETATM | 3715 | O | HOH | 1309 | 24.941 | 16.106 | 28.105 | 1.00 27.22 | O |
| HETATM | 3716 | O | HOH | 1310 | 48.767 | 36.362 | 53.067 | 1.00 39.18 | O |
| HETATM | 3717 | O | HOH | 1311 | 0.897 | 25.934 | 24.841 | 1.00 47.80 | O |
| HETATM | 3718 | O | HOH | 1312 | 41.531 | 54.883 | 30.082 | 1.00 37.92 | O |
| HETATM | 3719 | O | HOH | 1315 | 32.370 | 19.055 | 31.177 | 1.00 43.71 | O |
| HETATM | 3720 | O | HOH | 1316 | 19.469 | 15.072 | 45.662 | 1.00 48.16 | O |
| HETATM | 3721 | O | HOH | 1321 | 10.144 | 48.734 | 5.731 | 1.00 39.11 | O |
| HETATM | 3722 | O | HOH | 1322 | 29.076 | 56.977 | 42.203 | 1.00 46.38 | O |
| HETATM | 3723 | O | HOH | 1326 | 42.727 | 8.091 | 54.610 | 1.00 56.42 | O |
| HETATM | 3724 | O | HOH | 1330 | 41.316 | 20.071 | 29.052 | 1.00 39.86 | O |
| HETATM | 3725 | O | HOH | 1331 | 16.596 | 27.837 | 34.825 | 1.00 50.15 | O |
| HETATM | 3726 | O | HOH | 1332 | 19.903 | 45.162 | 47.256 | 1.00 52.33 | O |
| HETATM | 3727 | O | HOH | 1333 | 40.238 | -8.133 | 39.062 | 1.00 41.11 | O |
| HETATM | 3728 | O | HOH | 1335 | 32.007 | 37.168 | 46.170 | 1.00 43.84 | O |

*FIGURE 8A-73*

| | | | | | | | | | |
|---|---|---|---|---|---|---|---|---|---|
| HETATM | 3729 | O | HOH | 1337 | 8.866 | 32.982 | 29.638 | 1.00 51.57 | O |
| HETATM | 3730 | O | HOH | 1339 | 35.650 | 46.023 | 29.211 | 1.00 40.99 | O |
| HETATM | 3731 | O | HOH | 1340 | 52.825 | 32.335 | 38.756 | 1.00 50.57 | O |
| HETATM | 3732 | O | HOH | 1341 | 36.938 | 51.807 | 31.314 | 1.00 45.30 | O |
| HETATM | 3733 | O | HOH | 1342 | 18.790 | 42.705 | 33.580 | 1.00 43.47 | O |
| HETATM | 3734 | O | HOH | 1344 | 22.819 | 36.661 | 11.619 | 1.00 46.70 | O |
| HETATM | 3735 | O | HOH | 1345 | 19.465 | 28.669 | 34.714 | 1.00 39.89 | O |
| HETATM | 3736 | O | HOH | 1347 | 40.179 | 23.790 | 53.530 | 1.00 47.43 | O |
| HETATM | 3737 | O | HOH | 1353 | 3.487 | 36.484 | 13.806 | 1.00 40.41 | O |
| HETATM | 3738 | O | HOH | 1360 | 31.223 | 4.884 | 34.089 | 1.00 30.96 | O |
| HETATM | 3739 | O | HOH | 1361 | 19.647 | 3.819 | 14.444 | 1.00 26.16 | O |
| HETATM | 3740 | O | HOH | 1364 | 12.171 | -3.712 | 34.829 | 1.00 52.07 | O |
| HETATM | 3741 | O | HOH | 1366 | 14.715 | 10.503 | 15.414 | 1.00 47.98 | O |
| HETATM | 3742 | O | HOH | 1370 | 3.284 | 18.073 | 30.684 | 1.00 39.22 | O |
| HETATM | 3743 | O | HOH | 1371 | 16.114 | 12.267 | 13.222 | 1.00 41.79 | O |
| HETATM | 3744 | O | HOH | 1374 | 26.710 | -10.158 | 28.570 | 1.00 46.72 | O |
| HETATM | 3745 | O | HOH | 1376 | 13.842 | 2.095 | 17.391 | 1.00 51.23 | O |
| HETATM | 3746 | O | HOH | 1377 | 23.624 | 18.176 | 26.993 | 1.00 46.55 | O |
| HETATM | 3747 | O | HOH | 1378 | 17.679 | 9.897 | 14.906 | 1.00 29.42 | O |
| HETATM | 3748 | O | HOH | 1380 | 21.173 | -2.881 | 15.825 | 1.00 44.25 | O |
| HETATM | 3749 | O | HOH | 1381 | 25.990 | 6.184 | 14.411 | 1.00 40.98 | O |
| HETATM | 3750 | O | HOH | 1382 | 25.475 | 8.938 | 15.031 | 1.00 40.93 | O |
| HETATM | 3751 | O | HOH | 1384 | 27.045 | 17.549 | 12.911 | 1.00 44.46 | O |
| HETATM | 3752 | O | HOH | 1387 | 15.174 | -5.506 | 13.111 | 1.00 43.09 | O |
| HETATM | 3753 | O | HOH | 1388 | 3.093 | 25.580 | 28.841 | 1.00 47.33 | O |
| HETATM | 3754 | O | HOH | 1389 | 43.833 | 14.822 | 32.665 | 1.00 30.09 | O |
| HETATM | 3755 | O | HOH | 1390 | 27.283 | 3.257 | 16.277 | 1.00 28.50 | O |
| HETATM | 3756 | O | HOH | 1391 | 31.590 | 8.583 | 17.790 | 1.00 31.43 | O |
| HETATM | 3757 | O | HOH | 1392 | 28.183 | 8.699 | 15.618 | 1.00 37.69 | O |
| HETATM | 3758 | O | HOH | 1393 | 24.599 | 3.854 | 15.072 | 1.00 40.30 | O |
| HETATM | 3759 | O | HOH | 1404 | 39.148 | 30.436 | 32.035 | 1.00 17.64 | O |
| HETATM | 3760 | O | HOH | 1405 | 0.837 | 22.245 | 22.324 | 1.00 55.83 | O |
| HETATM | 3761 | O | HOH | 1406 | 29.799 | 34.134 | 27.910 | 1.00 28.75 | O |
| HETATM | 3762 | O | HOH | 1407 | 18.445 | 6.222 | 44.059 | 1.00 53.71 | O |
| HETATM | 3763 | O | HOH | 1409 | 30.392 | 39.323 | 25.039 | 1.00 34.89 | O |
| HETATM | 3764 | O | HOH | 1410 | 18.490 | 9.793 | 47.086 | 1.00 48.51 | O |
| HETATM | 3765 | O | HOH | 1411 | 13.220 | 32.748 | 8.629 | 1.00 49.26 | O |
| HETATM | 3766 | O | HOH | 1412 | 49.361 | 20.100 | 32.438 | 1.00 43.65 | O |
| HETATM | 3767 | O | HOH | 1414 | 51.855 | 33.864 | 41.242 | 1.00 64.26 | O |
| HETATM | 3768 | O | HOH | 1418 | 47.727 | 41.100 | 41.717 | 1.00 35.47 | O |
| HETATM | 3769 | O | HOH | 1419 | 24.466 | 54.548 | 43.747 | 1.00 53.28 | O |
| HETATM | 3770 | O | HOH | 1420 | 5.934 | 30.983 | 8.318 | 1.00 45.39 | O |
| HETATM | 3771 | O | HOH | 1421 | 32.399 | -4.433 | 42.259 | 1.00 41.31 | O |
| HETATM | 3772 | O | HOH | 1422 | 3.024 | 40.996 | 27.927 | 1.00 42.40 | O |
| HETATM | 3773 | O | HOH | 1424 | 36.321 | -0.489 | 35.913 | 1.00 41.12 | O |
| HETATM | 3774 | O | HOH | 1428 | 16.200 | 42.165 | 4.789 | 1.00 62.98 | O |
| HETATM | 3775 | O | HOH | 1429 | 4.930 | 40.213 | 24.269 | 1.00 53.41 | O |
| HETATM | 3776 | O | HOH | 1430 | 7.506 | 9.248 | 13.243 | 1.00 51.74 | O |
| HETATM | 3777 | O | HOH | 1434 | 16.093 | 51.978 | 11.936 | 1.00 39.24 | O |
| HETATM | 3778 | O | HOH | 1437 | 32.063 | 21.866 | 31.547 | 1.00 49.87 | O |
| HETATM | 3779 | O | HOH | 1438 | 54.621 | 26.247 | 29.147 | 1.00 48.62 | O |
| HETATM | 3780 | O | HOH | 1440 | 4.318 | 19.369 | 8.919 | 1.00 47.53 | O |
| HETATM | 3781 | O | HOH | 1441 | 5.136 | 2.358 | 29.831 | 1.00 44.25 | O |
| HETATM | 3782 | O | HOH | 1443 | 2.076 | 24.174 | 15.211 | 1.00 53.91 | O |
| HETATM | 3783 | O | HOH | 1444 | 15.474 | 42.729 | 30.690 | 1.00 38.63 | O |
| HETATM | 3784 | O | HOH | 1446 | 34.955 | 9.442 | 53.656 | 1.00 51.40 | O |
| HETATM | 3785 | O | HOH | 1447 | 28.597 | 17.387 | 31.041 | 1.00 40.53 | O |
| HETATM | 3786 | O | HOH | 1454 | 34.884 | -9.534 | 12.912 | 1.00 33.84 | O |
| HETATM | 3787 | O | HOH | 1455 | 56.971 | 31.610 | 49.136 | 1.00 44.36 | O |
| HETATM | 3788 | O | HOH | 1456 | 29.676 | 11.548 | 53.175 | 1.00 41.64 | O |

FIGURE 8A-74

```
HETATM 3789  O    HOH  1457    46.713  47.217  35.996  1.00 51.75           O
HETATM 3790  O    HOH  1458    22.556   3.172  12.871  1.00 35.99           O
HETATM 3791  O    HOH  1459    42.572  42.347  52.583  1.00 55.24           O
HETATM 3792  O    HOH  1461     0.573  13.064. 16.484  1.00 44.57           O
HETATM 3793  O    HOH  1462    50.467   6.260  32.228  1.00 46.40           O
HETATM 3794  O    HOH  1463     6.167  47.337   5.349  1.00 53.27           O
HETATM 3795  O    HOH  1464    24.604  -9.866  26.249  1.00 43.72           O
HETATM 3796  O    HOH  1466    22.806  17.220  45.236  1.00 61.41           O
HETATM 3797  O    HOH  1506    25.441  49.608  19.993  1.00 33.89           O
HETATM 3798  O    HOH  1507    39.709  -9.399  16.482  1.00 30.44           O
HETATM 3799  O    HOH  1509     9.926  24.411  36.529  1.00 37.21           O
HETATM 3800  O    HOH  1515    34.731  28.232  28.355  1.00 37.81.          O
HETATM 3801  O    HOH  1518    44.323  37.583  28.523  1.00 44.08           O
HETATM 3802  O    HOH  1519    30.194  -0.768  45.229  1.00 40.11           O
HETATM 3803  O    HOH  1521    42.425  48.375  34.242  1.00 50.42           O
HETATM 3804  O    HOH  1523    12.185   2.224  34.335  1.00 56.22           O
CONECT   109  108  110  119
CONECT   119  109  120
CONECT   120  119  121  123
CONECT   121  120  122  127
CONECT   122  121
CONECT   123  120  124
CONECT   124  123  125
CONECT   125  124  126
CONECT   126  125
CONECT   127  121  128
CONECT   187  186  188  189
CONECT   189  187  190
CONECT   190  189  191  193
CONECT   191  190  192  197
CONECT   192  191
CONECT   193  190  194
CONECT   194  193  195
CONECT   195  194  196
CONECT   196  195
CONECT   197  191  198
CONECT   248  247  905
CONECT   279  278  280  286
CONECT   286  279  287
CONECT   287  286  288  290
CONECT   288  287  289  294
CONECT   289  288
CONECT   290  287  291
CONECT   291  290  292
CONECT   292  291  293
CONECT   293  292
CONECT   294  288  295
CONECT   905  248  904
CONECT  1038 1037 1039 1048
CONECT  1048 1038 1049
CONECT  1049 1048 1050 1052
CONECT  1050 1049 1051 1056
CONECT  1051 1050
CONECT  1052 1049 1053
CONECT  1053 1052 1054
CONECT  1054 1053 1055
CONECT  1055 1054
CONECT  1056 1050 1057
CONECT  1116 1115 1117 1118
CONECT  1118 1116 1119
```

FIGURE 8A-75

```
CONECT 1119 1118 1120 1122
CONECT 1120 1119 1121 1126
CONECT 1121 1120
CONECT 1122 1119 1123
CONECT 1123 1122 1124
CONECT 1124 1123 1125
CONECT 1125 1124
CONECT 1126 1120 1127
CONECT 1177 1176 1874
CONECT 1208 1207 1209 1215
CONECT 1215 1208 1216
CONECT 1216 1215 1217 1219
CONECT 1217 1216 1218 1223
CONECT 1218 1217
CONECT 1219 1216 1220
CONECT 1220 1219 1221
CONECT 1221 1220 1222
CONECT 1222 1221
CONECT 1223 1217 1224
CONECT 1874 1177 1873
CONECT 1987 1986 1988 1997
CONECT 1997 1987 1998
CONECT 1998 1997 1999 2001
CONECT 1999 1998 2000 2005
CONECT 2000 1999
CONECT 2001 1998 2002
CONECT 2002 2001 2003
CONECT 2003 2002 2004
CONECT 2004 2003
CONECT 2005 1999 2006
CONECT 2065 2064 2066 2067
CONECT 2067 2065 2068
CONECT 2068 2067 2069 2071
CONECT 2069 2068 2070 2075
CONECT 2070 2069
CONECT 2071 2068 2072
CONECT 2072 2071 2073
CONECT 2073 2072 2074
CONECT 2074 2073
CONECT 2075 2069 2076
CONECT 2154 2153 2155 2161
CONECT 2161 2154 2162
CONECT 2162 2161 2163 2165
CONECT 2163 2162 2164 2169
CONECT 2164 2163
CONECT 2165 2162 2166
CONECT 2166 2165 2167
CONECT 2167 2166 2168
CONECT 2168 2167
CONECT 2169 2163 2170
CONECT 2813 2812 2814 2823
CONECT 2823 2813 2824
CONECT 2824 2823 2825 2827
CONECT 2825 2824 2826 2831
CONECT 2826 2825
CONECT 2827 2824 2828
CONECT 2828 2827 2829
CONECT 2829 2828 2830
CONECT 2830 2829
CONECT 2831 2825 2832
```

FIGURE 8A-76

```
CONECT 2891 2890 2892 2893
CONECT 2893 2891 2894
CONECT 2894 2893 2895 2897
CONECT 2895 2894 2896 2901
CONECT 2896 2895
CONECT 2897 2894 2898
CONECT 2898 2897 2899
CONECT 2899 2898 2900
CONECT 2900 2899
CONECT 2901 2895 2902
CONECT 2983 2982 2984 2990
CONECT 2990 2983 2991
CONECT 2991 2990 2992 2994
CONECT 2992 2991 2993 2998
CONECT 2993 2992
CONECT 2994 2991 2995
CONECT 2995 2994 2996
CONECT 2996 2995 2997
CONECT 2997 2996
CONECT 2998 2992 2999
CONECT 3522 3541 3542
CONECT 3524 3544 3545 3546
CONECT 3525 3526
CONECT 3526 3525 3527
CONECT 3527 3526 3528
CONECT 3528 3527 3530
CONECT 3529 3530 3531
CONECT 3530 3528 3529
CONECT 3531 3529 3533
CONECT 3532 3533 3534
CONECT 3533 3531 3532
CONECT 3534 3532 3536
CONECT 3535 3536 3537
CONECT 3536 3534 3535
CONECT 3537 3535 3539
CONECT 3538 3539 3540
CONECT 3539 3537 3538
CONECT 3540 3538
CONECT 3541 3522
CONECT 3542 3522
CONECT 3544 3524
CONECT 3545 3524
CONECT 3546 3524
MASTER      301    0  16  19  8  0  0  27 3796  4  147  84
END
```

Figure 9

```
submitted:
HETATM  4233   O   HOH   1021        36.890   32.430   27.721   1.00  24.58
HETATM  4234   O   HOH   1021        35.049   30.934   29.322   1.00  27.97
HETATM  4236   O   HOH   1022        31.347   42.865   52.839   1.00  31.45
HETATM  4238   O   HOH   1023        44.819   10.251   32.056   1.00  31.08
HETATM  4239   O   HOH   1023        47.508    7.695   33.365   1.00  35.15
HETATM  4240   O   HOH   1023        48.695    9.256   30.957   1.00  29.22 to this:
HETATM  4233   O   HOH   1021        36.890   32.430   27.721   1.00  24.58
HETATM  4234   O   HOH   1022        35.049   30.934   29.322   1.00  27.97
HETATM  4236   O   HOH   1023        31.347   42.865   52.839   1.00  31.45
HETATM  4238   O   HOH   1024        44.819   10.251   32.056   1.00  31.08
HETATM  4239   O   HOH   1025        47.508    7.695   33.365   1.00  35.15
HETATM  4240   O   HOH   1026        48.695    9.256   30.957   1.00  29.22

The LINKs are:

LINK     CA   CA   1021              O    HOH   1024
LINK     CA   CA   1021              O    HOH   1025
LINK     CA   CA   1023              O    HOH   1027
LINK     CA   CA   1023              O    HOH   1028
LINK     CA   CA   1023              O    HOH   1029
```

A. General model

B. Embodiment of the ligand head as an oligopeptide $F_1 - X_n - F_L(Cys) - X_m - F_2 - X_p - F_3$

SEQUENCE LISTING

<160> NUMBER OF SEQ ID NOS: 22

<210> SEQ ID NO 1
<211> LENGTH: 141
<212> TYPE: PRT
<213> ORGANISM: HOMO SAPIENS

<400> SEQUENCE: 1

Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
            20                  25                  30

Val Pro Gly Met Asp Val Leu Pro Ser His Gln Trp Ile Ser Glu Met
        35                  40                  45

Val Val Gln Leu Ser Asp Ser Leu Thr Asp Leu Leu Asp Lys Phe Ser
    50                  55                  60

Asn Ile Ser Glu Gly Leu Ser Asn Tyr Ser Ile Ile Asp Lys Leu Val
65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Lys Asp
        115                 120                 125

Phe Val Val Ala Ser Glu Thr Ser Asp Cys Val Val Ser
    130                 135                 140

<210> SEQ ID NO 2
<211> LENGTH: 150
<212> TYPE: PRT
<213> ORGANISM: HOMO SAPIENS

<400> SEQUENCE: 2

Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Cys Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Thr
    50                  55                  60

Met Arg Phe Arg Asp Asn Thr Pro Asn Ala Ile Ala Ile Val Gln Leu
65                  70                  75                  80

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu
        115                 120                 125

Asp Lys Asp Trp Asn Ile Phe Ser Lys Asn Cys Asn Asn Ser Phe Ala
    130                 135                 140

Glu Cys Ser Ser Gln Gly
145                 150

<210> SEQ ID NO 3

-continued

```
<211> LENGTH: 129
<212> TYPE: PRT
<213> ORGANISM: HOMO SAPIENS

<400> SEQUENCE: 3

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser

<210> SEQ ID NO 4
<211> LENGTH: 127
<212> TYPE: PRT
<213> ORGANISM: HOMO SAPIENS

<400> SEQUENCE: 4

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Ile Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 5
<211> LENGTH: 132
<212> TYPE: PRT
<213> ORGANISM: HOMO SAPIENS

<400> SEQUENCE: 5

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Tyr Met Pro Lys Lys
```

```
                35                  40                  45
Ala Thr Glu Leu Lys His Leu Gln Cys Leu Glu Glu Leu Lys Pro
         50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
        130

<210> SEQ ID NO 6
<211> LENGTH: 115
<212> TYPE: PRT
<213> ORGANISM: HOMO SAPIENS

<400> SEQUENCE: 6

Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Arg
                20                  25                  30

Ile Pro Val Pro Val His Lys Asn His Gln Leu Cys Thr Glu Glu Ile
            35                  40                  45

Phe Gln Gly Ile Gly Thr Leu Glu Ser Gln Thr Val Gln Gly Gly Thr
        50                  55                  60

Val Glu Arg Leu Phe Lys Asn Leu Ser Leu Ile Lys Lys Tyr Ile Asp
 65                  70                  75                  80

Gly Gln Lys Lys Lys Cys Gly Glu Glu Arg Arg Arg Val Asn Gln Phe
                85                  90                  95

Leu Asp Tyr Leu Gln Glu Phe Leu Gly Val Met Asn Thr Glu Trp Ile
            100                 105                 110

Ile Glu Ser
        115

<210> SEQ ID NO 7
<211> LENGTH: 164
<212> TYPE: PRT
<213> ORGANISM: RATTUS SP.

<400> SEQUENCE: 7

Glu Gly Ile Cys Arg Asn Arg Val Thr Asn Asn Val Lys Asp Val Thr
 1               5                  10                  15

Lys Leu Val Ala Asn Leu Pro Lys Asp Tyr Met Ile Thr Leu Lys Tyr
                20                  25                  30

Val Pro Gly Met Asp Val Leu Pro Ser His Cys Trp Ile Ser Glu Met
            35                  40                  45

Val Val Gln Leu Ser Asp Ser Leu Thr Asp Leu Leu Asp Lys Phe Ser
        50                  55                  60

Asn Ile Ser Glu Gly Leu Ser Asn Tyr Ser Ile Ile Asp Lys Leu Val
 65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
```

```
                    100                 105                 110
Glu Glu Phe Phe Arg Ile Phe Asn Arg Ser Ile Asp Ala Phe Lys Asp
            115                 120                 125

Phe Val Val Ala Ser Glu Thr Ser Asp Cys Val Val Ser Ser Thr Leu
        130                 135                 140

Ser Pro Glu Lys Asp Ser Arg Val Ser Val Thr Lys Pro Phe Met Leu
145                 150                 155                 160

Pro Pro Val Ala

<210> SEQ ID NO 8
<211> LENGTH: 164
<212> TYPE: PRT
<213> ORGANISM: MURINE SP.

<400> SEQUENCE: 8

Lys Glu Ile Cys Gly Asn Pro Val Thr Asp Asn Val Lys Asp Ile Thr
1               5                  10                  15

Lys Leu Val Ala Asn Leu Pro Asn Asp Tyr Met Ile Thr Leu Asn Tyr
            20                  25                  30

Val Ala Gly Met Asp Val Leu Pro Ser His Cys Trp Leu Arg Asp Met
        35                  40                  45

Val Ile Gln Leu Ser Leu Ser Leu Thr Thr Leu Leu Asp Lys Phe Ser
    50                  55                  60

Asn Ile Ser Glu Gly Leu Ser Asn Tyr Ser Ile Ile Asp Lys Leu Gly
65                  70                  75                  80

Lys Ile Val Asp Asp Leu Val Leu Cys Met Glu Asn Ala Pro Lys
                85                  90                  95

Asn Ile Lys Glu Ser Pro Lys Arg Pro Glu Thr Arg Ser Phe Thr Pro
            100                 105                 110

Glu Glu Phe Phe Ser Ile Phe Asn Arg Ser Ile Asp Ala Phe Lys Asp
            115                 120                 125

Phe Met Val Ala Ser Asp Thr Ser Asp Cys Val Leu Ser Ser Thr Leu
        130                 135                 140

Ser Pro Glu Lys Asp Ser Arg Val Ser Val Thr Lys Pro Phe Met Leu
145                 150                 155                 160

Pro Pro Val Ala

<210> SEQ ID NO 9
<211> LENGTH: 164
<212> TYPE: PRT
<213> ORGANISM: RATTUS SP.

<400> SEQUENCE: 9

Gln Glu Ile Cys Arg Asn Pro Val Thr Asp Asn Val Lys Asp Ile Thr
1               5                  10                  15

Lys Leu Val Ala Asn Leu Pro Asn Asp Tyr Met Ile Thr Leu Asn Tyr
            20                  25                  30

Val Ala Gly Met Asp Val Leu Pro Ser His Cys Trp Leu Arg Asp Met
        35                  40                  45

Val Thr His Leu Ser Val Ser Leu Thr Thr Leu Leu Asp Lys Phe Ser
    50                  55                  60

Asn Ile Ser Glu Gly Leu Ser Asn Tyr Ser Ile Ile Asp Lys Leu Gly
65                  70                  75                  80

Lys Ile Val Asp Asp Leu Val Ala Cys Met Glu Glu Asn Ala Pro Lys
                85                  90                  95
```

```
Asn Val Lys Glu Ser Leu Lys Lys Pro Glu Thr Arg Asn Phe Thr Pro
                100                 105                 110

Glu Glu Phe Phe Ser Ile Phe Asn Arg Ser Ile Asp Ala Phe Lys Asp
            115                 120                 125

Phe Met Val Ala Ser Asp Thr Ser Asp Cys Val Leu Ser Ser Thr Leu
        130                 135                 140

Ser Pro Glu Lys Asp Ser Arg Val Ser Val Thr Lys Pro Phe Met Leu
145                 150                 155                 160

Pro Pro Val Ala

<210> SEQ ID NO 10
<211> LENGTH: 165
<212> TYPE: PRT
<213> ORGANISM: CANIS SP.

<400> SEQUENCE: 10

Lys Gly Ile Cys Gly Lys Arg Val Thr Asp Asn Val Lys Asp Val Thr
1               5                   10                  15

Lys Leu Val Ala Asn Leu Pro Lys Asp Tyr Lys Ile Ala Leu Lys Tyr
            20                  25                  30

Val Pro Gly Met Asp Val Leu Pro Ser His Cys Trp Ile Ser Val Met
        35                  40                  45

Val Glu Gln Leu Ser Val Ser Leu Thr Asp Leu Asp Lys Phe Ser
    50                  55                  60

Asn Ile Ser Glu Gly Leu Ser Asn Tyr Ser Ile Ile Asp Lys Leu Val
65                  70                  75                  80

Lys Ile Val Asp Asp Leu Val Glu Cys Thr Glu Gly Tyr Ser Phe Glu
                85                  90                  95

Asn Val Lys Lys Ala Pro Lys Ser Pro Glu Leu Arg Leu Phe Thr Pro
                100                 105                 110

Glu Glu Phe Phe Arg Ile Phe Asn Arg Ser Ile Asp Ala Phe Lys Asp
            115                 120                 125

Phe Glu Thr Val Ala Ser Lys Ser Ser Glu Cys Val Val Ser Ser Thr
        130                 135                 140

Leu Ser Pro Asp Lys Asp Ser Arg Val Ser Val Thr Lys Pro Phe Met
145                 150                 155                 160

Leu Pro Pro Val Ala
                165

<210> SEQ ID NO 11
<211> LENGTH: 141
<212> TYPE: PRT
<213> ORGANISM: HOMO SAPIENS

<400> SEQUENCE: 11

Glu Gly Ile Cys Arg Asn Arg Val Thr Asn Asn Val Lys Asp Val Thr
1               5                   10                  15

Lys Leu Val Ala Asn Leu Pro Lys Asp Cys Met Ile Thr Leu Lys Tyr
            20                  25                  30

Val Pro Gly Met Asp Val Leu Pro Ser His Gln Trp Ile Ser Glu Met
        35                  40                  45

Val Val Gln Leu Ser Asp Ser Leu Thr Asp Leu Leu Asp Lys Phe Ser
    50                  55                  60

Asn Ile Ser Glu Gly Leu Ser Asn Tyr Ser Ile Ile Asp Lys Leu Val
65                  70                  75                  80

Asn Ile Val Asp Asp Leu Val Glu Cys Val Lys Glu Asn Ser Ser Lys
```

```
                85                  90                  95
Asp Leu Lys Lys Ser Phe Lys Ser Pro Glu Pro Arg Leu Phe Thr Pro
            100                 105                 110
Glu Glu Phe Phe Arg Ile Phe Asn Arg Ser Ile Asp Ala Phe Lys Asp
            115                 120                 125
Phe Val Val Ala Ser Glu Thr Ser Asp Cys Val Val Ser
        130                 135                 140

<210> SEQ ID NO 12
<211> LENGTH: 141
<212> TYPE: PRT
<213> ORGANISM: HOMO SAPIENS

<400> SEQUENCE: 12

Glu Gly Ile Cys Arg Asn Arg Val Thr Asn Asn Val Lys Asp Val Thr
1               5                   10                  15
Lys Leu Val Ala Asn Leu Pro Lys Cys Tyr Met Ile Thr Leu Lys Tyr
            20                  25                  30
Val Pro Gly Met Asp Val Leu Pro Ser His Gln Trp Ile Ser Glu Met
        35                  40                  45
Val Val Gln Leu Ser Asp Ser Leu Thr Asp Leu Leu Asp Lys Phe Ser
    50                  55                  60
Asn Ile Ser Glu Gly Leu Ser Asn Tyr Ser Ile Ile Asp Lys Leu Val
65                  70                  75                  80
Asn Ile Val Asp Asp Leu Val Glu Cys Val Lys Glu Asn Ser Ser Lys
                85                  90                  95
Asp Leu Lys Lys Ser Phe Lys Ser Pro Glu Pro Arg Leu Phe Thr Pro
            100                 105                 110
Glu Glu Phe Phe Arg Ile Phe Asn Arg Ser Ile Asp Ala Phe Lys Asp
            115                 120                 125
Phe Val Val Ala Ser Glu Thr Ser Asp Cys Val Val Ser
        130                 135                 140

<210> SEQ ID NO 13
<211> LENGTH: 141
<212> TYPE: PRT
<213> ORGANISM: HOMO SAPIENS

<400> SEQUENCE: 13

Glu Gly Ile Cys Arg Asn Arg Val Thr Asn Asn Val Lys Asp Val Thr
1               5                   10                  15
Lys Leu Val Ala Asn Leu Pro Lys Asp Tyr Met Ile Thr Leu Lys Tyr
            20                  25                  30
Val Pro Gly Met Asp Val Leu Pro Ser His Gln Trp Ile Ser Glu Met
        35                  40                  45
Val Val Gln Leu Ser Asp Ser Leu Thr Asp Leu Leu Asp Cys Phe Ser
    50                  55                  60
Asn Ile Ser Glu Gly Leu Ser Asn Tyr Ser Ile Ile Asp Lys Leu Val
65                  70                  75                  80
Asn Ile Val Asp Asp Leu Val Glu Cys Val Lys Glu Asn Ser Ser Lys
                85                  90                  95
Asp Leu Lys Lys Ser Phe Lys Ser Pro Glu Pro Arg Leu Phe Thr Pro
            100                 105                 110
Glu Glu Phe Phe Arg Ile Phe Asn Arg Ser Ile Asp Ala Phe Lys Asp
            115                 120                 125
Phe Val Val Ala Ser Glu Thr Ser Asp Cys Val Val Ser
```

130                 135                 140

<210> SEQ ID NO 14
<211> LENGTH: 141
<212> TYPE: PRT
<213> ORGANISM: HOMO SAPIENS

<400> SEQUENCE: 14

Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
                20                  25                  30

Val Pro Gly Met Asp Val Leu Pro Ser His Gln Trp Ile Ser Glu Met
            35                  40                  45

Val Val Gln Leu Ser Asp Ser Leu Thr Asp Leu Leu Asp Lys Phe Ser
    50                  55                  60

Asn Ile Ser Glu Gly Leu Ser Asn Tyr Ser Ile Ile Asp Asn Leu Val
65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Lys Asp
        115                 120                 125

Phe Val Val Ala Ser Glu Thr Ser Asp Cys Val Val Ser
    130                 135                 140

<210> SEQ ID NO 15
<211> LENGTH: 141
<212> TYPE: PRT
<213> ORGANISM: HOMO SAPIENS

<400> SEQUENCE: 15

Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
                20                  25                  30

Val Pro Gly Met Asp Val Leu Pro Ser His Gln Trp Ile Ser Glu Met
            35                  40                  45

Val Val Gln Leu Ser Asp Ser Leu Thr Asp Leu Leu Asp Lys Phe Ser
    50                  55                  60

Asn Ile Ser Glu Gly Leu Ser Asn Tyr Ser Ile Ile Asp Lys Leu Val
65                  70                  75                  80

Lys Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Lys Asp
        115                 120                 125

Phe Val Val Ala Ser Glu Thr Ser Asp Cys Val Val Ser
    130                 135                 140

<210> SEQ ID NO 16
<211> LENGTH: 141
<212> TYPE: PRT
<213> ORGANISM: HOMO SAPIENS

<400> SEQUENCE: 16

Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
                20                  25                  30

Val Pro Gly Met Asp Val Leu Pro Ser His Gln Trp Ile Ser Glu Met
            35                  40                  45

Val Val Gln Leu Ser Asp Ser Leu Thr Asp Leu Leu Asp Lys Phe Ser
        50                  55                  60

Asn Ile Ser Glu Gly Leu Ser Asn Tyr Ser Ile Ile Asp Lys Leu Val
65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
                100                 105                 110

Glu Glu Phe Phe Ala Ile Phe Asn Arg Ser Ile Asp Ala Phe Lys Asp
            115                 120                 125

Phe Val Val Ala Ser Glu Thr Ser Asp Cys Val Val Ser
130                 135                 140

<210> SEQ ID NO 17
<211> LENGTH: 141
<212> TYPE: PRT
<213> ORGANISM: HOMO SAPIENS

<400> SEQUENCE: 17

Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
                20                  25                  30

Val Pro Gly Met Asp Val Leu Pro Ser His Gln Trp Ile Ser Glu Met
            35                  40                  45

Val Val Gln Leu Ser Asp Ser Leu Thr Asp Leu Leu Asp Lys Phe Ser
        50                  55                  60

Asn Ile Ser Glu Gly Leu Ser Asn Tyr Ser Ile Ile Asp Lys Leu Val
65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
                100                 105                 110

Glu Glu Phe Phe Arg Ala Phe Asn Arg Ser Ile Asp Ala Phe Lys Asp
            115                 120                 125

Phe Val Val Ala Ser Glu Thr Ser Asp Cys Val Val Ser
130                 135                 140

<210> SEQ ID NO 18
<211> LENGTH: 141
<212> TYPE: PRT
<213> ORGANISM: HOMO SAPIENS

<400> SEQUENCE: 18

Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
                20                  25                  30

Val Pro Gly Met Asp Val Leu Pro Ser His Gln Trp Ile Ser Glu Met
            35                  40                  45

```
Val Val Gln Leu Ser Asp Ser Leu Thr Asp Leu Leu Asp Lys Phe Ser
     50                  55                  60

Asn Ile Ser Glu Gly Leu Ser Asn Tyr Ser Ile Ile Asp Lys Leu Val
 65                  70                  75                  80

Asn Ile Val Asp Asp Leu Val Glu Cys Val Lys Ala Asn Ser Ser Lys
                 85                  90                  95

Asp Leu Lys Lys Ser Phe Lys Ser Pro Glu Pro Arg Leu Phe Thr Pro
                100                 105                 110

Glu Glu Phe Phe Arg Ile Phe Asn Arg Ser Ile Asp Ala Phe Lys Asp
            115                 120                 125

Phe Val Val Ala Ser Glu Thr Ser Asp Cys Val Val Ser
        130                 135                 140

<210> SEQ ID NO 19
<211> LENGTH: 141
<212> TYPE: PRT
<213> ORGANISM: HOMO SAPIENS

<400> SEQUENCE: 19

Glu Gly Ile Cys Arg Asn Arg Val Thr Asn Asn Val Lys Asp Val Thr
 1               5                  10                  15

Lys Leu Val Ala Asn Leu Pro Lys Asp Tyr Met Ile Thr Leu Lys Tyr
                 20                  25                  30

Val Pro Gly Met Asp Val Leu Pro Ser His Gln Trp Ile Ser Glu Met
             35                  40                  45

Val Val Gln Leu Ser Asp Ser Leu Thr Asp Leu Leu Asp Lys Phe Ser
     50                  55                  60

Asn Ile Ser Glu Gly Leu Ser Asn Tyr Ser Ile Ile Asp Lys Leu Val
 65                  70                  75                  80

Asn Ile Val Asp Asp Leu Val Glu Cys Val Lys Glu Asn Ser Ala Lys
                 85                  90                  95

Asp Leu Lys Lys Ser Phe Lys Ser Pro Glu Pro Arg Leu Phe Thr Pro
                100                 105                 110

Glu Glu Phe Phe Arg Ile Phe Asn Arg Ser Ile Asp Ala Phe Lys Asp
            115                 120                 125

Phe Val Val Ala Ser Glu Thr Ser Asp Cys Val Val Ser
        130                 135                 140

<210> SEQ ID NO 20
<211> LENGTH: 141
<212> TYPE: PRT
<213> ORGANISM: HOMO SAPIENS

<400> SEQUENCE: 20

Glu Gly Ile Cys Arg Asn Arg Val Thr Asn Asn Val Lys Asp Val Thr
 1               5                  10                  15

Lys Leu Val Ala Asn Leu Pro Lys Asp Tyr Met Ile Thr Leu Lys Tyr
                 20                  25                  30

Val Pro Gly Met Asp Val Leu Pro Ser His Gln Trp Ile Ser Glu Met
             35                  40                  45

Val Val Gln Leu Ser Asp Ser Leu Thr Asp Leu Leu Asp Lys Phe Ser
     50                  55                  60

Asn Ile Ser Glu Gly Leu Ser Asn Tyr Ser Ile Ile Asp Lys Leu Val
 65                  70                  75                  80

Asn Ile Val Asp Asp Leu Val Glu Cys Val Lys Glu Asn Ser Ser Lys
                 85                  90                  95
```

```
Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Ala Ala Phe Lys Asp
            115                 120                 125

Phe Val Val Ala Ser Glu Thr Ser Asp Cys Val Val Ser
        130                 135                 140

<210> SEQ ID NO 21
<211> LENGTH: 141
<212> TYPE: PRT
<213> ORGANISM: HOMO SAPIENS

<400> SEQUENCE: 21

Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
            20                  25                  30

Val Pro Gly Met Asp Val Leu Pro Ser His Gln Trp Ile Ser Glu Met
        35                  40                  45

Val Val Gln Leu Ser Asp Ser Leu Thr Asp Leu Leu Asp Lys Phe Ser
    50                  55                  60

Asn Ile Ser Glu Gly Leu Ser Asn Tyr Ser Ile Ile Asp Lys Leu Val
65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Asp Asp
            115                 120                 125

Phe Val Val Ala Ser Glu Thr Ser Asp Cys Val Val Ser
        130                 135                 140

<210> SEQ ID NO 22
<211> LENGTH: 165
<212> TYPE: PRT
<213> ORGANISM: HOMO SAPIENS

<400> SEQUENCE: 22

Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
            20                  25                  30

Val Pro Gly Met Asp Val Leu Pro Ser His Cys Trp Ile Ser Glu Met
        35                  40                  45

Val Val Gln Leu Ser Asp Ser Leu Thr Asp Leu Leu Asp Lys Phe Ser
    50                  55                  60

Asn Ile Ser Glu Gly Leu Ser Asn Tyr Ser Ile Ile Asp Lys Leu Val
65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Lys Asp
            115                 120                 125

Phe Val Val Ala Ser Glu Thr Ser Asp Cys Val Val Ser Ser Thr Leu
        130                 135                 140
```

```
-continued

Ser Pro Glu Lys Asp Ser Arg Val Ser Val Thr Lys Pro Phe Met Leu
145                 150                 155                 160

Pro Pro Val Ala Ala
                165
```

CONJUGATED LIGANDS FOR THE STIMULATION OF BLOOD CELL PROLIFERATION BY EFFECTING DIMERIZATION OF THE RECEPTOR FOR STEM CELL FACTOR

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

FIELD OF THE INVENTION

This invention relates to stem cell factor (SCF) analogs, compositions containing such analogs, and related compositions. In another aspect, the present invention relates to nucleic acids encoding the present analogs or related nucleic acids, related host cells and vectors. In another aspect, the invention relates to computer programs and apparatuses for expressing the three dimensional structure of SCF and analogs thereof. In another aspect, the invention relates to methods for rationally designing SCF analogs and related compositions. In yet another aspect, the present invention relates to methods for treatment using the present SCF analogs.

BACKGROUND OF THE INVENTION

Stem cell factor (SCF) is an early-acting hematopoietic cytokine which elicits multiple biological effects. SCF is dimeric and occurs in soluble and membrane-bound forms. It transduces signals by ligand-mediated dimerization of its receptor, Kit. Kit is a receptor tyrosine kinase related to the receptors for platelet-derived growth factor (PDGF) and to those for vascular endothelial growth factor (VEGF), fibroblast growth factor (FGF), macrophage colony-stimulating factor (M-CSF) and Flt-3 ligand. The kinase portions of these receptors are closely related and their ligand-binding portions all comprise immunoglobulin-like (Ig) repeats, although these vary widely in sequence and also in a number. Determined here is the crystal structure of selenomethionyl soluble human SCF at 2.2 Å resolution by multiwavelength anomalous diffraction (MAD) phasing. SCF has the characteristic helical cytokine topology, but the structure is unique apart from core portions. The SCF dimer has a symmetric 'head-to-head' association. Potential Kit-binding sites on the SCF dimer surface are located. A superposition of this dimer onto VEGF in its complex with the Flt-1 receptor places the binding sites on SCF in positions of topographical and electrostatic complementarity with the Kit counterparts of Flt-1. Similar models can be made for the complex of PDGF with its receptor and FGF-heparin.

INTRODUCTION

Stem cell factor (SCF) is an early-acting hematopoietic cytokine that binds at the cell surface to its receptor, Kit, whereby it produces other biological effects in addition to those on hematopoiesis (see reviews by Galli et al., 1994; Lev et al., 1994; Besmer et al., 1997; Broudy, 1997). SCF, which is produced by various fibroblast-type cells including bone marrow stromal cells, has also been called Kit ligand (KL), mast-cell growth factor (MGF), and steel factor. The biochemistry and molecular biology that identified SCF and Kit as a ligand-receptor pair were preceded by an array of elegant animal biology studies that anticipated the underlying molecular mechanisms responsible for the genetics. (Russell, 1979). Mice with mutations in the S1 locus (gene for SCF) or in the dominant-spotting W locus (c-kit, the gene for Kit) show complex phenotypes that include macrocytic anemia, sterility from a deficiency of germ cells, lack of coat pigmentation (white spotting of the skin from absences of pigment cells) and mast cell deficiency. Kit mutations in man are responsible for the autosomal dominant congenital pigmentation disorder, piebaldism. Consistent with these phenotypes, in the last 10 years, a host of in vitro and in vivo experiments have clearly established Kit-mediated roles for SCP in early stages of hematopoiesis, in gametogenesis, in melanocyte proliferation and function and in mast cell proliferation, maturation and activation; (Galli et al., 1994, Lev et al., 1994, Besmer et al., 1997; Broudy, 1997). SCF has potential therapeutic applications in the treatment of anemias, boosting the mobilization of hematopoietic stem/progenitor cells to the peripheral blood for harvest and transplantation, and in increasing the efficiency of gene transduction for gene therapy (Galli et al., 1994, McNiece and Briddell, 1995, Glaspy, 1996, Broudy, 1997).

SCF is expressed as membrane-associated forms of either 248 or 220 amino acid residues (Galli et al., 1994, Lev et al., 1994, Besmer et al., 1997, Broudy, 1997). The two forms are a consequence of alternative mRNA splicing that includes or excludes exon 6. Exon 6 encodes a proteolytic cleavage site such that soluble $SCF^{1-165}$ is released from the 248 amino-acid precursor. Residues 166–189 represent a tether to the membrane, residues 190–221 represent a hydrophobic transmembrane segment, and residues 222–248 represent a cytoplasmic domain. The 220 amino acid residue form lacks the cleavage site and tends to remain membrane-bound. Soluble SCF exists as a non-covalently associated dimer (Arakawa et al., 1991). Each SCF monomer contains two intra-chain disulfide bridges, Cys4–Cys89 and Cys43–Cys138 (Langley et al, 1992). The N-terminal 141 residues of SCF have been identified as a functional core, $SCF^{1-141}$ (SEQ ID NO:1), that includes the dimer interface and portions that bind and activate the receptor Kit (Langley et al., 1994).

It has been proposed that SCF is a member of the helical cytokine structural superfamily characterized by a double-crossover four-helix bundle topology (Bazan, 1991). Three-dimensional structures are known for many of the family members and, from a comparison of the structures and sequences, the members have been classified into three subgroups (Sprang and Bazan, 1993): short-chain, long-chain and interferon-like.

The superfamily is highly divergent. Among five short-chain helical cytokines of known structure, sequence identity levels rarely exceed 20% and fewer than half of the residues constitute (41%–48%) a common framework of the fold with r.m.s. deviations ranging from 1.7 Å to 2.9 Å for the 61 $C_\alpha$ positions in common. Furthermore, many identical residues adopt different side chain conformations in the various structures. Nevertheless, sequence patterns do persist from the secondary structure and SCF has been proposed to be a short-chain helical cytokine (Bazan, 1991; Rozwarski et al., 1994).

Most helical cytokines signal through members of the hematopoietic cytokine receptor superfamily, which are without intrinsic kinase activity (Heldin, 1995). SCF, in contrast, signals through a class III receptor tyrosine kinase (i.e. Kit). This class of kinases also includes the receptors for platelet-derived growth factor (PDGF), macrophage colony-stimulating factor (M-CSF), granulocyte-macrophage colony-stimulating factor (GM-CSF), and Flt-3 ligand, and it is related to class V receptor tyrosine kinases (Flt-1, Flt-1/KDR and Flt-4) for vascular endothelial growth factors (VEGFs) (Fantl et al., 1993; Heldin, 1995; Rousset et al., 1995). The receptors in these classes have 'split' kinase domains intracellularly and multiple immunoglobulin(Ig)-like domains extracellularly.

The structures of PDGF (Oefner et al., 1992), M-CSF (Pandit et al., 1992), and VEGF (Muller et al., 1997), have all been determined by X-ray crystallography, as has the complex of VEGF with domain 2 of its receptor, Flt-1 (Wiesmann et al., 1997).

The ligands for the class III and class V receptors are all dimeric. As is the case for other ligands, SCF initiates signal transduction by dimerization of its receptor, Kit and the two juxtaposed receptors undergo tyrosine autophosphorylation (Heldin, 1995; Broudy, 1997), which initiates downstream intracellular signaling.

Here reported is the crystal structure of the core fragment of recombinant human stem cell factor, $SCF^{1-141}$, as determined at 2.2 Å resolution from multiwavelength anomalous diffraction (MAD) measurements. Incorporating data from mutagenesis and other structure-function studies, located were putative receptor-binding sites on the surface of the symmetric SCF dimer. From a comparison of these results with the structural and functional data for the related ligand-receptor systems, the complex of SCF with the receptor Kit is modeled and suggests a similar mode of association between other class III and class V receptors and their ligands.

Human SCF can be obtained and purified from a number of sources. SCF has been isolated from the rat and the mouse. Using the amino acid sequence of SCF protein isolated from the rat, the nucleic acid sequence encoding the rat protein sequence was obtained from a rat cDNA library and then was cloned. The cloned nucleic acid encoding rat SCF was used to isolate, by hybridization, the nucleic acid molecule encoding human SCF from a human cDNA library. The development of recombinant DNA technology, see, for instance, U.S. Pat. No. 4,810,643 (Souza) incorporated herein by reference, has enabled the production of commercial scale quantities of SCF in glycosylated form as a product of eukaryotic host cell expression, and of SCF in non-glycosylated form as a product of prokaryotic host cell expression.

SUMMARY OF THE INVENTION

The three dimensional structure of SCF has been determined herein to the atomic level. From this three-dimensional structure, one can now forecast with substantial certainty how changes in the composition of a SCF molecule may result in structural changes. These structural characteristics may be correlated with biological activity to design and produce SCF analogs.

This invention provides a computer based method for preparing a stem cell factor (SCF) analog comprising the steps of: (a) providing computer expression of the three dimensional structure of an SCF molecule using its crystal structure; (b) selecting from the computer expression of step (a) at least one site on the SCF molecule for alteration; (c) preparing an SCF molecule having an alteration at said at least one selected site; and (d), optionally, testing the SCF molecule for a desired characteristic.

This invention also provides an isolated SCF analog prepared according to the above-described computer based method for preparing a stem cell factor (SCF) analog comprising the steps of: (a) providing computer expression of the three dimensional structure of an SCF molecule using its crystal structure; (b) selecting from the computer expression of step (a) at least one site on the SCF molecule for alteration; (c) preparing a SCF molecule having an alteration at said at least one selected site; and (d) optionally, testing the SCF molecule for a desired characteristic. In an embodiment the above-described SCF analog binds to SCF receptor, Kit. As used herein SCF receptor and "Kit" are used interchangeably to reflect the varied nomenclature used in the art.

This invention provides a composition comprising an isolated SCF analog prepared according to the above-described computer based method for preparing a stem cell factor (SCF) analog comprising the steps of: (a) providing computer expression of the three dimensional structure of an SCF molecule using its crystal structure; (b) selecting from the computer expression of step (a) at least one site on the SCF molecule for alteration; (c) preparing a SCF molecule having an alteration at said at least one selected site; and (d) optionally, testing the SCF molecule for a desired characteristic, effective to treat a subject and a pharmaceutically acceptable carrier.

This invention provides a method of treating a subject comprising administration of an isolated SCF analog prepared by the above-described computer based method for preparing a stem cell factor (SCF) analog comprising the steps of: (a) providing computer expression of the three dimensional structure of an SCF molecule using its crystal structure; (b) selecting from the computer expression of step (a) at least one site on the SCF molecule for alteration; (c) preparing a SCF molecule having an alteration at said at least one selected site; and (d) optionally, testing the SCF molecule for a desired characteristic.

This invention provides a method for designing a compound (drug) capable of binding to the receptor of stem cell factor (SCF), Kit, comprising the steps of: a) determining a receptor binding site on the SCF based on the three dimensional structure of SCF (SEQ ID NO;1) or an SCF polypeptide capable of binding the receptor; and b) designing a compound comprising an entity that binds the SCF receptor. Accordingly, the designed compound is an SCF ligand analog, since a portion or part of the compound, "the entity", mimics the portion of SCF that binds to the SCF receptor, Kit. In step (a), and infra, the receptor binding site may be determined from atomic coordinates computed from X-ray diffraction data of a crystal comprising a polypeptide having an amino acid sequence portion of SCF capable of binding the receptor.

This invention provides a compound designed by the above-described method for designing a compound capable of binding to the receptor site of stem cell factor (SCF), Kit, comprising the steps of: a) determining a receptor binding site, on the SCF (SEQ ID NO;1) based on the atomic coordinates computed from X-ray diffraction data of a crystal comprising a polypeptide having an amino acid sequence portion of SCF capable of binding a ligand; and b) designing a compound comprising an entity that binds the SCF receptor. As used herein, the entity, i.e. the portion, of the designed compound fits the ligand binding site on the SCF receptor.

This invention provides a method of treating a subject comprising administration of a compound designed by the above-described method for designing a compound capable of binding to the SCF receptor site.

This invention also provides a method of stimulating the production of hematopoietic calls in a subject comprising administering an isolated stem cell factor (SCF) analog or SCF ligand analogs to the subject.

This invention provides an isolated stem cell factor (SCF) molecule, which is an altered SCF, comprising any portion of amino acids 1–165 of a human SCF polypeptide (SEQ ID NO;22), optionally comprising an N-terminal methionine before amino acid residue 1, wherein the polypeptide has an amino acid sequence portion of SCF capable of binding to the SCF receptor, Kit. Amino acid residue 1 of SCF is E, glutamic acid.

BRIEF DESCRIPTION OF THE FIGURES

FIGS. 1A–1C. Representative electron-density distributions in SCF. (FIG. 1A) MAD-phased experimental map calculated at 2.3 Å resolution. (FIG. 1B) The experimental map after four-fold averaging. (FIG. 1C) The current $2F_o$-$F_c$ map superimposed with the model refined at 2.2 Å resolution. Each map is contoured at $1.0\sigma$. Figures were drawn by the program O (Jones et al., 1991).

(FIG. 2A) Ribbon diagram. (FIG. 2B) $C_\alpha$ stereodiagram of the AB dimer. Figures were drawn using the program SETOR (Evans, 1993).

FIG. 3. Structure-based sequence alignment of SCF (SEQ ID NO:1) with other short-chain helical cytokines of human species. The dots denote gaps. M-CSF (SEQ ID NO:2), IL-4 (SEQ ID NO:3), GM-CSF (SEQ ID NO:4), IL-2 (SEQ ID NO:5) and IL-5 (SEQ ID NO:6) were aligned with SCF structure through structural superposition using TOSS (Hendrickson, 1979) and O (Jones et al., 1991). C$\alpha$ atoms were included if within 3.0 Å of their counterparts after superposition and at least three consecutive such residues are found in the fragment. The secondary structure elements were assigned according to the output of the PROCHECK program (Laskowski et al., 1993) except the helix assignment for residues 35–38, which was identified by inspection of the hydrogen-bond pattern. Secondary structures are shown shaded with filled boxes referring to $\alpha$-helices, half-filled boxes to $3_{10}$-helices and arrows to $\beta$-strands. The solvent accessibility of the SCF dimer is indicated for each residue by an open circle if the fractional solvent accessibility is >0.4, a half-filled circle if it is 0.1–0.4, and a filled circle if it is <0.1. Residues at the SCF dimer interface are identified by stars, and the N-linked glycosylation sites by Ys above the Asn residues.

(FIG. 4A) View as in FIG. 2. (FIG. 4B) View perpendicular to FIG. 4A, along the diad axis of M-CSF. Symmetry axes are shown as lines in FIG. 4A and dots in FIG. 4B. When one subunit of SCF dimer is superimposed onto a subunit of the M-CSF dimer, the other subunits are translated by 3.8 Å with a rotation of 4.7° to each other. Figures were generated using the program GRASP (Nicholls et al., 1991).

FIG. 5. Sequence alignment of SCF from human (SEQ ID NO:7), mouse (SEQ ID NO:8), rat (SEQ ID NO:9) and dog (SEQ ID NO:10). (Anderson et al., 1990; Huang et al., 1990; Martin et al. 1990; Shull et al., 1992). The residues that are conserved in human and dog but different from rat and mouse are shadowed. Five regions of divergent sequence are identified (Roman numerals). Dots denote gaps, and dashes indicate residues identical to the human residues.

(FIG. 6A) VEGF-Flt-1. (FIG. 6B) SCF-Kit. (FIG. 6C) PDGF-{DGF receptor. The used, without any modification, to approximate the receptor models. Receptor models are presented at the top. The ligand models are presented as worm models. Figures were drawn by the program GRASP (Nicholls et al., 1991).

FIGS. 7A–7B. Electrostatic and carbohydrate surfaces of SCF and homology-modeled receptor Kit. (FIG. 7A) Electrostatic surface of SCF and worm of D2D3 (Kit). (FIG. 7B) Electro-static surface of Kit and worm of SCF. Negative potential is dark gray and positive potential, light gray, with greatest saturations at −10 and +10 kT, respectively. Carbohydrate moieties are represented by CPK models of a $\beta$-D-N-acetylglucose Figures were drawn by the program GRASP (Nicholls et al., 1991).

FIGS. 8A-1 to 8A-76. X-ray crystallographic coordinates of truncated stem cell factor molecule comprising amino acids 1–141 of a human SCF polypeptide.

FIG. 9. Suggested renaming of the waters of the X-ray crystallographic coordinates set forth in FIG. 8.

Figure 1:
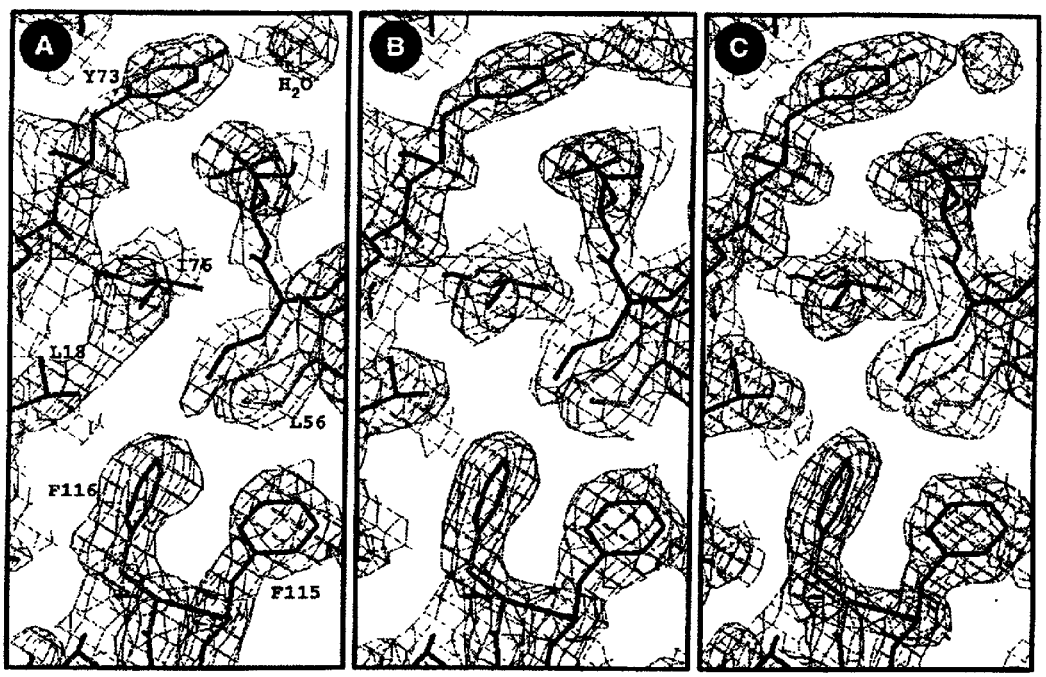

Ligand heads can be designed in at least four ways. (1) Ligand heads can be synthesized as oligopeptides wherein the functional moieties ($F_1$, $F_2$, $F_3$) are sequence elements from the SCF polypeptide; (2) The functional moieties ($F_1$, $F_2$, $F_3$) on such a ligand head can be selected by bacteriophage display for optimal receptor binding; (3) Chemical mimetice of the functional moieties and connecting segments in an active oligopeptide can be substituted for the respective moieties and segments; or (4) An appropriate chemical framework (scaffold) of connecting segments can be designed to present functional moieties ($F_1$, $F_2$, $F_3$) which can be selected by combinatorial chemistry for optimal receptor binding from a library of chemical moieties complementary to receptor-binding sites on the surface of SCF.

When an oligopeptide embodiment of a linker head is designed in accord with option (1) it can have a sequence wherein $F_1$ corresponds to a segment from within the N-terminal region of SCF, residues 1–10; $F_2$ corresponds to a segment from within residues 79–95 (mainly located on the $\alpha$C helix); $F_3$ is a segment from the C-terminal end of $\alpha$D, near residue 127; $F_L$ is a cysteine residue; and $X_n$, $X_m$, and $X_p$ are connecting-peptide segments, composed from appropriate linker residues such as alanine, glycine, serine or proline, and wherein n=0–5, m=0–5 and p=3–8 residues, respectively.

Linkers can be designed from an organic polymer such as polyethylene glycol $H[OCH_2CH_2]_nOH$, where n=10–20 may suffice to separate the heads appropriately, wherein a reactive capping moiety, $F_c$, is appended at each end. The capping moiety may be a thiol reactive group, such as N-ethyl maleimide, designed to bond covalently to the conjugation moiety, $F_L$, on the ligand head, wherein $F_L$ may be cysteine residue or another thiol-containing group.

DETAILED DESCRIPTION OF THE INVENTION

The present determination of the three-dimensional structure to the atomic level is the most complete analysis to date, and provides important information to those wishing to design and prepare SCF analogs. For example, from the present three dimensional structural analysis, precise areas of hydrophobicity and hydrophilicity have been determined.

Relative hydrophobicity is important because it directly relates to the stability of the molecule. Generally, biological molecules, found in aqueous environments, are externally hydrophilic and internally hydrophobic; in accordance with the second law of thermodynamics provides, this is the lowest energy state and provides for stability. Although one could have speculated that SCF's internal core would be hydrophobic, and the outer areas would be hydrophilic, one would have had no way of knowing specific hydrophobic or hydrophilic areas. With the presently provided knowledge of areas of hydrophobicity/-philicity, one may forecast with substantial certainty which changes to the SCF molecule will affect the overall structure of the molecule.

As a general rule, one may use knowledge of the geography of the hydrophobic and hydrophilic regions to design analogs in which the overall SCF structure is not changed, but change does affect biological activity ("biological activity" being used here in its broadest sense to denote function). One may correlate biological activity to structure. If the structure is not changed, and the mutation has no effect on biological activity, then the mutation has no biological function. If, however, the structure is not changed and the mutation does affect biological activity, then the residue (or atom) is essential to at least one biological function. Some of the present working examples were designed to provide no change in overall structure, yet have a change in biological function.

Based on the correlation of structure to biological activity, one aspect of the present invention relates to SCF analogs. These analogs are molecules which have more, fewer, different or modified amino acid residues from the SCF amino acid sequence. The modifications may be by addition, substitution, or deletion of one or more amino acid residues. The modification may include the addition or substitution of analogs of the amino acids themselves, such as peptidomimetics or amino acids with altered moieties such as altered side groups. The SCF used as a basis for comparison may be of human, animal or recombinant nucleic acid-technology origin (although the working examples disclosed herein are based on the recombinant production of the 141 amino acid species of human SCF (SEQ ID NO;1), optionally having an extra N-terminal methionine residue). The analogs may possess functions different from natural human SCF molecule, or may exhibit the same functions, or varying degrees of the same functions. For example, the analogs may be designed to have a higher or lower biological activity, have a longer shelf-life or a decrease in stability, be easier to formulate, or more difficult to combine with other ingredients. The analogs may bind receptor but elicit no biological activity and may therefore be useful as an antagonist against SCF effect (as, for example, in the overproduction of SCF). From time to time herein the present analogs are referred to as proteins or peptides for convenience, but contemplated herein are other types of molecules, such as peptidomimetics or chemically modified peptides.

In embodiment, the present invention relates to related compositions containing a SCP analog as an active ingredient. The term, "related composition," as used herein, is meant to denote a composition which may be obtained once the identity of the SCF analog is ascertained (such as a SCF analog labeled with a detectable label or pharmaceutical composition). Also considered a related composition are chemically modified versions of the SCF analog, such as those having attached at least one polyethylene glycol molecule.

For example, one may prepare a SCP analog to which a detectable label is attached, such as a fluorescent, chemiluminescent or radioactive molecule.

Another example is a pharmaceutical composition which may be formulated by known techniques using known materials, see, e.g., Remington's Pharmaceutical Sciences, 18th Ed. (1990, Mack Publishing Co., Easton, Pa. 28042) pages 1435–1712, which are herein incorporated by reference. Generally, the formulation will depend on a variety of factors such as administration, stability, production concerns and other factors. The SCF analog may be administered by injection or by pulmonary administration via inhalation. Enteric dosage forms may also be available for the present SCF analog compositions, and therefore oral administration may be effective. SCF analogs may be inserted into liposomes or other microcarriers for delivery, and may be formulated in gels or other compositions for sustained release. Although preferred compositions will vary depending on the use to which the composition will be put, generally, for SCF analogs having at least one of the biological activities of natural SCF, preferred pharmaceutical compositions are those prepared for subcutaneous injection or for pulmonary administration via inhalation, although the particular formulations for each type of administration will depend on the characteristics of the analog.

Another example of related composition is a receptor for the present analog. As used herein, the term "receptor" indicates a moiety which selectively binds to the present analog molecule. For example, antibodies, or fragments thereof, or "recombinant antibodies" (see Huse et al., Science 246:1275 (1989)) may be used as receptors. Selective binding does not mean only specific binding (although binding-specific receptors are encompassed herein), but rather that the binding is not a random event. Receptors may be on the cell surface or intra- or extra-cellular, and may act to effectuate, inhibit or localize the biological activity of the present analogs.

Receptor binding may also be a triggering mechanism for a cascade of activity indirectly related to the analog itself. Also contemplated herein are nucleic acids, vectors containing such nucleic acids and host cells containing such nucleic acids which encode such SCF analogs.

Another example of a related composition is a SCF analog with a chemical moiety attached. Generally, chemical modification may alter biological activity or antigenicity of a protein, or may alter other characteristics, and these factors will be taken into account by a skilled practitioner. As noted above, one example of such chemical moiety is polyethylene glycol. Modification may include the addition of one or more hydrophilic or hydrophobic polymer molecules, fatty acid molecules, or polysaccharide molecules. Examples of chemical modifiers include polyethylene glycol, alklpolyethylene glycols, DI-poly(amino acids), polyvinylpyrrolidone, polyvinyl alcohol, pyran copolymer, acetic acid/acylation, proprionic acid, palmitic acid, lecithin, stearic acid, dextran, carboxymethyl cellulose, pullulan, or agarose. See, Francis, *Focus on Growth Factors* 3: 4–10 (May 1992) (published by Mediscript, Mountview Court, Friern Barnet Lane, London N20 OLD, UK). Also, chemical modification may include an additional protein or portion thereof, use of a cytotoxic agent, or an antibody.

In another embodiment, the present invention relates to nucleic acids encoding such analogs. The nucleic acids may be DNAs or RNAs or derivatives thereof, and will typically be cloned and expressed on a vector, such as a phage or plasmid containing appropriate regulatory sequences. The nucleic acids may be labeled (such as using a radioactive, chemiluminescent, or fluorescent label) for diagnostic or prognostic purposes, for example. The nucleic acid sequence may be optimized for expression, such as including codons preferred for bacterial expression. The nucleic acid and its complementary strand, and modifications thereof which do not prevent encoding of the desired analog are here contemplated.

In another embodiment, the present invention relates to host cells containing the above nucleic acids encoding the present analogs. Host cells may be eukaryotic or prokaryotic, and expression systems may include extra steps relating to the attachment (or prevention) of sugar groups (glycosylation), proper folding of the molecule, the addition or deletion of leader sequences or other factors incident to recombinant expression.

In further embodiment the present invention relates to antisense nucleic acids which act to prevent or modify the type or amount of expression of such nucleic acid sequences. These may be prepared by known methods.

In another embodiment of the present invention, the nucleic acids encoding a present analog may be used for gene therapy purposes, for example, by placing a vector containing the analog-encoding sequence into a recipient so the nucleic acid itself is expressed inside the recipient who is in need of the analog composition. The vector may first be placed in a carrier, such as a cell, and then the carrier placed into the recipient. Such expression may be localized or systemic. Other carriers include non-naturally occurring carriers, such as liposomes or other microcarriers or particles, which may act to mediate gene transfer into a recipient.

The present invention also provides for computer programs for the expression (such as visual display) of the SCF or analog three dimensional structure, and further, a computer program which expresses the identity of each constituent of an SCF molecule and the precise location within the overall structure of that constituent, down to the atomic level. Set forth below is one example of such program. There are many currently available computer programs for the expression of the three dimensional structure of a molecule. Generally, these programs provide for inputting of the coordinates for the three dimensional structure of a molecule (i.e., for example, a numerical assignment for each atom of an SCF molecule along an x, y, and z axis), means to express (such as visually display) such coordinates, means to alter such coordinates and means to express an image of a molecule having such altered coordinates. One may program crystallographic information, i.e., the coordinates of the location of the atoms of an SCF molecule in three dimensional space, wherein such coordinates have been obtained from crystallographic analysis of said SCF molecule, into such programs to generate a computer program for the expression (such as visual display) of the SCF three dimensional structure. Also provided, therefore, is a computer program for the expression of SCF analog three dimensional structure. Preferred is the computer program Insight II, version 4, available from Biosym, San Diego, Calif., with the coordinates as set forth in FIG. 8 input. Preferred expression means is on a Silicon Graphics 320 VGX computer, with Crystal Eyes glasses (also available from Silicon Graphics), which allows one to view the SCF molecule or its analog stereoscopically. The above-listed computer programs are only examples, and the use of such programs in the claimed methods is not limited thereto, as one of skill may use any other computer program that provides the desired three dimensional expression. Alternatively, the present SCF crystallographic coordinates and diffraction data are also deposited in the Protein Data Bank, Chemistry Department, Rutgers University, New Jersey, USA [formerly at Brookhaven National Laboratory, Upton, N.Y. 11912]. One may use these data in preparing a different computer program for expression of the three dimensional structure of a SCF molecule or analog thereof. Therefore, another aspect of the present invention is a computer program for the expression of the three dimensional structure of a SCF molecule. Also provided is said computer program for visual display of the three dimensional structure of an SCF molecule; and further, said program having means for altering such visual display. Apparatus useful for expression of such computer program, particularly for the visual display of the computer image of said three dimensional structure of an SCF molecule or analog thereof is also therefore here provided, as well as means for preparing said computer program and apparatus.

The computer program is useful for preparation of SCF analogs because one may select specific sites on the SCF molecule for alteration and readily ascertain the effect the alteration will have on the overall structure of the SCF molecule. Selection of said site for alteration will depend on the desired biological characteristic of the SCF analog. If one were to randomly change said SCF molecule there would be substitutions, additions or deletions, and even more analogs having multiple changes. By viewing the three dimensional structure wherein said structure is correlated with the composition of the molecule, the selection for sites for alteration is no longer a random event, but sites for alteration may be determined rationally.

Identity of the three dimensional structure of SCF, including the placement of each constituent down to the atomic level has now yielded information regarding which moieties are necessary to maintain the overall structure of the SCF molecule. One may therefore select whether to maintain the overall structure of the SCF molecule when preparing an SCF analog of the present invention, or whether (and how) to change the overall structure of the SCF molecule when preparing a SCF analog of the present invention. Optionally, once one has prepared such analog, one may test such analog for a desired characteristic.

One may, for example, seek to maintain the overall structure possessed by a non-altered natural or recombinant SCF molecule. The overall structure is presented in FIGS. 2A–2B, and is described in more detail below. Maintenance of the overall structure may ensure receptor binding, a necessary characteristic for an analog possessing the biologic capabilities of natural SCF (if no receptor binding, signal transduction does not result from the presence of the analog). It is contemplated that one class of SCF analogs will possess the three dimensional core structure of a natural or recombinant (non-altered) SCF molecule, yet possess different characteristics, such as an increased ability to selectively stimulate neutrophils. Another class of SCF analogs are those with a different overall structure which diminishes the ability of an SCF analog molecule to bind to a SCF receptor, Kit, and possesses a diminished ability to selectively stimulate hematopoiesis, for example, as compared to non-altered natural or recombinant SCF.

For example, it is now known which moieties within the internal regions of the SCF molecule are hydrophobic, and, correspondingly, which moieties on the external portion of the SCF molecule are hydrophilic. Without knowledge of the overall three dimensional structure, preferably to the atomic level as provided herein, one could not forecast which alterations within this hydrophobic internal area would result in a change in the overall structural conformation of the molecule. An overall structural change could result in a functional change, such as lack of receptor binding, for example, and therefore, diminishment of biological activity as found in non-altered SCF. Another class of SCF analogs is therefore SCF analogs, which possess the same hydrophobicity as (non-altered) natural or recombinant SCF. More particularly, another class of SCF analogs possesses the same hydrophobic moieties within the four helical bundle of its internal core as those hydrophobic moieties possessed by (non-altered) natural or recombinant SCF yet have a composition different from said non-altered natural or recombinant SCF.

Another example relates to external loops which are structures which connect the internal core (helices) of the SCF molecule. From the three dimensional structure—including information regarding the spatial location of the amino acid residues—one may forecast that certain changes in certain loops will not result in overall conformational changes.

Therefore, another class of SCF analogs provided herein is that having an altered external loop but possessing the same overall structure as (non-altered) natural or recombinant SCF. More particularly, another class of SCF analogs provided herein are those having an altered external loop, said loop being selected from the loops discussed infra. More particularly, said loops, are altered to increase the half life of the molecule by stabilizing said loops. Such stabilization may be by connecting all or a portion of said loop(s) to a portion of an alpha helical bundle found in the core of a SCF (or analog) molecule. Such connection may be via beta sheet, salt bridge, disulfide bonds, hydrophobic interaction or other connecting means available to those skilled in the art, wherein such connecting means serves to stabilize said external loop or loops.

Additionally, such external loops may be the site(s) for chemical modification because in (non-altered) natural or recombinant SCF such loops are relatively flexible and tend not to interfere with receptor binding. Thus, there would be additional room for a chemical moiety to be directly attached (or indirectly attached via another chemical moiety which serves as a chemical connecting means). The chemical moiety may be selected from a variety of moieties available for modification of one or more function of an SCF molecule. For example, an external loop may provide sites for the addition of one or more polymer which serves to increase serum half-life, such as a polyethylene glycol molecule. Such polyethylene glycol molecule(s) may be added wherein said loop is altered to include additional lysines which have reactive side groups to which polyethylene glycol moieties are capable of attaching. Other classes of chemical moieties may also be attached to one or more external loops, including but not limited to other biologically active molecules, such as receptors, other therapeutic proteins (such as other hematopoietic factors which would engender a hybrid molecule), or cytotoxic agents (such as diphtheria toxin). This list is of course not complete; one skilled in the art possessed of the desired chemical moiety will have the means to effect attachment of said desired moiety to the desired external loop. Therefore, another class of the present, SCF analogs includes those with at least one alteration in an external loop wherein said alteration provides for the addition of a chemical moiety such as at least one polyethylene glycol molecule.

Deletions, such as deletions of sites recognized by proteins for degradation of the molecule, may also be effectual in the external loops. This provides alternative means for increasing half-life of a molecule otherwise having the SCF receptor binding and signal transduction capabilities (e.g., the ability to selectively stimulate hematopoiesis). Therefore, another class of the present SCF analogs includes those with at least one alteration in an external loop wherein said alteration decreases the turnover of said analog by proteases. One may prepare an abbreviated SCF molecule by deleting a portion of the amino acid residues found in any of the the external loops (discussed infra), said abbreviated SCF molecule may have additional advantages in preparation or in biological function.

Another example relates to the relative charges between amino acid residues which are in proximity to each other. As noted above, the SCF molecule contains a relatively tightly packed four helical bundle. Some of the faces on the helices face other helices. At the point (such as a residue) where a helix faces another helix, the two amino acid moieties which face each other may have the same charge, and thus tend to repel each other, which lends instability to the overall molecule. This may be eliminated by changing the charge (to an opposite charge or a neutral charge) of one or both of the amino acid moieties so that there is no repelling. Therefore, another class of SCP analogs includes those SCF analogs having been altered to modify instability due to surface interactions, such as electron charge location.

The present invention provides methods for designing SCF analogs and related compositions and the products of those methods. The end products of the methods may be the SCF analogs as defined above or related compositions. For instance, the examples disclosed herein demonstrate (a) the effects of changes in the constituents (i.e., chemical moieties) of the SCF molecule on the SCF structure and (b) the effects of changes in structure on biological function.

Accordingly, therefore, the present invention provides a computer based method for preparing a stem cell factor (SCF) analog comprising the steps of: (a) providing computer expression of the three dimensional structure of of an SCF molecule using its crystal structure; (b) selecting from the computer expression of step (a) at least one site on the SCF molecule for alteration; (c) preparing an SCF molecule having an alteration at said one said selected site; and (d) optionally, testing the SCF molecule for a desired characteristic. The SCF molecule of step (a) may be naturally occurring wild type SCF or any portion or fragment thereof which is capable of binding to SCF receptor.

In an embodiment of the above-described method the computer expression allows for display of the amino acids of the SCF molecule. In another embodiment of the method the computer expression allows for display of each atom of the SCF molecule. In a further embodiment of the method the SCF molecule is a native or a selenomethionyl SCF. In another embodiment of the method the site on the SCF molecule for alteration is a receptor binding site on the surface of the SCF molecule. In a further embodiment of the method the receptor binding site comprises amino acid residues 79–85 (of SEQ ID NO:1). The SCF molecule may be a recombinant human SCF or a wild type naturally occurring human SCF. SCF wild type and recombinant may also be of other sources such as but not limited to rat or mouse. In an embodiment of the above-described method, the atomic coordinates of the crystal structure are set forth in FIG. 8. In another embodiment the SCF analog comprises a polypeptide having an amino acid sequence portion of SCF capable of binding a receptor and having the overall three-dimensional conformation as shown in FIGS. 2A–2B, wherein the three-dimensional conformation is: a) anti-parallel, double-cross over 4-alpha helical bundle with a left hand twist; and b) overall dimensions of approximately 85 Å×30 Å×20 Å. In an embodiment the SCF analog comprises electron density distributions as set forth in FIGS. 1A, 1B, and 1C. In a further embodiment the SCF molecule is a native SCF or a selenomethionyl SCF.

In an embodiment the site on the SCF molecule for alteration is a receptor binding site on the surface of the SCF molecule or a non-receptor site of the SCF.

Alteration of a non-receptor binding site will result in a designed SCF analog that binds to the SCF receptor but is less active such that such an analog may be used for blocking activity of the SCF.

In another embodiment the receptor binding site comprises approximately amino acid residues 79–95 (of SEQ ID NO:1).

This invention provides an isolated SCF analog prepared according to the above-described method. In an embodiment the isolated SCF analog which binds to SCF receptor, Kit. In another embodiment the isolated SCF analog has an alteration in at least one atom of the atomic coordinates of the crystal structure set forth in FIG. 8. In a further embodiment the SCF analog comprises a polypeptide having an amino acid sequence portion of SCF capable of binding a receptor and having the overall three-dimensional conformation as shown in FIGS. 2A–2B, wherein the three-dimensional conformation is: a) anti-parallel, double-cross over 4-alpha helical bundle with a left hand twist; and b) overall dimensions of approximately 85 Å×30 Å×20 Å. In an embodiment the SCF analog comprises electron density distributions altered from those set forth in FIGS. 1A, 1B, and 1C.

This invention provides a composition comprising an isolated SCF analog prepared according to the above-described method effective to treat a subject and a pharmaceutically acceptable carrier. In an embodiment of the composition, the isolated SCF analog has an alteration in at least one atom of the atomic coordinates of the crystal structure set forth in FIG. 8. In another embodiment the isolated SCF analog comprises a polypeptide having an amino acid sequence portion of SCF capable of binding a receptor and having the overall three-dimensional conformation as shown in FIGS. 2A–2B, or an alteration thereof, wherein the three-dimensional conformation is: a) anti-parallel, double-cross over 4-alpha helical bundle with a left hand twist; and b) overall dimensions of approximately 85 Å×30 Å×20 Å. In a further embodiment the isolated SCF analog comprises electron density distributions as set forth in FIGS. 1A, 1B, and 1C. In an embodiment the isolated SCF analog comprises a native SCF1-165 (SEQ ID NO:22), a recombinant seleno-methionyl SCF1-141 (of SEQ ID NO:1), or a recombinant selenomethionyl SCF1-165 (of SEQ ID NO:22).

Any of the aforementioned SCF analogs may optionally have before the first N-terminal amino acid residue a methionine at position "−1".

In an embodiment of the composition the site on the isolated SCF molecule for alteration is a receptor binding site on the surface of the SCF molecule. In a further embodiment the receptor binding site comprises approximately amino acid residues 79–95 of SEQ ID NO:1.

This invention provides a method of treating a subject having a disorder requiring SCF comprising administration of a composition comprising an isolated SCF analog prepared by the method of preparing a SCF analog or a compound designed by the method of designing a compound capable of binding to the SCF receptor as described infra. In an embodiment the subject has a blood disorder. In another embodiment the disorder which the subject has is anemia, myeloproliferative disorder, neoplasia, nerve damage, infertility, intestinal damage, a pigmentation disorder, or immunodeficiency. In an embodiment the administration of the isolated SCF analog is for ex vivo or in vivro production of peripheral blood progenitors, ex vivo or in vivro stem cell expansion, ex vivo or in vitro growth of epithelial cells, ex vivo or in vitro growth of stromal cells, ex vivo or in vitro dendritic cell stimulation, and in vivo cell mobilization. In an embodiment the isolated SCF analog is administered orally or by any other routes described infra. In an embodiment the isolated SCF analog has an alteration in at least one atom of the atomic coordinates of the crystal structure set forth in FIG. 8. In a further embodiment the isolated SCF analog comprises a native SCF1-165 (SEQ ID NO:22) or a recombinant selenomethionyl SCF1-141 (of SEQ ID NO:1). In another embodiment the site on the isolated SCF molecule for alteration is a receptor binding site on the surface of the SCF molecule. In a further embodiment the receptor binding site comprises approximately amino acid residues 79–95. In an embodiment the isolated SCF analog comprises a native or recombinant SCF1-165 (SEQ ID NO:22 or a recombinant selenomethionyl SCF1-141 (of SEQ ID NO:1). As used herein throughout SCF receptor is Kit.

This invention provides a method for designing a compound capable of binding to the stem cell factor (SCF) receptor site of comprising the steps of: a) determining a binding site for the SCF receptor on the SCF based on the three-dimensional structure of SCF or an SCF polypeptide or portion/fragment thereof, atomic coordinates computed from X-ray diffraction data of a crystal comprising a polypeptide having an amino acid sequence portion of SCF capable of binding the receptor; and b) designing a compound comprising an entity that binds the SCF receptor. The designed compound mimics, i.e. is a copy or simulation of the overall portion of SCF that binds to SCF receptor, Kit.

Figure 6:
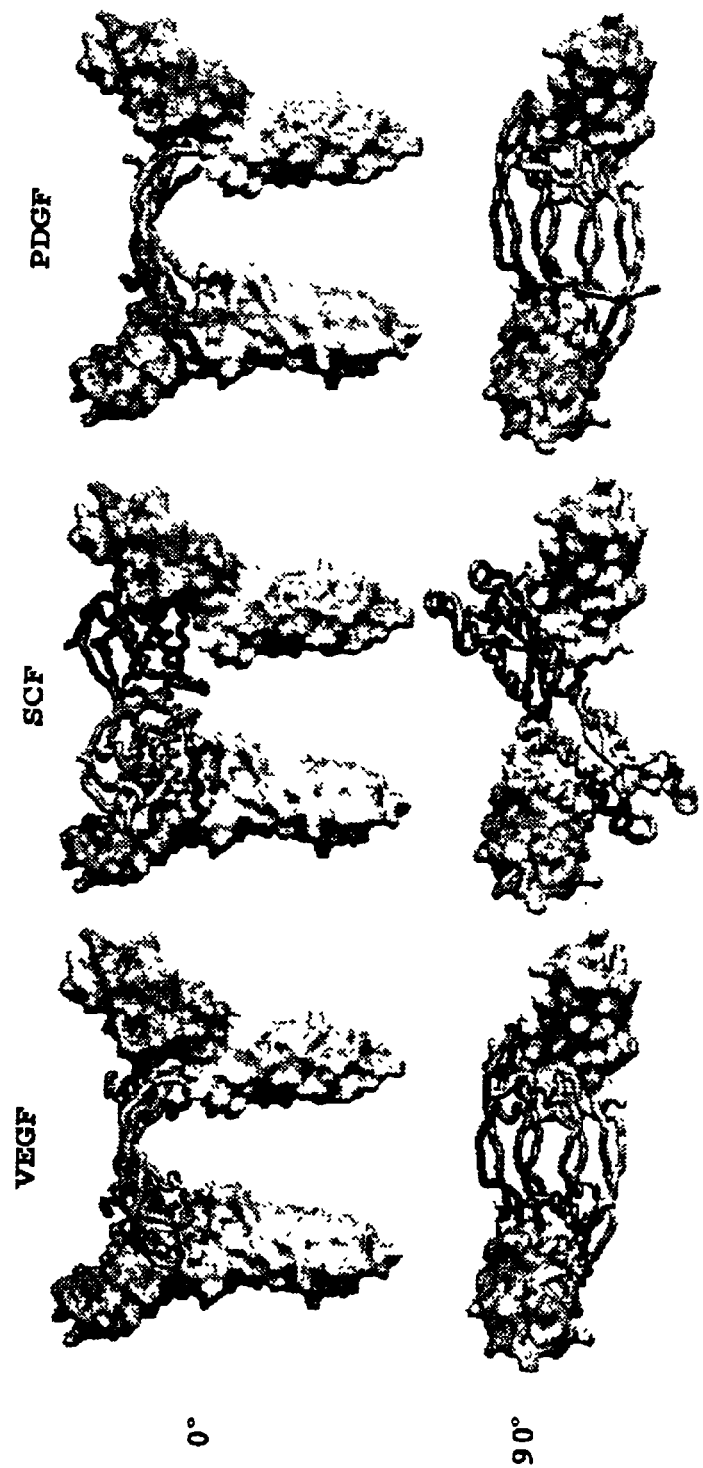
FIGS. 6A–6C. Ligand (worm structures)-receptor models.
Figure 10:
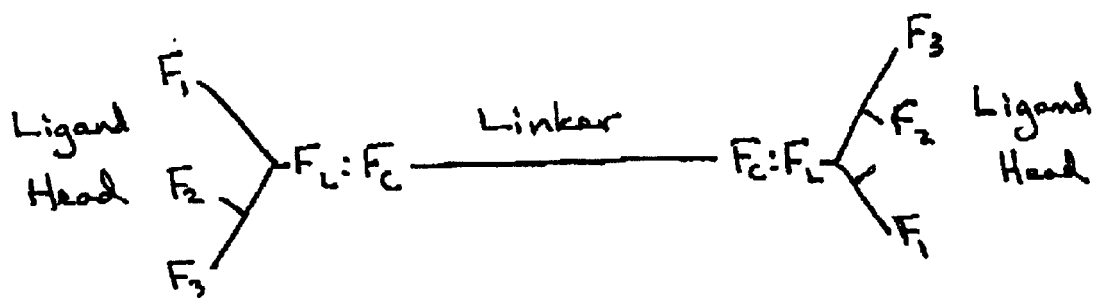
FIGS. 10A–10B Design for a double-headed SCF ligand analog. (10A) General model (10B) Embodiment of the ligand head as an oligopeptide. The compound is the conjugation of a linker molecule with two ligand-head molecules. Each ligand head is composed of up to three functional moieties, $F_1$, $F_2$ and $F_3$, which serve to mimic receptor-binding sites on the surface of SCF. Each ligand head also contains a conjugation moiety, $F_L$, endowed with chemical reactivity for conjugation with a reactive group at the end of the linker molecule. The capping moiety, $F_c$, at each end of the linker molecule is endowed with chemical reactivity for conjugation with the conjugation moiety from the ligand head. Double-headed molecules of this structure can have the property of binding to the SCF receptor, Kit, in such a way as to dimerize the receptor molecules and thereby lead to Kit activation in a manner analogous to the natural activity of SCF.

In an embodiment the design of the compound of step (b) is determined by shape complementarity or by estimated interaction energy. In another embodiment the designed compound fits an SCF receptor binding site on SCF receptor as shown in FIG. 6. In a further embodiment the designed compound fits an SCF receptor binding site on SCF receptor as shown in FIG. 7A or 7B. In an embodiment the designed compound has an alteration in at least one atom of the atomic coordinates of the crystal structure set forth in FIG. 8. In yet another embodiment the designed compound is a double-headed SCF ligand analog having the structure set forth in FIG. 10A. In a still further embodiment each ligand head of the double-headed SCP ligand analog is an oligopeptide having the structure set forth in FIG. 10B. The designed compound comprises two conjugated ligand having a linker between the two ligands.

In an embodiment, the oligopeptide comprises a sequence, wherein functional moiety $F_1$ corresponds to a segment of amino acid residues from within N-terminal residues 1–10 of SCF, functional moiety $F_2$ corresponds to a segment of amino acid residues from within residues 79–95 of SCF (SEQ ID NO:1), and functional moiety $F_3$ corresponds to a segment of amino acid residues located within three amino acid residues of amino acid residue 127, wherein $F_1$, $F_2$, and $F_3$ are connected by connecting peptide segments $X_n$, $X_m$, and $X_p$, respectively, wherein n=0–5, m=0–5 and p=3–8 amino acid residues, respectively, and the conjugation moiety $F_L$ is a cysteine residue.

A functional moiety is defined as en entity that has a particular binding property, i.e. it mimics receptor-binding sites on the surface of SCF, i.e. the ligand portion of SCF.

The amino acid residues located within 3 amino acid residues of amino acid residue 127 (SEQ ID NO:1) may be located within 3 residues in either direction of residue 127. In further embodiments the amino acid residues may be from 4 to 10 amino acid residues in either direction of amino acid residue 127.

In another embodiment of the above-described method the functional moieties $F_1$, $F_2$, and $F_3$ on the ligand heads have been selected by bacterial phage display for optimal receptor binding. In an embodiment the functional moieties and connecting peptide segments of an active oligopeptide ligand head are replaced by chemical mimetics. In another embodiment an appropriate chemical scaffold of connecting segments has been designed to comprise (present) functional moieties $F_1$, $F_2$ and $F_3$ which have been selected by combinatorial chemistry for optimal receptor binding from a library of chemical moieties complementary to receptor-binding sites on the surface of SCF. In an embodiment the linker comprises an organic polymer having two ends capped at each end by a reactive capping moiety, $F_c$, which react covalently with the conjugation moiety, $F_L$, on the ligand head. In an embodiment the organic polymer is polyethyleneglycol (PEG) comprising the structure $H[OCH_2CH_2]_nOH$, wherein n is 10–20. In an embodiment the capping moiety, $F_c$, is a thiol-reactive group such as N-ethyl maleimide. In an embodiment the conjugating moiety, $F_L$, is a thiol containing group such as cysteine.

This invention provides a compound designed by the method of claim 32.

A composition comprising the compound designed by the above described method and a pharmaceutically acceptable carrier. In an embodiment the compound comprises an isolated SCF analog, whose alteration site is a receptor-binding site on the surface of the altered SCF molecule. In another embodiment the composition comprises a double-headed receptor SCF ligand analog having the structure set forth in FIG. 10A. In an embodiment each ligand head of the double-headed SCF ligand analog is an oligopeptide having the structure set forth in FIG. 10B.

In another embodiment the oligopeptide comprises a sequence, wherein functional moiety $F_1$ corresponds to a segment of amino acid residues from within N-terminal residues 1–10 of SCF (SEQ ID NO:1), functional moiety $F_2$ corresponds to a segment of amino acid residues from within residues 79–95 of SCF, and functional moiety $F_3$ corresponds to a segment of amino acid residues located within three amino acid residues of amino acid residue 127, wherein $F_1$, $F_2$, and $F_3$ are connected by connecting peptide segements $X_n$, $X_m$, and $X_p$, respectively, wherein n=0–5, m=0–5 and p=3–8 amino acid residues, respectively, and the conjugation moiety $F_L$ is a cysteine residue. In a further embodiment the functional moieties $F_1$, $F_2$, and $F_3$ on the ligand heads have been selected by bacterial phage display for optimal receptor binding. In an embodiment the functional moieties and connecting peptide segments of an active oligopeptide ligand head are replaced by chemical mimetics. In another embodiment an appropriate chemical scaffold of connecting segments has been designed to comprise (present) functional moieties $F_1$, $F_2$, and $F_3$, which have been selected by combinatorial chemistry for optimal receptor binding from a library of chemical moieties complementary to receptor-binding sites on the surface of SCF. In another embodiment the linker comprises an organic polymer having two ends capped at each end by a reactive capping moiety, $F_c$, which react covalently with the conjugation moiety, $F_L$, on the ligand head. In a further embodiment the organic polymer is polyethyleneglycol (PEG) comprising the structure $H[OCH_2CH_2]_nOH$, wherein n is 10–20. In another embodiment the capping moiety, $F_c$, is a thiol-reactive group such as N-ethyl maleimide. In an embodiment the conjugating moiety, $F_L$, is a thiol containing group such as cysteine.

This invention provides a method of treating a subject comprising administration of a compound designed by the above described method. In an embodiment the subject has a blood disorder. In a further embodiment the blood disorder is anemia or immunodeficiency. In an embodiment the compound is administered orally or any other routes. In an embodiment the compound is an isolated SCF analog. In another embodiment the compound comprises an isolated SCF analog, whose alteration site is a receptor binding site on the surface of the altered SCF molecule. In another embodiment of the method the composition comprises a double-headed receptor SCF ligand analog having the structure set forth in FIG. 10A. In an embodiment each ligand head of the double-headed SCF ligand analog is an oligopeptide having the structure set forth in FIG. 10B. In another embodiment the ooligopeptide comprises a sequence, wherein functional moiety $F_1$ corresponds to a segment of amino acid residues from within N-terminal residues 1–10 of SCF, functional moiety $F_2$ corresponds to a segment of amino acid residues from within residues 79–95 of SCF, and functional moiety $F_3$ corresponds to a segment of amino acid residues located within three amino acids residues of amino acid residue 127, wherein $F_1$, $F_2$, and $F_3$ are connected by connecting peptide segements $X_n$, $X_m$, and $X_p$, respectively, wherein n=0–5, m=0–5 and p=3–8 amino acid residues, respectively, and the conjugation moiety $F_L$ is a cysteine residue. In a further embodiment the functional moieties $F_1$, $F_2$, and $F_3$ on the ligand heads have been selected by bacterial phage display for optimal receptor binding. In an embodiment the functional moieties and connecting peptide segments of an active oligopeptide ligand head are replaced by chemical mimetics. In another embodiment an appropriate chemical scaffold of connecting segments has been designed to comprise (present) functional moieties $F_1$, $F_2$, and $F_3$, which have been selected by combinatorial chemistry for optimal receptor binding from a library of chemical moieties complementary to receptor-binding sites on the surface of SCF. In another embodiment the linker comprises an organic polymer having two ends capped at each end by a reactive capping moiety, $F_c$, which react covalently with the conjugation moiety, $F_L$, on the ligand head. In a further embodiment the organic polymer is polyethyleneglycol (PEG) comprising the structure $H[OCH_2CH_2]_nOH$, wherein n is 10–20. In another embodiment the capping moiety, $F_c$, is a thiol-reactive group such as N-ethyl maleimide. In an embodiment the conjugating moiety, $F_L$, is a thiol containing group such as cysteine.

This invention provides a method of stimulating the production of hematopoietic cells in a subject comprising administering an isolated stem cell factor (SCF) analog. In an embodiment isolated stem cell factor (SCF) analog is prepared by the method of claim 1 or designed by the above described method. In another embodiment the administration is oral or any other route. In an embodiment the isolated SCF analog has an alteration in at least one atom of the atomic coordinates of the crystal structure as set forth in FIG. 8. In another embodiment the isolated SCF analog comprises amino acid residues of native or recombinant SCF1-165 or amino acid residues of a recombinant selenomethionyl SCF1-141. In an embodiment of this method the isolated SCF analog, comprises an isolated altered SCF molecule, whose alteration site is a receptor binding site on the surface of the altered SCF molecule. In another embodiment of the above-described the compound comprises an isolated SCF analog, whose alteration site is a receptor-binding site on the surface of the altered SCF molecule. In another embodiment of said method the composition comprises a double-headed receptor SCF ligand analog having the structure set forth in FIG. 10A. In an embodiment each ligand head of the double-headed SCF ligand analog is an oligopeptide having the structure set forth in FIG. 10B. In another embodiment the ooligopeptide comprises a sequence, wherein functional moiety $F_1$ corresponds to a segment of amino acid residues from within N-terminal residues 1–10 of SCF, functional moiety $F_2$ corresponds to a segment of amino acid residues from within residues 79–95 of SCF, and functional moiety $F_3$ corresponds to a segment of amino acid residues located within three amino acid residues of amino acid residue 127, wherein $F_1$, $F_2$, and $F_3$ are connected by connecting peptide segements $X_n$, $X_m$, and $X_p$, respectively, wherein n=0–5, m=0–5 and p=3–8 amino acid residues, respectively, and the conjugation moiety $F_L$ is a cysteine residue. In a further embodiment the functional moieties $F_1$, $F_2$, and $F_3$ on the ligand heads have been selected by bacterial phage display for optimal receptor binding. In an embodiment the functional moieties and connecting peptide segments of an active oligopeptide ligand head are replaced by chemical mimetics. In another embodiment an appropriate chemical scaffold of connecting segments has been designed to comprise (present) functional moieties $F_1$, $F_2$, and $F_3$ which have been selected by combinatorial chemistry for optimal receptor binding from a library of chemical moieties complementary to receptor-binding sites on the surf ace of SCP. In another embodiment the linker comprises an organic polymer having two ends capped at each end by a reactive capping moiety, $F_c$, which react covalently with the conjugation moiety, $F_L$, on the ligand head. In a further embodiment the organic polymer is polyethyleneglycol (PEG) comprising the structure $H[OCH_2CH_2]_nOH$, wherein n is 10–20. In another embodiment the capping moiety, $F_c$, is a thiol-reactive group such as N-ethyl maleimide. In an embodiment the conjugating moiety, $F_L$, is a thiol containing group such as cysteine.

This invention provides an isolated stem cell factor (SCF) molecule, which is an altered SCF, comprising any portion of amino acids 1–165 of a human SCF polypeptide (SEQ ID NO:7), optionally comprising an N-terminal methionine before amino acid residue 1, wherein the polypeptide has an amino acid sequence portion of SCF capable of binding to the SCF receptor. In an embodiment of the altered isolated stem cell factor molecule an alteration is selected from the group consisting of deletion, insertion and substitution of at least one amino acid residue from the naturally occurring amino acid sequence of SCF.

In a further embodiment an alteration is a truncated SCF comprising amino acids 1–141 of a human SCF polypeptide (SEQ ID NO:1), optionally comprising an N-terminal methionine before amino acid residue 1, E. In another embodiment the three-dimensional structure is altered from the atomic coordinates are set forth in FIG. 8. In yet another embodiment the electron density distribution map is altered from the atomic coordinates are set forth in FIGS. 1A, 1B, or 1C. In a still further embodiment the substitution of at least one amino acid residue is selected from the group consisting of SCF(Y26C) (SEQ ID NO:11) disulfide-linked dimer, SCF(D25C)(SEQ ID NO:12), SCF(K62C)(SEQ ID NO:13), SCF(K78N, (SEQ ID NO:14); N81K (SEQ ID NO:15)), SCF(R117A, (SEQ ID NO:16); I118A (SEQ ID NO:17)), SCF(E92, (SEQ ID NO:18); S95A (SEQ ID NO:19)), and SCF(D124A, (SEQ ID NO:21); K127D (SEQ ID NO:22)). In another embodiment the overall three-dimensional conformation of the stem cell factor molecule has an altered three-dimensional structure of the αC-β2 loop.

This invention provides a pharmaceutical composition comprising the above described altered isolated SCF molecule and a pharmaceutically acceptable carrier. In an embodiment the altered SCF molecule molecule is a hybrid molecule of the altered stem cell factor molecule and a second protein or fragment thereof. As used herein, an SCF hybrid molecule is defined as a molecule wherein analog SCF is combined with with part or all of another protein such as another cytokine or another protein, which for example, effects signal transduction via entry through the cell through a SCF-SCF receptor transport mechanism. In an embodiment the alteration of the αC-β2 loop is a change in length of the amino acid sequence of the αC-β2 loop by a deletion or an insertion of at least one amino acid residue or a change in at least one amino acid residue from the naturally occurring amino acid residue(s) of the αC-β2 loop. In another embodiment the change in said at least one amino acid residue from the naturally occurring amino acid residue (s) is selected from the group consisting of SCF(Y26C) (SEQ ID NO:11) disulfide-linked dimer, SCF(D25C)(SEQ ID NO:12), SCF(K62C) (SEQ ID NO:13), SCF(K78N, (SEQ ID NO:14); N81K (SEQ ID NO:15)), SCF(R117A, (SEQ ID ND:16); I118A (SEQ ID NO:17)), SCF(E92A, (SEQ ID NO:18); S95A (SEQ ID NO:19)), and SCF (D124A, (SEQ ID NO:21); K127D (SEQ ID NO:22)).

Generally, for design of drugs as described in the above-described methods, certain changes are known to have certain structural effects. For example, deleting one cysteine could result in the unfolding of a molecule which is, in its unaltered state, is normally folded via a disulfide bridge. There are other known methods for in adding deleting or substituting amino acids in order to change the function of a protein.

The atomic coordinates may be determined in the above-described method by multiwave anomalous diffraction (MAD) measurements, but is not limited htereto, since any means determined suitable by one of skill in the art may also be used.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods

SCF Expression, Purification and Analyses

Human SCF$^{1-141}$ (SEQ ID NO:1) was expressed recombinantly in *E. coli* as described previously (Langley et al., 1994). For expression of SeMet SCF$^{1-141}$, the expression vector was transfected into the methionine auxotrophic *E. coli* strain FM5. Fermentation was carried out at 30° C. in 8 liters of minimal medium consisting of ammonium sulfate (10 g/liter), glucose (5 g/liter), methionine (0.125 g/liter), phosphate salts, magnesium, citric acid, trace metals, and vitamins. When an OD$_{600}$ of 3–5 was reached, a feed medium was added that consisted of the following components in a total volume of 1 liter: 100 g of ammonium sulfate, 450 g of glucose, 2 g of methionine, magnesium, trace metals, and vitamins. At an OD$_{600}$ of 12.4, induction medium (one liter containing 100 g of ammonium sulfate, 300 g of glucose, and 1 g of selenomethionine) was added and fermentation proceeded at 30° C. Five hours later (at an OD$_{600}$ of approximately 16), the temperature was raised to 42° C. to induce SCF expression and additional selenomethionine (1 g) was added. Cells were harvested 4 hours after the temperature shift (OD$_{600}$ of approximately 16). SeMet SCF$^{1-141}$ expression was estimated as 0.5 g/liter. Both SCF$^{1-141}$ and SeMetSCF$^{1-141}$ were purified with minor modifications to previously described procedures (Langley et al., 1992, 1994). Both retain the initiating methionine (or SeMet) residue [position (−1)] (Langley et al., 1994). N-terminal amino acid sequencing was performed as described (Lu et al., 1991). About 90% SeMet was present in SeMetSCF$^{1-141}$ at each of the Met positions, based on amino acid analysis and N-terminal sequencing results (i.e. lack of recovery of Met residues for SeMetSCF$^{1-141}$ in comparison with SCF$^{1-141}$; data not shown).

Crystallization

Crystals were obtained by the use of hanging drop vapor diffusion method under aerobic conditions. The initial crystals were grown by mixing 1 μl of protein solution [44 mg/ml for SCF$^{1-141}$ or 38 mg/ml for SeMet SCF$^{1-141}$) in 10 mM sodium phosphate pH 6.5, 80 mM NaCl] with 1 μl crystallization reservoir solution. The crystallization reservoir solution included 25% (w/w) PEG 400, 240 mM CaCl$_3$, 100 mM HEPES pH 7.4 for SCF$^{1-141}$, and 22% PEG400, 220 mM CaCl$_2$, 100 mM HEPES pH 7.2 and 5–10 mM dithiothreitol (DTT) for SeMetSCF$^{1-141}$. Crystallization trays were incubated at 20° C. and crystals reached full size in approximately 3 days with typical dimensions of 0.5× 0.2×0.2 mm. Microseeding and lower concentrations of DTT solution (2 mM) were needed to reproduce SeMetSCF$^{1-141}$ crystals subsequently. An extant SeMetSCF$^{1-141}$ crystal was washed with its reservoir solution and then crushed to produce microseeds, which were stored in 50 μl of a stabilizing solution of 32% (w/w) PEG400, 260 mM CaCl$_2$, 100 mM HEPES (pH 7.4) at room temperature. For microseeding experiments, the seed stock was diluted by 10–10,000-fold with crystallization reservoir solution. A 1 μl aliquot of this prepared precipitant was mixed with 1 μl of the protein solution to make the droplet. The crystal for MAD phasing was grown from a crystallization reservoir solution containing 2 mM DTT concentration.

Diffraction Measurements

X-ray diffraction data from SCF$^{1-141}$ crystals were recorded on two Hamlin-Xuong area detectors at 293K at a home source. The data were integrated using the UCSD software package and scaled using AGROVATA and ROTAVATA as implemented in CCP4 suite (CCP4, 1994). The MAD experiments for SeMetSCF$^{1-141}$ were conducted at the X4A synchrotron beam line of Brookhaven National Laboratory using Fuji image plates. A single crystal was frozen at 110K using paratone-N (Exxon) as a cryoprotectant. The MAD data were collected at four wavelengths (before the edge, at the SeK edge, at the peak and after the peak) in oscillations of 1.3–1.5° without overlap. The SaMetSCF$^{1-141}$ crystal was oriented such that b-axis was parallel to the oscillation axis and a mirror geometry was used during data collection. The MAD data were processed using DENZO and Scalepack (Otwinowski, 1993; Gewirth, 1995)(Table I).

TABLE I

MAD data collection and phasing statistics.

Data collection (25–2.0Å)$^a$

| Wavelength (Å) | Unique reflections | Completeness (%) | Signal (I/σ) | R$_{sym}$ (%) |
|---|---|---|---|---|
| λ1 = 0.9919 (pre-edge) | 65,810 | 95.1 | 18.4 | 6.7 |
| λ2 = 0.9793 (inflection) | 65,759 | 95.0 | 16.7 | 5.8 |
| λ3 = 0.9791 (peak) | 65,665 | 94.9 | 15.2 | 6.7 |
| λ4 = 0.9686 (remote) | 65,689 | 94.9 | 16.0 | 5.6 |

Anomalous diffraction ratios (20–2.6Å)$^b$

| | λ1 | λ2 | λ3 | λ4 | f' (e) | f" (e) |
|---|---|---|---|---|---|---|
| λ1 | 0.035 (0.030) | 0.051 | 0.042 | 0.035 | −4.0 | −0.5 |
| λ2 | | 0.052 (0.029) | 0.033 | 0.051 | −10.3 | 3.8 |
| λ3 | | | 0.070 (0.031) | 0.041 | −8.1 | 5.6 |
| λ4 | | | | 0.055 (0.030) | −3.9 | 3.8 |

MAD phasing (25–2.6Å)$^c$

R(°|F$_T$|) = 0.044  R(°|F$_A$|) = 0.39  <Δ(ΔΦ)> = 41.6°  <σ(ΔΦ)> = 18.7°

$^a$Unique reflections are determined by point group 222 (not mmm) to distinguish Bijvoet-related reflections. R$_{sym}$ = 100 × Σ$_{hkl}$ Σ$_i$ |I$_i$ − <I>|</ Σ$_{hkl}$Σ$_i$I$_i$, where I$_i$ is the ith measurement of reflection hkl and <I> is the weighted mean of all measurements of I.
$^b$Anomalous diffraction ratios = <Δ|F|$^2$>"/<|F|$^2$>", where Δ|F| is the absolute value of the Bijvoet (diagonal elements) or dispersive difference (off-diagonal elements), respectively. Values in parentheses are for centric data.
$^c$R = Σ$_{hkl}$ Σ$_i$ | | F$_i$ | − < F > | / Σ | F |. °F$_T$ is the structure factor due to normal scattering from all the atoms. °F$_A$ is the structure factor due to normal scattering from the anomalous scatterers only, and ΔΦ is the phase difference between °F$_T$ and °F$_A$. Δ(ΔΦ) is the difference between two independent determinations of ΔΦ.

Molecular Replacement Attempts

Structure determination by the molecular replacement method was attempted for the home source data set. The MERLOT (Fitzgerald, 1988) and AmoRe (CCP4, 1994) programs were used with various four-helix bundle structures as search models, and a good rotation solution was obtained. The rotation solution agreed well with the orientation of helical bundles (approximately along the b-axis of unit cell) that was deduced from native Patterson maps. Dissimilarities among the helical cytokines and the multiplicity of subunits (four) hampered detection of any significant translational function peaks.

Phase Evaluation

The processed MAD data were passed through the MAD-SYS programs (Hendrickson, 1985). Algebraic and probabilistic MAD phasing procedures (Hendrickson, 1965; Pahler et al., 1990) were applied for phase determination (Table II). Selenium sites were located by HASSP program (CCP4, 1994) in $F_A$ Patterson and difference Fourier maps and refined by MADSYS programs. The choice of enantiomer was determined by comparison of the electron density maps computed from the two enantiomorphic selenium structures to maximum Bragg spacings of 2.6 Å. The phases were improved by 4-fold non-crystallographic symmetry (NCS) averaging. The rotation-translation matrices of the NCS axes were determined by TOSS (Hendrickson, 1979) from the selenium sites and subsequently refined by LSQRHO (W. A. Hendrickson, unpublished) and RAVE (Kleywegt and Jones, 1994), and the averaging procedure by DM (CCP4, 1994).

Model Building and Refinement

The initial model of SeMetSCF$^{1-141}$ was built into the averaged map at 2.3 Å by using program O (Jones et al., 1991). The model includes 98 core residues for each of the four molecules in an asymmetric unit. The remote wavelength after the SeK peak was used for the refinement with the Bijvoet difference applied to Se scattering factors. The R-value for this model, before any refinement, was 42.1% in the resolution range of 10.0–2.3 Å. NCS restraints were applied during the initial rounds of refinements. After several iterations of least square and simulated annealing refinement with X-PLOR (Brunger et al., 1987) and manual rebuilding against SIGMAA (Read, 1986) and 2|F$_o$|-|F$_c$| maps, the crystallographic R-value is 19.9% for the current model (Table III). The sites of Ca$^{2+}$ ions, a component of the crystallization medium, were located from a Bijvoet difference Patterson map at the remote wavelength before the SeK edge. The SCF$^{1-141}$ model was obtained by subjecting the refined SeMetSCF$^{1-141}$ model to refinement against the area-detector data set from the SCF$^{1-141}$ crystal using the XPLOR program (Brünger et al., 1987). The atomic coordinates have been deposited in the Brookhaven Protein Data Bank with accession code 1scf.

TABLE II

Lattice and Refinement Statistics

|  | SeMeSCF$^{1-141}$(λ4) | Native |
|---|---|---|
| Lattice | | |
| Space group | P2$_1$2$_1$2$_1$ | P2$_1$2$_2$2$_1$ |
| Cell constants (a, b, c) (Å) | 71.8, 82.6, 88.2 | 73.0, 84.7, 88.8 |
| Z$_a$$^a$ | 4 | 4 |
| Refinement$^b$ | | |
| Resolution range (Å) | 20.0–2.2 | 8.0–3.3 |
| Completeness (%) | 96.6 | 98.6 |
| Unique reflections$^c$ | 49851 | 7990 |
| R-value$^d$ (|F| > 2σ) (%) | 19.9 | 20.8 |
| R$_{free}$$^b$ (%) | 24.2 | 27.3 |
| R$_{sym}$$^f$ (%) | 5.6 | 15.2 |
| Model parameter | | |
| Total non-H atoms | 3804 | 3502 |
| Total residues | 448 | 447 |
| Total water molecules | 264 | 0 |
| Total metal ions | 3 | 0 |
| rms bond length/angle | 0.016/2.5° | 0.017/3.0° |
| Average B-factor (Å$^2$) | 32.1 | 18.7 |
| main-chain rms B (bond, angle) (Å$^2$) | 1.2/1.6 | 1.9/2.2 |
| side-chain rms B (bond, angle) (Å$^2$) | 2.1/2.4 | 3.0/3.3 |

$^a$Z$_a$ = number of molecules in the asymmetric unit.
$^b$The reflection data higher that the resolution range were not included in the refinement due to poor R$_{sym}$ in these resolution shells.
$^c$Unique reflections are determined by point group 222 for the SeMetSCF$^{1-141}$ dataset to distinguish Bijvoet-related reflections and by point group mmm for native dataset.
$^d$R-value = $\Sigma_{hkl}||F_m| - |F_c||/\Sigma_{hkl}|F_o|$.
$^e$A subset of the data (6%) was excluded from the refinement and used for the free R-value calculation.
$^f$R$_{sym}$ for SeMetSCF$^{1-141}$ data set was calculated in the resolution range of 25–2.2Å and for the SCF$^{1-141}$ data set in the resolution range of 13–3.3 Å.

Structure Analysis

Solvent accessibilities were defined as compared with the corresponding Gly-X-Gly peptide (Shrake and Rupley, 1973) as calculated by XPLOR (Brunger et al., 1987). Structural superimpositions were performed based on a-carbon atoms alone. The coordinates were taken from the Brookhaven Data Bank with entry codes: M-CSF, 1hmc (Pandit et al., 1992); IL-4, 1rcb (Wlodawer et al., 1992); GM-CSF, 1gmf (Diederichs et al., 1991) IL-2, 3ink (McKay, 1992); IL-5, 1hul (Milburn et al., 1993). Initial segments of equivalence between two structures were defined according to equivalent secondary structure elements. These structures were then superimposed using program TOSS (Hendrickson, 1979) and the number of equivalent atoms were extended using Lsq_imp command in program O (Jones et al., 1991). A cutoff distance of 3.0 Å and at least three residues in a consecutive fragment were used as the criteria of defining equivalent atom sets. Different initial equivalent segments did give different results in the structural alignment, as Rozwarski et al observed in their study (Rozwarski et al., 1994). In this study, several initial sets of equivalent segments for each alignment were tried and the one that generated in the greatest number of equivalent atoms after the Lsq_imp extension was retained.

Results and Discussion

Structure Determination

Both native and selenomethionyl (SeMet) human SCF$^{1-141}$ were expressed as recombinant proteins in *E. coli* (Langley et al., 1994). Crystals grew in space group. P2$_1$2$_1$2$_1$ with four SCF subunits and 39% solvent in the asymmetric unit. The attempts to solve the crystal structure of SCF$^{1-141}$ by molecular replacement from other cytokine models gave good rotation solutions, but no significant translation function peaks. Experimental phases for SeMetSCF$^{1-141}$ were then evaluated in a multiwavelength anomalous diffraction (MAD) experiment. Four-wavelength data were measured from, a single, frozen SeMetSCF$^{1-141}$ crystal and analyzed with MADSYS (Hendrickson, 1985). Twelve selenium sites were found in four congruent sets that proved to be associated with the respective SCF subunits in the crystal. A MAD-phased electron-density map was calculated at 2.3 Å resolution (FIG. 1A) and improved by molecular averaging (FIG. 1B) and refinement (FIG. 1C).

An atomic model was fitted to the experimental maps and refined at 2.2 Å resolution to an R-value of 0.199 (|F|>20) with stereochemical ideality typified by the r.m.s. deviation from bond ideality of 0.016 Å. There are no residues in energetically disfavored regions of the Ramachandran plot.

This model for SeMetSCF$^{1-141}$ has 3804 non-hydrogen atoms from 448 amino acid residues, 264 water molecules, three Ca$^+$ ions and one polyethylene glycol (PEG) moiety. All four polypeptide chains (designated A, B, C, and D) are sufficiently disordered before residue 11 to preclude modeling of this portion, and none of them is fully ordered through to the end. Specifically, A92–103, B130–136, B139–141, C92–103, C127–141, and D91–103 and D128–141 are all disordered. This disorder is such that, of the eight disulfide bridges, only two are seen. To test whether the reducing agent used to crystallize SeMetSCF$^{1-141}$ (see Materials and Methods) might have broken these bonds and caused the disorder, the native SCF$^{1-141}$ structure which was crystallized without reducing agent was also refined. The two crystals are nearly isomorphous (differences are due to temperature at data collection), and the two structures show the same pattern of order-disorder.

Structure of SCF

The four independent SCF subunits in the crystal are similar but distinctive, and identification of the AB and CD pairs as the molecular dimers is unmistakable. None of the SCF monomer copies is complete, but each flexible portion except for the N-terminus is stabilized by lattice contacts to another monomer. Thus, through the combination of chains A and B there are images for all but residues 1–10, and the position of Cys89 to which Cys 4 must bridge, determines the approximate course of this disordered segment. The overall structure of this composite SCF dimer is shown in FIG. 2A and the C$_\alpha$ backbone for the actual AB dimer is drawn in stereo in FIG. 2B. Topologically, SCF structure is similar to other short-chain helical cytokines (Rozwarski et al., 1994) with a core of four helices (αA, αB, αC and αD) and two beta strands, β1 between αA and αB and β2 between αC and αD. Apart from the tight β2-αD connection, however, the segments outside these core elements are unique in conformation if not in length. In particular, there is an additional one-turn helix, αB', between β1 and αB, there is an exceptional hairpin loop between αB and αC at the dimer interface, and there is another extra one-turn helix, αD', in the C-terminal extension. The bounds of secondary-structure elements are given in FIG. 3.

Figure 2:
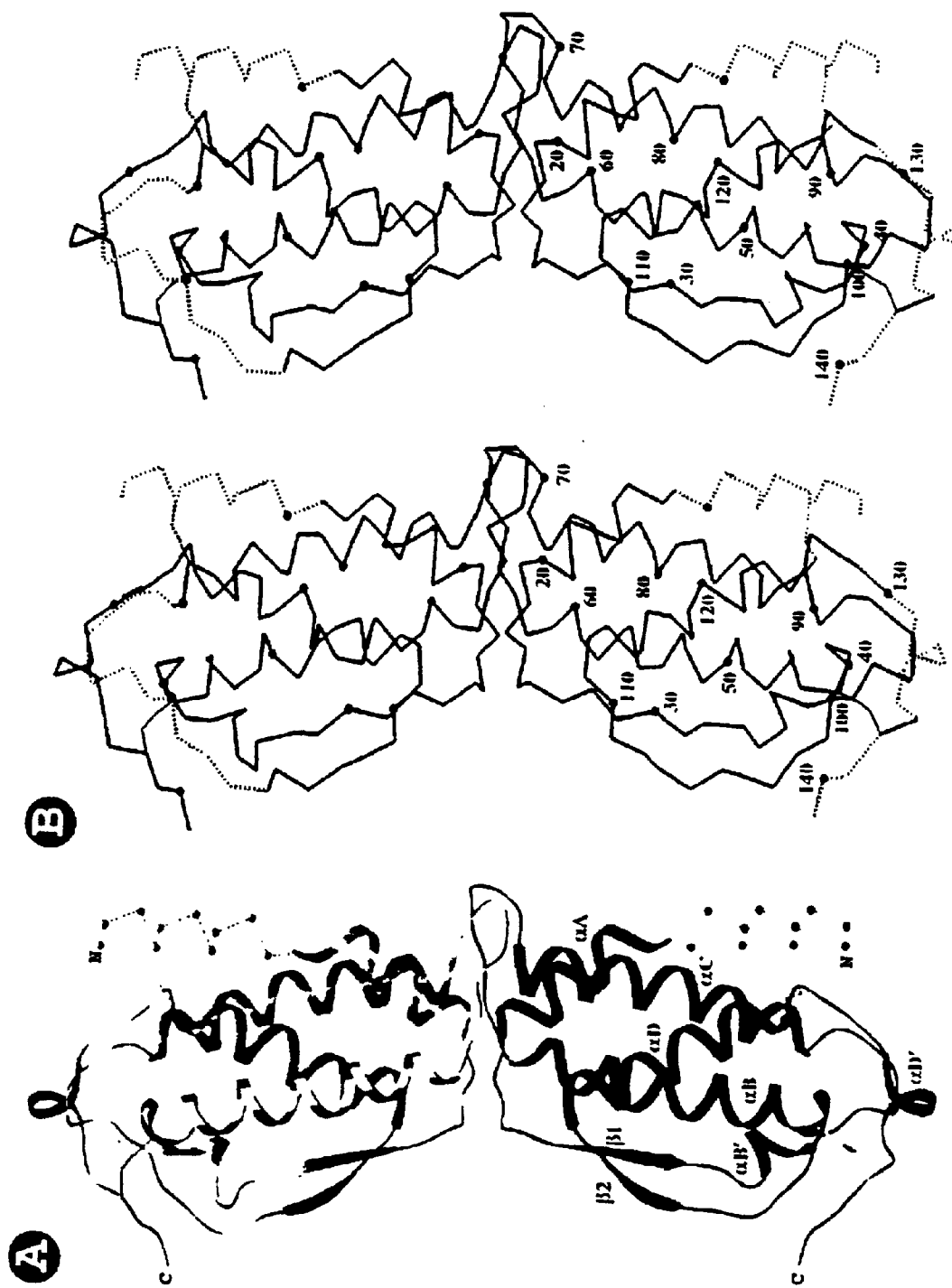
FIGS. 2A–2B. Overall structure of an SCF dimer.

The core SCF diner has its subunits arranged in a head-to-head manner with the opposed four-helix bundle axes nearly coincident (FIG. 2). This gives the molecule an elongated shape, ~85 Å×30 Å×20 Å. Approximately 855 Å$^3$ of surface area is buried from each protomer into the dimer interface. The interface is dominated by contacts from the C-terminal end of αA and the αA-β1 connection of one monomer to the αB-αC loop of the other monomer (FIG. 2), and the reciprocal pair is related by an approximate dyad axis of symmetry. The actual symmetry operators have rotational and translational components of 176.3° and 0.33°, respectively, for the AB dimer and 177.4° and 0.04° Å for the CD dimer. The two dimers thereby deviate significantly and similarly (with A matched to C and B matched to D) from true 2-fold symmetry. Nevertheless, since interatomic contacts at the interface are symmetric, it is presumed that theses deviations reflect flexibility rather than inherent asymmetry.

Then the r.m.s. deviation for the C$_{\alpha}$ positions in common between the two dimers is 0.80 Å (208 C$_\alpha$ atoms) is comparable to that of pairwise comparisons among the four independent molecules (from 0.57 Å to 0.94 Å for 103 C$_\alpha$ atoms). If D alone is superimposed onto B, a rotation of 2.1° brings A and C into optimal superposition. In the contrary match-up, with D onto A, a rotation of 6.7° is needed to superimpose B and C.

The crystal structure is compatible with solution biochemistry. Consistent with the relative rates of in vitro oxidation of methionyl residues (Hsu et al. 1996), Met36 and Met48 are buried in the hydrophobic core whereas Met27 is solvent accessible. Furthermore, as predicted on the basis of fluorescence spectroscopy studies (Arakawa et al., 1991), Trp41 is buried within the hydrophobic core.

Natural SCF and Chinese hamster ovary(CHO) cell-expressed recombinant SCF are heavily glycosylated by both N-linked and O-linked carbohydrates. All four potential N-linked sites are in the SCF$^{1-165}$ are in the SCF$^{1-141}$ portion that has been crystallized (Langley et al., 1992; Lu et al., 1992). Although the recombinant proteins expressed in bacteria are non-glycosylated, both human and rat SCF expressed in *E. coli* and then refolded in vitro have native structures, as judged by biophysical methods and in vitro biopotency assays (Arakawa et al., 1991; Langley et al., 1992). The crystal structure of the recombinant SCF in this study is compatible with, the glycosylation pattern found for SCF expressed from mammalian cells.

Thus, the potential site at Asn72, which is unglycosylated in both human and rat natural SCF expressed from mammaliam cells, is buried in the dimer interface, whereas the site at Asn120, which is fully glycosylated in both species, is accessible in the atomic model. Other sites (Asn65 in both human and rat, human Asn93 and rat Asn109) are glycosylated in some molecules but not others. These sites are also accessible in the atomic model. Asn93 is located in the highly flexible region between αC and β2, and its side chain is disordered.

Although natural SCF is a noncovalently associated dimer, recombinant human SCF produced in *E. coli* can fold alternatively in vitro into a covalently-linked dimer. These dimers have Cys4–Cys89' and Cys43–Cys138' intermolecular disulfide bonds (Lu et al., 1996). The disulfide-linked and natural non-covalently associated SCF dimers are similar with regard to biochemical and biophysical properties, biopotency and receptor-binding affinity. The disulfide-linked SCF is also biologically active with higher biopotency in supporting growth of hematopoietic cell line and stimulating hematopoietic cell colony formation but slightly lower binding affinity to c-Kit than the noncovalently associated dimer. It was proposed that the disulfide-linked dimer arises from a double-swap of αA and αD helices between the monomers (Lu et al., 1996). The crystal structure of SCF, however, suggests that a single-swap at the αB-αC loop near residue 68 is more likely.

Comparison with other Short-chain Helical Cytokines

Figure 3:
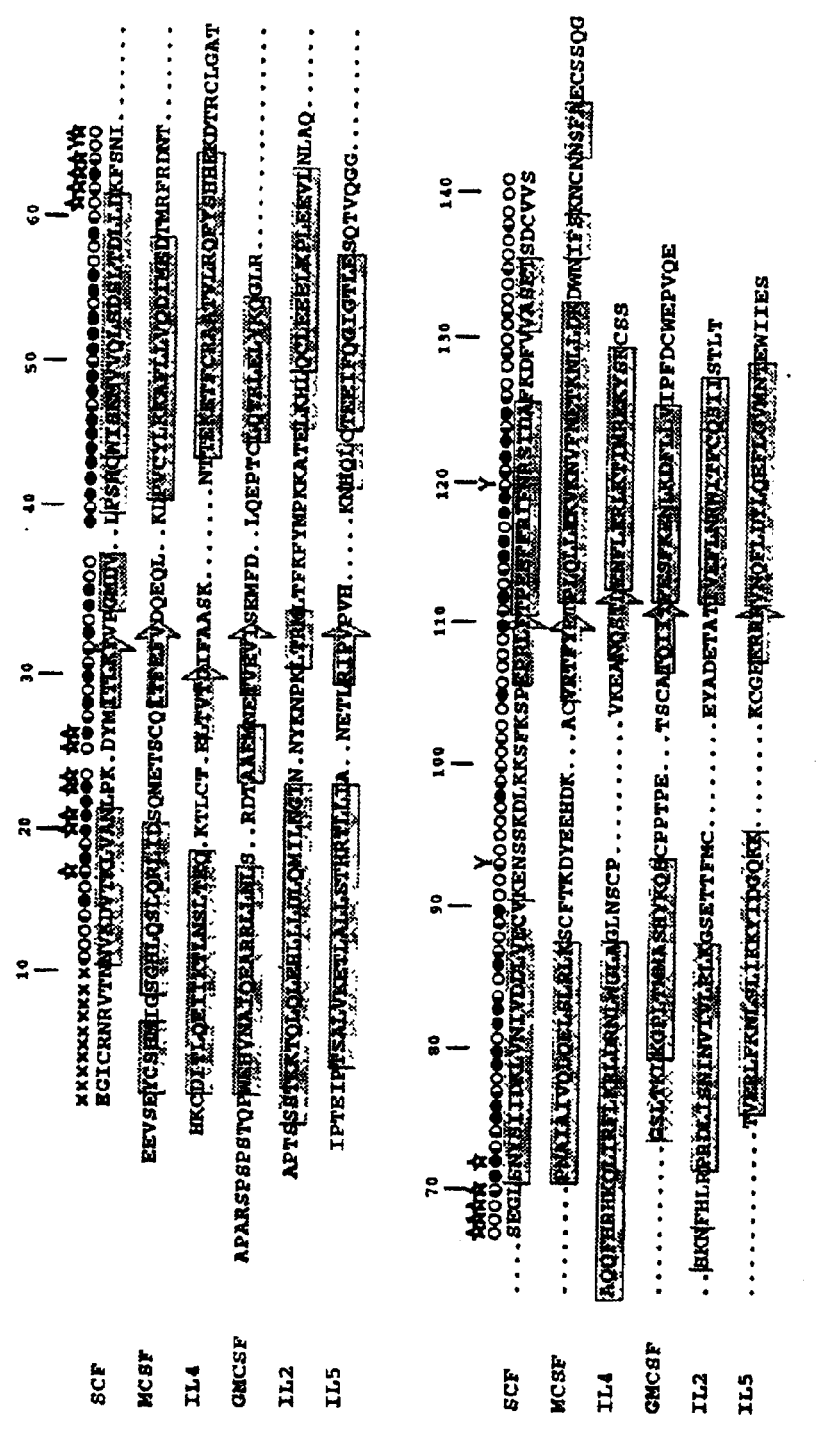

Although SCF has the characteristic features of short-chain helical cytokines, as among other members, both sequence and structure are highly divergent. If anything, SCF (SEQ ID NO:l) resembles the others less than they resemble one another (Table III). The comparison in this study of SCF with other short-chain helical cytokine structures [granulocyte-macrophage colony-stimulating factor (GM-CSF) Diederichs et al., 1991), M-CSF (Pandit et al., 1992), and IL-5 (Milburn et al., 1993)] shows greatest structural similarity with M-CSF (SEQ ID NO:2) or IL-4 (SEQ ID NO:3), but even here fewer than half of the residues can be superimposed (Table III). Sequence similarities are essentially random. A structure-based sequence alignment (FIG. 3) of SCF with other short-chain helical cytokines has pairwise identities ranging from 6.7% to 18.8% (Table III) and not even a single residue in SCF is conserved in all the others. Moreover, the best alignment presented in FIG. 3 is only valid for the specified criteria herein, and it differs somewhat from that given by Rozwarski et al. (Rozwarski et al., 1994). Indeed, because of variability in the core structures in this divergent superfamily, a self-consistent pairwise alignment of the family members has not been able to be achieved. Nevertheless, the core elements are remarkably similar in structure.

TABLE III

Structural and sequence comparisons of short-chain helical cytokines.

| | SCF | M-CSF | IL-4 | GM-CSF | IL-2 | IL-5 |
|---|---|---|---|---|---|---|
| SCF | | 14.1 | 12.7 | 12.5 | 18.8 | 6.7 |
| | | (13.0) | (12.3) | (23.5) | (16.4) | (21.1) |
| M-CSF | 64 | | 14.8 | 13.8 | 17.5 | 10.5 |
| | (1.755) | | (18.9) | (18.3) | (17.1) | (18.6) |
| Il-4 | 63 | 54 | | 26.6 | 14.5 | 18.9 |
| | (1.578) | (1.820) | | (25.0) | (22.2) | (18.9) |
| GM-CSF | 48 | 58 | 64 | | 9.8 | 20.4 |
| | (1.632) | (1.814) | (1.559) | | (26.0) | (14.7) |
| IL-2 | 48 | 57 | 69 | 61 | | 14.5 |
| | (1.700) | (1.581) | (1.330) | (1.482) | | (22.2) |
| IL-5 | 45 | 38 | 53 | 49 | 62 | |
| | (1.695) | (1.721) | (1.324) | (1.334) | (1.371) | |

Structural comparisons and sequence comparisons between the short-chain helical cytokines are given in the lower and upper triangles, respectively. Structural comparisons are given as the maximum number of equivalent α-carbon atoms between two short-chain helical cytokines, and the r.m.s. deviation (Å), (in parentheses). Sequence comparisons are given as the percentage of sequence identity from sequence alignment based on structural superimposition, and that based on the sequence alignment from BESTFIT program of the GCG package (in parentheses). The latter alignment is based only on maximizing the percentage of identity, similarities and length of the matching sequences, and the sequences submitted to the BESTFIT program were restricted within the region as defined in the PDB files, including the disordered residues. With the advantage of the relatively large number of independent data points (15 pairs), the correlation between sequence similarity and structural deviation was analyzed. Without any restriction of structural alignment, the correlation coefficient (C) between structural deviation and sequence identity is −0.21 and the student's t probability (P) is 0.44, suggesting little correlation between a specific sequence and the tertiary fold. With the restriction of structural alignment, however, C is −0.30 and P 0.28, indicating that the structure-based sequence identity and structural deviation are weakly connected (as also observed in another highly diverged protein family, hemoglobin; Aronson et al., 1994).

Core portions aside, SCF differs markedly from other short-chain helical cytokines, as indeed they differ from one another (FIG. 3; Rozwarski et al., 1994)). First, helix αA of SCF is unusually shortened at its N-terminus. Its disordered extension must deviate toward αC, as in M-CSF but not in the others, by virtue of the Cys4–Cys89' disulfide bridge in common with M-CSF. Secondly, the conformation of the αA-β1 connection is distinctive as required for the dimer interface, and the β1-αB connection uniquely has αB'. Again at the dimer interface, in the αB-αC loop extends out distinctively along the dyad axis. Thirdly, the unusually long αC-β2 loop of SCF is both highly flexible (only one ordered copy) and with a path of its own when ordered. Finally, the C-terminal extension after αD compares only to that of M-CSF, and then only in its general direction of exit out past αB and the β-strands.

Figure 4:
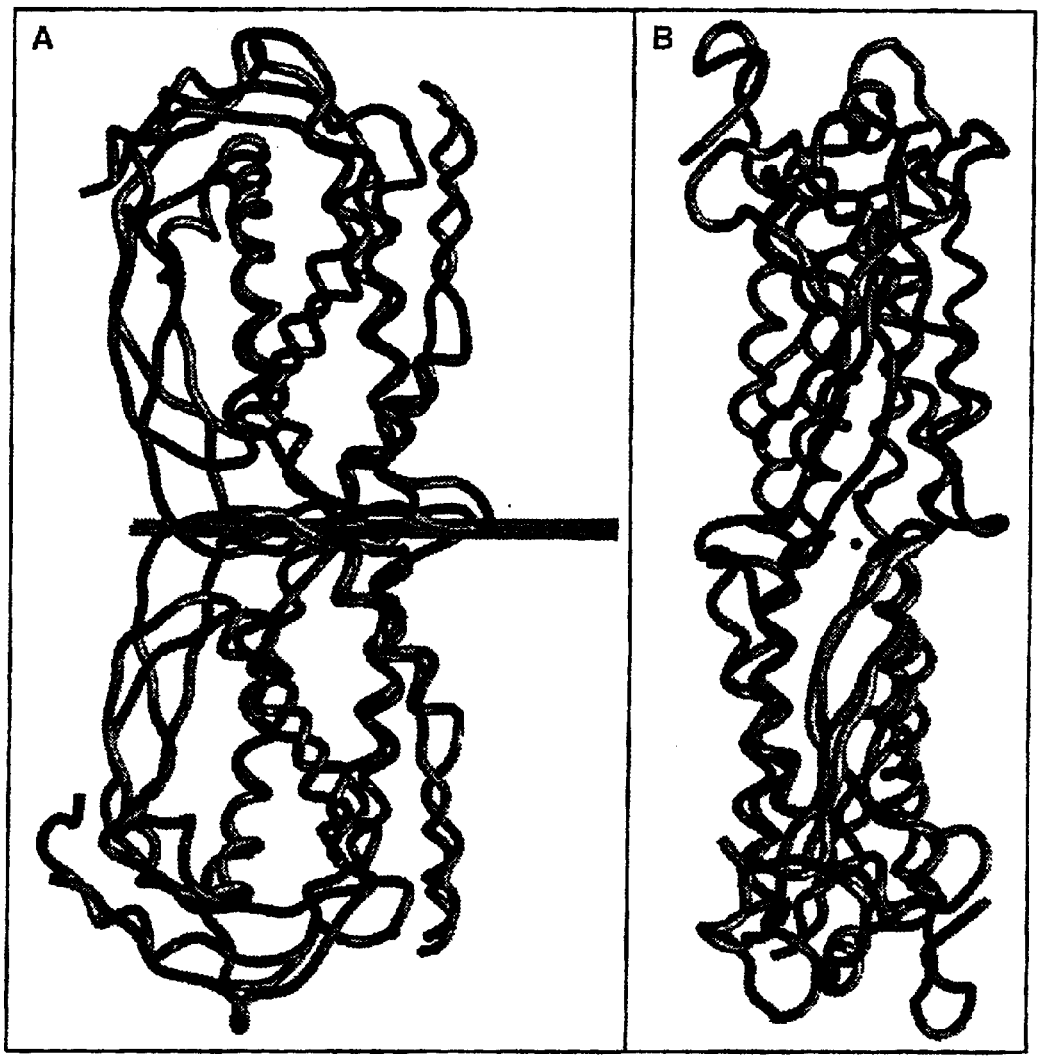
FIGS. 4A–4B. Comparison of SCF dimer (shades of green) and M-CSF dimer (shades of brown).

Among the short-chain helical cytokines, SCF is most closely related to M-CSF. These two have similarities in gene structure, alternative splicing, proteolytic maturation, disulfide bridging, dimer assembly, and receptor type (these similarities also extend to the Flt-3igand; Lyman and Jacobsen, 1998). Despite negligible sequence identity, an alignment and secondary structure prediction prompted by these relationships (Bazan, 1991) fits the actual structure amazingly well, except for shifts in αB and in the αC-β2 loop. Here reality confounds logic; unexpectedly, compa-rable glycosylation sites (Asn120 in SCF and Asn122 in M-CSF) are displaced by one helical turn and comparable disulfide bridges (Cys43–Cys138' in SCF and Cys48–Cys139' in M-CSF) are not superimposible structurally (FIG. 4).

Both were roughly correct in secondary-structure prediction for helices αA and αC, but substantial misplacements were made for helices αB and αD and strand β2. In the study of Rozwarski et al. (Rozwarski et al., 1994), the alignment for αB is incorrect by a shift of 14 residues and that for β2 and αD by a shift of 7 residues. Bazan's earlier sequence alignment (Bazan, 1991) fits to the structural alignment herein amazingly well, except for a shift of one residue for αB and a three-residue gap in the αC-β2 loop.

Comparison with other Cytokine Dimers

Helical cytokines dimerize in various ways (Sprang and Bazan, 1993). Among the five dimeric helical cytokines for which crystal structures have been described [M-CSF, IL-5, ciliary neurotrophic factor (CNTF), interferon-γ (IFN-γ) and IL-10], only IFN-γ and IL-10 are similar dimers. These latter two have a 'tip-to-tip' packing with helix axes approximately perpendicular. Otherwise, the only salient feature in common is having the subunits oriented with bundle axes aligned in parallel and helix dipoles positioned to compensate. There is 'head-to-head' packing of the four-helix bundles in M-CSF, 'tail-to-tail' packing in IL-5, and 'side-to-side' packing in CNTF. Moreover, IFN-γ, IL-10 and IL-5 are all interdigitated dimers with helices swapped between subunits. Thus, although SCF relates most closely to M-CSF, the dimer structure could not be deduced readily beforehand.

SCF in keeping with its relationship to M-CSF, is a non-interdigitated 'head-to-head' dimer (FIG. 4). The two interfaces between promoters are completely different, however. One αA-β1 loop of M-CSF is situated between the αA-β1 and αB-αC loops of the other protomer, whereas in SCF each αA-β1loop interacts only with αB-αC loop of the partner. This staggered mode of M-CSF dimerization (FIG. 4B) is dictated by the position of the Cys31–Cys31' intermolecular disulfide bond in M-CSF. The dyad axes are similarly oriented in the two cases (perpendicular to the bundle axis and parallel to the αA-αD and αB-αC helix planes), but whereas the dyad axis in SCF nearly intersects the bundle axis, that in M-CSF is offset toward the αA-αD helix pair (FIG. 4). Thus, when one protomer of an SCF dimer is superimposed onto one from M-CSF, the superimposition of the two mates requires a translation of 3.8 Å but a rotation of only 4.7°.

Location of the Binding Site for the Receptor Kit

SCF binds with high affinity (nM range) to its receptor (Philo et al., 1996; Broudy, 1997)). Various structure-function studies and analyses help to define residues of SCF that may be involved in this binding. These studies include mutagenesis experiments, immunochemical mapping, comparative analyses of inter-species ligand-receptor interactions, and analyses of glycosylation. Residues thereby implicated in receptor binding can then be mapped onto the surface of SCF as defined by the crystal structure. Although a precise definition of the receptor-binding site on SCF will require direct structural information on the complex of SCF with the Kit receptor, this mapping of the binding site provides a crude picture that is useful when coupled with information on Kit and related receptors.

From studies of truncation and point mutants, Langley et al (1994) demonstrated that the N-terminal residues 1–4 and 1–10 and the Cys4–Cys89 disulfide bond are required for receptor binding and bioactivity, and that the Cys43–Cys138 disulfide bond and C-terminal residues past 127 are not required for receptor binding but may have some roles in cell proliferation activity. Moreover, alterations at Asn10 and Asn11 brought about by chemical isomerization or by mutagenesis have positive or negative effects depending on the substitution (Hsu et al., 1998). A quadruple mutant of SCF (Arg121Asn, Asp124Asn, Lys127Asp and Asp128Lys) was found to be defective in bioactivity (Matous et al., 1996). The molecular cause of this deficiency may be specific to Lys127 or due to indirect electrostatic effects. Arg121 and Asp124 are adjacent to the main N-linked glycosylation site, which is not involved in binding (see infra), and Asp128 is absent in the 1–127 truncation mutant (SEQ ID NO:4) that retains full receptor-binding activity (Langley et al., 1994). Moreover, a study of human-murine SCF chimeras narrowed the important receptor recognition epitopes to within residues 1 to 35 and 79 to 97 (Matous et al., 1996), and the epitope of a neutralizing antibody was mapped to the region of residues 60–95 (Mendiaz et al., 1996) and 79–97 (Matous et al., 1996).

Although SCF molecules from different mammalian species are very similar (>75% identity), there are substantial differences in inter-species receptor activation. Human SCF activates murine Kit very poorly, rodent SCF has only slightly lower potency than human SCF in binding/activating human Kit Martin et al., 1990; Lev et al., 1992), and canine SCF activates human Kit slightly better than human SCF does itself (K. E. Lang, unpublished data). It is likely that the receptor-binding regions involve residues that are different between man and mouse but conserved between man and dog. These residues can be classified into five groups in the sequence (FIG. 5). Most residues in group III are buried and those in group II are close to the dimer interface. The residues in groups III (45–58) are buried and those in group II (24–34) are close to the dimer interface. The results in groups I (1–15), IV (80–117) and and V (130–140) are more likely to be involved in direct receptor binding.

The heavy glycosylation of natural and CHO cell-derived recombinant SCFs sheds light on the question whether residues in vicinity of αD, the equivalent of the major receptor binding site in GH, are involved in receptor binding. Human SCF expressed in CHO cells is approximately 30% by weight (Arakawa et al., 1991) The main glycosylation site is at Asn120 (Langley et al., 1992). Glycosylation at this site, which is near the center of the αD helix, does not appear to influence biological activity; therefore, the area around this residue cannot be involved in receptor binding. Glycosylation of human SCF at either Asn65 or Asn93 lowers the biological activity approximately 10-fold; therefore, these residues may be near but not directly at the binding site.

Taken together, these observations indicate that the receptor-binding site may include residues from the first few N-terminal residues, the 79–95 region (mainly located on αC helix) and the C-terminal end of αD (around 127). These regions are contiguous on the SCF surface in the atomic model provided herein. The putative receptor-binding site of M-CSF was mapped to a similar region (Taylor et al., 1994).

Structural Characteristics of SCF-Kit and Related Ligand-receptor Complexes

Kit, the receptor for SCF, is a class III receptor tyrosine kinase. This class, which includes the receptors for PDGF and M-CSF, is also closely related to the class IV receptors for FGF and the class V receptors for VEGF, Flt-3 ligand and KDR (Fantl et al., 1993). The ligand-binding portions of these receptors are all composed of immunoglobulin(Ig)-like domains and the kinase domains all include kinase insert sequences. The three classes are distinguished by the number of Ig repeats (five for class III, three for class IV and seven for class V) and by the length of kinase insert, which corresponds to an excursion between two helices of the kinase structure. These Ig-like receptors share similar signal transduction pathways, chromosomal localization and gene organization (Rousset et al., 1995), but their ligands come with completely unrelated topologies as typified by VEGF (cystine knot) on the one hand, versus M-CSF, SCF and Flt-3 ligand (helical cytokine) on the other. Even receptors of the same class have unrelated ligands; thus both SCF and PDGF use class III receptors and VEGF anf Flt-3 ligand use class V receptors. The amino acid sequences of the ligands are extremely dissimilar even when the fold is the same, as for PDGF vs. VEGF (25% identity) and M-CSF vs SCF (14% identity).

Although Ig-like receptors have very similar kinase portions (70% amino acid sequence identity between III and V) and about 50% identity for III or V with IV) their Ig-like domains are dissimilar in sequence both between repeats within a molecule and also at comparable positions between different receptors. (Rousset et al., 1995) Nevertheless, there are features of the receptor-ligand interaction that the class III and class V receptors have in common. First, for every studied example, the ligand binding function has been localized to the first three Ig-like domains and, where defined, to domains D2 and D3 specifically (Heidaran et al., 1990; Blechman et al., 1993, Lev et al., 1993; Wang et al., 1993; Davis-Symyth et al., 1996; Barleon et al., 1997). Secondly, the ligands for all of these receptors are functional as dimers; M-CSF, VEGF and PDGF are covalently dimers, while SCF and Flt-3 ligand are non-covalently linked dimers. In each case, signaling occurs through ligand-mediated receptor oligomerization (Heldin, 1995). For SCF-Kit, it has been shown directly by biophysical methods that complexes containing toe SCF subunits and two Kit extracellular domain molecules can form in solution (Philo et al., 1996). The genetic organization of these receptor genes has the placements and phases of introns in common (Agnes et al., 1997) and the extracellular domains can be recognized from sequence motifs as telokin-like, I-set members of the Ig superfamily (Bateman and Chothia, 1995; Harpaz and Chothia, 1994).

The structure of domain D2 of Flt-1 receptor in complex with VEGF (Wiesmann et al., 1997) provides a template for ligand interactions with PDGF-related receptors. Wiesmann et al. (1997) modeled the interaction of VEGF with D1D2D3D4(Flt-1) and discussed the likelihood that other ligand complexes with class III and class V receptors may be similar. In light of the structure of SCF and the identified location of receptor-binding sites, the SCF-Kit complex is modeled herein.

The D2(Flt-1) domain is similar in structure to telokin, as predicted (Harpaz and Chothia, 1994), and thereby also to both domains in the structure of vascular cell adhesion molecule (VCAM)-1 (Jones et al., 1995). To test the validity of VCAM-1 as a model for D2D3 (Flt-1) and D2D3 (Kit), used herein was a prediction-based threading program (Fisher and Eisenberg, 1996) to thread the sequences of the Ig-like domains of Flt-1 and Kit into the telokin and VCAM-1 structures. Fits were achieved with moderate to very high confidence of similarity. The resulting structure-based sequence alignment of D2D3(Kit) with the VCAM-1 template (five gaps) has a continuous domain boundary, and residues Cys151 and Cys183 in D2 (Kit) are positioned properly to make an additional dioulfide bridge between strands C and F.

Characteristics of the SCF-Kit Interaction

Although it has been suggested (Matous et al., 1996; Mendiaz et al., 1996) that SCF may interact with its receptor in a manner analogous to the ligand-receptor interactions of another helical cytokine, growth hormone (de Vos et al., 1992), an alternative mode of interaction can be contemplated given the similarities among Ig-like tyrosine-kinase receptors described above. If these similarities extend to the signaling interaction, the structure of the complex of VEGF with domain D2 of Flt-1 (Wiesmann et al, 1997) should provide a fu template for the interaction despite the disparate structures of the ligands.

To test this hypothesis next constructed was a model of the VEGF-D2D3(Flt-1) receptor complex from a rigid-body superposition of VEGF (Muller et al., 1997) and VCAM-1 such as to mimic the reported VEGF- D2(Flt-1) structure (Wiesmann et al., 1997). Then, keeping the dyad-symmetric receptor pair fixed, VEGF was successively replaced with the other Ig-like receptors ligands of known three-dimensional structure: PDGF (Oefner et al., 1992), M-CSF (Pandit et al., 1992), and SCF (this work). Each was placed on the dyad axis and positioned to optimize contacts between the VEGF-binding site on the receptor and the putative receptor-binding regions of the ligands. Remarkably, these disparate dimeric ligands have similar spacings between binding sites and a satisfactory fit is possible for each (FIG. 6). Also constructed were simple homology models of the various receptors with changes in the backbone only to accommodate insertions and deletions. The model for SCF with D2D3 (Kit) shows a striking electrostatic complementarity between a highly negative binding surface on SCF and a positive surface on Kit (FIGS. 7A and 7B). The glycosylation sites on both molecules are also compatible with unimpeded interaction.

The Kit receptor is activated by both soluble and membrane-bound forms of SCF, and signaling from the membrane-bound form appears to be have in vivo roles (se Lyman and Jacobsen, 1998). Moreover, as in the case of Flt-1 (Barleon et al., 1997), the D4 (Kit) may be involved in inter-receptor contacts in the signaling dimer (Blechman et al., 1995) [although this proposal for Kit has been questioned (Philo et al., 1996; Lemmon et al., 1997)]. The model constructed herein for the SCF-Kit complex is compatible with these properties (FIGS. 7A and 7B). The C-termini of the SCF dimer are directed oppositely from those of Kit, as would be appropriate for a cell-cell contact, and the receptor units cross naturally at D4. It is noteworthy that the ligands of other Ig-like receptors also have membrane-bound forms (M-CSF and Flt-3 ligand) or are typically complexed to the extracellular matrix (Kawasaki and Ladner, 1990; Lyman and Jacobsen, 1998).

The ligand-receptor structures that are suggested herein for the Ig-like kinase receptors are remarkable. Despite marked differences in ligand structure as typified by VEGF (cystine knot), SCF (helical cytokine) and FGF (beta trefoil), the geometrical configurations of receptor binding sites on these ligands are alike. Coupled with features in common among the receptors and in their biology, a similar mode of ligand-receptor interaction across the Ig-like subfamily of receptor tyrosine kinases seems plausible.

SECOND SERIES OF EXPERIMENTS

Based on the X-ray crystallographic structure of SCF, several analogs were made and their biological activities were measured and compared to that of SCF wild type.

Analogs Biological Activity (Approximate, compared to wild type SCF)

SCF(Y26C) disulfide linker 2 to 3 fold higher (SEQ ID NO:11)

SCF(D25C) 100 fold lower (SEQ ID NO:12)

SCF(K62C) 7 fold lower (SEQ ID NO:13)

These analogs were designed based on the structure of the dimer interface of SCF, which is a non-covalent dimer. Leu22, Pro23, Lys24, Asp25, Tyr26, Lys62 and Phe63 are in the dimer surface. The side chains of Leu22, Pro23, Tyr26, and Phe63 reside in the buried center of the dimerization site and are involved in hydrophobic interactions. The hydrophilic side chains of Lys24, Asp25 and Lys62 from each monomer residue in the solvent accessible surface, and are involved in ionic interactions. By replacing Tyr26 with Cys, [SCF(Y26C)], it was anticipated that a dimer covalently linked by a disulfide bond between the C26 residue of each monomer would form because the distance between the β carbons of the two Cys26 residues would be less than 3 Å.

Analogs Biological Activity (Approximate, compared to wild type SCF)

SCF(K78N, N81K) 3 fold lower (SEQ ID NO:14 & SEQ ID NO:15)

SCF(R117A, I118A) 10 fold lower (SEQ ID NO:16 & SEQ ID NO:17)

SCF(E92A, S95A) no change (SEQ ID NO:19 & SEQ ID NO:20)

SCF(D124A, K127D) no change (SEQ ID NO:21 & SEQ ID NO:22)

These analogs were designed based on the assumption that there may be two distinct receptor binding sites, per monomer, as with growth hormone. One site would be on the face between helix A and helix C, and the other site would be on the face between helix A and helix D.

References

Agnes, F., et al. (1997) Genomic organization of the extracellular coding region of the human FGFR4 and FLT4 genes: Evolution of the genes encoding receptor tyrosine kinases with immunoglobulin-like domains. *J. Mol. Evol.*, 45, 45–49.

Anderson, D. M., et al. (1990) Molecular cloning of mast cell growth factor, a hematopoietin that is active in both membrane bound and soluble forms. *Cell*, 63, 235–243.

Andre, C., et al. (1992) Genomic organization of the human c-kit gene: Evolution of the receptor tyrosine kinase subclass III. *Oncogene*, 7, 685–691.

Arakawa, T., et al. (1992) Molecular weights of glycosylated and nonglycosylated forms of recombinant human stem cell factor determined by low-angle laser scattering. *Analytical Biochem.*, 203, 52–57.

Arakawa, T., et al. (1991) Glycosylated and unglycosylated recombinant-derived human stem cell factor are dimeric and have extensive regular secondary structure. *J. Biol. Chem.*, 266, 18942–18948.

Aronson, H.-E. G., et al. (1994) Quantification of tertiary structural conservation despite primary sequence drift in the globin fold. *Prot. Sci.*, 3, 1706–1711.

Barleon, B., et al. (1997) Mapping of the sites for ligand binding and receptor dimerization at the extracellular domain of the vascular endothelial growth factor receptor flt-1. *J. Biol. Chem.*, 272, 10382–10388.

Bateman, A. and Chothia, C. 11995) Outline structures for the extracellular domains of the fibroblast growth factor receptors. *Nature Structural Biology*, 2, 1068–1074.

Bazan, J. F. (1991) Genetic and structural homology of stem cell factor and macrophage colony-stimulating factor. *Cell*, 65, 9–10.

Bella, J., et al. (1998) The structure of the two amino-terminal domains of human ICAM-1 suggests how it functions as a rhinovirus receptor and as an LFA-1 integrin ligand. *Proc. Natl. Acad. Sci. USA*, 95, 4140–4145.

Besmer, P. (1997) Kit-ligand-stem cell factor. In Garland, J. M., Quesenberry, P. J. and Hilton, D. J. (eds), Colony-Stimulating Factors: Molecular and Cellular Biology, 2$^{nd}$ edn., Marcel Dekker, Inc., New York, N.Y., PP. 369–404.

Blechman, J. M., et al. (1993) Soluble c-kit proteins and antireceptor monoclonal antibodies confine the binding site of the stem cell factor. *J. Biol. Chem.*, 268, 4399–4406.

Blechman, J. M., et al. (1995) The fourth immunoglobulin domain of the stem cell factor receptor couples ligand binding to signal transduction. *Cell*, 80, 103–113.

Broudy, V. C. (1997) Stem cell factor and hematopoiesis. *Blood*, 90, 1345–1364.

Brünger, A. T., et al. (1987) Crystallographic R-factor refinement by molecular dynamics. *Science*, 235, 458–460.

Casasnovas, J. M., et al. (1997) Crystal structure of ICAM-2 reveals a distinctive integrin recognition surface. *Nature*, 387, 312–315.

Casasnovas, J. M., et al. (1998) A dimeric crystal structure for the N-terminal two domains of intercellular adhesion molecule-1. *Proc. Natl. Acad. Sci. USA*, 95, 4134–4139.

Collaborative Computational Project Number 4 (1994) The CCP4 suite: programs for protein crystallography. *Acta Czystallogr.*, D, 50, 252–276.

Davis-Symyth, T., et al. (1996) The second immunoglubulin-like domain of the VEGF tyrosine kinase receptor Flt-1 determines ligand binding and may initiate a signal transduction cascade. *EMBO J.*, 15, 4919–4927.

de Vos, A. M., et al. (1992) Human growth hormone and extracellular domain of its receptor: crystal structure of the complex. *Science*, 255, 306–312.

Diederichs, K., et al. (1991) Novel fold and putative receptor binding site of granulocyte-macrophage colony-stimulating factor. *Science*, 254, 1779–1782.

DiGabriele, A. D., et al. (1998) Structure of a heparin-linked biologically active dimer of fibroblast growth factor. *Nature*, 393, 812–817.

DiMario, J., et al. (1989) Fibroblast growth factor in the extracellular matrix of dystrophic (mdx) mouse muscle. *Science*, 244, 688–690.

Ealick, S. E., et al. (1991) Three-dimensional structure of recombinant human interferon-gamma. *Science*, 252, 698–702.

Evans, S. V. (1993) SETOR: Hardware lighted three dimensional solid model representations of macromolecules. *J. Mol. Graphics*, 11, 134–138.

Fantl, W. J., et al. (1993) Signalling by receptor tyrosine kinases. *Annu. Rev. Biochem.*, 62, 453–481.

Fenstermaker et al., (1993) A cationic region of the platelet-derived growth factor (PDGF) A-chain (Arg159-Lys160nLys161) is required for receptor binding and mitogenic activity of the PDGF-AA homodimer., *J. Biol. Chem.*, 268, 10482–10489.

Fisher, D. and Eisenberg, D. (1996) Fold recognition using sequence-derived predictions. *Prot. Sci.*, 5, 947–955.

Fitzgerald, P. M. D. (1988) MERLOT, an integrated package of computer programs for the determination of crystal structures by molecular replacement. *J. Appl. Crystallogr.*, 21, 273–278.

Flanagan, J. G. and Leder, P. (1990) The kit ligand: a cell surface molecule altered in steel mutant fibroblasts. *Cell*, 63, 185–194.

Fukuda, N., et al. (1997) Role of long-form PDGF A-chain in the growth of vascular smooth muscle cells from spontaneously hypertensive rats. *Am. J. Hypertens.*, 10(10 Pt 1), 1117–1124.

Galli, S. J., et al. (1994) The kit ligand, stem cell factor. *Adv. Immunol.*, 55, 1–96.

Gewirth, D. (1995) *The HKL Manual*. Yale University, New Haven, Conn.

Glaspy, J. (1996) Clinical applications of stem cell factor. *Curr. Opin. Hematol.*, 3, 223–229.

Harpaz, Y. and Chothia, C. (1994) Many of the immunoglobulin superfamily domains in cell adhesion molecules and surface receptors belong to a new structural set which is close to that containing variable domains. *J. Mol. Biol.*, 238, 528–539.

Heidaran, M. A., et al. (1990) Chimeric alpha- and beta-platelet-derived growth factor (PDGF) receptors define three immunoglobulin-like domains of the alpha-PDGF receptor that determine PDGF-AA binding specificity. *J. Biol. Chem.*, 265, 18741–18744.

Heldin, C.-H. (1995) Dimerization of cell surface receptors in signal transduction. *Cell*, 80, 213–223.

Hendrickson, W. A. (1979) Transformations to optimize the superposition of similar structures. *Acta Cryst*, A, 35, 158–163.

Hendrickson, W. A. et al. (1985) Direct phase determination based on anomalous scattering. *Methods Enzymology*, 115, 41–55.

Houck, K. A., et al. (1991) The vascular endothelial growth factor family: identification of a fourth molecular species and characterization of alternative splicing of RNA. *Mol. Endocrinol.*, 5, 1906–1814.

Hsu, Y.-R., et al. (1996) In vitro methionine oxidation of *Escherichia coli*-derived human stem cell factor: effects on molecular structure, biological activity, and dimerization. *Protein Sci.*, 5, 1165–1173.

Hsu, Y.-R., et al. (1998) Selective deamidation of recombinant human stem cell factor during in vitro aging: isolation and characterization of the aspartyl and isoaspartyl homodimers and heterodimers. *Biochemistry*, 37, 2251–2262.

Huang, E., et al. (1990) The hematopoietic growth factor KL is encoded by the S1 locus and is the ligand of the c-kit receptor, the product of the W locus, *Cell*, 63, 225–233.

Jones, D. T., et al. (1992) A new approach to protein fold recognition. *Nature*, 358, 86–89.

Jones, E. Y., et al. (1995) Crystal structure of integrin-binding fragment of vascular cell adhesion molecule-1 at 1.8 angstroms resolution. *Nature*, 373, 539–544.

Jones, T. A. (1992) a, yaap, asap, @#*? A set of averaging programs, In S. Bailey, Hubbard, R. & Waller, D. (ed.) *Molecular Replacement, Proceedings of the CCP4 Study Weekend*, Daresbury Laboratory, Warrington, UK, pp. 92–105.

Jones, T. A., et al. (1991) Improved methods for building protein models in electron density maps and the location of errors in these models. *Acta Crystallogr.*, A, 47, 110–119.

Kawasaki, E. S. and Ladner, M. B. (1990) Molecular biology of macrophage colony-stimulating factor. *Immunol. Ser.*, 49, 155–176.

Kelvenbach, C. G., et al. (1991) Densimetric determination of carbohydrate content in glycoproteins. *J. Biochem. Biophys Methods*, 23, 295–300.

Kleywegt, G. J. and Jones, T. A. (1994) Halloween . . . masks and bones. In Bailey, S. Hubbard, R., and Waller, D. (eds), From First Map to Final Model, Proceedings of the CCP4 Study Weekend. Daresbury Laboratory, Warrington, UK, pp 59–66.

Koths, K. (1997) Structure-function studies on human macrophage colony-stimulating factor. *Mol. Reprod. Dev.*, 46, 31–37.

Langley, K. E., et al. (1992) Purification and characterization of soluble forms of human and rat stem cell factor recombinantly expressed by *Escherichia Coli* and by Chinese hamster ovary cells. *Arch. Biochem. Biophys.*, 295, 21–28.

Langley, K. E., et al. (1994) Properties of variant forms of human stem cell factor recombinantly expressed in *Escherichia coli*. *Arch. Biochem. Biophys.*, 311, 55–61.

Laskowski, R. A., et al. (1993) PROCHECK: a program to check stereochemical quality of protein structures. *J. Appl. Crystallogr.*, 26, 283–291.

Lemmon, M. A., et al. (1997) Kit receptor dimerization is driven by bivalent of stem cell factor, *J. Biol. Chem.*, 272, 6311–6317.

Lev, S., et al., (1992) Dimerization and activation of the Kit receptor by monovalent and bivalent binding of the stem cell factor. *J. Biol. Chem.*, 267, 15970–15977.

Lev, S., et al., (1993) Interspecies molecular chimeras of Kit help define the binding site of the stem cell factor. *Mol. Cell. Biol.*, 13, 2224–2234.

Lev, S., et al., (1994) Steel factor and c-kit protooncogene: genetic lessons in sugnal transduction, *Crit. Rev. Oncog.*, 5, 141–168.

Lu, H. S., et al., (1991) Amino acid sequence and post-translational modification of stem cell factor isolated from buffalo rat liver cell-conditioned medium. *J. Biol. Chem.*, 266, 8102–8107.

Lu, H. S., et al., (1992) Post-translational processing of membrane-associated recombinant human stem cell factor expressed in Chinese hamster ovary cells. *Arch. Biochem. Biophys.*, 298, 150–158.

Lu, H. S., et al., (1996) Isolation and characterization of a disulfide-linked human stem cell factor dimer. *J. Biol. Chem.*, 271, 11309–11316.

Lyman, S. D, and Jacobsen, S. E. W. (1998) c-Kit ligand and Flt3 ligand: stem/progenitor cell factors with overlapping yet distinct activities, *Blood*, 91, 1101–1134.

Martin, F. H., et al., (1990) Primary structure and functional expression of rat and human stem cell factor DNAs. *Cell*, 63, 203–211.

Matous, J. V., et al., (1996) Structure-function relationships of stem cell factor: an analysis based on a series of human-murine SCF chimera and the mapping of a neutralizing monoclonal antibody. *Blood*, 88, 437–444.

McDonald, N. Q., et al., (1995) Crystal structure of dimeric human ciliary neurotrophic factor determined by MAD phasing. *EMBO J.*, 14, 2689–2699.

McKay, D. B. (1992) Unraveling the structure of IL-2, *Science*, 257, 412–413.

McNiece, I. K. and Briddell, R. A. (1995) Stem cell factor. *J. Leukoc. Biol.*, 57, 14–22.

Mendiaz, E. A., et al. (1996) Epitope mapping and immunoneutralization of recombinant human stem cell factor. *Eur. J. Biochem.*, 239, 842–649.

Milburn, M. V., et al. (1993) A novel dimer configuration revealed by the crystal structure at 2.4 Å resolution of human interleukin-5. *Nature*, 363, 172–176.

Muller, Y. A., et al. (1997) Vascular endothelial growth factor: crystal structure and functional mapping of the kinase domain receptor binding site. *Proc. Natl. Acad. Sci. USA*, 94, 7192–7197.

Neufeld, G., et al. (1994). Vascular endothelial growth factor and its receptors. *Prog. Growth Factor Res.*, 5, 89–97.

Nicholls, A., et al. (1991) Protein folding and association: insights from the interfacial and thermodynamic properties of hydrocarbons. *Proteins*, 11, 281–296.

Oefner, C., et al. (1992) Crystal structure of human platelet-derived growth factor BB. *EMBO J.*, 11, 3921–3926.

Otwinowski, Z. (1993) Oscillation data reduction program, In N. I. L. Sawyer, and S. Bailey (eds.) *Data Collection and Processing*, Science and Engineering Research Council, Warrington, UK, Vol. pp. 55–62.

Pähler, A., et al. (1990) A probability representation for phase information from multiwavelength anomalous dispersion. *Acta Cryst*, A, 46, 537–540.

Pandit, J., et al., (1992) Three-dimensional structure of dimeric huam recombinant macrophage colony-stimulating factor. *Science*, 258, 1358–1362.

Philo, J. S., et al., (1i996) Human stem cell factor dimer forms a complex with two molecules of the extracellular domain of its receptor, Kit. *J. Biol. Chem.*, 271, 6895–6902.

Qiu, F., et al., (1988) Primary structure of c-kit: relationship with the CSF-1/PDGF receptor kinase family-oncogenic activation of v-kit involves deletion of extracellular domain and C terminus. *EMBO J.*, 7, 1003–1011.

Raines, E. W. and Ross, R. (1992) Compartmentalization of PDGF on extracellular binding sites dependent on exon-6-encoded sequences. *J. Cell Biol.*, 116, 533–543.

Read, R. J. (1986) Improved Pourier coefficients for maps using phases from partial structures with errors. *Acta Crystallogr*, A, 42, 140–149.

Rousset, D., et al., (1995) Molecular evolution of the genes encoding receptor tyrosine kinase with immunoglobulin-like domains. *J. Mol. Evol.*, 41, 421–430.

Rozwarski, D. A., et al., (1994) Structural comparisons among the short-chain helical cytokines. *Structure*, 2, 159–173.

Russell, E. S. (1979) Hereditary anemias of the mouse: a review for geneticists. *Adv. Genet.*, 20, 357–459.

Shrake, A. and Rupley, J. A. (1973) Environment and exposure to solvent of protein atoms: lysozyme and insulin. *J. Mol. Biol.*, 79, 351–371.

Shull, R. M. et al., (1992) Canine stem cell factor (c-kit ligand) supports the survival of hematopoietic progenitors in long-term canine marro Stanley, E. R. and Guilbert,.L. J. (1981) Methods for the purificaiton, assay, characterization and target cell binding of a colony stimulating factor (CSF-1). *J. Immunol. Methods*, 42, 253–284.

Sprang, S. R. and Bazan J. F. (1993) Cytokine structural taxonomy and mechanisms of receptor engagement, *Curr. Opin. Struct. Biol.*, 3, 815–827.

Stein, J., et al. (1990) Direct stimulation of cells expressing receptors for macrophage colony-stimulating factor (CSF-1) by a plasma membrane-bound precursor of human CSF-1. *Blood*, 76, 1308–1314.

Tan, K., et al., (1998) The structure of immunoglobulin superfamily domains 1 and 2 of MAdCAM-1 reveals novel features important for integrin recognition. *Structure*, 6, 793–801.

Taylor, E. W., et al., (1994) Structure-function studies on recombinant human macrophage colony-stimulating factor (M-CSF). *J. Biol. Chem.*, 269, 31171–31177.

Toksoz, D., et al., (1992) Support of human hematopoiesis in long-term bone marrow cultures by murine stromal cells selectively expressing the membrane-bound and secreted forms of the human homolog of the steel gene product, stem cell factor. *Proc. Natl. Acad. Sci. USA*, 89, 7350–7354.

Wang, J. H., et al., (1995) The crystal structure of an N-terminal two-domain fragment of vascular cell adhesion molecule 1 (VCAM-1): a cyclic peptide based on the domain 1 C-D loop can inhibit VCAM-1-alpha 4 integrin interaction. *Proc. Natl. Acad. Sci. USA*, 92, 5714–5718.

Wang, Z., et al., (1993) Identification of the ligand-binding regions in the macrophage colony-stimulating factor receptor extracellular domain. *Mol. Cell. Biol.*, 13, 5348–5359.

Wiesmann, C., et al., (1997) Crystal structure at 1.7 Å resolution of VEGF in complex with domain 2 of the Flt-1 receptor. *Cell*, 91, 695–704.

Wlodawer, A.; et al., (1992) Crystal structure of human recombinant interleukin-4 at 2.25 Å, *FEBS Lett.*, 309, 59–64.

Zdanov, A., et al., (1995) Crystal structure of interleukin-10 reveals the functional dimer with an unexpected topological similarity to interferon gamma. *Structure*, 3, 591–601.

Zimmer, Y., et al., (1993) Multiple structural elements determine ligand binding of fibroblast growth factor receptors: Evidence that both Ig domain 2 and 3 define receptor specificity. *J. Biol. Chem.*, 268, 7899–7903.

What is claimed is:

1. A method of preparing a compound capable of binding to a Stem Cell Factor-binding site of a Stem Cell Factor receptor comprising the steps of:
   a) determining the 3-D structure of a fragment of a Stem Cell Factor (SCF) by computing atomic co-ordinates from X-ray diffraction data of a crystal of the fragment of SCF, wherein the fragment of SCF consists of consecutive amino acids the sequence of which is set forth in SEQ ID NO:1;
   b) identifying a Stem Cell Factor receptor-binding site on the fragment of SCF based on the 3-D structure of the SCF fragment;
   c) designing a compound capable of binding to the Stem Cell Factor-binding site of the Stem Cell Factor receptor based on a 3-D structure shape complementarity or estimated interaction energy of the Stem Cell Factor receptor-binding site on the fragment of SCF; and
   d) preparing the compound capable of binding to the Stem Cell Factor-binding site of the Stem Cell Factor receptor designed in step c).

2. The method of claim 1, wherein the compound capable of binding to a Stem Cell Factor receptor comprises two ligand heads linked by a linker molecule, wherein the linker molecule is an organic polymer attached at each end to a separate capping moiety, each capping moiety attached in turn to a single ligand head via a cysteine residue, wherein the ligand head comprises the elements $F_1$—$X_n$—$F_L$(Cys)—$X_m$—$F_2$—$X_p$—$F_3$, wherein each of $F_1$, $F_2$ and $F_3$ is a peptide each comprising consecutive amino acids having a sequence corresponding to a sequence of consecutive amino acid residues of Stem Cell Factor (SCF) (SEQ ID NO:1); each of $X_n$, $X_m$, and $X_p$ is a peptide of n, m, and p amino acid residues, respectively where each of n, m, and p is an integer representing a number of amino acid residues; $F_L$ (Cys) is the cysteine residue; and each dash (—) represents a peptide bond.

3. The method of claim 2, wherein the sequence of $F_1$ corresponds to a sequence of amino acid residues present within N-terminal residues 1–10 of SCF (SEQ ID NO:1); $F_2$ corresponds to a sequence of amino acid residues present within residues 79–95 of SCF, and the sequence of $F_3$ corresponds to a sequence of amino acid residues present within three amino acid residues of amino acid residue 127 of SCF; and wherein n=0–5, m=0–5 and p=3–8.

4. The method of claim 2, wherein each of $F_1$, $F_2$, $F_3$ has been selected by bacterial phage display for optimal receptor binding.

5. The method of claim 2, wherein the organic polymer is polyethyleneglycol (PEG) comprising the structure H[OCH$_2$CH$_2$]$_n$OH, wherein n is integer from 10 to 20.

6. The method of claim 2, wherein the capping moiety is a thiol-reactive group.

7. The method of claim 6, wherein the thiol-reactive group is N-ethyl malemide.

* * * * *